US012441707B2

(12) United States Patent
Hudkins et al.

(10) Patent No.: US 12,441,707 B2
(45) Date of Patent: Oct. 14, 2025

(54) INDAZOLE COMPOUNDS

(71) Applicant: TYRA BIOSCIENCES, INC., Carlsbad, CA (US)

(72) Inventors: Robert L. Hudkins, Virginia Beach, VA (US); Daniel C. Bensen, Carlsbad, CA (US)

(73) Assignee: TYRA BIOSCIENCES, INC., Carlsbad, CA (US)

( * ) Notice: Subject to any disclaimer, the term of this patent is extended or adjusted under 35 U.S.C. 154(b) by 603 days.

(21) Appl. No.: 17/788,346

(22) PCT Filed: Dec. 30, 2020

(86) PCT No.: PCT/US2020/067415

§ 371 (c)(1),
(2) Date: Jun. 23, 2022

(87) PCT Pub. No.: WO2021/138391

PCT Pub. Date: Jul. 8, 2021

(65) Prior Publication Data

US 2023/0115528 A1 Apr. 13, 2023

Related U.S. Application Data

(60) Provisional application No. 63/047,600, filed on Jul. 2, 2020, provisional application No. 62/954,939, filed on Dec. 30, 2019.

(51) Int. Cl.
*C07D 401/14* (2006.01)
*A61P 35/00* (2006.01)
*C07D 401/12* (2006.01)

(52) U.S. Cl.
CPC ............ *C07D 401/14* (2013.01); *A61P 35/00* (2018.01); *C07D 401/12* (2013.01)

(58) Field of Classification Search
CPC ...... C07D 401/14; C07D 401/12; A61P 35/00
See application file for complete search history.

(56) References Cited

U.S. PATENT DOCUMENTS

| | | | |
|---|---|---|---|
| 4,775,612 | A | 10/1988 | Abe et al. |
| 4,940,703 | A | 7/1990 | Baker et al. |
| 5,041,453 | A | 8/1991 | Huang et al. |
| 5,461,146 | A | 10/1995 | Lewis et al. |
| 5,792,778 | A | 8/1998 | De et al. |
| 5,859,041 | A | 1/1999 | Liverton et al. |
| 6,063,930 | A | 5/2000 | Dinsmore et al. |
| 6,200,968 | B1 | 3/2001 | Dickason et al. |
| 6,329,412 | B1 | 12/2001 | Goldstein et al. |
| 6,391,872 | B1 | 5/2002 | Marfat |
| 6,562,817 | B1 | 5/2003 | Tanimoto et al. |
| 6,579,983 | B1 | 6/2003 | Batchelor et al. |
| 6,600,037 | B1 | 7/2003 | Davis et al. |
| 6,660,729 | B1 | 12/2003 | Dickason et al. |
| 6,689,778 | B2 | 2/2004 | Bemis et al. |
| 6,716,978 | B2 | 4/2004 | Marfat |
| 6,746,729 | B1 | 6/2004 | Cherkaoui et al. |
| 6,953,857 | B2 | 10/2005 | Nazare et al. |
| 6,969,714 | B2 | 11/2005 | Breault et al. |
| 6,982,274 | B2 | 1/2006 | Oinuma et al. |
| 6,995,144 | B2 | 2/2006 | Ozaki et al. |
| 7,008,954 | B1 | 3/2006 | Arimura et al. |
| 7,018,999 | B2 | 3/2006 | Aimone et al. |
| 7,067,665 | B2 | 6/2006 | Nazare et al. |
| 7,186,716 | B2 | 3/2007 | Wei et al. |
| 7,244,739 | B2 | 7/2007 | Cheng et al. |
| 7,265,108 | B2 | 9/2007 | Ozaki et al. |
| 7,276,502 | B2 | 10/2007 | Brenchley et al. |
| 7,429,609 | B2 | 9/2008 | Ohi et al. |
| 7,456,191 | B2 | 11/2008 | Luecking et al. |
| 7,485,638 | B2 | 2/2009 | Newcombe et al. |
| 7,541,376 | B2 | 6/2009 | Oinuma et al. |
| 7,615,562 | B2 | 11/2009 | Bollbuck et al. |
| 7,635,698 | B2 | 12/2009 | Rosse et al. |
| 7,776,890 | B2 | 8/2010 | Oinuma et al. |
| 7,781,442 | B2 | 8/2010 | Cheng et al. |
| 7,795,246 | B2 | 9/2010 | Dickason et al. |
| 7,799,808 | B2 | 9/2010 | Cheng et al. |
| 7,825,128 | B2 | 11/2010 | Luecking et al. |
| 7,834,036 | B2 | 11/2010 | Wood et al. |
| 7,880,002 | B2 | 2/2011 | Carson et al. |
| 7,910,741 | B2 | 3/2011 | Nishizawa et al. |
| 7,915,274 | B2 | 3/2011 | Ozaki et al. |
| 7,968,543 | B2 | 6/2011 | James et al. |
| 8,008,481 | B2 | 8/2011 | Ericsson et al. |

(Continued)

FOREIGN PATENT DOCUMENTS

| | | |
|---|---|---|
| CN | 103420906 A | 12/2013 |
| CN | 103664878 A | 3/2014 |

(Continued)

OTHER PUBLICATIONS

Lucking, "Sulfoximines: A Neglected Opportunity in Medicinal Chemistry" Angew. Chem. Int. Ed., 52 (36) 2013, pp. 9399-9408. (Year: 2013).*

Sirvent et al. "Novel Pieces for the Emerging Picture of Sulfoximines in Drug Discovery: Synthesis and Evaluation of Sulfoximine Analogues of Marketed Drugs and Advanced Clinical Candidates" ChemMedChem, 12 (7) 2017, pp. 487-501. (Year: 2017).*

Carlson et al., Systematically Mitigating the p38a Activity of Triazole-based BET Inhibitors, ACS Med. Chem. Lett., vol. 10, No. 9, 2019, pp. 1296-1301.

Fricker et al., Substituting c-Jun N-terminal kinase-3 (JNK3) ATP-binding site amino acid residues with their p38 counterparts affects binding of JNK- and p38-selective inhibitors, Archives of Biochemistry and Biophysics, vol. 438, Issue 2, 2005, pp. 195-205.

(Continued)

*Primary Examiner* — Joseph K Mckane
*Assistant Examiner* — Jalisa Holmes Ferguson
(74) *Attorney, Agent, or Firm* — BakerHostetler

(57) ABSTRACT

Disclosed herein are indazole compounds and methods of treating diseases and/or conditions (e.g., cancer) with the indazole compounds disclosed herein.

23 Claims, No Drawings

(56) References Cited

U.S. PATENT DOCUMENTS 8,017,629 B2 9/2011 Cheng et al.
8,119,680 B2 2/2012 Cheng et al.
8,143,404 B2 3/2012 Takaoka et al.
8,168,788 B2 5/2012 Carson et al.
8,211,429 B2 7/2012 Watts et al.
8,277,830 B2 10/2012 De et al.
8,309,550 B2 11/2012 Luo et al.
8,324,231 B2 12/2012 Koltun et al.
8,329,737 B2 12/2012 Styles et al.
8,338,439 B2 12/2012 Singh et al.
8,338,458 B2 12/2012 Meinke et al.
8,399,006 B2 3/2013 De et al.
8,399,455 B2 3/2013 Rosse et al.
8,410,276 B2 4/2013 Takaoka et al.
8,426,417 B2 4/2013 Caruso et al.
8,450,335 B2 5/2013 Singh et al.
8,455,516 B2 6/2013 Gochin et al.
8,481,279 B2 7/2013 Rikova et al.
8,546,433 B2 10/2013 Hitoshi et al.
8,598,374 B2 12/2013 Shi et al.
8,604,207 B2 12/2013 Takaoka et al.
8,609,679 B2 12/2013 Singh et al.
8,642,587 B2 2/2014 Lange et al.
8,648,197 B2 2/2014 Carson et al.
8,669,289 B2 3/2014 Li
8,710,222 B2 4/2014 Singh et al.
8,722,903 B2 5/2014 Buchstaller et al.
8,735,412 B2 5/2014 Lucking et al.
8,759,337 B2 6/2014 Asberom et al.
8,791,136 B2 7/2014 Goff et al.
8,795,660 B2 8/2014 Watts et al.
8,809,370 B2 8/2014 Goff et al.
8,883,793 B2 11/2014 Chen et al.
8,957,073 B2 2/2015 Allen et al.
8,962,618 B2 2/2015 Reddy et al.
8,975,235 B2 3/2015 Buckman et al.
8,980,921 B2 3/2015 Goff et al.
8,987,303 B2 3/2015 Goff et al.
9,000,175 B2 4/2015 Thotapally et al.
9,016,221 B2 4/2015 Brennan et al.
9,040,547 B2 5/2015 Cheng et al.
9,089,574 B2 7/2015 Gavegnano et al.
9,109,227 B2 8/2015 Valmier
9,120,779 B2 9/2015 Li et al.
9,140,689 B2 9/2015 Byron et al.
9,155,723 B2 10/2015 Jain et al.
9,212,181 B2 12/2015 Singh et al.
9,216,172 B2 12/2015 Kohno et al.
9,248,185 B2 2/2016 Rubin et al.
9,254,288 B2 2/2016 Pollock
9,266,856 B2 2/2016 Goff et al.
9,296,737 B2 3/2016 Singh et al.
9,315,848 B2 4/2016 Haick et al.
9,340,489 B2 5/2016 Atzrodt et al.
9,340,566 B2 5/2016 Reddy et al.
9,351,943 B2 5/2016 Mcleay
9,402,901 B2 8/2016 Binder
9,415,118 B2 8/2016 Batt et al.
9,464,065 B2 10/2016 Schultz et al.
9,476,050 B2 10/2016 Westermarck et al.
9,498,532 B2 11/2016 Batt et al.
9,517,238 B2 12/2016 Rochman et al.
9,523,130 B2 12/2016 Rikova et al.
9,546,162 B2 1/2017 Donde et al.
9,550,000 B2 1/2017 Robinson et al.
9,550,770 B2 1/2017 Qian et al.
9,617,256 B2 4/2017 Moser et al.
9,663,496 B2 5/2017 Irving et al.
9,669,068 B2 6/2017 Shaw
9,676,802 B2 6/2017 Qiu et al.
9,695,178 B2 7/2017 Zhang
9,718,803 B2 8/2017 Allen et al.
9,724,421 B2 8/2017 Denys et al.
9,730,877 B2 8/2017 Christiano et al.
9,732,055 B2 8/2017 Li et al.
9,782,417 B2 10/2017 Rubin et al.
9,782,418 B2 10/2017 Lee et al.
9,801,853 B2 10/2017 Grandori et al.
9,840,516 B2 12/2017 Li et al.
9,884,900 B2 2/2018 Kumar et al.
9,890,147 B2 2/2018 Siegel et al.
9,908,884 B2 3/2018 Gray et al.
9,918,972 B2 3/2018 Civin et al.
9,931,347 B2 4/2018 Cowley et al.
9,931,400 B2 4/2018 Jeong et al.
9,931,401 B2 4/2018 Urano et al.
9,938,264 B2 4/2018 Crews et al.
9,951,064 B2 4/2018 Bryan et al.
9,968,608 B2 5/2018 Khattar et al.
9,987,276 B2 6/2018 Singh et al.
10,000,814 B2 6/2018 Cronin et al.
10,010,548 B2 7/2018 Singh et al.
10,034,891 B2 7/2018 Reddy et al.
10,045,979 B2 8/2018 Long et al.
10,094,834 B2 10/2018 Westermarck et al.
10,100,042 B2 10/2018 Chen et al.
10,124,003 B2 11/2018 Sootome
10,166,237 B2 1/2019 Schultz et al.
10,172,868 B2 1/2019 Qian et al.
10,180,626 B2 1/2019 Fujiwara et al.
10,208,017 B2 2/2019 Hommes et al.
10,246,424 B2 4/2019 Li et al.
10,294,207 B2 5/2019 Choi et al.
10,308,648 B2 6/2019 Ciblat et al.
10,329,270 B2 6/2019 Qiu et al.
10,351,527 B2 7/2019 Rennie et al.
10,377,742 B2 8/2019 Goff et al.
10,414,757 B2 9/2019 Li et al.
10,414,875 B2 9/2019 Cannas et al.
10,463,661 B2 11/2019 Long et al.
10,519,133 B2 12/2019 Chen et al.
10,544,106 B2 1/2020 Qian et al.
10,550,121 B2 2/2020 Gray et al.
10,550,326 B2 2/2020 Wittek et al.
10,562,883 B2 2/2020 Hommes et al.
10,596,172 B2 3/2020 Singh et al.
10,633,338 B2 4/2020 Rennie et al.
10,653,701 B2 5/2020 Qian et al.
10,662,174 B2 5/2020 Wang et al.
10,709,718 B2 7/2020 Reddy et al.
10,736,897 B2 8/2020 Li et al.
10,781,218 B2 9/2020 Wu et al.
10,828,300 B2 11/2020 Singh et al.
10,829,458 B2 11/2020 Li et al.
10,870,651 B2 12/2020 Gray et al.
10,941,134 B2 3/2021 Goff et al.
10,959,966 B2 3/2021 Su et al.
11,040,976 B2 6/2021 Maianti et al.
11,059,795 B2 7/2021 Zhou et al.
11,124,628 B2 9/2021 Zhang et al.
11,351,168 B1 6/2022 Singh et al.
2002/0049220 A1 4/2002 Revesz et al.
2002/0169154 A1 11/2002 Ruggeri et al.
2003/0087899 A1 5/2003 Aimone et al.
2003/0149061 A1 8/2003 Nishihara et al.
2003/0212269 A1 11/2003 Davis et al.
2003/0232391 A1 12/2003 Prescott et al.
2004/0014776 A1 1/2004 Breault et al.
2004/0171630 A1 9/2004 Kim et al.
2004/0220176 A1 11/2004 Dickason et al.
2004/0235876 A1 11/2004 Davis et al.
2005/0004150 A1 1/2005 Brenchley et al.
2005/0049246 A1 3/2005 Bemis et al.
2005/0171134 A1 8/2005 Davis et al.
2005/0176760 A1 8/2005 Cezanne et al.
2005/0203151 A1 9/2005 Malecha et al.
2005/0282880 A1 12/2005 Oinuma et al.
2006/0004033 A1 1/2006 Breault et al.
2006/0058250 A1 3/2006 Denmeade et al.
2006/0094674 A1 5/2006 Neel et al.
2007/0043048 A1 2/2007 Bollbuck et al.
2007/0135401 A1 6/2007 Dziki et al.
2007/0135485 A1 6/2007 Gillig et al.
2007/0135628 A1 6/2007 Dziki et al.

(56) References Cited

U.S. PATENT DOCUMENTS

| | | | |
|---|---|---|---|
| 2007/0185069 | A1 | 8/2007 | Plum et al. |
| 2007/0244140 | A1 | 10/2007 | Hu et al. |
| 2008/0021013 | A1 | 1/2008 | Dobrzanski et al. |
| 2008/0066741 | A1 | 3/2008 | Lemahieu et al. |
| 2008/0299215 | A1 | 12/2008 | Czarnik |
| 2009/0047246 | A1 | 2/2009 | Beigelman et al. |
| 2009/0048282 | A1 | 2/2009 | Hauze et al. |
| 2009/0054358 | A1 | 2/2009 | Small et al. |
| 2009/0155352 | A1 | 6/2009 | Drager et al. |
| 2009/0156475 | A1 | 6/2009 | Rikova et al. |
| 2009/0203691 | A1 | 8/2009 | Oinuma et al. |
| 2009/0203709 | A1 | 8/2009 | Steinberg et al. |
| 2009/0209496 | A1 | 8/2009 | Chaplin et al. |
| 2009/0226431 | A1 | 9/2009 | Habib |
| 2009/0227650 | A1 | 9/2009 | Bierlmaier et al. |
| 2009/0275567 | A1 | 11/2009 | Jones et al. |
| 2009/0312319 | A1 | 12/2009 | Ren et al. |
| 2010/0048533 | A1 | 2/2010 | Dziki et al. |
| 2010/0048534 | A1 | 2/2010 | Dziki et al. |
| 2010/0075965 | A1 | 3/2010 | Ni et al. |
| 2010/0135983 | A1 | 6/2010 | Hyde et al. |
| 2010/0135984 | A1 | 6/2010 | Hyde et al. |
| 2010/0136094 | A1 | 6/2010 | Hyde et al. |
| 2010/0136095 | A1 | 6/2010 | Hyde et al. |
| 2010/0136096 | A1 | 6/2010 | Hyde et al. |
| 2010/0136097 | A1 | 6/2010 | Hyde et al. |
| 2010/0137246 | A1 | 6/2010 | Hyde et al. |
| 2010/0137247 | A1 | 6/2010 | Hyde et al. |
| 2010/0143459 | A1 | 6/2010 | Liepold et al. |
| 2010/0179318 | A1 | 7/2010 | Stoner |
| 2010/0298255 | A1 | 11/2010 | Ballesteros et al. |
| 2011/0009421 | A1 | 1/2011 | Setoh et al. |
| 2011/0070232 | A1 | 3/2011 | Lepage et al. |
| 2011/0129463 | A1 | 6/2011 | Erez et al. |
| 2011/0130374 | A1 | 6/2011 | Erez et al. |
| 2011/0245210 | A1 | 10/2011 | Greig et al. |
| 2011/0263541 | A1 | 10/2011 | Luo et al. |
| 2011/0294784 | A1 | 12/2011 | Asberom et al. |
| 2012/0039805 | A1 | 2/2012 | Lisanti et al. |
| 2012/0040977 | A1 | 2/2012 | Li et al. |
| 2012/0135952 | A1 | 5/2012 | Kim et al. |
| 2012/0157500 | A1 | 6/2012 | Tao |
| 2012/0244116 | A1 | 9/2012 | Hiwase et al. |
| 2012/0245156 | A1 | 9/2012 | Nguyen |
| 2013/0028978 | A1 | 1/2013 | Mao et al. |
| 2013/0079348 | A1 | 3/2013 | Velicelebi et al. |
| 2013/0129675 | A1 | 5/2013 | Priebe et al. |
| 2013/0131034 | A1 | 5/2013 | Follmann et al. |
| 2013/0156764 | A1 | 6/2013 | Levis et al. |
| 2013/0209452 | A1 | 8/2013 | Rikova et al. |
| 2013/0252924 | A1 | 9/2013 | Penninger et al. |
| 2013/0266666 | A1 | 10/2013 | Moneo et al. |
| 2013/0267515 | A1 | 10/2013 | Sawyer et al. |
| 2013/0288915 | A1 | 10/2013 | Seligmann et al. |
| 2013/0310340 | A1 | 11/2013 | Payan et al. |
| 2013/0310379 | A1 | 11/2013 | Albrecht et al. |
| 2013/0338161 | A1 | 12/2013 | Hitoshi et al. |
| 2014/0004516 | A1 | 1/2014 | Sattler et al. |
| 2014/0065142 | A1 | 3/2014 | Roschke et al. |
| 2014/0135377 | A1 | 5/2014 | Westermarck et al. |
| 2014/0213538 | A1 | 7/2014 | Buckman et al. |
| 2014/0221404 | A1 | 8/2014 | Kohno et al. |
| 2014/0235558 | A1 | 8/2014 | Kim et al. |
| 2014/0235559 | A1 | 8/2014 | Kim et al. |
| 2014/0303163 | A1 | 10/2014 | Luo |
| 2014/0343128 | A1 | 11/2014 | Bentires-Alj et al. |
| 2014/0349969 | A1 | 11/2014 | Penninger et al. |
| 2014/0357557 | A1 | 12/2014 | Cole et al. |
| 2014/0364420 | A1 | 12/2014 | Carson et al. |
| 2015/0050274 | A1 | 2/2015 | Elenitoba-Johnson et al. |
| 2015/0056193 | A1 | 2/2015 | Crosby et al. |
| 2015/0073036 | A1 | 3/2015 | Hawryluk et al. |
| 2015/0087673 | A1 | 3/2015 | Hitoshi et al. |
| 2015/0093355 | A1 | 4/2015 | Hiwase et al. |
| 2015/0148345 | A1 | 5/2015 | Lannutti et al. |
| 2015/0155494 | A1 | 6/2015 | Wei et al. |
| 2015/0177246 | A1 | 6/2015 | Shibata et al. |
| 2015/0203502 | A1 | 7/2015 | Cheng et al. |
| 2015/0204877 | A1 | 7/2015 | Westermarck et al. |
| 2015/0209369 | A1 | 7/2015 | Westermarck et al. |
| 2015/0210765 | A1 | 7/2015 | Roschke et al. |
| 2015/0218652 | A1 | 8/2015 | Doebele et al. |
| 2015/0297598 | A1 | 10/2015 | Friedman et al. |
| 2015/0366866 | A1 | 12/2015 | Ali et al. |
| 2016/0009785 | A1 | 1/2016 | Lipson et al. |
| 2016/0045498 | A1 | 2/2016 | Ernst et al. |
| 2016/0046678 | A1 | 2/2016 | Roschke et al. |
| 2016/0128974 | A1 | 5/2016 | Jain et al. |
| 2016/0158353 | A1 | 6/2016 | Kielian |
| 2016/0166571 | A1 | 6/2016 | Janes et al. |
| 2016/0235812 | A1 | 8/2016 | Bruhn et al. |
| 2016/0243150 | A1 | 8/2016 | Wood et al. |
| 2016/0251696 | A1 | 9/2016 | Georgopoulos et al. |
| 2016/0272707 | A1 | 9/2016 | Levine et al. |
| 2016/0279135 | A1 | 9/2016 | Lannutti et al. |
| 2016/0289663 | A1 | 10/2016 | Kiyokawa et al. |
| 2016/0304613 | A1 | 10/2016 | Watts et al. |
| 2016/0304616 | A1 | 10/2016 | Hiwase et al. |
| 2016/0317499 | A1 | 11/2016 | Nakanishi et al. |
| 2016/0317660 | A1 | 11/2016 | Mcleay |
| 2016/0355503 | A1 | 12/2016 | Zhou et al. |
| 2017/0008964 | A1 | 1/2017 | Batt et al. |
| 2017/0042891 | A1 | 2/2017 | Hitoshi et al. |
| 2017/0071877 | A1 | 3/2017 | Kim et al. |
| 2017/0087156 | A1 | 3/2017 | Allen et al. |
| 2017/0096409 | A1 | 4/2017 | Singh et al. |
| 2017/0106003 | A1 | 4/2017 | Berenson |
| 2017/0106095 | A1 | 4/2017 | Batt et al. |
| 2017/0114415 | A1 | 4/2017 | Doebele et al. |
| 2017/0136021 | A1 | 5/2017 | Einav et al. |
| 2017/0143725 | A1 | 5/2017 | Sawyer et al. |
| 2017/0157275 | A1 | 6/2017 | Panyam et al. |
| 2017/0172920 | A1 | 6/2017 | Li et al. |
| 2017/0205395 | A1 | 7/2017 | Ballesteros et al. |
| 2017/0246174 | A1 | 8/2017 | Amatangelo et al. |
| 2017/0248616 | A1 | 8/2017 | Sarraf |
| 2017/0258922 | A1 | 9/2017 | Kinoh et al. |
| 2017/0281566 | A1 | 10/2017 | Ciceri et al. |
| 2017/0296669 | A1 | 10/2017 | Denys et al. |
| 2017/0349953 | A1 | 12/2017 | Lovejoy et al. |
| 2017/0362328 | A1 | 12/2017 | Hiwase et al. |
| 2017/0369780 | A1 | 12/2017 | Adlem et al. |
| 2018/0044672 | A1 | 2/2018 | Zehendner et al. |
| 2018/0050085 | A1 | 2/2018 | Kumar et al. |
| 2018/0057898 | A1 | 3/2018 | Tabibiazar et al. |
| 2018/0086764 | A1 | 3/2018 | Gelman et al. |
| 2018/0117061 | A1 | 5/2018 | Lee et al. |
| 2018/0117148 | A1 | 5/2018 | Holman |
| 2018/0117168 | A1 | 5/2018 | Cole et al. |
| 2018/0127426 | A1 | 5/2018 | Kinsella et al. |
| 2018/0153858 | A1 | 6/2018 | Grandori et al. |
| 2018/0162807 | A1 | 6/2018 | Dixon et al. |
| 2018/0185372 | A1 | 7/2018 | Schinazi et al. |
| 2018/0185382 | A1 | 7/2018 | Narla et al. |
| 2018/0200213 | A1 | 7/2018 | Kelley et al. |
| 2018/0201614 | A1 | 7/2018 | Bunker et al. |
| 2018/0214449 | A1 | 8/2018 | Kim et al. |
| 2018/0222886 | A1* | 8/2018 | Chen .................... C07D 413/14 |
| 2018/0256678 | A1 | 9/2018 | Khodarev et al. |
| 2018/0263992 | A1 | 9/2018 | Richardson et al. |
| 2018/0289717 | A1 | 10/2018 | Keilhack et al. |
| 2018/0305331 | A1 | 10/2018 | Rzymski et al. |
| 2018/0305334 | A1 | 10/2018 | Larsen et al. |
| 2019/0011435 | A1 | 1/2019 | Cagan et al. |
| 2019/0015417 | A1 | 1/2019 | Sootome |
| 2019/0055444 | A1 | 2/2019 | Fujiwara et al. |
| 2019/0177617 | A1 | 6/2019 | Adlem et al. |
| 2019/0298691 | A1 | 10/2019 | Valmier |
| 2019/0300480 | A1 | 10/2019 | Rennie et al. |
| 2019/0375743 | A1 | 12/2019 | Hudson et al. |
| 2020/0102321 | A1 | 4/2020 | Li et al. |
| 2020/0123117 | A1 | 4/2020 | Zhou et al. |
| 2020/0165224 | A1 | 5/2020 | Li et al. |
| 2020/0172495 | A1 | 6/2020 | Qian et al. |

(56) References Cited

U.S. PATENT DOCUMENTS

| | | | |
|---|---|---|---|
| 2020/0181118 | A1 | 6/2020 | Malhotra et al. |
| 2020/0181123 | A1 | 6/2020 | Li et al. |
| 2020/0247792 | A1 | 8/2020 | Burris et al. |
| 2020/0361913 | A1 | 11/2020 | Chen et al. |
| 2020/0392083 | A1 | 12/2020 | Jiang et al. |
| 2021/0009582 | A1 | 1/2021 | Vechorkin et al. |
| 2021/0101908 | A1 | 4/2021 | Wu et al. |
| 2021/0106588 | A1 | 4/2021 | Vechorkin et al. |
| 2021/0187902 | A1 | 6/2021 | Fujiwara et al. |
| 2021/0198213 | A1 | 7/2021 | Zhou et al. |
| 2021/0220408 | A1 | 7/2021 | Boitano et al. |
| 2021/0317127 | A1 | 10/2021 | Li et al. |
| 2021/0359226 | A1 | 11/2021 | Ko et al. |
| 2022/0015338 | A1 | 1/2022 | Zhang et al. |
| 2022/0016146 | A1 | 1/2022 | Wei et al. |
| 2022/0045293 | A1 | 2/2022 | Kim et al. |
| 2022/0079928 | A1 | 3/2022 | Lou et al. |
| 2022/0259201 | A1 | 8/2022 | Su et al. |
| 2022/0273665 | A1 | 9/2022 | Mcgovern et al. |

FOREIGN PATENT DOCUMENTS

| | | | |
|---|---|---|---|
| CN | 105712998 | A | 6/2016 |
| CN | 108276352 | A | 7/2018 |
| CN | 109438447 | A | 3/2019 |
| CN | 111039942 | A | 4/2020 |
| CN | 112079830 | A | 12/2020 |
| CN | 112409331 | A | 2/2021 |
| CN | 112812014 | A | 5/2021 |
| EP | 0768312 | A2 | 4/1997 |
| EP | 1011648 | A2 | 6/2000 |
| EP | 1046631 | A1 | 10/2000 |
| EP | 1102758 | A1 | 5/2001 |
| EP | 1187816 | A1 | 3/2002 |
| EP | 1224180 | A2 | 7/2002 |
| EP | 1351958 | A1 | 10/2003 |
| EP | 1389100 | A2 | 2/2004 |
| EP | 1439174 | A1 | 7/2004 |
| EP | 1597251 | A2 | 11/2005 |
| EP | 1605946 | A2 | 12/2005 |
| EP | 1615898 | A1 | 1/2006 |
| EP | 1663223 | A2 | 6/2006 |
| EP | 1685137 | A2 | 8/2006 |
| EP | 1778224 | A2 | 5/2007 |
| EP | 1968607 | A1 | 9/2008 |
| EP | 2170839 | A1 | 4/2010 |
| EP | 2205244 | A1 | 7/2010 |
| EP | 2387395 | A1 | 11/2011 |
| EP | 2433124 | A1 | 3/2012 |
| EP | 2447359 | A1 | 5/2012 |
| EP | 2456444 | A1 | 5/2012 |
| EP | 2547698 | A1 | 1/2013 |
| EP | 2646000 | A1 | 10/2013 |
| EP | 2723450 | A2 | 4/2014 |
| EP | 2740742 | A1 | 6/2014 |
| EP | 2830662 | A1 | 2/2015 |
| EP | 2872631 | A1 | 5/2015 |
| EP | 2890986 | A1 | 7/2015 |
| EP | 2918589 | A1 | 9/2015 |
| EP | 2935331 | A1 | 10/2015 |
| EP | 3111931 | A1 | 1/2017 |
| EP | 3254698 | A1 | 12/2017 |
| EP | 3333157 | A1 | 6/2018 |
| EP | 3722282 | A1 | 10/2020 |
| JP | 62-135830 | A | 6/1987 |
| JP | 62-135834 | A | 6/1987 |
| JP | 62-135835 | A | 6/1987 |
| JP | 62-136650 | A | 6/1987 |
| JP | 62-136651 | A | 6/1987 |
| JP | 62-136654 | A | 6/1987 |
| JP | 5763937 | B2 | 8/2015 |
| KR | 10-1648141 | B1 | 8/2016 |
| KR | 10-2032418 | B1 | 10/2019 |
| KR | 10-2127006 | B1 | 6/2020 |
| WO | 99/08668 | A2 | 2/1999 |
| WO | 00/08004 | A1 | 2/2000 |
| WO | 01/53268 | A2 | 7/2001 |
| WO | 01/76582 | A1 | 10/2001 |
| WO | 02/00651 | A2 | 1/2002 |
| WO | 02/55484 | A1 | 7/2002 |
| WO | 03035638 | A1 | 5/2003 |
| WO | 2004/074244 | A2 | 9/2004 |
| WO | 2005/066156 | A1 | 7/2005 |
| WO | 2006/038594 | A1 | 4/2006 |
| WO | 2007/044085 | A2 | 4/2007 |
| WO | 2007/050124 | A1 | 5/2007 |
| WO | 2007/058626 | A1 | 5/2007 |
| WO | 2007/149427 | A2 | 12/2007 |
| WO | 2008/008650 | A1 | 1/2008 |
| WO | 2008/155140 | A1 | 12/2008 |
| WO | 2009/061446 | A1 | 5/2009 |
| WO | 2009/158571 | A1 | 12/2009 |
| WO | 2010/048149 | A2 | 4/2010 |
| WO | 2010/075273 | A1 | 7/2010 |
| WO | 2010/081443 | A2 | 7/2010 |
| WO | 2010/083465 | A1 | 7/2010 |
| WO | 2010/088518 | A2 | 8/2010 |
| WO | 2010/108051 | A2 | 9/2010 |
| WO | 2010/129053 | A2 | 11/2010 |
| WO | 2010/129509 | A1 | 11/2010 |
| WO | 2010/135468 | A1 | 11/2010 |
| WO | 2011/008302 | A1 | 1/2011 |
| WO | 2011/056764 | A1 | 5/2011 |
| WO | 2011/094890 | A1 | 8/2011 |
| WO | 2011/097300 | A1 | 8/2011 |
| WO | 2011/109217 | A2 | 9/2011 |
| WO | 2011/115937 | A1 | 9/2011 |
| WO | 2012/025811 | A1 | 3/2012 |
| WO | 2012/073188 | A1 | 6/2012 |
| WO | 2012/126181 | A1 | 9/2012 |
| WO | 2012/146933 | A1 | 11/2012 |
| WO | 2012/146936 | A1 | 11/2012 |
| WO | 2013/019058 | A2 | 2/2013 |
| WO | 2013/149194 | A1 | 10/2013 |
| WO | 2013/167743 | A1 | 11/2013 |
| WO | 2014/029016 | A1 | 2/2014 |
| WO | 2014/040555 | A1 | 3/2014 |
| WO | 2014/087018 | A1 | 6/2014 |
| WO | 2014/105810 | A1 | 7/2014 |
| WO | 2014/152716 | A1 | 9/2014 |
| WO | 2014/182521 | A1 | 11/2014 |
| WO | 2015/039006 | A1 | 3/2015 |
| WO | 2015/103527 | A1 | 7/2015 |
| WO | 2015/170266 | A1 | 11/2015 |
| WO | 2016/025641 | A1 | 2/2016 |
| WO | 2016/040449 | A1 | 3/2016 |
| WO | 2016/059086 | A1 | 4/2016 |
| WO | 2016/066582 | A1 | 5/2016 |
| WO | 2016/081364 | A1 | 5/2016 |
| WO | 2016/089208 | A2 | 6/2016 |
| WO | 2016/112637 | A1 | 7/2016 |
| WO | 2016/123086 | A1 | 8/2016 |
| WO | 2016/135046 | A1 | 9/2016 |
| WO | 2016/144637 | A1 | 9/2016 |
| WO | 2016/160617 | A2 | 10/2016 |
| WO | 2016/160833 | A1 | 10/2016 |
| WO | 2016/168612 | A1 | 10/2016 |
| WO | 2016/172199 | A1 | 10/2016 |
| WO | 2016/179605 | A1 | 11/2016 |
| WO | 2017/051188 | A1 | 3/2017 |
| WO | 2017/083592 | A1 | 5/2017 |
| WO | 2017/120600 | A1 | 7/2017 |
| WO | 2017/143014 | A1 | 8/2017 |
| WO | 2017/168454 | A2 | 10/2017 |
| WO | 2017/175238 | A1 | 10/2017 |
| WO | 2017/197301 | A1 | 11/2017 |
| WO | 2017/201089 | A1 | 11/2017 |
| WO | 2017/211937 | A1 | 12/2017 |
| WO | 2017/214463 | A1 | 12/2017 |
| WO | 2017/216584 | A1 | 12/2017 |
| WO | 2018/005737 | A1 | 1/2018 |
| WO | 2018/013918 | A2 | 1/2018 |
| WO | 2018/039557 | A1 | 3/2018 |
| WO | 2018/052120 | A1 | 3/2018 |

(56) References Cited

FOREIGN PATENT DOCUMENTS

| | | | |
|---|---|---|---|
| WO | 2018/053142 | A2 | 3/2018 |
| WO | 2018/058098 | A1 | 3/2018 |
| WO | 2018/085275 | A1 | 5/2018 |
| WO | 2018/126192 | A1 | 7/2018 |
| WO | 2018/144773 | A1 | 8/2018 |
| WO | 2019/018795 | A1 | 1/2019 |
| WO | 2019/101182 | A1 | 5/2019 |
| WO | 2019/101183 | A1 | 5/2019 |
| WO | 2019/141250 | A1 | 7/2019 |
| WO | 2019/209948 | A1 | 10/2019 |
| WO | 2020/028706 | A1 | 2/2020 |
| WO | 2020/081572 | A1 | 4/2020 |
| WO | 2020/113759 | A1 | 6/2020 |
| WO | 2020/131627 | A1 | 6/2020 |
| WO | 2020/231990 | A1 | 11/2020 |
| WO | 2020/236524 | A1 | 11/2020 |
| WO | 2020/243457 | A1 | 12/2020 |
| WO | 2021/104305 | A1 | 6/2021 |
| WO | 2021/127333 | A1 | 6/2021 |
| WO | 2021/127337 | A1 | 6/2021 |
| WO | 2021/138391 | A1 | 7/2021 |
| WO | 2021/155253 | A1 | 8/2021 |
| WO | 2021/161230 | A1 | 8/2021 |
| WO | 2021/183970 | A1 | 9/2021 |
| WO | 2022/015979 | A1 | 1/2022 |
| WO | 2022/147246 | A1 | 7/2022 |
| WO | 2022/182972 | A1 | 9/2022 |
| WO | 2023/279041 | A1 | 1/2023 |

OTHER PUBLICATIONS

Frings et al., Sulfoximines from a Medicinal Chemist's Perspective: Physicochemical and in vitro Parameters Relevant for Drug Discovery, Eur. J. Med. Chem., vol. 126, 2017, pp. 225-245.

International Patent Application No. PCT/US2020/067415; Int'l Written Opinion and Search Report; dated Apr. 20, 2021; 9 pages.

International Patent Application No. PCT/US2020/067417; Int'l Preliminary Report on Patentability; dated Jul. 14, 2022; 9 pages.

International Patent Application No. PCT/US2020/067417; Int'l Search Report and the Written Opinion; dated Apr. 20, 2021; 14 pages.

Kang et al., DBM1285 Suppresses Tumor Necrosis Factor a Production by Blocking p38 Mitogen-Activated Protein Kinase/Mitogen-Activated Protein Kinase-Activated Protein Kinase 2 Signaling Pathway, Journal of Pharmacology and Experimental Therapeutics, vol. 334, No. 2, 2010, pp. 657-664.

Lücking, Sulfoximines: A Neglected Opportunity in Medicinal Chemistry, Angew. Chem. Int. Ed. Engl., vol. 52, No. 36, 2013, pp. 9399-9408.

Matralis et al., Development of Chemical Entities Endowed with Potent Fast-Killing Properties against *Plasmodium falciparum* Malaria Parasites, J. Med. Chem., vol. 62, No. 20, 2019, pp. 9217-9235.

Shirahashi Hiromitsu et al: "The discovery of novel 3-aryl-indazole derivatives as peripherally restricted pan-Trk inhibitors for the treatment of pain", Bioorganic & Medicinal Chemistry Letters, Elsevier, Amsterdam, NL, vol. 29, No. 16, Jun. 17, 2019 (Jun. 17, 2019) , pp. 2320-2326, XP085759046.

Siemeister et al., Bay 1000394, a Novel Cyclin-Dependent Kinase Inhibitor, with Potent Antitumor Activity in Mono- and in Combination Treatment upon Oral Application, Mol. Cancer Ther., vol. 11, No. 10, 2012, pp. 2265-2273.

Sirvent et al., Novel Pieces for the Emerging Picture of Sulfoximines in Drug Discovery: Synthesis and Evaluation of Sulfoximine Analogues of Marketed Drugs and Advanced Clinical Candidates, ChemMedChem, vol. 12, No. 7, 2017, pp. 487-501.

* cited by examiner

INDAZOLE COMPOUNDS

CROSS-REFERENCE TO RELATED APPLICATIONS

This application is the National Stage Application of International Patent Application No. PCT/US2020/067415, filed Dec. 30, 2020, which claims the benefit of U.S. Provisional Application No. 62/954,939, filed Dec. 30, 2019, and U.S. Provisional Application No. 63/047,600, filed Jul. 2, 2020, the entireties of which are incorporated by reference herein.

FIELD OF THE INVENTION

Disclosed herein are indazole compounds containing a sulfoximine group, including pharmaceutical compositions that include one or more indazole sulfoximines.

BACKGROUND OF THE INVENTION

Various approaches have been employed in the past to block the activity of various tyrosine kinases. These kinase inhibitors are often small molecules. These small molecules can be used to target these kinases to block the development, growth or spread of cancer.

Fibroblast growth factors (FGFs) and their receptors (FGFRs) regulate a wide range of physiologic cellular processes, such as embryonic development, differentiation, proliferation, survival, migration, and angiogenesis. The FGF family comprises 18 secreted ligands (FGFs) which are readily sequestered to the extracellular matrix by heparin sulfate proteoglycans (HPSGs). For signal propagation, FGFs are released from the extracellular matrix by proteases or specific FGF-binding proteins, with the liberated FGFs subsequently binding to a cell surface FGF-receptor (FGFR) in a ternary complex consisting of FGF, FGFR and HPSG (Beenken, A., Nat. Rev. Drug Discov. 2009; 8:235-253).

FGFR signaling components are frequently altered in human cancer, and several preclinical models have provided compelling evidence for the oncogenic potential of aberrant FGFR signaling in carcinogenesis, thereby validating FGFR signaling as an attractive target for cancer treatment.

Compounds that inhibit FGFR are needed.

SUMMARY OF THE INVENTION

The disclosure is directed to compounds of Formula (I), and pharmaceutically acceptable salts thereof:

(I)

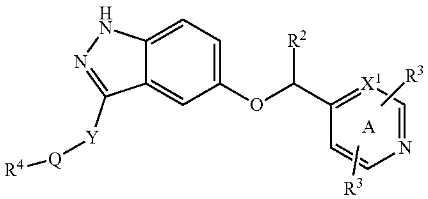

wherein Y is —C(O)—$NR^8$—, —$NR^8$C(O)—, —$CR^1$═$CR^1$—, or Y is absent;

each $R^1$, where present, is independently —H, —F, —Cl, —$C_{1-6}$alkyl, $C_{1-6}$haloalkyl, $C_{1-6}$alkoxy, or $C_{1-6}$hydroxyalkyl;

$R^8$, where present, is —H or —$C_{1-6}$alkyl;

$R^2$ is —H or optionally substituted $C_1$-$C_3$ alkyl;

$X^1$ is CH, $CR^3$, or N;

each instance of $R^3$ can replace any —H of a CH within Ring A and each instance of $R^3$ is independently —F, —Cl, Br, optionally substituted $C_1$-$C_3$-alkyl, $C_3$-$C_6$-cycloalkyl, or —$OR^9$;

each instance of $R^9$, where present, is independently —H or optionally substituted $C_1$-$C_6$-alkyl;

Q is optionally substituted phenyl, optionally substituted pyridinyl, optionally substituted pyrimidinyl, optionally substituted pyridazinyl, optionally substituted pyrazolyl, optionally substituted imidazolyl, optionally substituted thiazole, or optionally substituted pyrrolopyridinyl;

$R^4$ is:

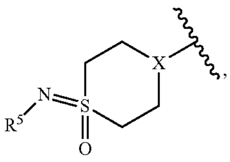, 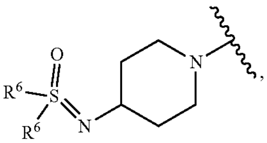,

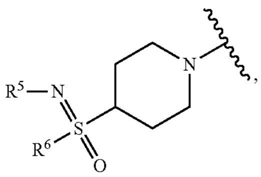, 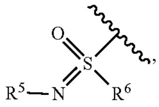,

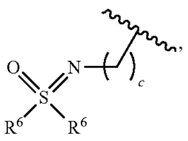, 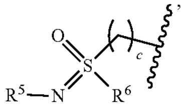, 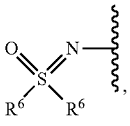, or

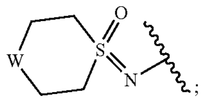;

X is C—H or N;

$R^5$ is —H, optionally substituted $C_1$-$C_6$-alkyl, or optionally substituted $C_3$-$C_6$-cycloalkyl;

each instance of $R^6$ is independently optionally substituted $C_1$-$C_6$-alkyl, optionally substituted $C_3$-$C_6$-cycloalkyl, or two $R^6$ groups, together with the atoms to which they are attached, form a 4- to 7-membered ring W is —$CH_2$—, —C(O)—, CH(OH), or —N($R^7$)—;

$R^7$ is —H, optionally substituted —$C_1$-$C_6$-alkyl, —$C_1$-$C_6$-alkenyl, or optionally substituted —$C_3$-$C_6$-cycloalkyl;

c is 1 or 2;

each instance of $R^9$, where present, is independently —H or optionally substituted $C_1$-$C_6$-alkyl;

wherein each instance of Q, phenyl, pyridine, pyrimidine, pyridazine, pyrazole, imidazole, pyrrolopyridinyl, thiazolyl, $C_1$-$C_6$-alkyl, and $C_3$-$C_6$-cycloalkyl, when substituted, is independently substituted with one or more of —F, —Cl, Br, —OH, $C_1$-$C_6$-alkyl, —$OR^9$, or —$N(R^9)_2$.

Methods of making and using these compounds is also described.

Several embodiments disclosed herein pertain to sulfoximine indazole compounds, their use as kinase inhibitors, their methods of manufacture, and their methods of use as therapeutics for treating kinase-related disease states (e.g., cancer). In several embodiments, the indazole sulfoximine compound comprises a sulfoximine and an indazole. Several embodiments comprise or consist essentially of to a sulfoximine compound of Formula (I) (or any other structure disclosed herein), their pharmaceutically acceptable salts, enantiomers, methods of manufacture, and/or their methods of use in treating disease states. In several embodiments, by using one or more compounds of Formula (I) (or any other structure disclosed herein) to inhibit a kinase in a subject, a disease state can be treated. In several embodiments, the disease state is cancer. In several embodiments, the kinase is a wild-type kinase. In several embodiments, the kinase is a mutant or variant kinase whose activity is not influenced by other standard kinase inhibitors.

DETAILED DESCRIPTION OF THE INVENTION

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

Several embodiments disclosed herein provide compounds useful in treating diseases caused by dysregulated protein kinase activity. Several embodiments also provide methods of treating diseases utilizing these compounds or pharmaceutical compositions comprising these compounds. In several embodiments, the compounds are sulfoximine compounds. In several embodiments, the sulfoximine functionalities are bound to a core aryl structure. In several embodiments, the core aryl structure is a heteroaryl. In several embodiments, the heteroaryl sulfoximine is an indazole sulfoximine. In several embodiments, the heteroaryl sulfoximine compound has a structure as represented by one of Formula (I), as shown below. In several embodiments, the disclosed heteroaryl sulfoximines can be used in methods of treating cancer.

(I)

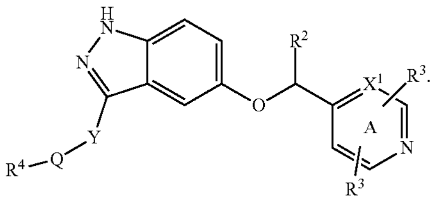

The following description provides context and examples, but should not be interpreted to limit the scope of the inventions covered by the claims that follow in this specification or in any other application that claims priority to this specification. No single component or collection of components is essential or indispensable. For example, some embodiments one or more variables, such as Y or Y and Q may be omitted. Any feature, structure, component, material, step, or method that is described and/or illustrated in any embodiment in this specification can be used with or instead of any feature, structure, component, material, step, or method that is described and/or illustrated in any other embodiment in this specification.

As used herein, any "R" group(s) such as, without limitation, $R^1$, $R^2$, $R^3$, etc., represent substituents that can be attached to the indicated atom. An R group may be substituted or unsubstituted. If two "R" groups are described as being "taken together" the R groups and the atoms they are attached to can form a cycloalkyl, aryl, heteroaryl or heterocycle. For example, without limitation, if $R^{1a}$ and $R^{1b}$ of an $NR^{1a}R^{1b}$ group are indicated to be "taken together," it means that they are covalently bonded to one another to form a ring:

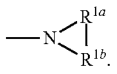

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from hydroxy, halogen, an amino, a mono-substituted amino group, and a di-substituted amino group.

As used herein, "$C_a$ to $C_b$" or $C_{a-b}$ in which "a" and "b" are integers refer to the number of carbon atoms in a moiety as described herein. For example, "a" and "b" refer to the number of carbon atoms in an alkyl, alkenyl or alkynyl group, or the number of carbon atoms in the ring of a, e.g., cycloalkyl, aryl, or heteroaryl group. That is, the alkyl, alkenyl, alkynyl, ring of the cycloalkyl, ring of the aryl, or the ring of the heteroaryl can contain from "a" to "b", inclusive, carbon atoms. Thus, for example, a "$C_1$ to $C_4$ alkyl" group or a "$C_{1-4}$alkyl" group refers to all alkyl groups having from 1 to 4 carbons (e.g., 1, 2, 3, or 4), that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. A "$C_1$ to $C_6$ alkyl" group refers to all alkyl groups having from 1 to 6 carbons (e.g., 1, 2, 3, 4, 5, or 6). If no "a" and "b" are designated with regard to an alkyl, alkenyl, alkynyl, cycloalkyl, aryl, or heteroaryl group, the broadest range described in these definitions is to be assumed.

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms, although the present definition also covers the occurrence of the term "alkyl" where no numerical range is designated). The "alkyl" group may also be a medium size alkyl having 1 to 12 carbon atoms. The "alkyl" group could also be a lower alkyl having 1 to 6 carbon atoms. An alkyl group may be substituted or unsubstituted. By way of example only, "$C_1$-$C_5$ alkyl" indicates that there are one to five carbon atoms in the alkyl chain, i.e., the alkyl chain is selected from methyl, ethyl, n-propyl, isopropyl, n-butyl, isobutyl, tert-butyl, pentyl (branched and straight-chained), etc. Typical alkyl groups include, but are in no way limited to, methyl, ethyl, propyl, isopropyl, butyl, isobutyl, tertiary butyl, pentyl and hexyl. In several embodiments, "Me" is methyl (e.g., $CH_3$).

As used herein, the term "alkylene" refers to a bivalent fully saturated straight chain aliphatic hydrocarbon group. Examples of alkylene groups include, but are not limited to, methylene, ethylene, propylene, butylene, pentylene, hexylene, heptylene and octylene. An alkylene group may be represented by , followed by the number of carbon atoms, followed by a "*". For example,

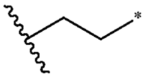 [SMILES: *CC*]

to represent ethylene. The alkylene group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkylene" where no numerical range is designated). The alkylene group may also be a medium size alkyl having 1 to 12 carbon atoms. The alkylene group could also be a lower alkyl having 1 to 6 carbon atoms. An alkylene group may be substituted or unsubstituted. For example, a lower alkylene group can be substituted by replacing one or more hydrogen of the lower alkylene group and/or by substituting both hydrogens on the same carbon with a $C_{3-6}$ monocyclic cycloalkyl group (e.g.,  ).

The term "$C_1$-$C_6$alk" when used alone or as part of a substituent group refers to an aliphatic linker having 1, 2, 3, 4, 5, or 6 carbon atoms and includes, for example, $—CH_2—$, $—CH(CH_3)—$, $—CH(CH_3)—CH_2—$, and $—C(CH_3)_2—$. The term "$—C_0$alk-" refers to a bond.

As used herein, "alkenyl" refers to an alkyl group that contains in the straight or branched hydrocarbon chain one or more double bonds. An alkenyl group may be unsubstituted or substituted.

The term "alkynyl" refers to $C_2$-$C_{12}$ alkyl group that contains at least one carbon-carbon triple bond. In some embodiments, the alkenyl group is optionally substituted. In some embodiments, the alkynyl group is a $C_2$-$C_6$ alkynyl.

The term "haloalkyl" refers to an alkyl group wherein one or more of the hydrogen atoms has been replaced with one or more halogen atoms. Halogen atoms include chlorine, fluorine, bromine, and iodine. Examples of haloalkyl groups of the disclosure include, for example, trifluoromethyl ($—CF_3$), chloromethyl ($—CH_2Cl$), and the like.

The term "hydroxyalkyl" refers to an alkyl group wherein one or more of the hydrogen atoms has been replaced with one or more OH moieties.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. Heteroaryl rings may also include bridge head nitrogen atoms. For example, but not limited to: pyrazolo[1,5-a]pyridine, imidazo[1,2-a]pyridine, and pyrazolo[1,5-a]pyrimidine. A heteroaryl group may be substituted or unsubstituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s), or as otherwise noted herein. A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "heterocycloalkyl," "heterocyclyl" or "heteroalicyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogen in a heteroalicyclic may be quaternized. Heterocyclyl or heteroalicyclic groups may be unsubstituted or substituted. Examples of such "heterocycloalkyl," "heterocyclyl," or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3, 5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

As used herein, the term "amino" refers to a —$NH_2$ group.

As used herein, the term "hydroxy" refers to a —OH group.

As used herein, the terms "ester" and "C-carboxy" refer to a "—C(═O)OR" group in which R can be the same as defined with respect to O-carboxy. An ester and C-carboxy may be substituted or unsubstituted.

As used herein, the term "halogen atom" or "halogen" refers to any one of the radio-stable atoms of column 7 of the Periodic Table of the Elements, such as, fluorine, chlorine, bromine and iodine.

As used herein, "alkoxy" and "alkylthio" (or thioalkoxy) refer to alkyl groups attached to the remainder of a molecule via an oxygen atom or a sulfur atom, respectively.

As used herein, a "sulfenyl" group refers to an "—SR" group in which R can be hydrogen, an alkyl, an alkenyl, an alkynyl, or a cycloalkyl. A sulfenyl may be substituted or unsubstituted.

As used herein, the term "sulfoximine" refers to a functional group having a sulfur atom with a double bond to each of an oxygen atom and a nitrogen atom, where the sulfur atom is additionally bonded to two other R groups (which may or may not be different atoms of the same molecule) and where the nitrogen is bonded to one other R group.

The term "pharmaceutically acceptable salt" refers to a salt of a compound that does not cause significant irritation to an organism to which it is administered and does not abrogate the biological activity and properties of the compound. In several embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. It is understood that, in any compound described herein having one or more chiral centers, all possible diastereomers are also envisioned. It is understood that, in any compound described herein all tautomers are envisioned. It is also understood that, in any compound described herein, all isotopes of the included atoms are envisioned. For example, any instance of hydrogen, may include hydrogen-1 (protium), hydrogen-2 (deuterium), hydrogen-3 (tritium) or other isotopes; any instance of carbon may include carbon-12, carbon-13, carbon-14, or other isotopes; any instance of oxygen may include oxygen-16, oxygen-17, oxygen-18, or other isotopes; any instance of fluorine may include one or more of fluorine-18, fluorine-19, or other isotopes; any instance of sulfur may include one or more of sulfur-32, sulfur-34, sulfur-35, sulfur-36, or other isotopes.

The term "gatekeeper mutation" when used herein denotes mutations in a kinase enzyme that modulate the accessibility of the kinase ATP-binding pocket.

The term "target sequence" or "target nucleic acid sequence" shall be given its ordinary meaning and shall also include and also refer to the particular nucleotide sequence of the target nucleic acid to be detected (e.g., through amplification). The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence. In several embodiments, the target sequence is one or more of the particular sequences for FGFR mutants provided herein (such as Tables 0.1 or 0.2).

As used herein, the term "kinase inhibitor" means any compound, molecule or composition that inhibits or reduces the activity of a kinase. The inhibition can be achieved by, for example, blocking phosphorylation of the kinase (e.g., competing with adenosine triphosphate (ATP), a phosphorylating entity), by binding to a site outside the active site, affecting its activity by a conformational change, or by depriving kinases of access to the molecular chaperoning systems on which they depend for their cellular stability, leading to their ubiquitylation and degradation.

As used herein, "subject," "host," "patient," and "individual" are used interchangeably and shall be given its ordinary meaning and shall also refer to an organism that has FGFR proteins. This includes mammals, e.g., a human, a non-human primate, ungulates, canines, felines, equines, mice, rats, and the like. The term "mammal" includes both human and non-human mammals. In some aspects, the "subject," "host," "patient," or "individual" is human.

"Diagnosis" as used herein shall be given its ordinary meaning and shall also include determination of a subject's susceptibility to a disease or disorder, determination as to whether a subject is presently affected by a disease or disorder, prognosis of a subject affected by a disease or disorder (e.g., identification of cancer or cancerous states, stages of cancer, or responsiveness of cancer to therapy), and use of therametrics (e.g., monitoring a subject's condition to provide information as to the effect or efficacy of therapy).

The term "sample" or "biological sample" shall be given its ordinary meaning and also encompasses a variety of sample types obtained from an organism and can be used in an imaging, a diagnostic, a prognostic, or a monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment," "treating," "treat" and the like shall be given its ordinary meaning and shall also include herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein shall be given its ordinary meaning and shall also cover any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, e.g., arresting its development; and/or (c) relieving the disease symptom, e.g., causing regression of the disease or symptom.

The terms "cancer," "neoplasm," and "tumor" are used interchangeably herein, shall be given its ordinary meaning and shall also refer to cells which exhibit relatively autonomous growth, so that they exhibit an aberrant growth phenotype characterized by a significant loss of control of cell proliferation. In general, cells of interest for detection or treatment in the present application include precursors, precancerous (e.g., benign), malignant, pre-metastatic, metastatic, and non-metastatic cells. As used herein, "FGFR related cancer" denotes those cancers that involve an increased activity in a mutant FGFR kinase, for example, the continued activation of FGFR.

"Cancerous phenotype" shall be given its ordinary meaning and shall also generally refer to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc. In several embodiments, a subject is identified as a potential recipient if they have a cancerous phenotype. In several embodiments, a subject is identified as a potential recipient if they exhibit a new cancerous phenotype when they are already on a cancer therapy (other than a compound as disclosed herein (e.g., Formula (I), as well as all subgenera disclosured herein)).

The term "control" refers shall be given its ordinary meaning and shall also include a sample or standard used for comparison with a sample which is being examined, processed, characterized, analyzed, etc. In several embodiments, the control is a sample obtained from a healthy patient or a non-tumor tissue sample obtained from a patient diagnosed with a tumor. In several embodiments, the control is a historical control or standard reference value or range of values. In several embodiments, the control is a comparison to a wild-type FGFR arrangement or scenario.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the general description and the following detailed description are exemplary and explanatory only and are not restrictive. The term "and/or" denotes that the provided possibilities can be used together or be used in the alternative. Thus, the term "and/or" denotes that both options exist for that set of possibilities.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," or the like; the term "comprising" as used herein is synonymous with "including," "containing," or "characterized by," and is inclusive or open-ended and does not exclude additional, unrecited elements or method steps; the term "having" should be interpreted as "having at least;" the term "includes" should be interpreted as "includes but is not limited to;" the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment of the invention. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds of the Disclosure

Several embodiments pertain to indazolyl sulfoximine compounds. In several embodiments, the indazole sulfoximine is a compound having the structure of Formula (I) (or a pharmaceutically acceptable salt thereof):

(I)

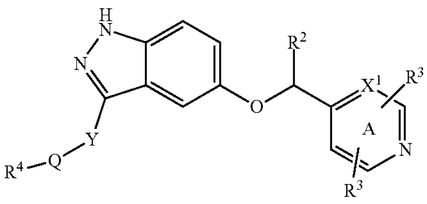

According to the disclosure, Y is —C(O)—$NR^8$—, —$NR^8$C(O)—, —$CR^1$═$CR^1$—, or Y is absent (e.g., Y is a single bond connecting Q and the indazole ring). In some aspects, Y is —C(O)—$NR^8$—. In other aspects, Y is —$NR^8$C(O)—. In these aspects, $R^8$ is H or $C_{1-6}$alkyl (e.g., methyl).

In some aspects, Y is —$CR^1$═$CR^1$—, wherein each $R^1$ is independently selected from the group consisting —H, —F, —Cl, —$C_{1-6}$alkyl (e.g., methyl), $C_{1-6}$haloalkyl (e.g, $CF_3$), $C_{1-6}$alkoxy e.g., ($OCH_3$), or $C_{1-6}$hydroxyalkyl (e.g., $CH_2CH_2OH$). In some aspects, both $R^1$ are H. In some aspects, one $R^1$ is H and the other $R^1$ is —F, —Cl, —$C_{1-6}$ alkyl, $C_{1-6}$haloalkyl, $C_{1-6}$alkoxy, or $C_{1-6}$hydroxyalkyl. In some aspects, at least one $R^1$ is F. In some aspects, at least one $R^1$ is Cl. In some aspects, at least one $R^1$ is $C_{1-6}$alkyl. In some aspects, at least one $R^1$ is $C_{1-6}$haloalkyl. In some aspects, at least one $R^1$ is $C_{1-6}$alkoxy. In some aspects, at least one $R^1$ is $C_{1-6}$hydroxyalkyl.

In some aspects, Y is absent, that is, Y is a single bond connecting moiety Q to the indazolyl ring.

According to the disclosure $R^2$ is selected from the group consisting of —H, $C_1$-$C_6$ alkyl (e.g., $C_1$-$C_3$alkyl), and substituted $C_1$-$C_6$ alkyl (e.g., substituted $C_1$-$C_3$alkyl) When $R^2$ is not H, $R^2$ may be in the R or S configuration.

According to the disclosure, $X^1$ is selected from the group consisting of CH, $CR^3$, and N. In some aspects, $X^1$ is CH. In other aspects $X^1$ is N. In other aspects, $X^1$ is $CR^3$.

Other than for $CR^3$, each instance of $R^3$ is located on any available carbon (e.g., one or more of positions 2, 3, 5, and/or 6) of Ring A (e.g., the terminal heterocyclyl ring). Also in these aspects, each instance of $R^3$ is independently selected from the group consisting of —F, —Cl, —Br, optionally substituted $C_1$-$C_6$-alkyl, $C_{1-6}$haloalkyl, $C_3$-$C_6$-cycloalkyl, and —$OR^9$. In some aspects, one or more $R^3$ is independently F. In some aspects, one or more $R^3$ is independently Cl. In some aspects, one or more $R^3$ is independently —Br. In some aspects, one or more $R^3$ is independently $C_1$-$C_3$-alkyl. In some aspects, one or more $R^3$ is independently substituted $C_1$-$C_3$-alkyl. In some aspects, one or more $R^3$ is independently $C_1$-$C_6$haloalkyl. In some aspects, one or more $R^3$ is independently $C_3$-$C_6$-cycloalkyl. In some aspects, one or more $R^3$ is independently substituted $C_3$-$C_6$-cycloalkyl. In some aspects, one or more $R^3$ is independently $C_{1-6}$alkoxy. In some aspects, one or more $R^3$ is independently —$OR^9$, wherein each $R^9$ is independently selected from the group consisting of H, $C_1$-$C_3$-alkyl, $C_{1-6}$haloalkyl and substituted $C_1$-$C_3$-alkyl. In some aspects, each $R^9$ is H. In some aspects, each $R^9$ is independently $C_1$-$C_3$-alkyl. In some aspects each $R^9$ is independently substituted $C_1$-$C_3$-alkyl. In some aspects, each $R^9$ is independently $C_{1-6}$haloalkyl.

According to the disclosure, Q is selected from the group consisting of optionally substituted phenyl, optionally substituted pyridine, optionally substituted pyrimidine, optionally substituted pyridazine, optionally substituted pyrazole, optionally substituted imidazole, optionally substituted thiazolyl, and optionally substituted pyrrolopyridinyl.

In some aspects Q is phenyl. In other aspects, Q is substituted phenyl.

In some aspects Q is pyridinyl. In other aspects, Q is substituted pyridinyl.

In some aspects Q is pyrimidinyl. In other aspects, Q is substituted pyrimidinyl.

In some aspects Q is pyridazinyl. In other aspects, Q is substituted pyridazinyl.

In some aspects Q is pyrazolyl. In other aspects, Q is substituted pyrazolyl.

In some aspects Q is imidazolyl. In other aspects, Q is substituted imidazolyl.

In some aspects Q is thiazolyl. In other aspects, Q is substituted thiazolyl.

In some aspects, Q is pyrrolopyridinyl. In some aspects, Q is substituted pyrrolopyridinyl.

According to the disclosure, $R^4$ is positioned at any available position of Q.

According to the disclosure, $R^4$ is selected from the group consisting of:

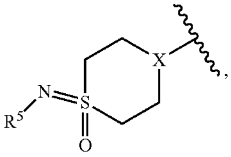,
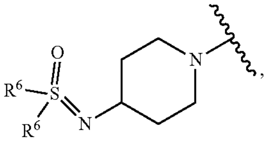,
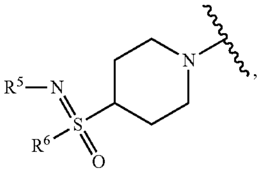,
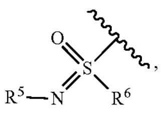,
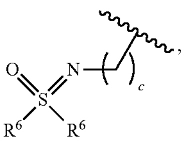,
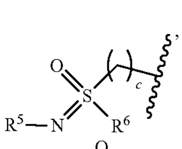,
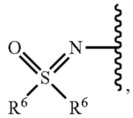, and
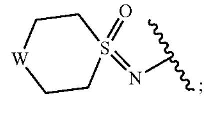;

wherein X is N or C—H. In some aspects, X is N. In other aspects, X is CH.

According to the disclosure, c is an integer equal to 1 or 2. In some aspects, c is 1. In some aspects, c is 2.

According to the disclosure, $R^5$ is selected from the group consisting of —H, optionally substituted $C_1$-$C_6$-alkyl, and optionally substituted $C_3$-$C_6$-cycloalkyl. In some aspects, $R^5$ is H. In some aspects, $R^5$ is $C_1$-$C_6$-alkyl. In some aspects, $R^5$ is substituted $C_1$-$C_6$-alkyl. In some aspects, $R^5$ is $C_3$-$C_6$-cycloalkyl. In some aspects, $R^5$ is substituted $C_3$-$C_6$-cycloalkyl.

According to the disclosure, each instance of $R^6$ is independently selected from optionally substituted $C_1$-$C_6$-alkyl, and optionally substituted $C_3$-$C_6$-cycloalkyl. In some aspects, at least one $R^6$ is independently $C_1$-$C_6$-alkyl. In some aspects, at least one $R^6$ is independently substituted $C_1$-$C_6$-alkyl. In some aspects, at least one $R^6$ is independently $C_3$-$C_6$-cycloalkyl. In some aspects, at least one $R^6$ is independently substituted $C_3$-$C_6$-cycloalkyl. In some aspects, two $R^6$ groups, together with the atoms to which they are attached, form a 4- to 7-membered ring.

According to the disclosure, W is selected from the group consisting of —$CH_2$—, —C(O)—, CH(OH), and —N($R^7$)—. In some aspects, W is —$CH_2$—. In some aspects, W is —C(O)—. In some aspects, W is CH(OH). In some aspects, W is —N($R^7$)—.

In those aspects wherein W is —N($R^7$)—, $R^7$ is selected from the group consisting of —H, optionally substituted —$C_1$-$C_6$-alkyl, —$C_1$-$C_6$-alkenyl, and optionally substituted —$C_3$-$C_6$-cycloalkyl. In some aspects, $R^7$ is H. In some aspects, $R^7$ is —$C_1$-$C_6$-alkyl. In some aspects, $R^7$ is substituted —$C_1$-$C_6$-alkyl. In some aspects, $R^7$ is —$C_1$-$C_6$-alkenyl. In some aspects, $R^7$ is substituted —$C_1$-$C_6$-alkenyl. In some aspects, $R^7$ is —$C_3$-$C_6$-cycloalkyl. In some aspects, $R^7$ is substituted —$C_3$-$C_6$-cycloalkyl.

In some aspects, $R^4$ is

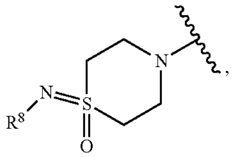

with the following moieties being particularly preferred:

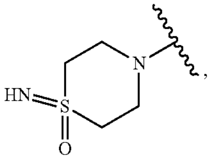

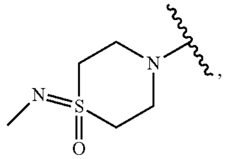

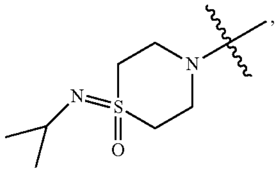

-continued

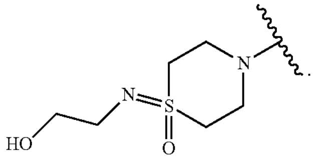

In some aspects, $R^4$ is

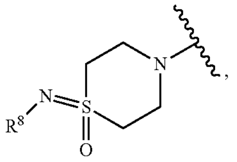

with the following moieties being particularly preferred:

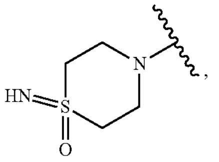

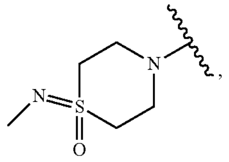

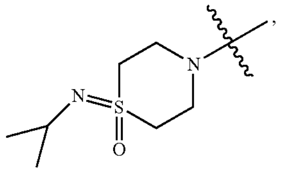

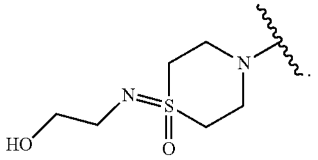

In some aspects, $R^4$ is

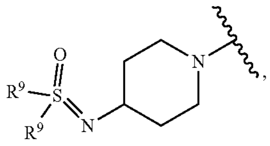

with the following moieties being particularly preferred:

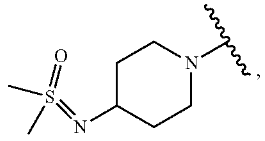

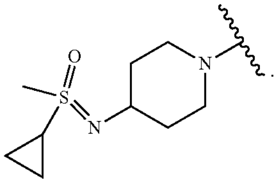

In some aspects, $R^4$ is

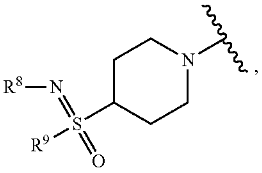

with the following moieties being particularly preferred:

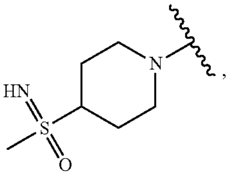
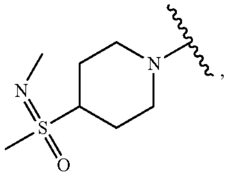
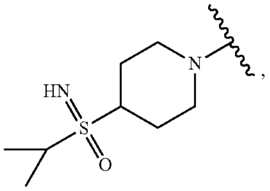
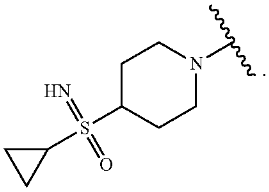

In some aspects, $R^4$ is

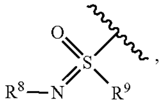

with the following moieties being particularly preferred:

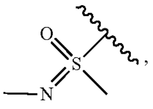
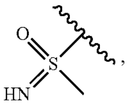
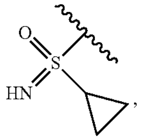
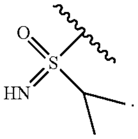

In some aspects, $R^4$ is

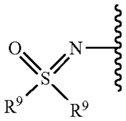

with the following moieties being particularly preferred:

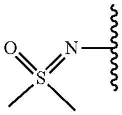
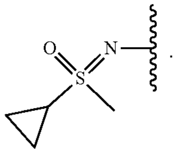

In some aspects, $R^4$ is

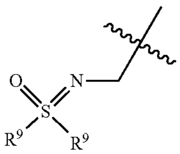

with the following moieties being particularly preferred:

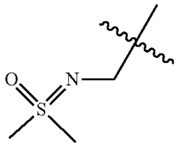
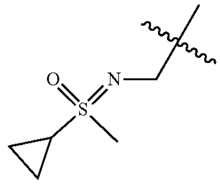

In some aspects, $R^4$ is

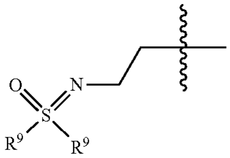

with the following moieties being particularly preferred:

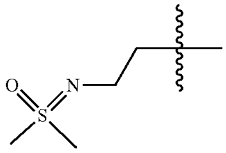
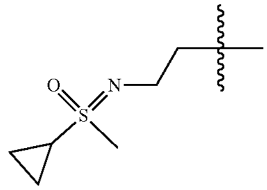

In some aspects, $R^4$ is

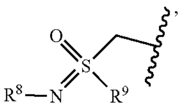

with the following moieties being particularly preferred:

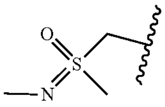,
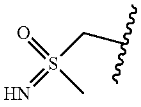,
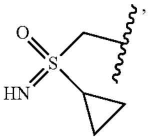,

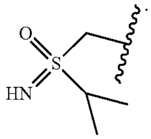.

In some aspects, $R^4$ is

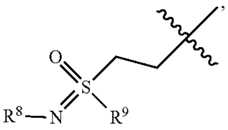, with the following moieties being particularly preferred:

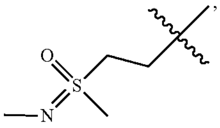,
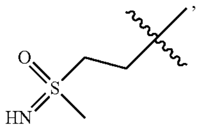,

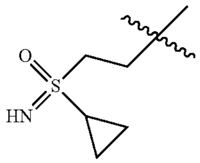 or 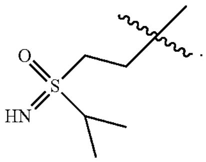.

In some aspects, $R^4$ is

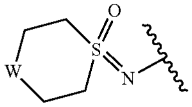

with the following moieties being particularly preferred:

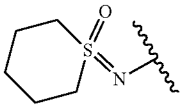
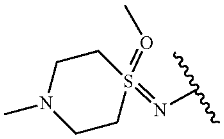
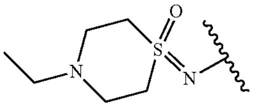
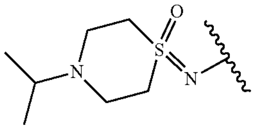.

In some aspects, $R^4$ is

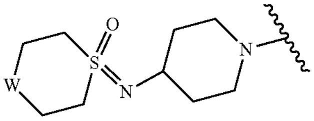

with the following moieties being particularly preferred:

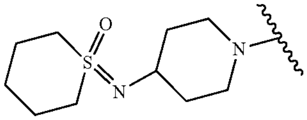
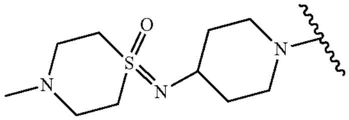
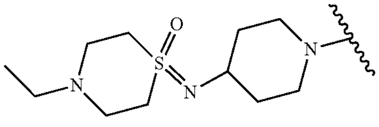
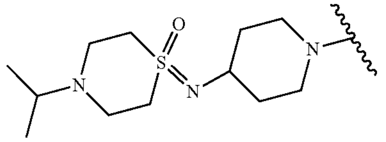.

In some embodiments, $R^4$ is

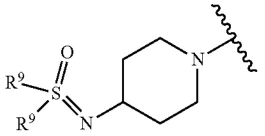, 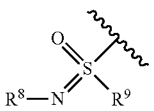, or

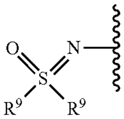.

In yet other aspects, $R^4$ is

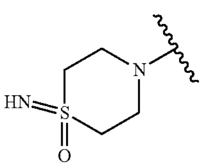, 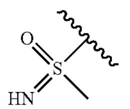,

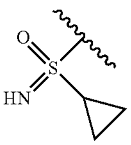, 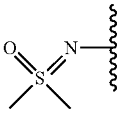.

In several embodiments of the disclosure, each of Q, phenyl, pyridine, pyrimidine, pyridazine, pyrazole, imidazole, thiazole, $C_1$-$C_6$-alkyl (where present), and $C_3$-$C_6$-cycloalkyl (where present), may independently be substituted with one or more of —F, —Cl, —Br, —OH, $C_1$-$C_6$-alkyl, —$OR^9$, and —$N(R^9)_2$, where $R^9$ is as disclosed elsewhere herein.

In several embodiments, the Q may be represented by one or more of the following optionally substituted pyridine, optionally substituted pyrimidine, optionally substituted pyridazine, optionally substituted pyrazole, optionally substituted imidazole structures, optionally substituted thiazole, and optionally substituted pyrrolopyrimidine structures:

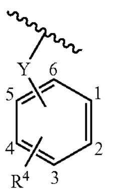

Phenyl

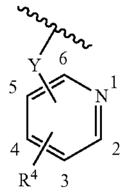

pyridine or pyridinyl

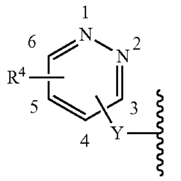

pyridazine or pyridazinyl

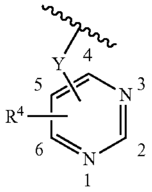

pyrimidine or pyrimidinyl

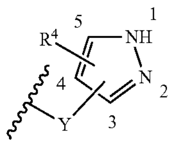

pyrazole or pyrazolyl

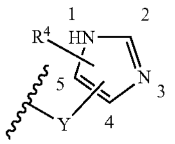

imidazole or imidazolyl

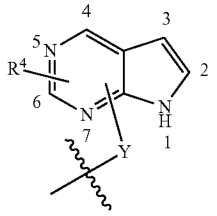

pyrrolopyrimidine or pyrrolopyrimidinyl

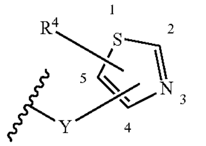

thiazole or thiazolyl wherein $R^4$ and Y can independently be located at any one of the 1, 2, 3, 4, 5, or 6 positions of the phenyl, at any one of the 2, 3, 4, 5, or 6 positions of the pyridine, at any one of the 3, 4, 5, or 6 positions of the pyridazine, at any one of the 2, 4, 5, or 6 positions of the pyrimidine, at any one of the 1, 3, 4, or 5 positions of the pyrazole, at any one of the 1, 2, 4, or 5 positions of the imidazole, at any one of the 1, 2, 4, or 5 positions of the thiazole, or at any one of the 1, 2, 3, 4, 5, 6, or 7 positions of the pyrrolopyrimidine.

In several embodiments, where Y is absent, a direct single bond connects the indazole ring of the compound of the disclosure and Q. As disclosed elsewhere herein, Q may be represented by one or more of the following optionally substituted pyridine, optionally substituted pyrimidine, optionally substituted pyridazine, optionally substituted pyrazole, optionally substituted imidazole structures, optionally substituted thiazole structures, and optionally substituted pyrrolopyrimidine structures:

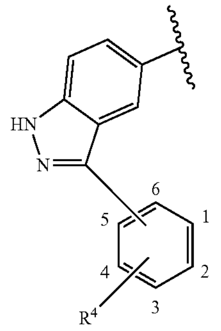

Phenyl

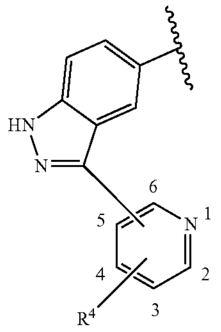

pyridine or pyridinyl

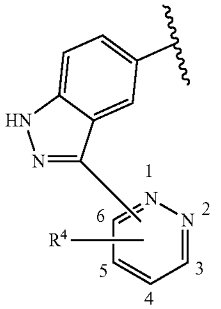

pyridazine or pyridazinyl

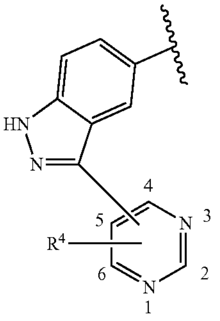

pyrimidine or pyrimidinyl

-continued

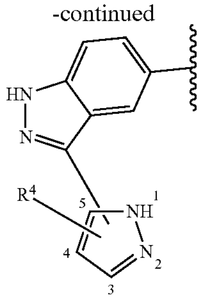

pyrazole or pyrazolyl

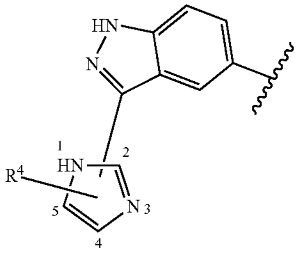

imidazole or imidazolyl

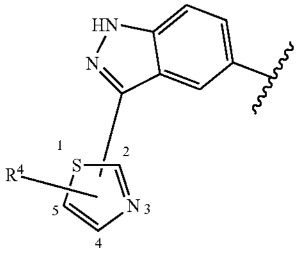

thiazole or thiazolyl

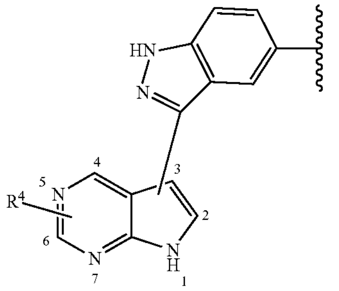

pyrrolopyrimidine or pyrrolopyrimidinyl where $R^4$ and the indazole can independently be located at any one of the 1, 2, 3, 4, 5, or 6 positions of the phenyl, at any one of the 2, 3, 4, 5, or 6 positions of the pyridine, at any one of the 3, 4, 5, or 6 positions of the pyridazine, at any one of the 2, 4, 5, or 6 positions of the pyrimidine, at any one of the 1, 3, 4, or 5 positions of the pyrazole, at any one of the 1, 2, 4, or 5 positions of the imidazole, at any one of the 1, 2, 4, or 5 positions of the thiazole, or at any one of the 1, 2, 3, 4, 5, 6, or 7 positions of the pyrrolopyrimidine. In several embodiments, where Q is a six membered ring (e.g., phenyl, pyridyl, etc.), $R^4$ and the indazole may be para to one another or meta to one another.

In several embodiments, each instance of Q, phenyl, pyridine, pyrimidine, pyridazine, pyrazole, imidazole, thiazole, pyrrolopyridinine, $C_1$-$C_6$-alkyl, and $C_3$-$C_6$-cycloalkyl, when substituted, is independently substituted with one or more of —F, —Cl, —Br, $C_1$-$C_6$-alkyl, —OH, —$OR^9$, and —$N(R^{11})_2$. In several embodiments, each instance of $R^9$ or $R^{11}$, where present, is independently selected from the group consisting of —H and optionally substituted $C_1$-$C_3$-alkyl, or each $R^{11}$ combine to form a cyclic pyrrolidine, piperidine, or methylpiperazine.

Formula IA Compounds

Several exemplary embodiments of structures of Formula (I) may be represented by the structure of Formula (IA), a vinyl indazole, where Y is —$CR^1$=$CR^1$— and each other variable is as defined elsewhere herein (e.g., as defined in Formula (I)):

(IA)

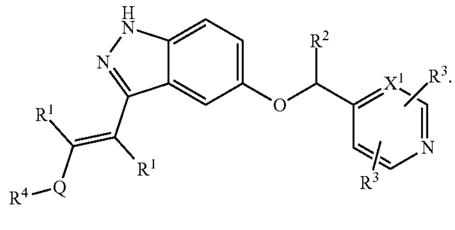

In several embodiments, each instance of $R^1$ is independently selected from the group consisting —H, —F, —Cl, and -Me. In several embodiments, $R^2$ is selected from the group consisting of —H and optionally substituted $C_1$-$C_3$ alkyl. In several embodiments, $X^1$ is selected from the group consisting of $CR^3$ and N. In several embodiments, each instance of $R^3$ can replace any —H of a CH within Ring A (which is shown as "A" in Formula (I)) and each instance of $R^3$ is independently selected from the group consisting of —H, —F, —Cl, optionally substituted $C_1$-$C_3$-alkyl, $C_3$-$C_6$-cycloalkyl, and —$OR^9$ (where each instance of $R^9$, where present, is independently selected from the group consisting of —H and optionally substituted $C_1$-$C_3$-alkyl). In several embodiments, Q is selected from the group consisting of optionally substituted phenyl, optionally substituted pyridine, optionally substituted pyrimidine, optionally substituted pyridazine, optionally substituted pyrazole, optionally substituted imidazole, optionally substituted thiazolyl, and optionally substituted pyrrolopyrimidine. In several embodiments, $R^4$ is selected from the group consisting of:

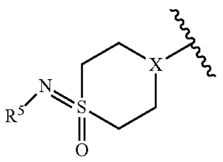
,
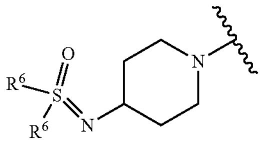
,
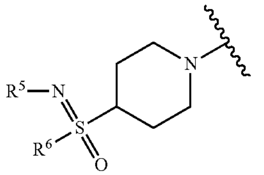
,
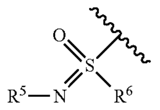
,
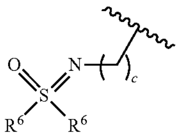
,
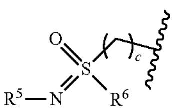
,
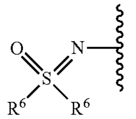
, and
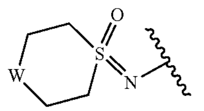
.

In several embodiments, X is N or C—H. In several embodiments, $R^5$ is selected from the group consisting of —H, optionally substituted $C_1$-$C_6$-alkyl, and optionally substituted $C_3$-$C_6$-cycloalkyl. In several embodiments, each instance of $R^6$ is independently selected from optionally substituted $C_1$-$C_6$-alkyl, and optionally substituted $C_3$-$C_6$-cycloalkyl. In several embodiments, W is selected from the group consisting of —$CH_2$—, —C(O)—, CH(OH), and —N($R^7$)—. In several embodiments, $R^7$ is selected from the group consisting of —H, optionally substituted —$C_1$-$C_6$-alkyl, —$C_1$-$C_6$-alkenyl, and optionally substituted —$C_3$-$C_6$-cycloalkyl; and c is an integer equal to 1 or 2. In several embodiments, wherein each instance of Q, phenyl, pyridine, pyrimidine, pyridazine, pyrazole, imidazole, thiazole, $C_1$-$C_6$-alkyl, and $C_3$-$C_6$-cycloalkyl, when substituted, is independently substituted with one or more of —F, —Cl, $C_1$-$C_6$-alkyl, —OH, —$OR^9$, and —$N(R^{11})_2$. In several embodiments, each instance of $R^9$ or $R^{11}$, where present, is independently selected from the group consisting of —H and optionally substituted $C_1$-$C_3$-alkyl, or each $R^{11}$ combine to form a cyclic pyrrolidine, piperidine, or methylpiperazine, (shown below).

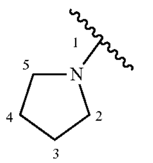

pyrrolidine

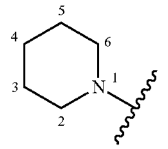

piperidine

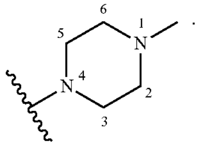

methylpiperazine

Several embodiments of Formula (IA) are represented by the structure of Formula (IAi), where each instance of $R^1$ is —H or —F, $R^2$ is -Me, $X^1$ is $CR^3$, each instance of $R^3$ is —Cl located at the 5 and 3 positions of the terminal heteroaryl ring (e.g., terminal pyridyl ring), and each other variable is as defined elsewhere herein:

(IAi)

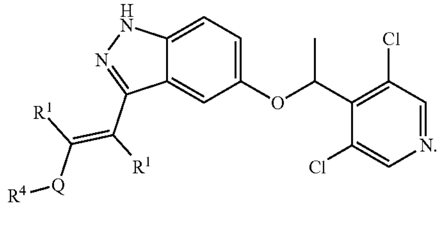

In several embodiments, as disclosed elsewhere herein, Q is pyridine and each other variable of the structure of Formula (IAi) is as defined elsewhere herein. In several embodiments, where Q is pyridine, $R^1$ are each —H, $R^4$ is selected from:

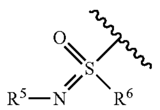,

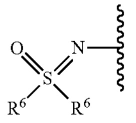,

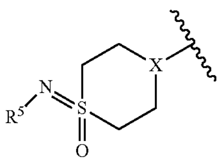, and

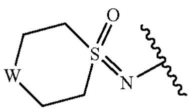, and each other variable is as defined elsewhere herein, Formula (IAi) may be represented by any one of the following compounds (or others):

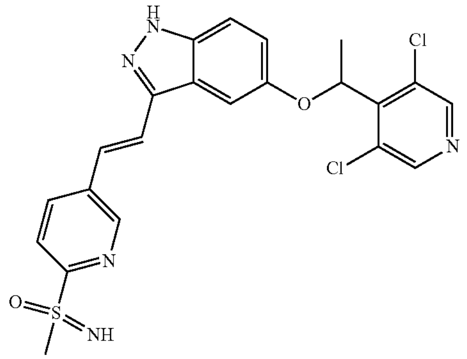

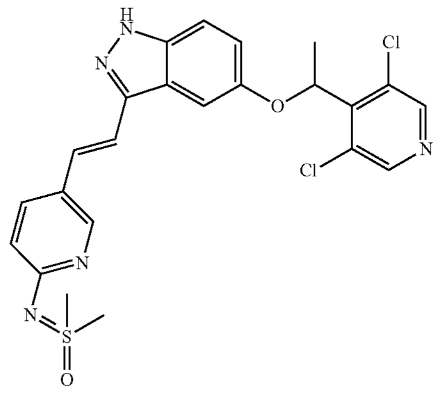

-continued
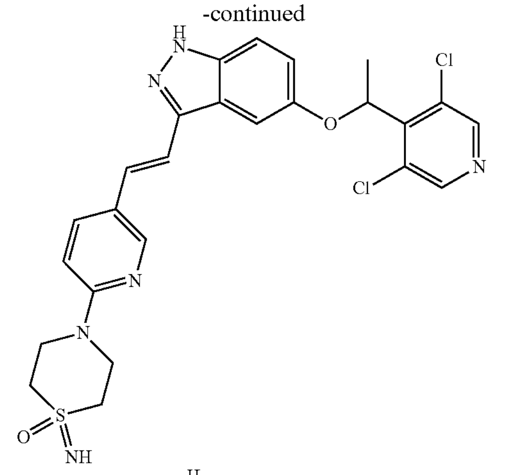
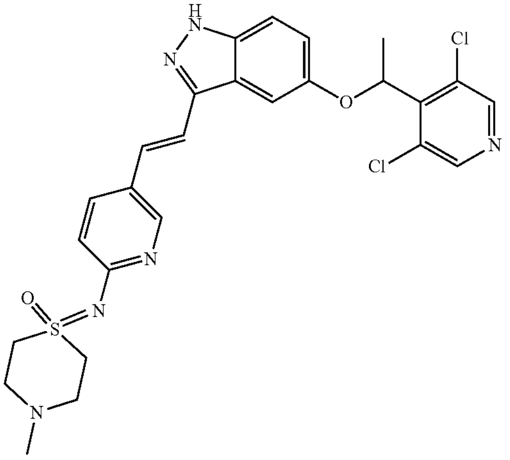
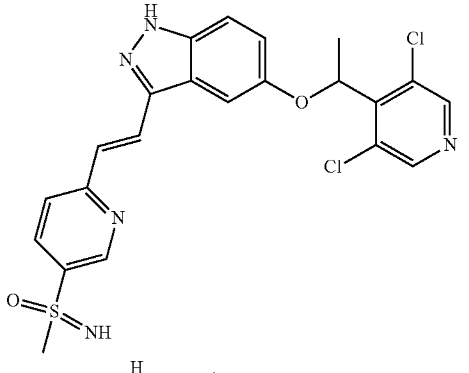
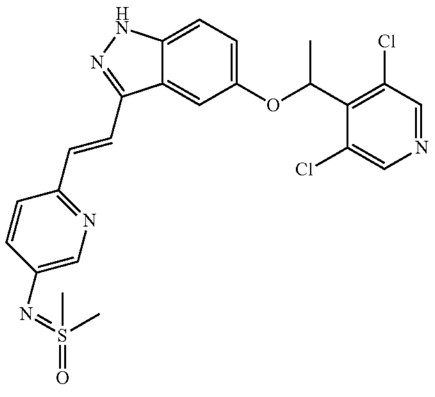
-continued
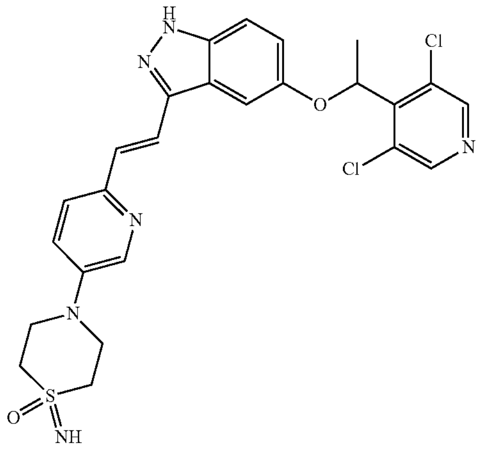
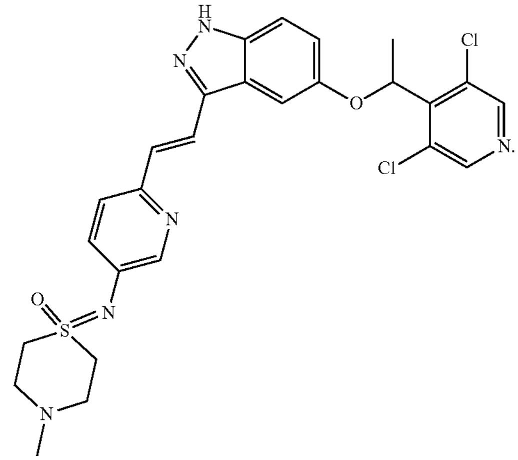
In several embodiments, where Q is pyridine, $R^1$ are each —H, $R^2$ is methyl (and may be in the R or S configuration), $R^4$ is selected from:
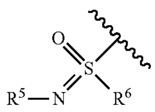
, and
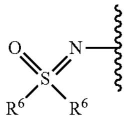
,
and each other variable is as defined elsewhere herein, Formula (IAi) may be represented by any one of the following compounds (or others):

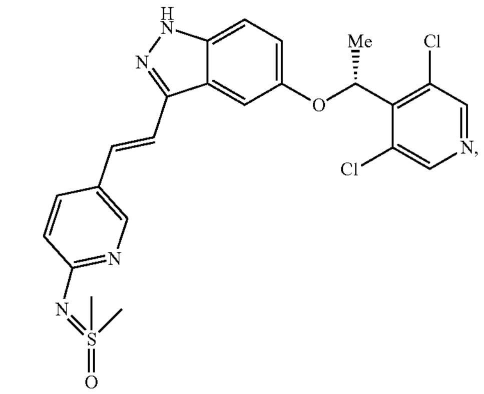

,

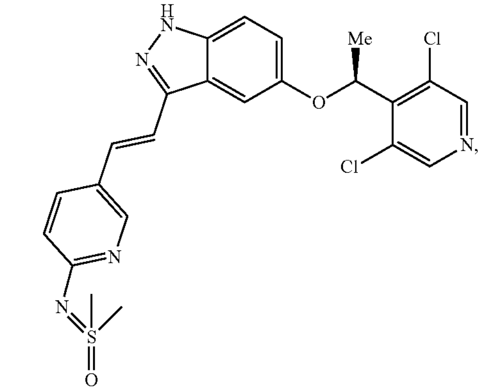

,

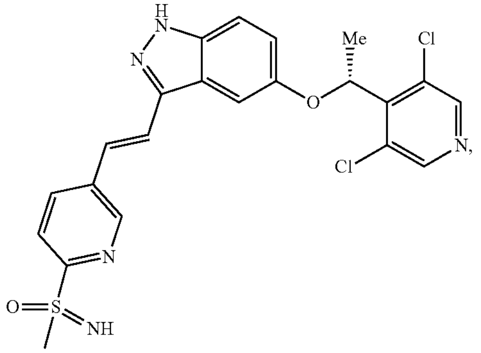

and

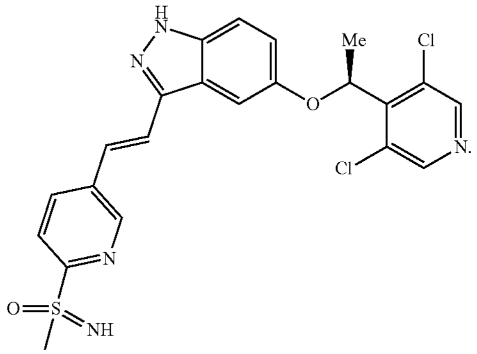

.

In several embodiments, as disclosed elsewhere herein, Q is pyridazine, $R^1$ are each —H, and each other variable of the structure of Formula (IAi) is as defined elsewhere herein. In several embodiments, where Q is pyridazine, $R^1$ are each —H, $R^4$ is selected from:

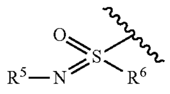

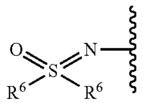

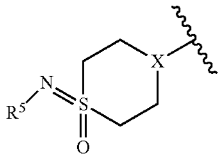

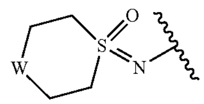

, and each other variable is as defined elsewhere herein, Formula (IAi) may be represented by any one of the following compounds (or others):

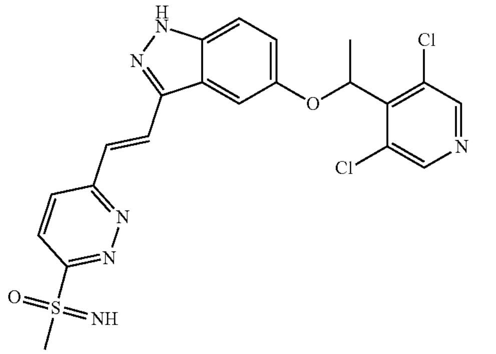

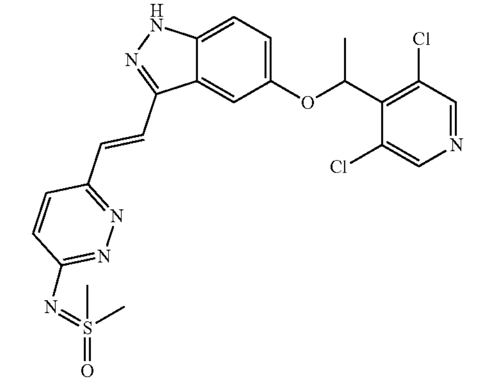

-continued

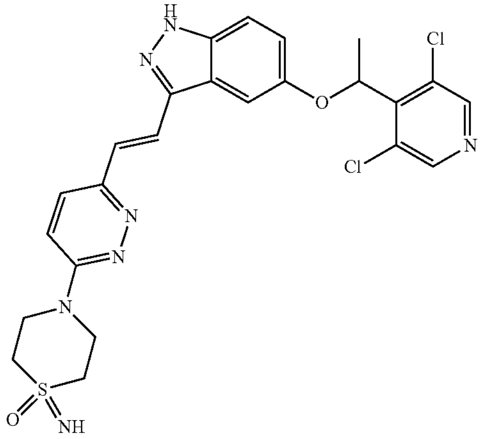

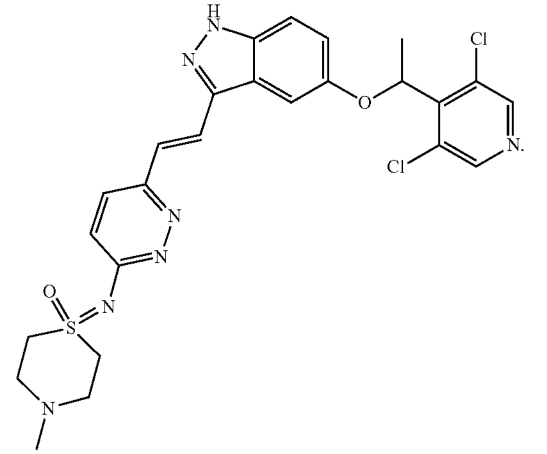

In several embodiments, as disclosed elsewhere herein, Q is pyrazole and each other variable of the structure of Formula (IAi) is as defined elsewhere herein. In several embodiments, where Q is pyrazole, $R^1$ are each —H, $R^4$ is selected from:

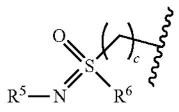

and

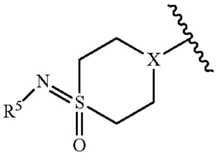

, c is 2, and each other variable is as defined elsewhere herein, Formula (IAi) may be represented by any one of the following compounds (or others):

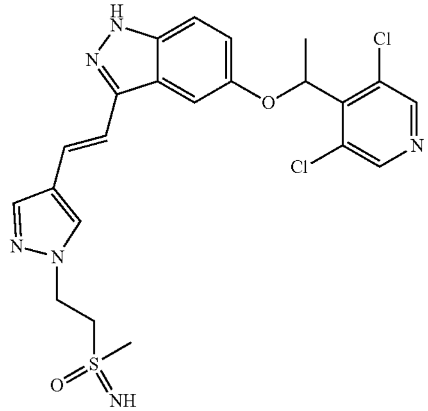

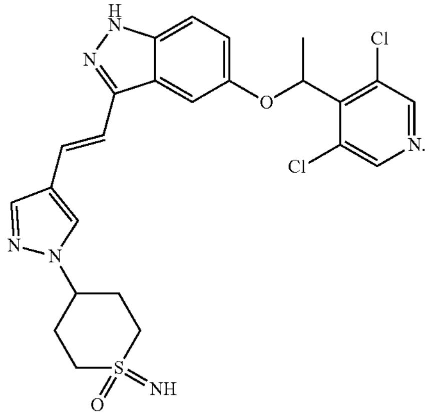

In several embodiments, as disclosed elsewhere herein, Q is imidazole and each other variable of the structure of Formula (IAi) is as defined elsewhere herein. In several embodiments, where Q is imidazole, $R^1$ are each —H, $R^4$ is:

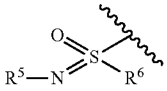

, and each other variable is as defined elsewhere herein, Formula (IAi) may be represented by the following compound:

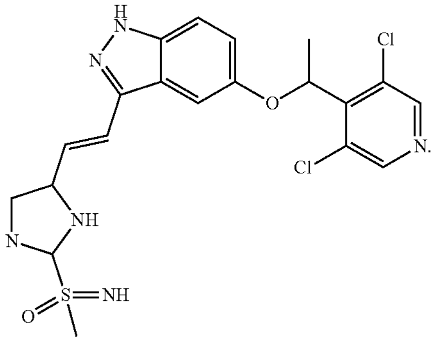

Several embodiments of Formula (IA) are represented by the structure of Formula (IAi), where an instance of $R^1$ is —H and another instance of $R^1$ is —F, $R^2$ is -Me, $X^1$ is $CR^3$, and each instance of $R^3$ is —Cl. In several embodiments, where Q is pyridine, $R^4$ is selected from:
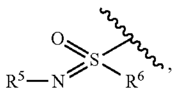
,
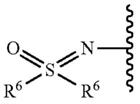
,
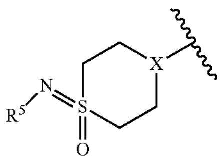
, and
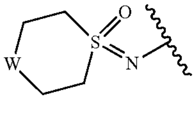
,
and each other variable is as defined elsewhere herein, Formula (IAi) may be represented by any one of the following compounds (or others):
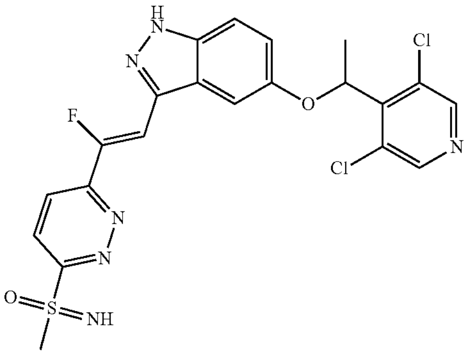
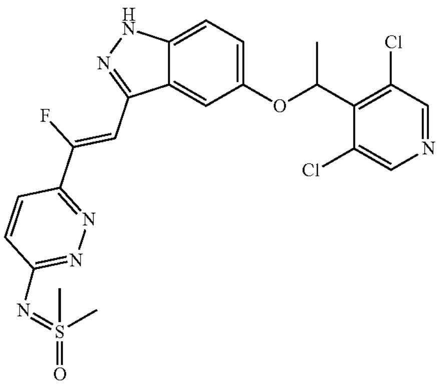
-continued
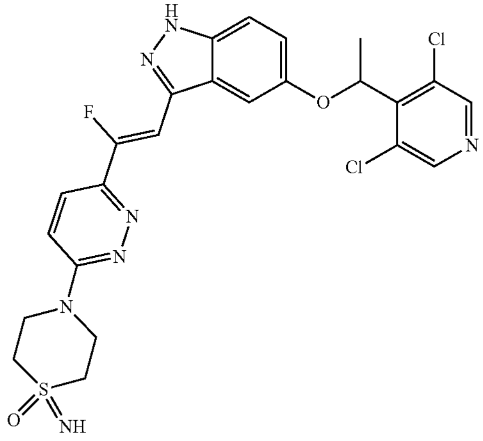
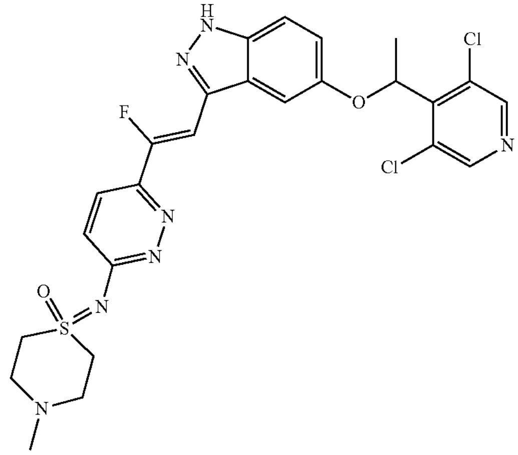
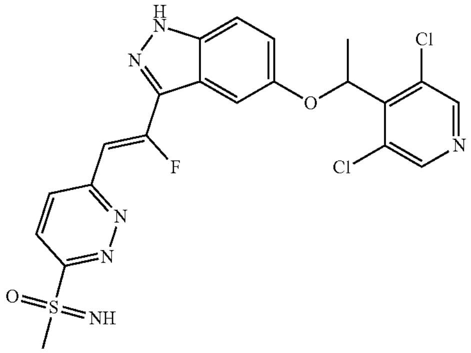
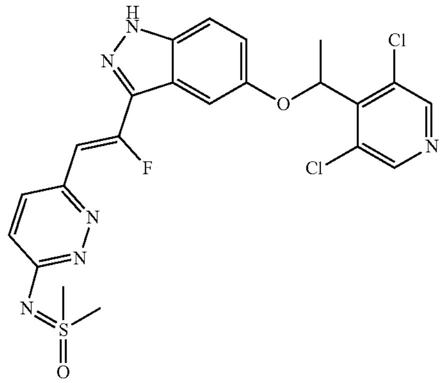

-continued

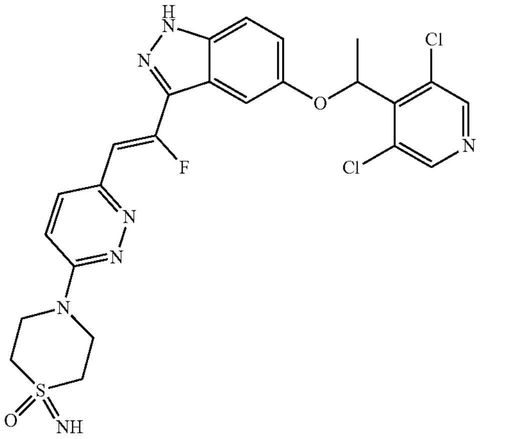

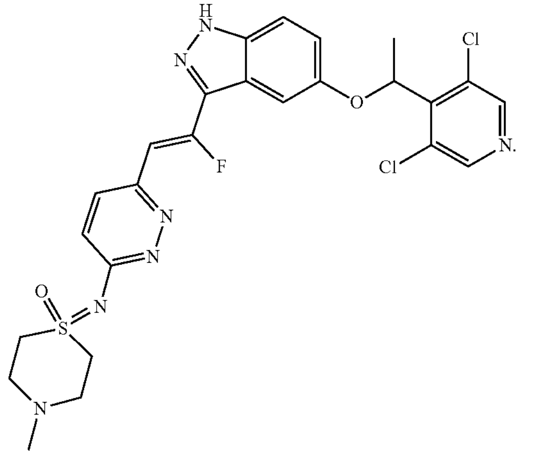

Several embodiments of Formula (IA) are represented by the structure of Formula (IAii), where each instance of $R^1$ is —H or —F, $R^2$ is -Me, $X^1$ is $CR^3$, an instance of $R^3$ is —H and another instance of $R^3$ is $C_3$-$C_6$-cycloalkyl (e.g., cyclopropyl), and $R^4$ is as defined elsewhere herein:

(IAii)

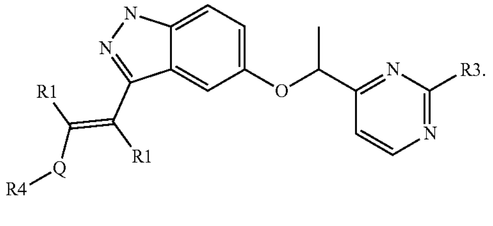

In several embodiments, as disclosed elsewhere herein, Q is pyridine and each other variable of the structure of Formula (IAii) is as defined elsewhere herein. In several embodiments, where Q is pyridine, an instance of $R^1$ is —F and another instance of $R^1$ is —H, $R^4$ is selected from:

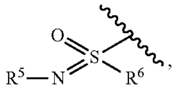,

-continued

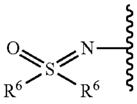,

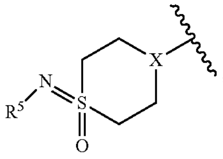, and

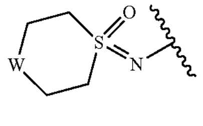, and each other variable is as defined elsewhere herein, Formula (IAii) may be represented by any one of the following compounds (or others):

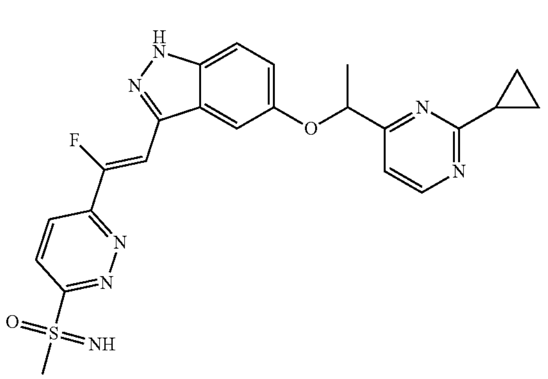

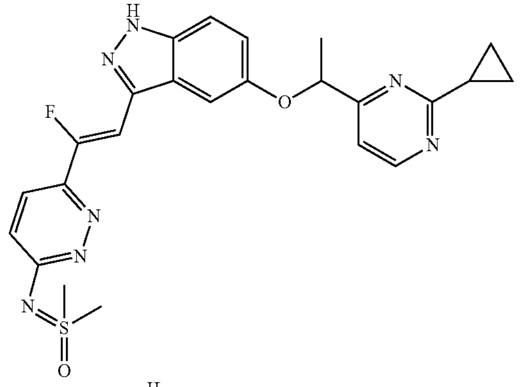

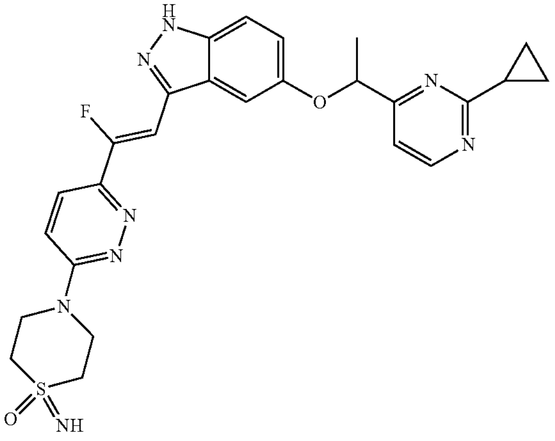

-continued

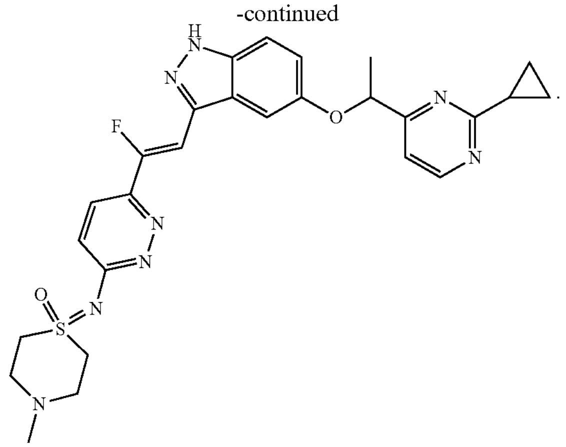

In several embodiments, as disclosed elsewhere herein, Q is pyrazole and each other variable of the structure of Formula (IAii) is as defined elsewhere herein. In several embodiments, where Q is pyrazole, $R^1$ are each —H, $R^4$ is:

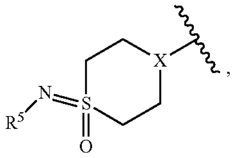

X is CH, and each other variable is as defined elsewhere herein, Formula (IAii) may be represented the following compound:

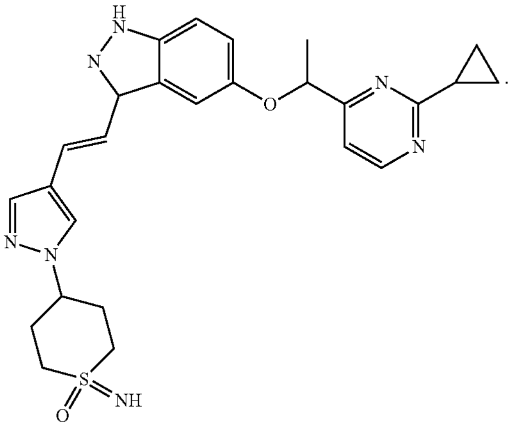

Formula IB Compounds

Several exemplary embodiments of structures of Formula (I) may be represented by the structure of Formula (IB), an indazole amide, where Y is —C(O)—$NR^8$— and each other variable is as defined elsewhere herein (e.g., as defined in Formula (I)):

(IB)

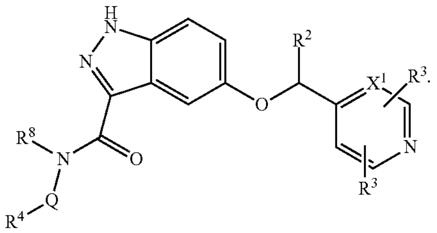

In several embodiments, $R^8$ is selected from —H and -Me. In several embodiments, $R^2$ is selected from the group consisting of —H and optionally substituted $C_1$-$C_3$ alkyl. In several embodiments, $X^1$ is selected from the group consisting of $CR^3$ and N. In several embodiments, each instance of $R^3$ can replace any —H of a CH within Ring A (which is shown as "A" in Formula (I)) and each instance of $R^3$ is independently selected from the group consisting of —H, —F, —Cl, Br, optionally substituted $C_1$-$C_3$-alkyl, $C_3$-$C_6$-cycloalkyl, and —$OR^9$ (where each instance of $R^9$, where present, is independently selected from the group consisting of —H and optionally substituted $C_1$-$C_3$-alkyl). In several embodiments, Q is selected from the group consisting of optionally substituted phenyl, optionally substituted pyridine, optionally substituted pyrimidine, optionally substituted pyridazine, optionally substituted pyrazole, optionally substituted imidazole, and optionally substituted pyrrolopyrimidine. In several embodiments, $R^4$ is selected from the group consisting of:

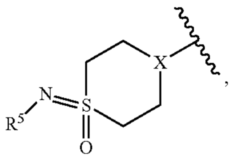

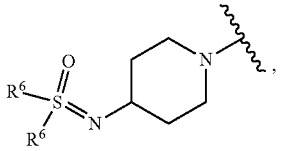

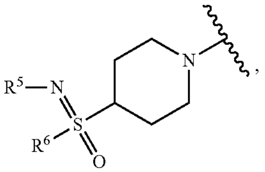

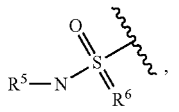

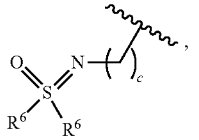

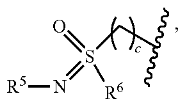

-continued

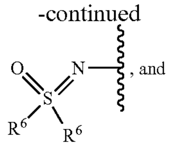

, and

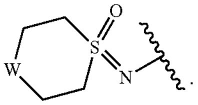

.

In several embodiments, X is N or C—H. In several embodiments, $R^5$ is selected from the group consisting of —H, optionally substituted $C_1$-$C_6$-alkyl, and optionally substituted $C_3$-$C_6$-cycloalkyl. In several embodiments, each instance of $R^6$ is independently selected from optionally substituted $C_1$-$C_6$-alkyl, optionally substituted $C_3$-$C_6$-cycloalkyl or two $R^6$ groups, together with the atoms to which they are attached, form a 4- to 7-membered ring. In several embodiments, W is selected from the group consisting of —$CH_2$—, —C(O)—, CH(OH), and —$N(R^7)$—. In several embodiments, $R^7$ is selected from the group consisting of —H, optionally substituted —$C_1$-$C_6$-alkyl, —$C_1$-$C_6$-alkenyl, and optionally substituted —$C_3$-$C_6$-cycloalkyl; and c is an integer equal to 1 or 2. In several embodiments, wherein each instance of Q, phenyl, pyridine, pyrimidine, pyridazine, pyrazole, imidazole, thiazole, $C_1$-$C_6$-alkyl, and $C_3$-$C_6$-cycloalkyl, when substituted, is independently substituted with one or more of —F, —Cl, Br, $C_1$-$C_6$-alkyl, —OH, —$OR^9$, and —$N(R^{11})_2$. In several embodiments, each instance of $R^9$ or $R^{11}$, where present, is independently selected from the group consisting of —H and optionally substituted $C_1$-$C_3$-alkyl, or each $R^{11}$ combine to form a cyclic pyrrolidine, piperidine, or methylpiperazine, (shown below).

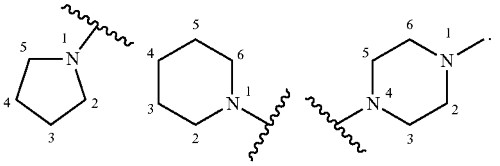

pyrrolidine piperidine methylpiperazine

Several embodiments of Formula (IB) are represented by the structure of Formula (IBi), where $R^8$ is —H, $R^2$ is -Me, $X^1$ is $CR^3$, each instance of $R^3$ is —Cl located at the 5 and 3 positions of the terminal heteroaryl ring (e.g., terminal pyridyl ring), and each other variable is as defined elsewhere herein:

(IBi)

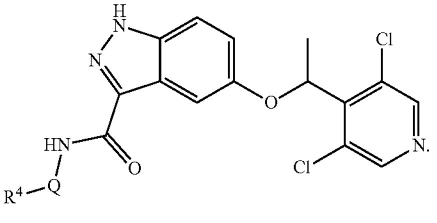

In several embodiments, as disclosed elsewhere herein, Q is optionally substituted phenyl and each other variable of the structure of Formula (IBi) is as defined elsewhere herein.

In several embodiments, where Q is phenyl substituted with —$OR^9$, $R^9$ is $C_1$-$C_3$-alkyl (e.g., -Me), $R^8$ is —H, $R^4$ is selected from:

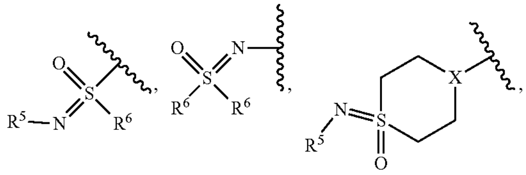

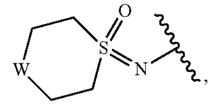

and each other variable is as defined elsewhere herein, Formula (IBi) may be represented by any one of the following compounds (or others):

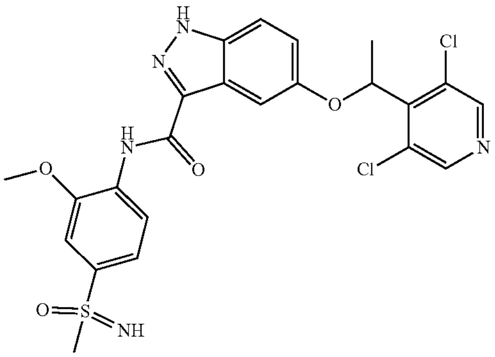

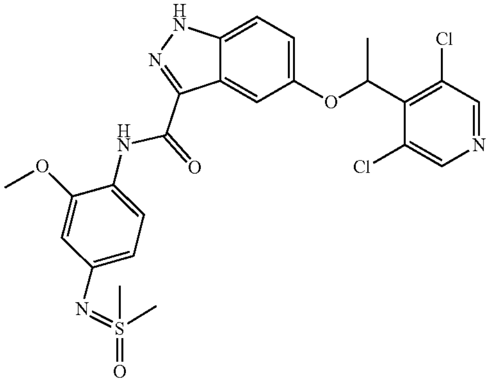

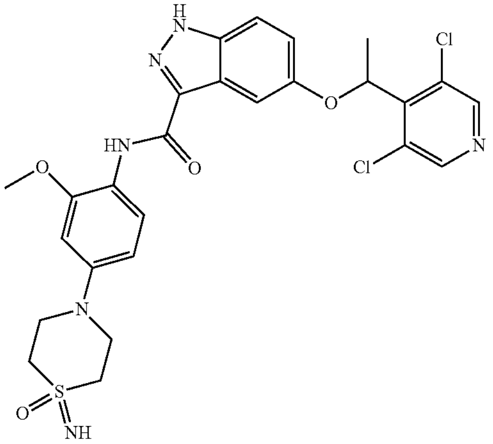

-continued

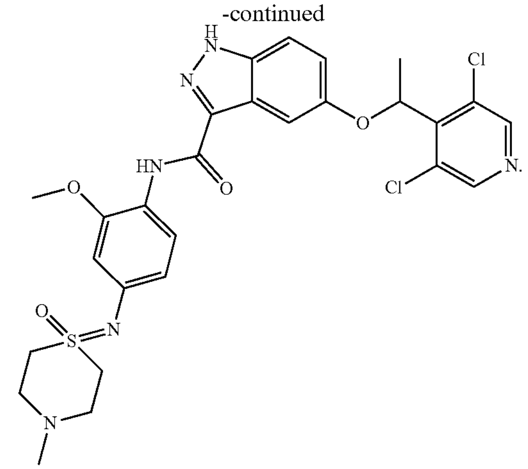

In several embodiments, where Q is phenyl, $R^8$ is —H, $R^4$ is:

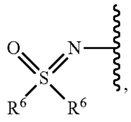, $R^4$ is methyl, and each other variable is as defined elsewhere herein, Formula (IBi) may be represented by any one of the following compounds (or others):

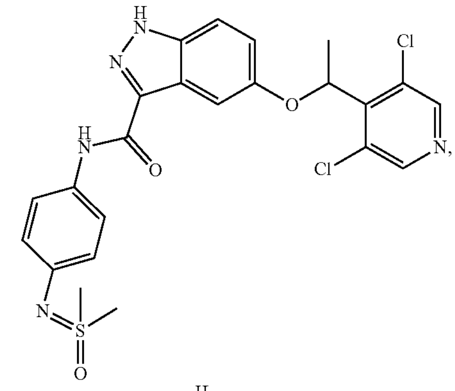, and

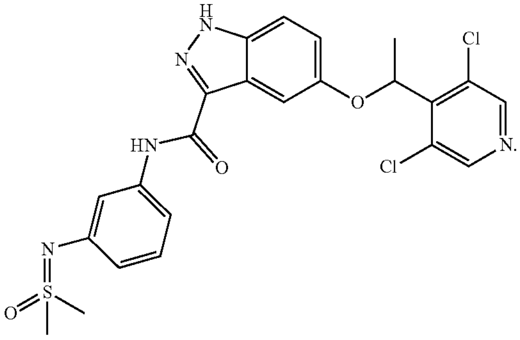.

In several embodiments, as disclosed elsewhere herein, Q is pyridine and each other variable of the structure of Formula (IBi) is as defined elsewhere herein. In several embodiments, where Q is pyridine, $R^8$ is —H, $R^4$ is selected from:

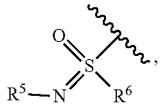, 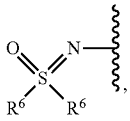, 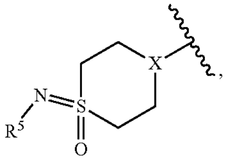, and

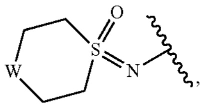, and each other variable is as defined elsewhere herein, Formula (IBi) may be represented by any one of the following compounds (or others):

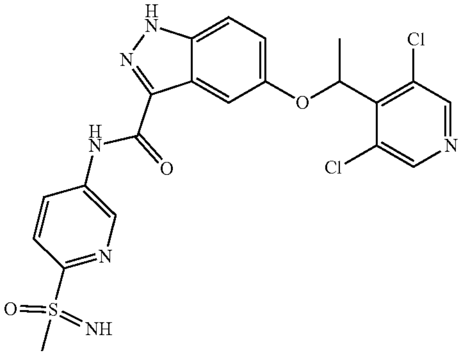

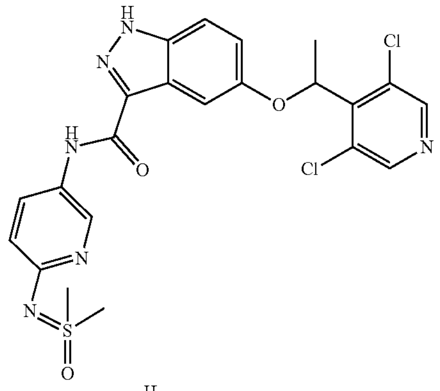

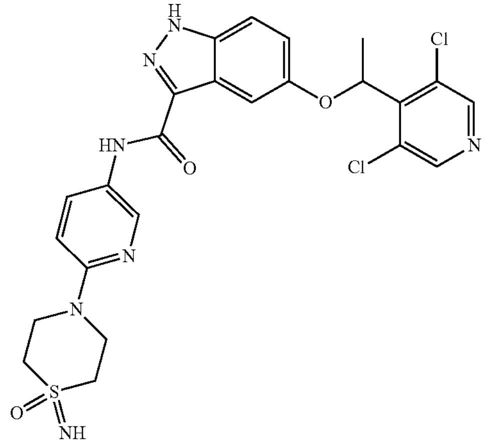

-continued
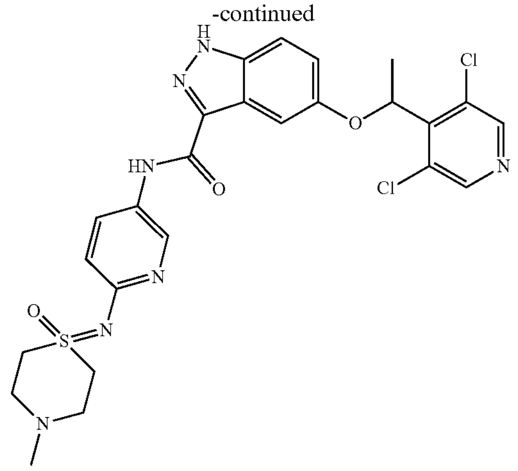
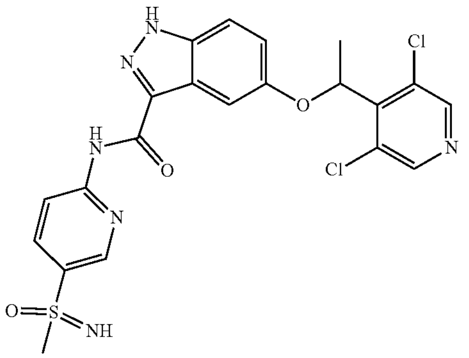
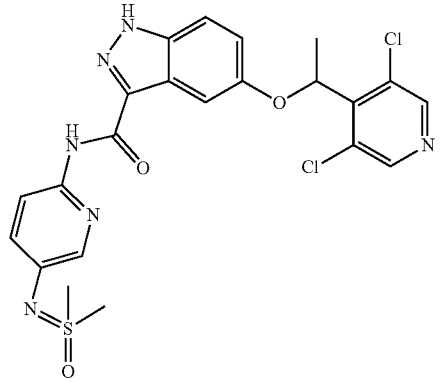
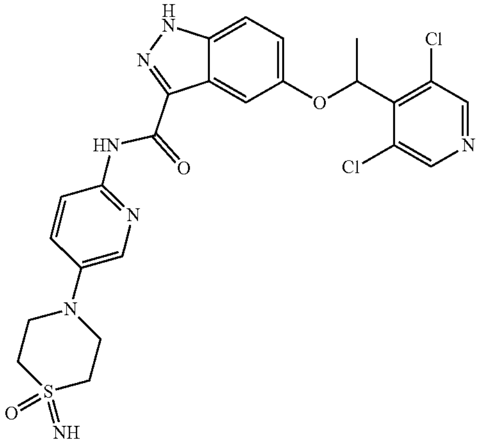
-continued
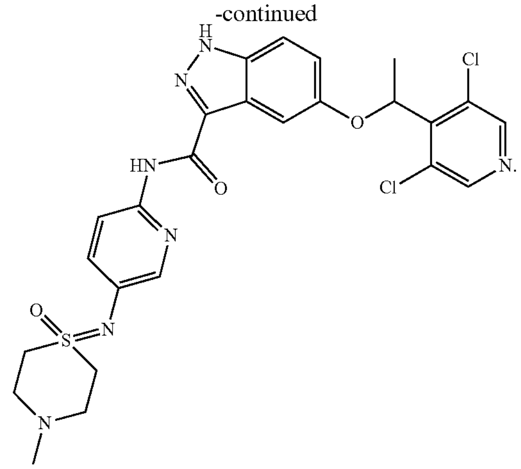
In several embodiments, where Q is pyridine, $R^4$ is selected from:
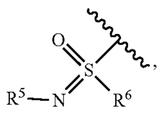
, and
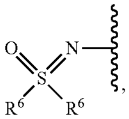
,
and each other variable is as defined elsewhere herein, Formula (IBi) may be represented by any one of the following compounds (or others):
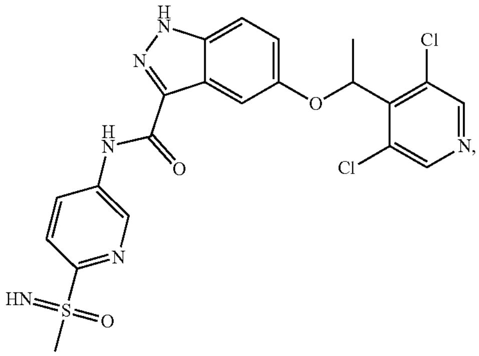
, and
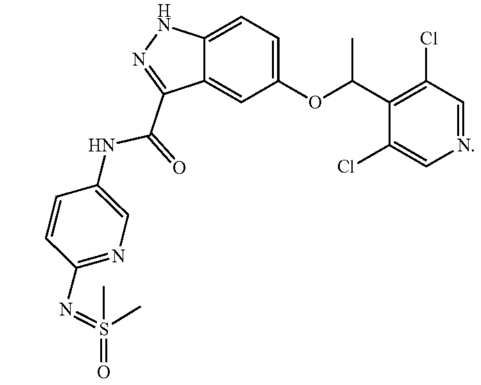
In several embodiments, as disclosed elsewhere herein, Q is pyrazole and each other variable of the structure of Formula (IBi) is as defined elsewhere herein. In several embodiments, where Q is pyrazole, $R^8$ is —H, $R^4$ is selected from:

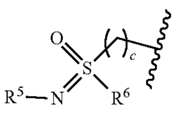

and

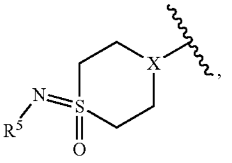

c is 2, and each other variable is as defined elsewhere herein, Formula (IAi) may be represented by any one of the following compounds (or others):

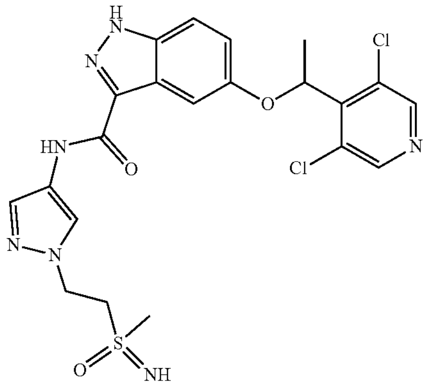

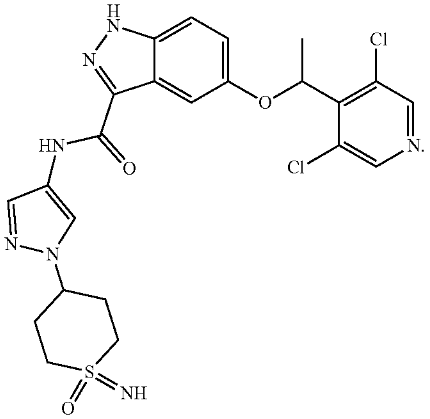

In several embodiments, as disclosed elsewhere herein, Q is imidazole and each other variable of the structure of Formula (IBi) is as defined elsewhere herein. In several embodiments, where Q is imidazole, $R^8$ is —H, $R^4$ is selected from:

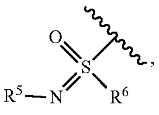

and each other variable is as defined elsewhere herein, Formula (IBi) may be represented by the following compound:

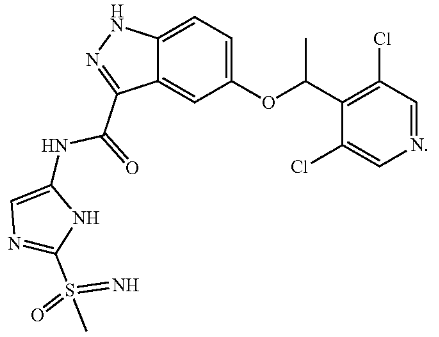 [SMILES: CC(Oc1ccc2[nH]nc(C(=O)Nc3cnc(S(C)(=N)=O)[nH]3)c2c1)c1c(Cl)cncc1Cl]

Several embodiments of Formula (IB) are represented by the structure of Formula (IBii), where $R^8$ is —H, $R^2$ is -Me, $X^1$ is $CR^3$, an instance of $R^3$ is —H and another instance of $R^3$ is $C_3$-$C_6$-cycloalkyl (e.g., cyclopropyl), and $R^4$ is as defined elsewhere herein:

(IBii)

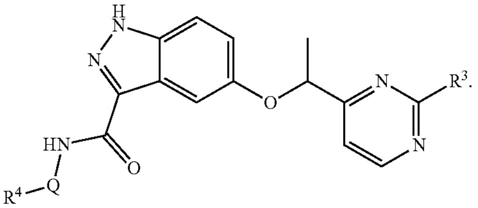

In several embodiments, as disclosed elsewhere herein, Q is pyrazole and each other variable of the structure of Formula (IAii) is as defined elsewhere herein. In several embodiments, where Q is pyrazole, $R^4$ is:

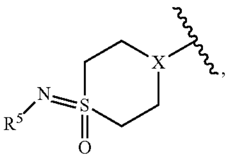

X is CH, and each other variable is as defined elsewhere herein, Formula (IBii) may be represented the following compound:

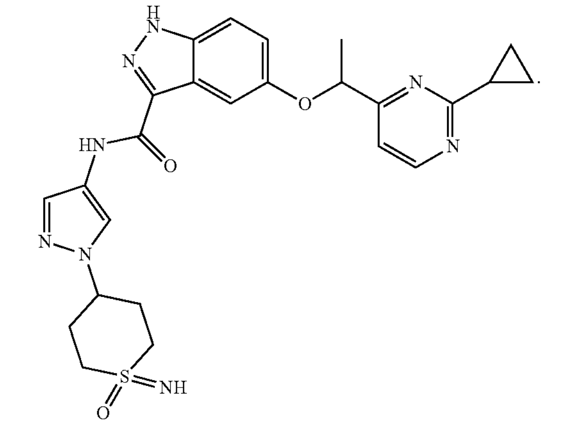 [SMILES: CC(Oc1ccc2[nH]nc(C(=O)Nc3cnn(C4CCS(=N)(=O)CC4)c3)c2c1)c1ccnc(C2CC2)n1]

Formula IC Compounds

Several exemplary embodiments of structures of Formula (I) may be represented by the structure of Formula (IC), an indazole amide, where Y is —C(O)—NR$^8$— and each other variable is as defined elsewhere herein (e.g., as defined in Formula (I)):

(IC)

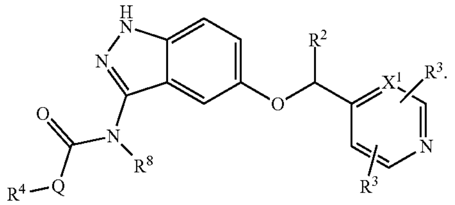

In several embodiments, R$^8$ is selected from —H and -Me. In several embodiments, R$^2$ is selected from the group consisting of —H and optionally substituted $C_1$-$C_3$ alkyl. In several embodiments, X$^1$ is selected from the group consisting of CR$^3$ and N. In several embodiments, each instance of R$^3$ can replace any —H of a CH within Ring A (which is shown as "A" in Formula (I)) and each instance of R$^3$ is independently selected from the group consisting of —H, —F, —Cl, Br, optionally substituted $C_1$-$C_3$-alkyl, $C_3$-$C_6$-cycloalkyl, and —OR$^9$ (where each instance of R$^9$, where present, is independently selected from the group consisting of —H and optionally substituted $C_1$-$C_3$-alkyl). In several embodiments, Q is selected from the group consisting of optionally substituted phenyl, optionally substituted pyridine, optionally substituted pyrimidine, optionally substituted pyridazine, optionally substituted pyrazole, optionally substituted imidazole, optionally substituted thiazolyl, and optionally substituted pyrrolopyrimidine. In several embodiments, R$^4$ is selected from the group consisting of:

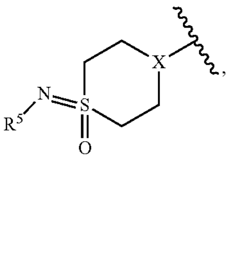,
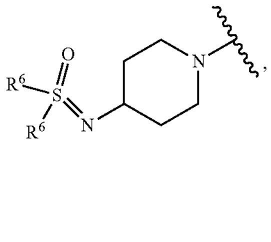,

-continued

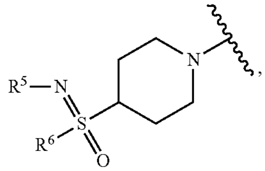,
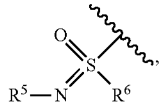,

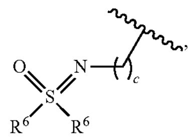,
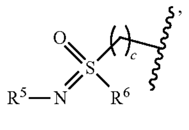,

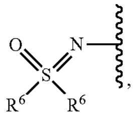, and
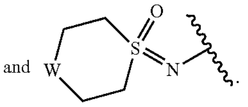.

In several embodiments, X is N or C—H. In several embodiments, R$^5$ is selected from the group consisting of —H, optionally substituted $C_1$-$C_6$-alkyl, and optionally substituted $C_3$-$C_6$-cycloalkyl. In several embodiments, each instance of R$^6$ is independently selected from optionally substituted $C_1$-$C_6$-alkyl and optionally substituted $C_3$-$C_6$-cycloalkyl or two R$^6$ groups, together with the atoms to which they are attached, form a 4- to 7-membered ring. In several embodiments, W is selected from the group consisting of —$CH_2$—, —C(O)—, CH(OH), and —N(R$^7$)—. In several embodiments, R$^7$ is selected from the group consisting of —H, optionally substituted —$C_1$-$C_6$-alkyl, —$C_1$-$C_6$-alkenyl, and optionally substituted —$C_3$-$C_6$-cycloalkyl; and c is an integer equal to 1 or 2. In several embodiments, wherein each instance of Q, phenyl, pyridine, pyrimidine, pyridazine, pyrazole, imidazole, thiazole, $C_1$-$C_6$-alkyl, and $C_3$-$C_6$-cycloalkyl, when substituted, is independently substituted with one or more of —F, —Cl, Br, $C_1$-$C_6$-alkyl, —OH, —OR$^9$, and —N(R$^{11}$)$_2$. In several embodiments, each instance of R$^9$ or R$^{11}$, where present, is independently selected from the group consisting of —H and optionally substituted $C_1$-$C_3$-alkyl, or each R$^{11}$ combine to form a cyclic pyrrolidine, piperidine, or methylpiperazine, (shown below).

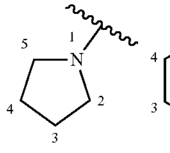
pyrrolidine

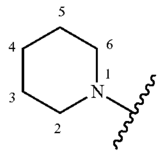
piperidine

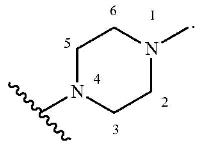
methylpiperazine

Several embodiments of Formula (IC) are represented by the structure of Formula (ICi), where R$^8$ is —H, R$^2$ is -Me, X$^1$ is CR$^3$, each instance of R$^3$ is —Cl located at the 5 and 3 positions of the terminal heteroaryl ring (e.g., terminal pyridyl ring), and each other variable is as defined elsewhere herein:

(ICi)

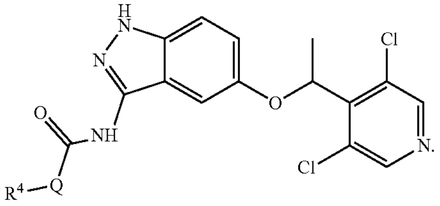

In several embodiments, as disclosed elsewhere herein, Q is pyridine and each other variable of the structure of Formula (ICi) is as defined elsewhere herein. In several embodiments, where Q is pyridine, $R^8$ is —H, $R^4$ is selected:

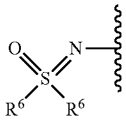, and each other variable is as defined elsewhere herein, Formula (ICi) may be represented by any one of the following compounds (or others):

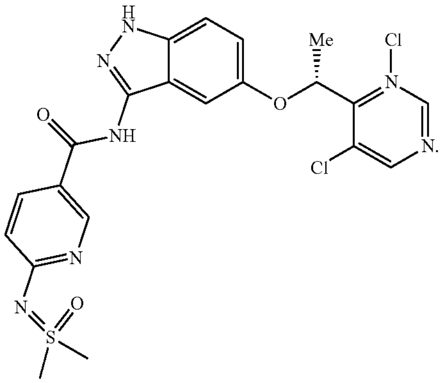

Formula ID Compounds

Several exemplary embodiments of structures of Formula (I) may be represented by the structure of Formula (ID), an indazole where Y is absent, a direct bond connects the Q and the indazole ring of the compound, and each other variable is as defined elsewhere herein (e.g., as defined in Formula (I)):

(ID)

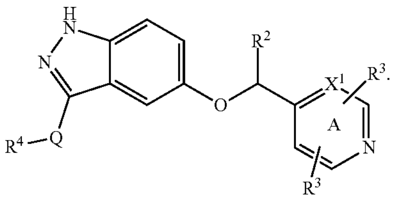

In several embodiments, $R^2$ is selected from the group consisting of —H and optionally substituted $C_1$-$C_3$ alkyl. In several embodiments, $X^1$ is selected from the group consisting of $CR^3$ and N. In several embodiments, each instance of $R^3$ can replace any —H of a CH within Ring A and each instance of $R^3$ is independently selected from the group consisting of —H, —F, —Cl, Br, optionally substituted $C_1$-$C_3$-alkyl, $C_3$-$C_6$-cycloalkyl, and —$OR^9$ (where each instance of $R^9$, where present, is independently selected from the group consisting of —H and optionally substituted $C_1$-$C_3$-alkyl). In several embodiments, Q is selected from the group consisting of optionally substituted phenyl, optionally substituted pyridine, optionally substituted pyrimidine, optionally substituted pyridazine, optionally substituted pyrazole, optionally substituted imidazole, optionally substituted thiazole, and optionally substituted pyrrolopyrimidine. In several embodiments, $R^4$ is selected from the group consisting of:

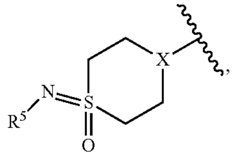, 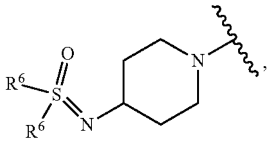,

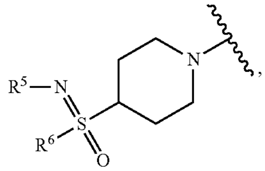, 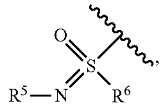,

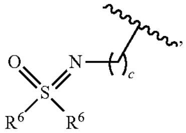, 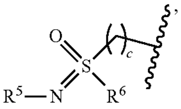,

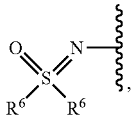, and 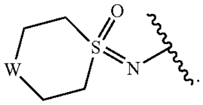.

In several embodiments, X is N or C—H. In several embodiments, $R^5$ is selected from the group consisting of —H, optionally substituted $C_1$-$C_6$-alkyl, and optionally substituted $C_3$-$C_6$-cycloalkyl. In several embodiments, each instance of $R^6$ is independently selected from optionally substituted $C_1$-$C_6$-alkyl, optionally substituted $C_3$-$C_6$-cycloalkyl or two $R^6$ groups, together with the atoms to which they are attached, form a 4- to 7-membered ring. In several embodiments, W is selected from the group consisting of —$CH_2$—, —C(O)—, CH(OH), and —$N(R^7)$—. In several embodiments, $R^7$ is selected from the group consisting of —H, optionally substituted —$C_1$-$C_6$-alkyl, —$C_1$-$C_6$-alkenyl, and optionally substituted —$C_3$-$C_6$-cycloalkyl; and c is an integer equal to 1 or 2. In several embodiments, wherein each instance of Q, phenyl, pyridine, pyrimidine, pyridazine, pyrazole, imidazole, thiazole, $C_1$-$C_6$-alkyl, and $C_3$-$C_6$-cycloalkyl, when substituted, is independently substituted with one or more of —F, —Cl, Br, $C_1$-$C_6$-alkyl, —OH, —$OR^9$, and —$N(R^{11})_2$. In several embodiments, each instance of $R^9$ or $R^{11}$, where present, is independently selected from the group consisting of —H and optionally substituted $C_1$-$C_3$-alkyl, or each $R^{11}$ combine to form a cyclic pyrrolidine, piperidine, or methylpiperazine, (shown below).

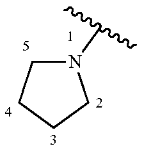

pyrrolidine

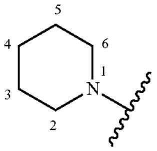

piperidine

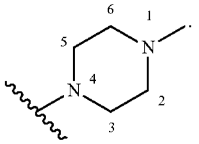

methylpiperazine

Several embodiments of Formula (ID) are represented by the structure of Formula (IDi), where each instance of Q is phenyl, $X^1$ is $CR^3$, each instance of $R^3$ is —Cl located at the 5 and 3 positions of the terminal heteroaryl ring (e.g., terminal pyridyl ring), and each other variable is as defined elsewhere herein:

(IDi)

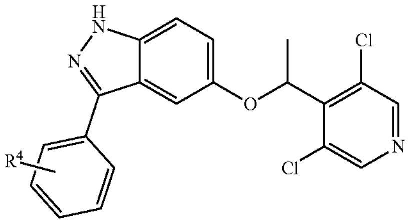

In other aspects of the disclosure are compounds of the following formulas:

(IDia)

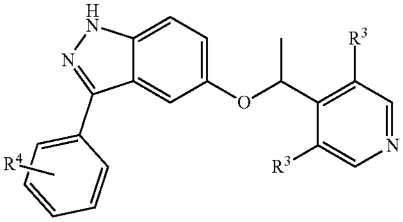

(IDib)

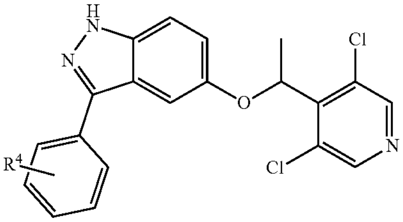

(IDib)

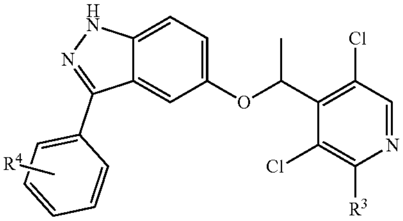

-continued (IDib)

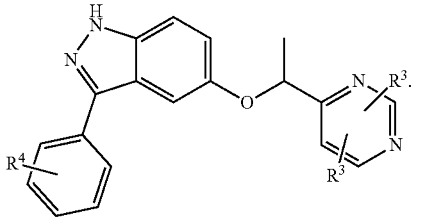

wherein each $R^3$ is independently $C_{1-6}$alkyl, F, Cl, or Br.

In several embodiments, as disclosed elsewhere herein, Q is phenyl and each other variable of the structure of Formula (IDi) is as defined elsewhere herein. In several embodiments, where Q is phenyl, $R^4$ is selected from:

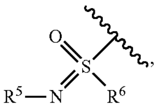

,

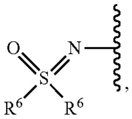

, and

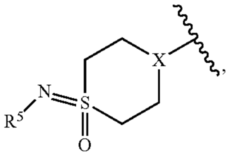

, and each other variable is as defined elsewhere herein, Formula (IDi) may be represented by any one of the following compounds (or others):

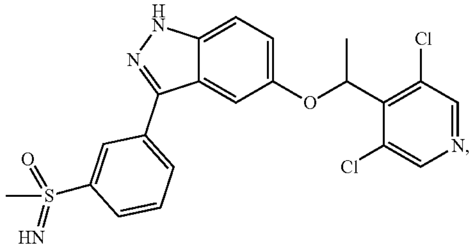

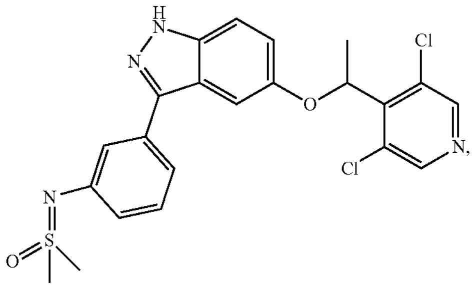

-continued

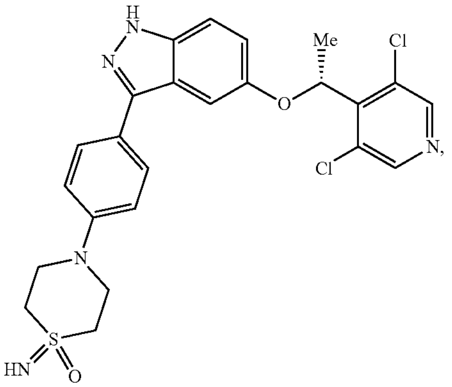

, and

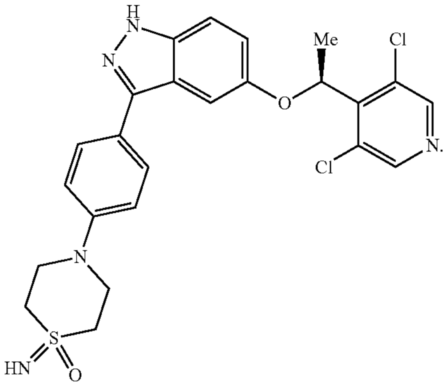

.

In several embodiments, as disclosed elsewhere herein, Q is pyridyl and each other variable of the structure of Formula (IC) is as defined elsewhere herein. In several embodiments, where Q is optionally substituted pyridine (e.g., optionally substituted with a halogen), $R^2$ is selected from the group consisting of —H and methyl (and, where methyl, may be in the (R) or (S) configuration), $X^1$ is selected from the group consisting of $CR^3$ and N, $R^3$ is independently selected from the group consisting of —H, —F, —Cl, and methyl, $R^4$ is selected from:

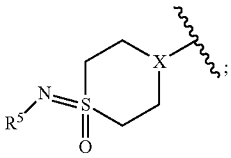

;

and each other variable is as defined elsewhere herein, Formula (ID) may be represented by any one of the following compounds (or others):

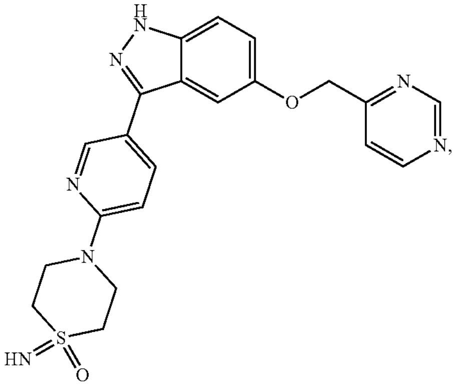

,

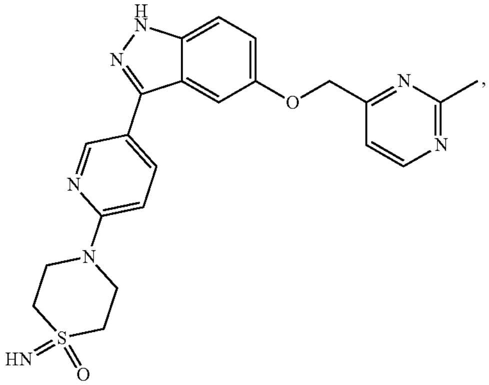

,

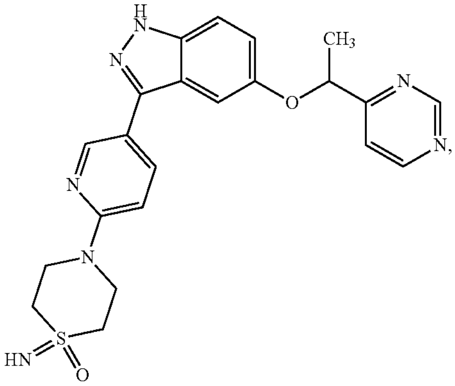

,

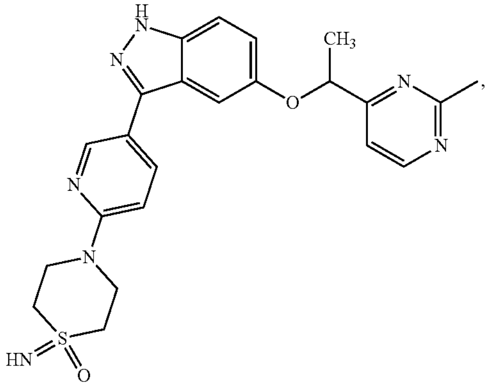

,

-continued
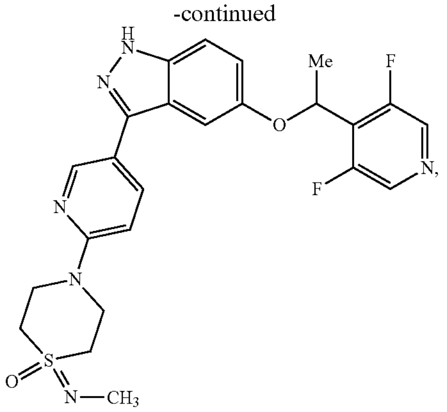
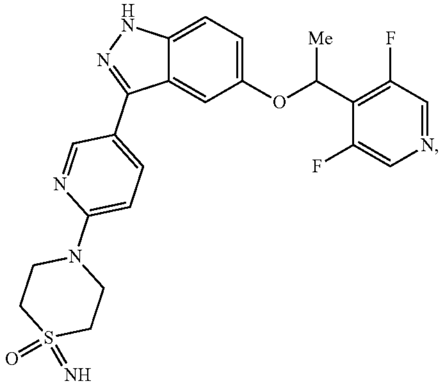
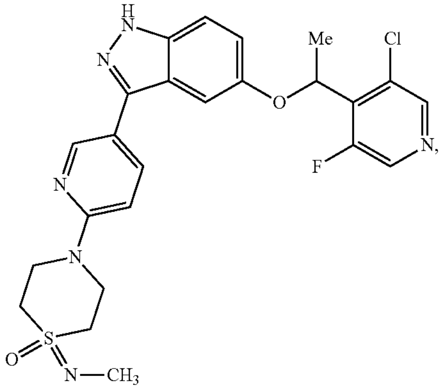
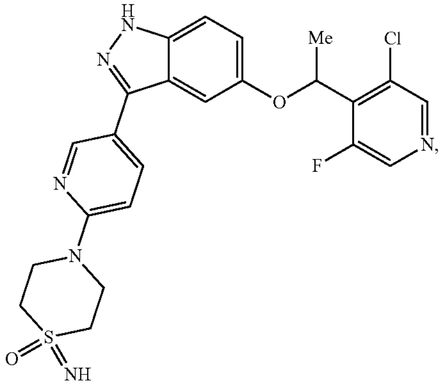
-continued
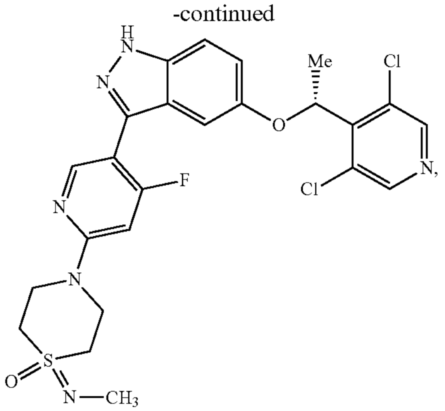
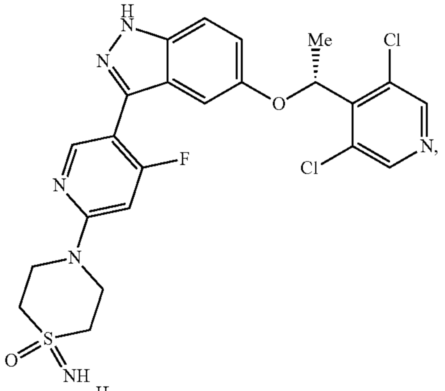
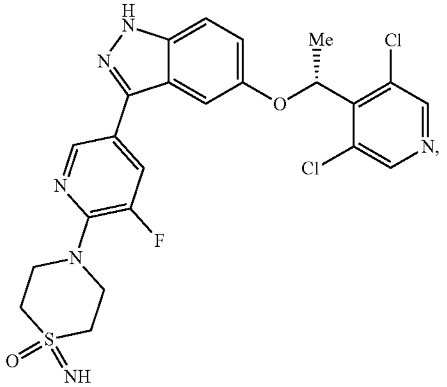
and
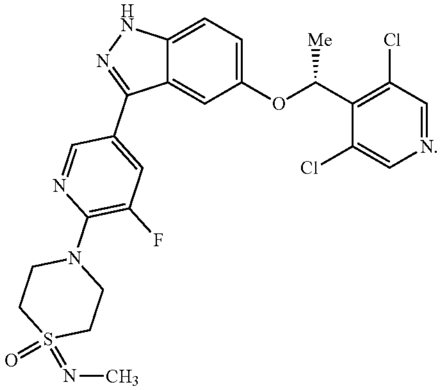
Several embodiments of Formula (ID) are represented by the structure of Formula (IDii), where each instance of Q is pyridyl, $X^1$ is $CR^3$, each instance of $R^3$ is —Cl located at the 5 and 3 positions of the terminal heteroaryl ring (e.g., terminal pyridyl ring), and each other variable is as defined elsewhere herein:

(IDii)

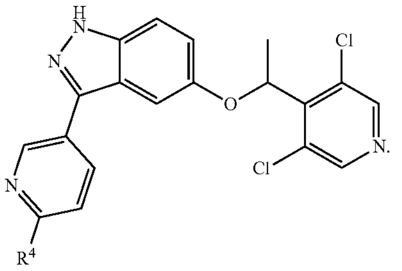

Also within the scope of the disclosure are compounds of the formula:

(IDii)

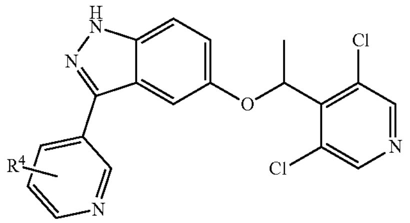

(IDiia)

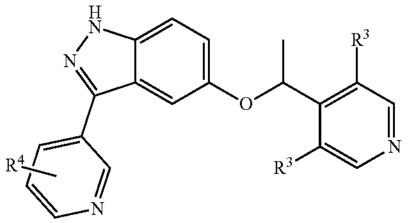

(IDiib)

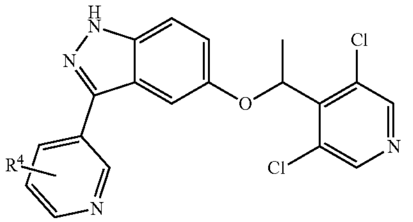

(IDiib)

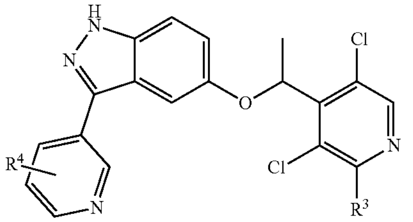

(IDiib)

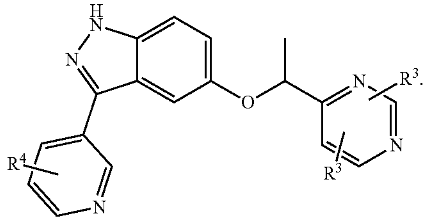

In several embodiments, as disclosed elsewhere herein, Q is pyridyl and each other variable of the structure of Formula (IDii) is as defined elsewhere herein. In several embodiments, where Q is pyridyl, $R^4$ is:

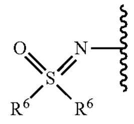

and

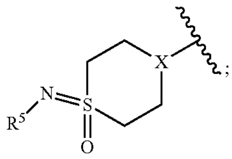

;

and each other variable is as defined elsewhere herein, and the $R^2$, when methyl, is in the R or S configuration, Formula (IDii) may be represented by any one of the following compounds (or others):

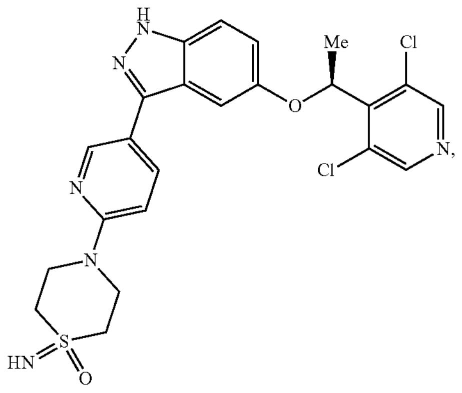

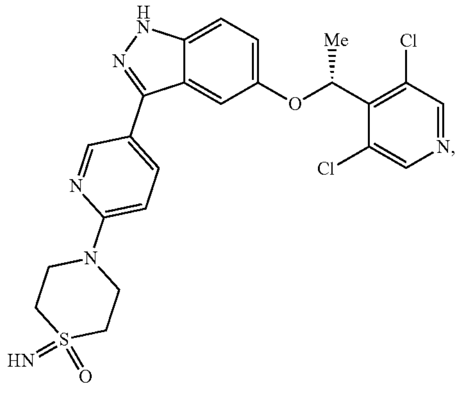

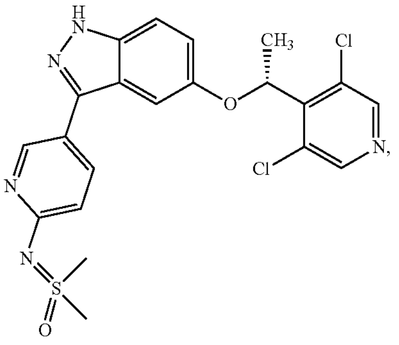

-continued

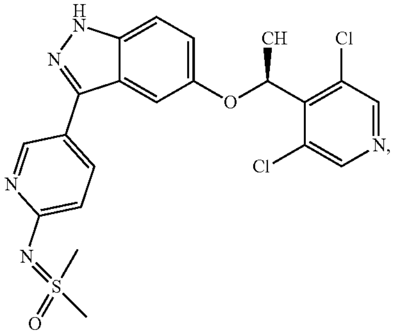

and

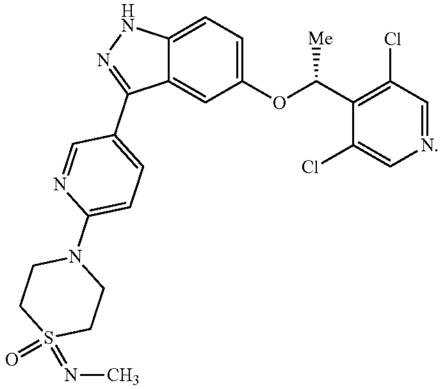

Several embodiments pertain to a compound of Formula (I), or a pharmaceutically acceptable salt thereof, further represented by compounds of the formula:

(IEii)

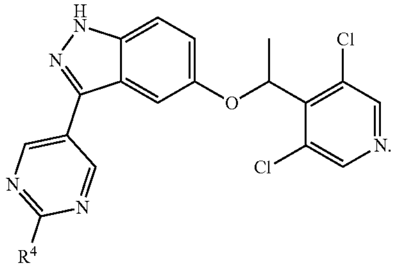

(IEii)

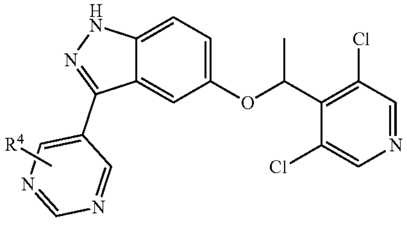

(IEiia)

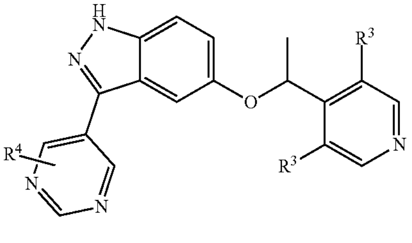

-continued (IEiib)

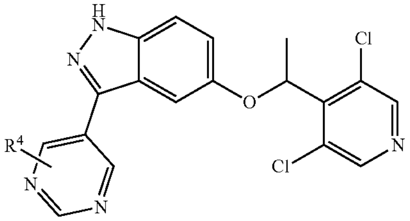

(IEiib)

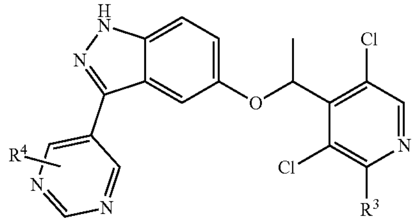

(IEiib)

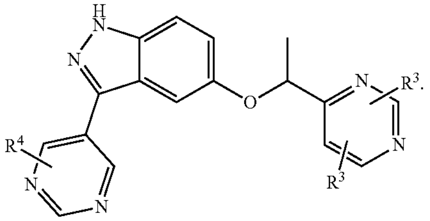

In several embodiments, as disclosed elsewhere herein, Q is pyrimidinyl and each other variable of the structure of Formula (IC) is as defined elsewhere herein. In several embodiments, where Q is pyrimidinyl, $R^2$ is methyl, each instance of $R^3$ is independently —Cl, $R^4$ is selected from:

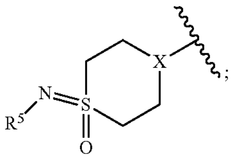

$R^5$ is methyl or H, and each other variable is as defined elsewhere herein, Formula (ID) may be represented by any one of the following compounds (or others):

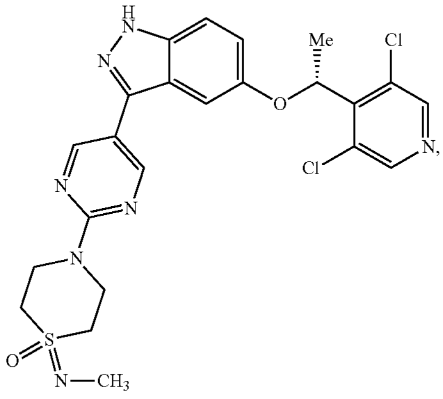

and

-continued

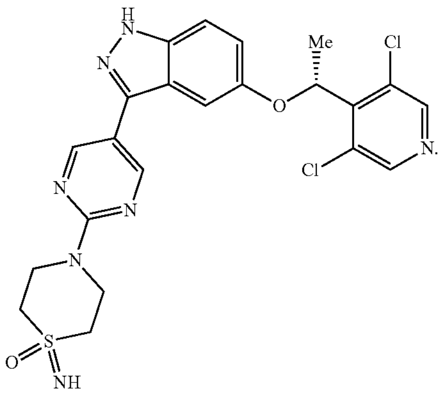

Also within the scope of the disclosure are compounds of the formula (IFa)

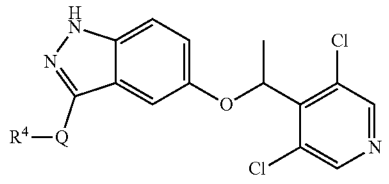

(IFb)

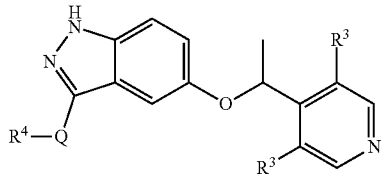

(IFc)

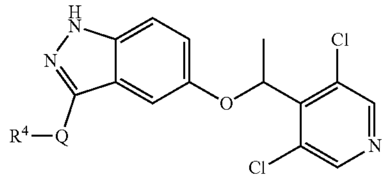

(IFd)

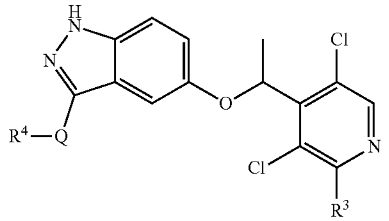

(IFe)

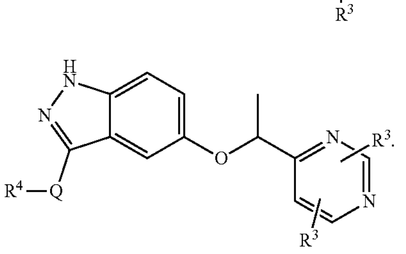

Methods of Making Compounds of the Disclosure

Several exemplary embodiments pertain to methods of synthesizing compounds of the disclosure and intermediate compounds of the disclosure. Schemes 1-5 show embodiments synthetic routes for the preparation of embodiment as disclosed herein.

Scheme 1

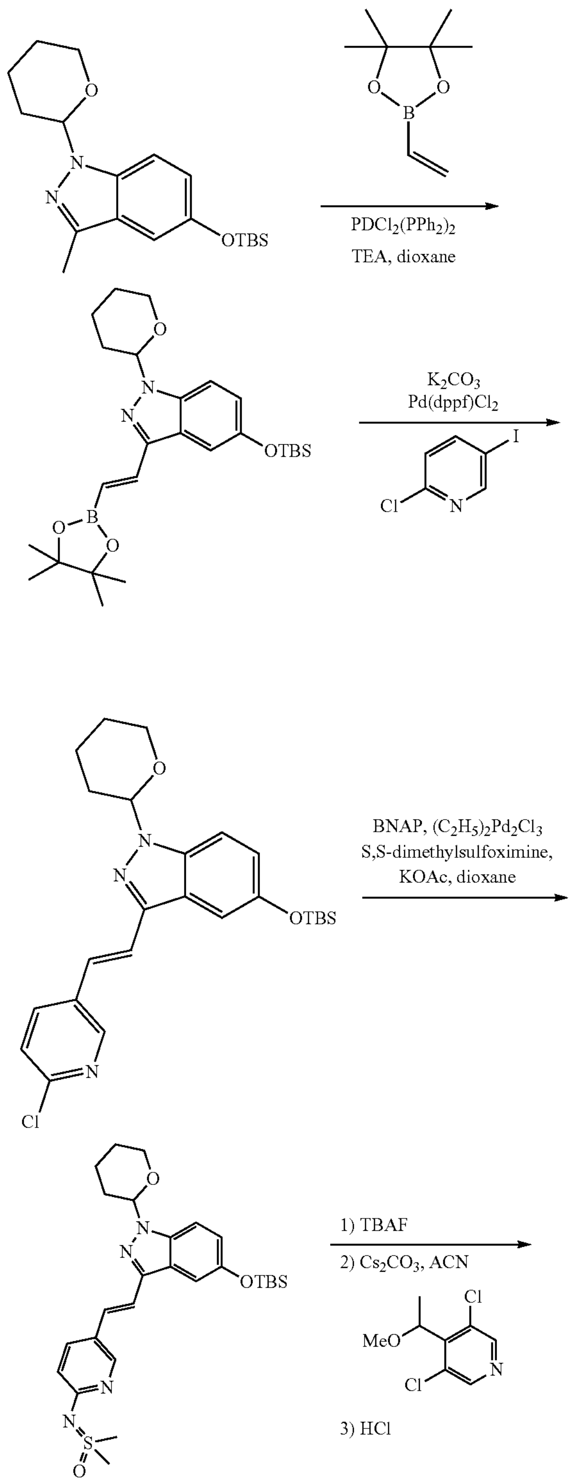

-continued
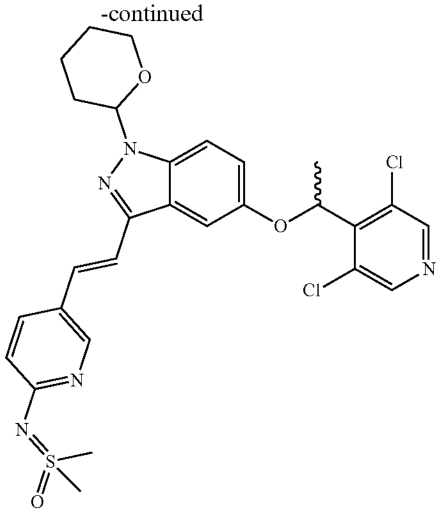
Ex. 3-4
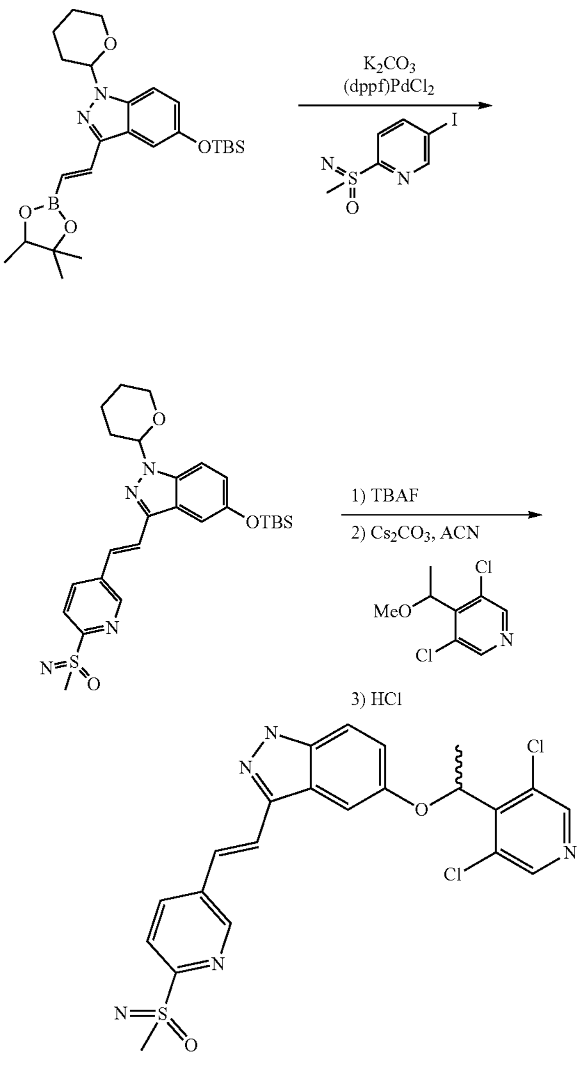
Ex. 9-10
Scheme 2
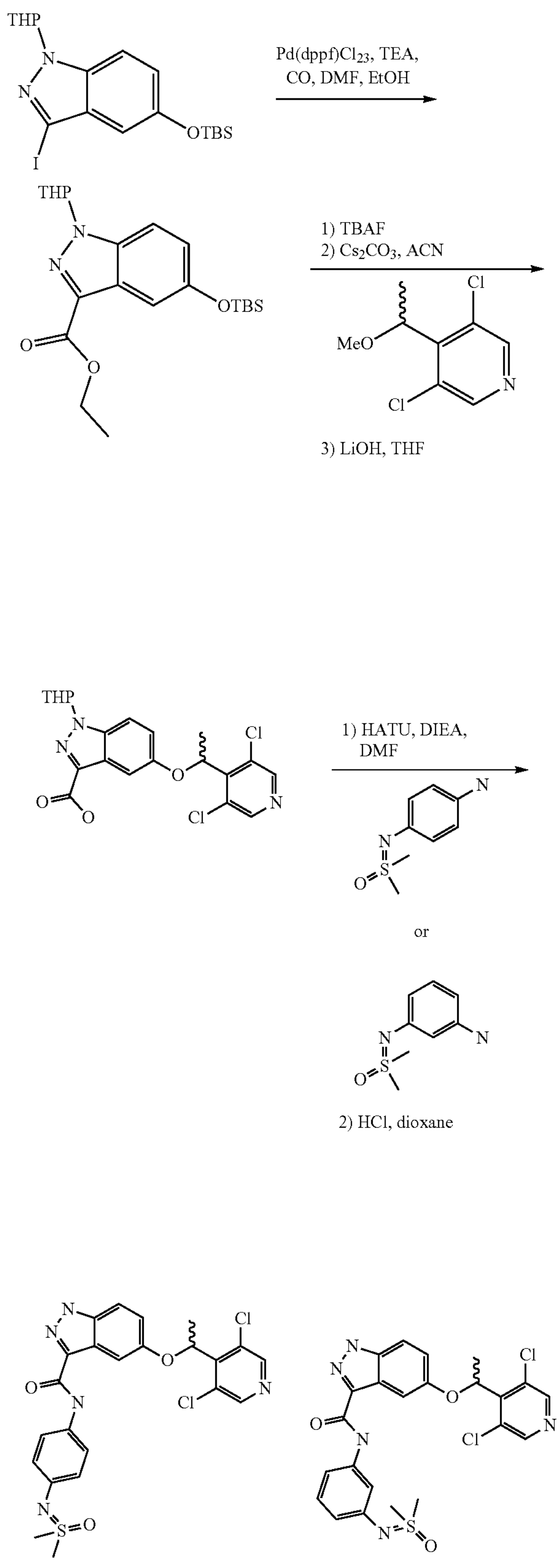
Ex. 5
Ex. 7

Scheme 3
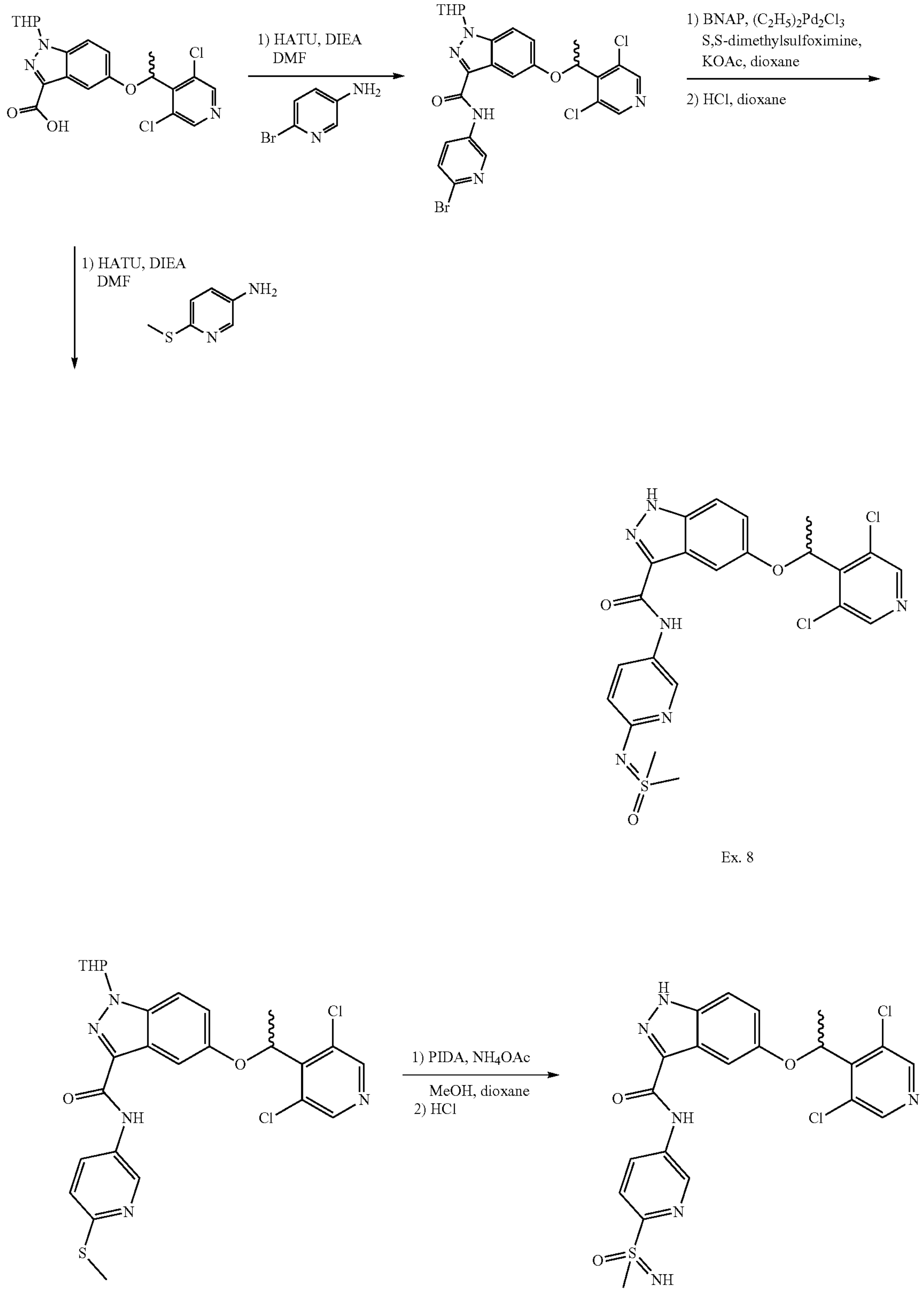
Ex. 8
Ex. 6

Scheme 4
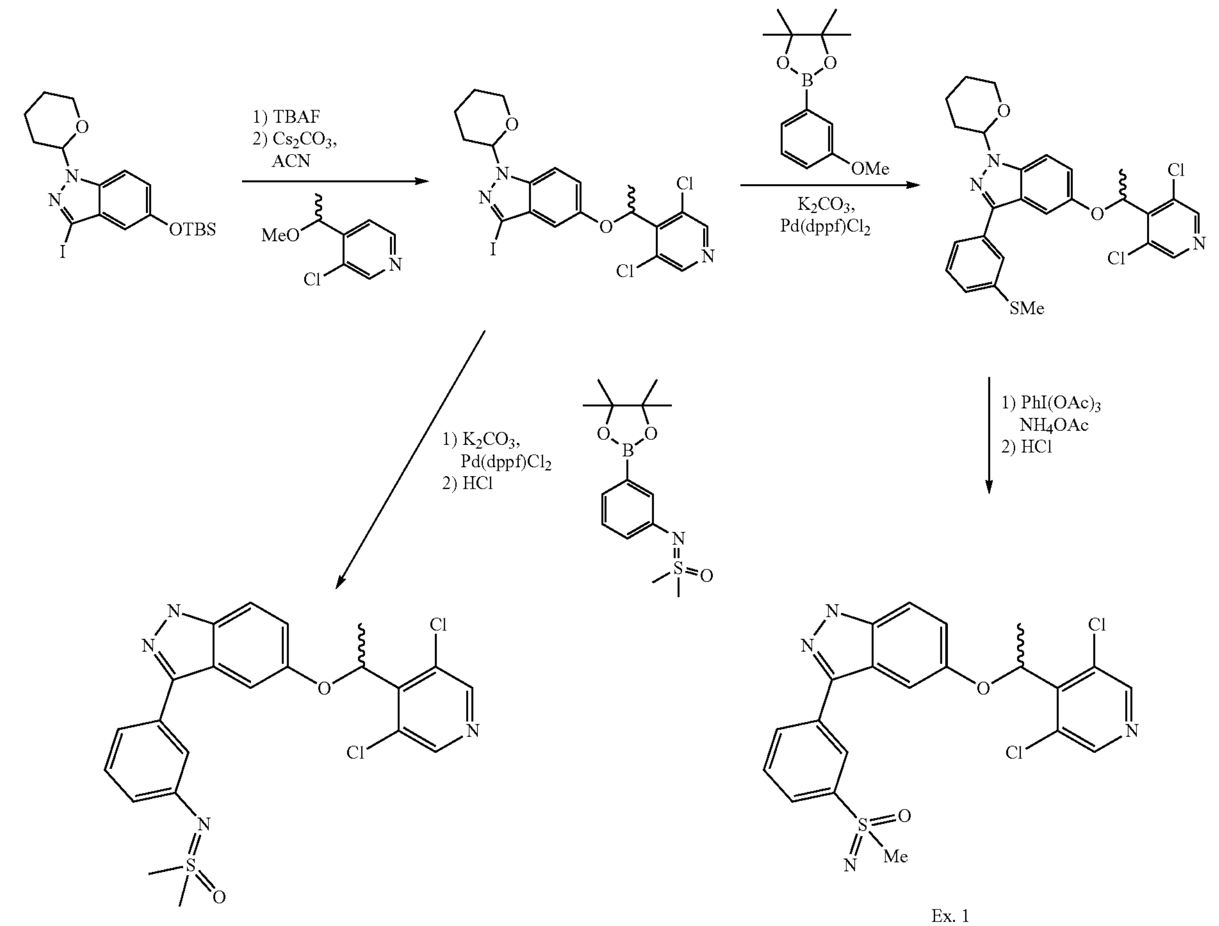
Ex. 2
Ex. 1

Scheme 5
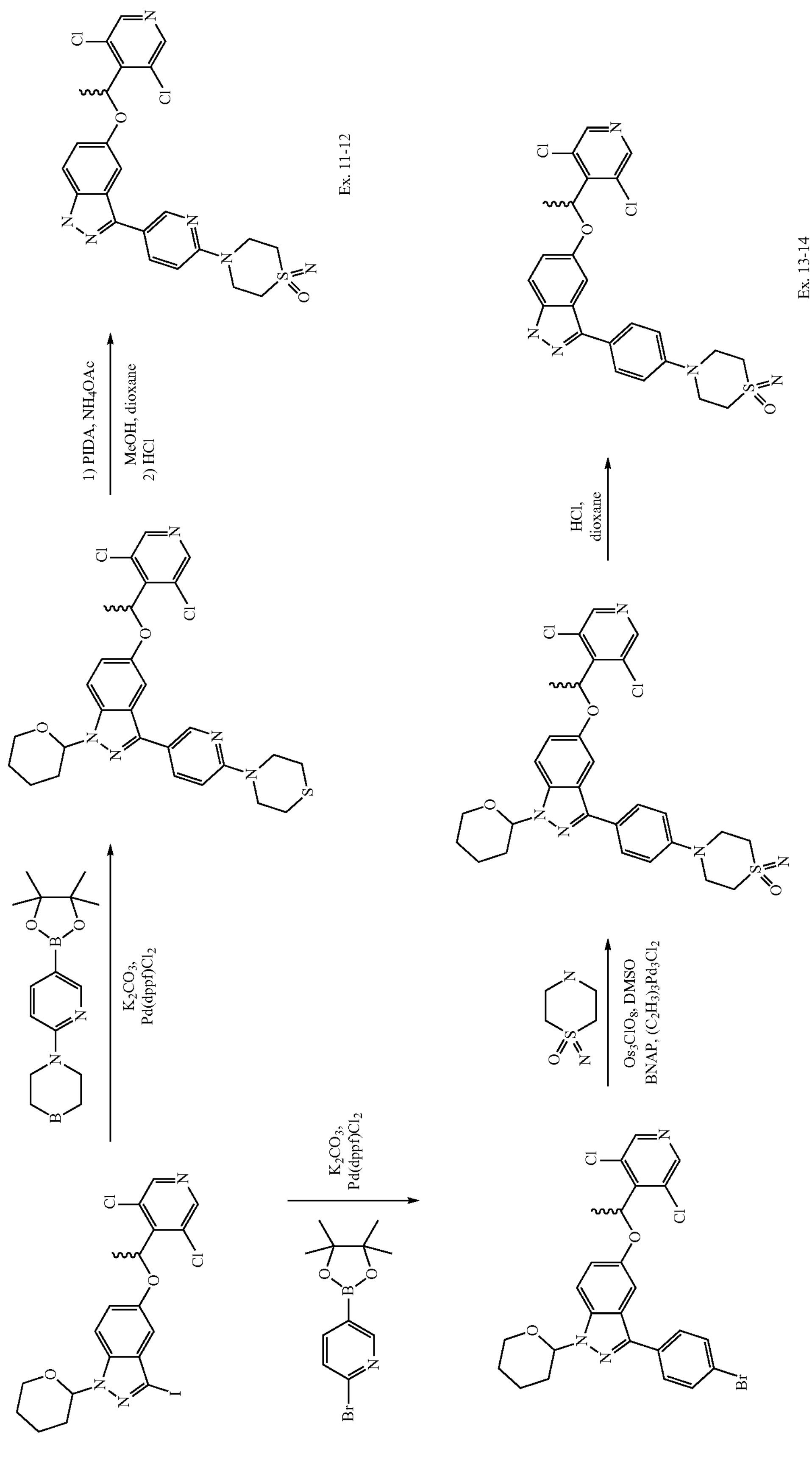
Ex. 11-12
Ex. 13-14

In several embodiments, to prepare a compound of Formula (1) a protected indazole (S1) is prepared and/or acquired, as shown below:

S1

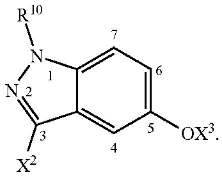

In several embodiments, S1 comprises a protecting group on the 1 position amine ($R^{10}$), a protecting group on the 5-position oxygen ($X^3$), and a halogen bonded to the 3 position (as $X^2$). In several embodiments, the amine protecting group $R^{10}$ is a tetrahydropyranyl ether. In several embodiments, $X^3$ is a silyl protecting group (e.g., trimethylsilyl (TMS), tert-butyldiphenylsilyl (TBDPS), tert-butyldimethylsilyl (TBS/TBDMS) and triisopropylsilyl (TIPS)).

In several embodiments, to prepare a structure of Formula (IA), a coupling is performed using a boronic acid, as shown below, to provide Sa2. In several embodiments, a iodo and chloro substituted Q group, as disclosed elsewhere herein is coupled to Sa2 under coupling conditions, thereby providing Sa3. In several embodiments, as shown in Scheme 1 and below, $R^4$ is introduced to Q of Sa3 by displacing the chloro group to provide Sa4.

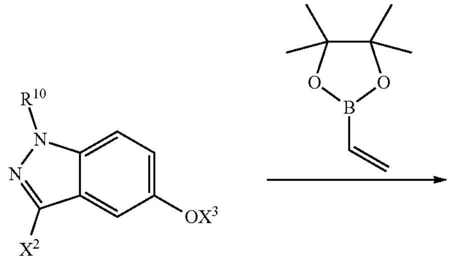

S1

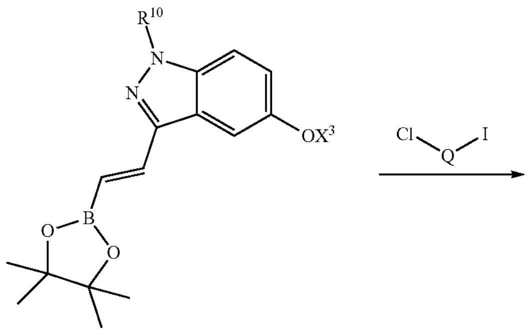

Sa2

-continued

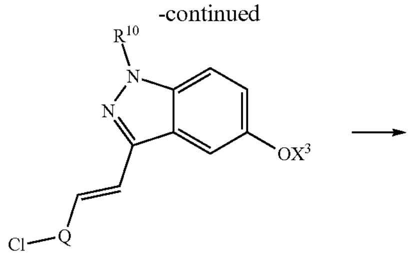

Sa3

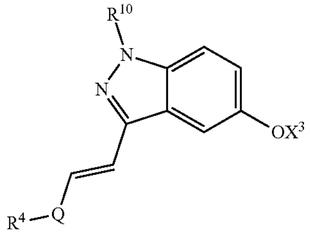

Sa4

Alternatively, also as shown in Scheme 1, in several embodiments, $R^4$ may be introduced to compound Sa2 as part of the Q moiety to provide Sa4, as shown in the following:

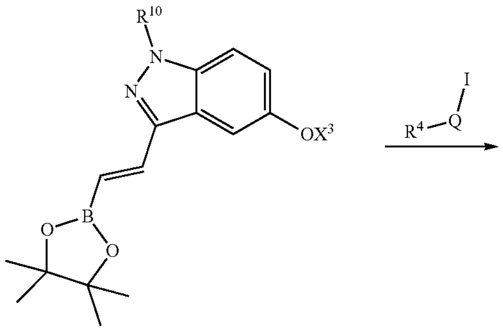

Sa2

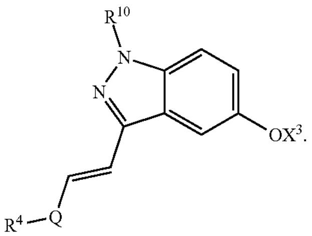

Sa4

As shown in the following (and as depicted in Scheme 1), in several embodiments, the $X^3$ group is removed using deprotecting conditions to provide Sa5 and the deprotected OH of Sa5 displaces a leaving group (e.g., tosylate, mesylate, etc.) on the A ring moiety to couple the A ring moiety to Sa4 (thereby providing Sa5). In several embodiments, the $R^{10}$ substituent of Sa5 is removed using deprotecting conditions to provide a structure of Formula (IA).

S4 →

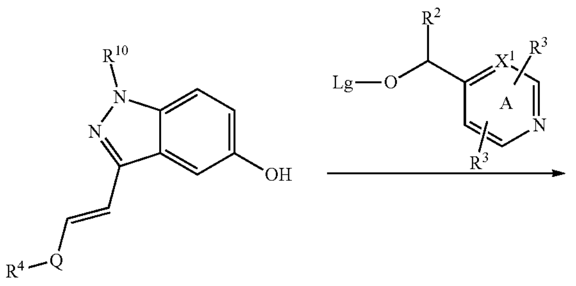

Sa5

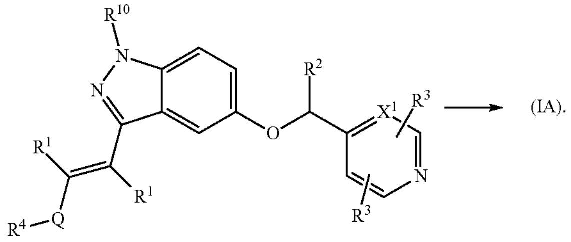

Sa6

In several embodiments, to prepare a structure of Formula (IB) (as shown in Schemes 2 and 3, above), S1 is again used. In several embodiments, a coupling reaction is performed in the presence of a catalyst (e.g., a Pd catalyst), CO and ethanol (or any $C_1$ to $C_6$ alkanol), thereby providing Sb2. As shown in the following (and as depicted in Scheme 2, above), in several embodiments, the $X^3$ group is removed using deprotecting conditions to provide Sb3 and the deprotected OH of Sb3 displaces a leaving group (e.g., tosylate, mesylate, etc.) on the A ring moiety to couple the A ring moiety to Sb3 (thereby providing Sb4).

S1 →

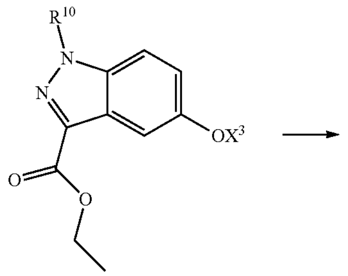

Sb2

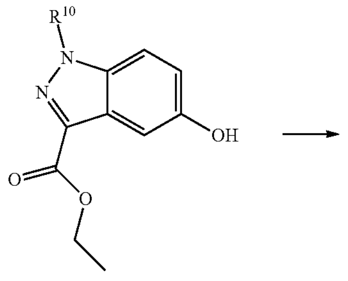

Sb3

-continued

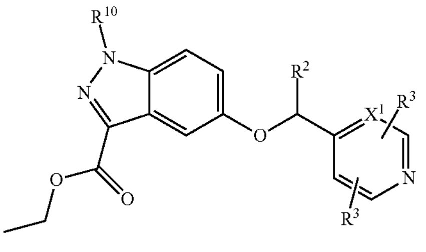

Sb4

In several embodiments, an ester saponification is performed to provide the carboxylic acid Sb5 (as shown in FIG. 2, above). At that time, $R^8$NH-Q-$R^4$ is coupled to Sb5 under coupling conditions, thereby providing Sb6. In several embodiments, as shown in Scheme 2, the $R^{10}$ substituent of Sb6 is removed using deprotecting conditions to provide the structure of Formula (IB):

Sb4 →

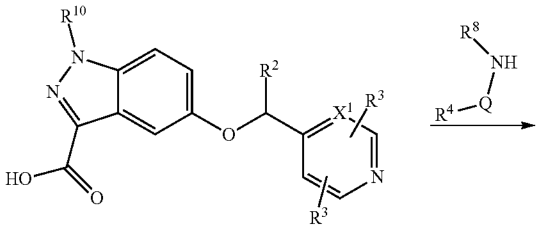

Sb5

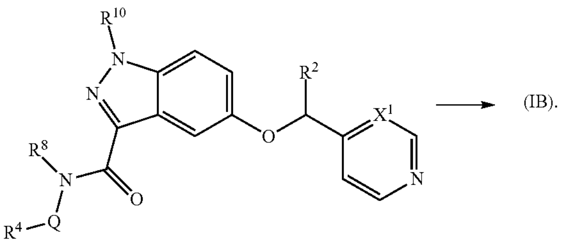

Sb6

Alternatively, in several embodiments, as shown in Scheme 3, $R^4$ may be introduced after an $R^8$NH-Q-$X^4$ unit is coupled with Sb5. In several embodiments, $R^8$NH-Q-$X^4$ is coupled to Sb5 under coupling conditions, thereby providing Sb7. In several embodiments, $X^4$ of Sb7 is a halogen or a sulfenyl group.

Sb4 →

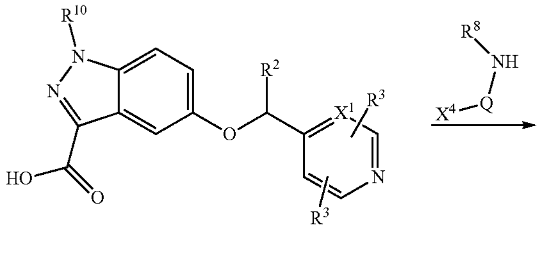

Sb5

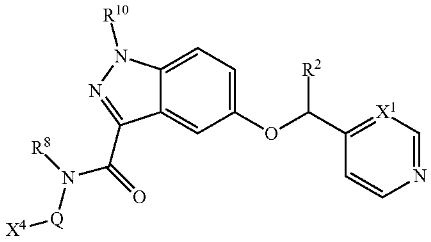

Sb7

In several embodiments, $R^4$ is introduced by displacing the $X^4$ halogen, or by coupling an amine to the sulfur of the sulfenyl group and oxidizing the sulfur atom. In several embodiments, as shown in Scheme 3 (above), the $R^{10}$ substituent of Sb6 is removed using deprotecting conditions to provide the structure of Formula (IB):

Sb7 →

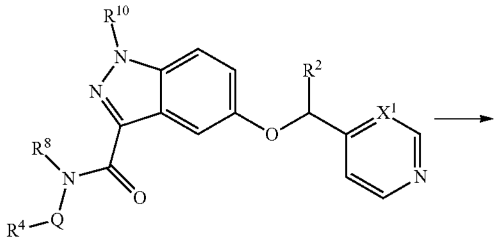

(IB).

Sb6

In several embodiments, to prepare a structure of Formula (ID), as shown in the following (and as depicted in Scheme 4 and Scheme 5, above), the $X^3$ group of S1 is removed using deprotecting conditions to provide Sc2 and the deprotected OH of Sc2 displaces a leaving group (e.g., tosylate, mesylate, etc.) on the A ring moiety to couple the A ring moiety to Sc2 (thereby providing Sb3).

S1 →

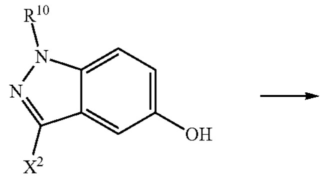

Sc2

-continued

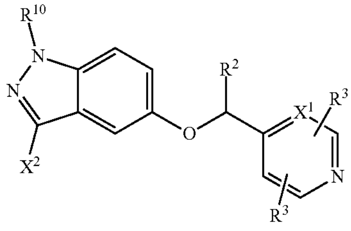

Sc3

In several embodiments, using a boronic acid and coupling conditions, Q-$R^4$ is coupled to Sc3 to provide Sc4. In several embodiments, as shown in Scheme 4, the $R^{10}$ substituent of Sb4 is removed using deprotecting conditions to provide the structure of Formula (ID):

Sc3 →

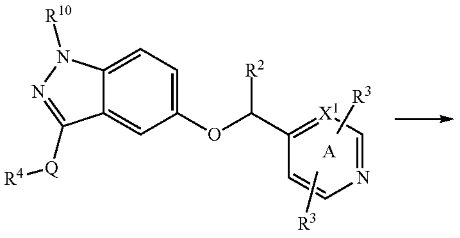

(IC).

Sc4

Alternatively, in several embodiments, as shown in Scheme 5, $R^4$ may be introduced after a boronic acid of Q-$X^5$ is coupled with Sc3. In several embodiments, Q-$X^5$ is coupled to Sb3 under coupling conditions, thereby providing Sb5. In several embodiments, $X^5$ of Sb5 is a halogen or a sulfenyl group. In several embodiments, $R^4$ is introduced by displacing the $X^4$ halogen (e.g., with $R^4$), or by coupling an amine to the sulfur of the sulfenyl group and oxidizing the sulfur atom. In several embodiments, as shown in Scheme 5, the $R^{10}$ substituent of Sc4 is removed using deprotecting conditions to provide the structure of Formula (ID).

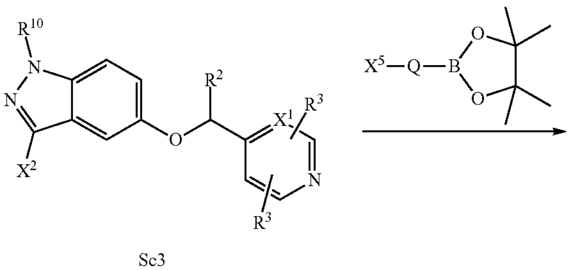

Sc3

-continued

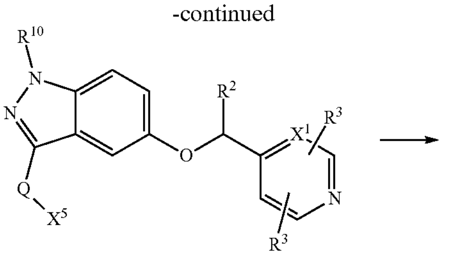

Sc5

Sc4 (IC)

In several embodiments, where the variables of S1, S2, Sa1 to Sa6, Sb1 to Sb7, or Sc1 to Sc5 are not defined, the are as defined as elsewhere herein (e.g., as for Formulae (I), (IA), (IB), (IC), (ID), etc.).

In several embodiments, where single enantiomers are provided (e.g., of the compounds of Formula (I), (IA), (IB), (IC), (ID), etc.), the enantiomers may be separated by conventional means (chiral chromatography, preparing diastereomeric salts, chiral derivatization, crystallization, enzymatic reactions, etc.). In several embodiments, a chiral intermediate compound is purified to prepare an enantiomerically pure (or substantially enantiomerically pure, enantiomerically enriched, etc.) intermediate. For example, compound S2 below may be separated by any one of chiral chromatography, preparing a diastereomeric salt, chiral derivatization, crystallization, etc. In several embodiments, chiral chromatography (e.g., HPLC using a chiral column) is used to prepare the enantiomerically pure (or substantially enantiomerically pure, enantiomerically enriched, etc.).

S2

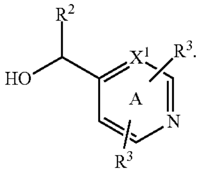

In several embodiments of S2, the variables are as defined elsewhere herein. For example, the following separation may be carried out to provide compounds that are enantiomerically pure (or substantially enantiomerically pure, enantiomerically enriched, etc.):

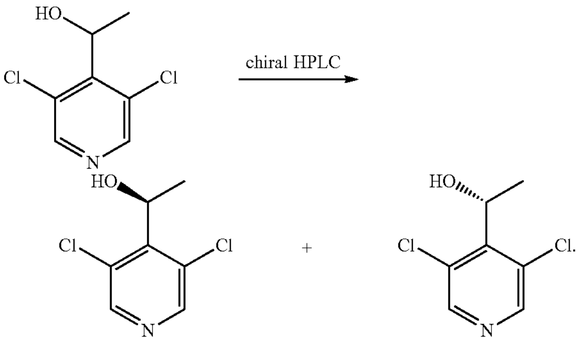

S R

The FGFR receptors (FGFRl, FGFR2, FGFR3, and FGFR4) share several structural features in common, including three extracellular immunoglobulin-like (Ig) domains, a hydrophobic transmembrane domain, and an intracellular tyrosine kinase domain split by a kinase insert domain, followed by a cytoplasmic c-terminal tail (Johnson et al., Adv. Cancer Res. 60:1-40, 1993; and Wilkie et al., Curr. Biol. 5:500-507, 1995). In FGFRl, the kinase insert domain spans positions 582 to 595 of the alpha Al isoform of FGFRl. In FGFR2, the kinase insert domain spans positions 585 to 598 of the FGFR2 Ille isoform. In FGFR3, the kinase insert domain spans positions 576 to 589 of the FGFR3 Ille isoform. In FGFR4, the kinase insert domain spans positions 571 to 584 of FGFR4 isoform 1. The c-terminal tail of FGFRs begins following the end of the tyrosine kinase domain and extends to the c-terminus of the protein. Several isoforms of each FGFR have been identified and are the result of alternative splicing of their mRNAs (Johnson et al., Mol. Cell. Biol. 11:4627-4634, 1995; and Chellaiah et al., J. Biol. Chem. 269:11620-11627, 1994).

A few of the receptor variants that result from this alternative splicing have different ligand binding specificities and affinities (Zimmer et al., J. Biol. Chem. 268:7899-7903, 1993; Cheon et al., Proc. Natl. Acad. Sci. U.S.A. 91:989-993, 1994; and Miki et al., Proc. Natl. Acad. Sci. U.S.A. 89:246-250, 1992). Protein sequences for FGFR proteins and nucleic acids encoding FGFR proteins are known in the art. Signaling by FGFRs regulates key biological processes including cell proliferation, survival, migration, and differentiation. Dysregulation of a FGFR gene, a FGFR protein, or expression or activity, or level of the same, has been associated with many types of cancer. For example, dysregulation of FGFRs can occur by multiple mechanisms, such as FGFR gene overexpression, FGFR gene amplification, activating mutations (e.g., point mutations or truncations), and chromosomal rearrangements that lead to FGFR fusion proteins. Dysregulation of a FGFR gene, a FGFR protein, or expression or activity, or level of the same, can result in (or cause in part) the development of a variety of different FGFR-associated cancers.

FGFR fusion proteins are known in the art. See, e.g., Baroy et al., *PloS One;* 11(9):e0163859. doi: 10.1371/journal.pone.0163859, 2016; Ren et al., *Int. J. Cancer,* 139(4):836-40, 2016; Marchwicka et al., *Cell Biosci.,* 6:7. doi: 10.1186/s13578-016-0075-9, 2016; PCT Patent Application Publication No. WO 2014/071419A2; U.S. Patent Application Publication No. 2015/0366866Al; PCT Patent Application Publication No. WO 2016/084883Al; PCT Patent Application Publication No. WO 2016/030509Al; PCT Patent Application Publication No. WO 2015/150900A2; PCT Patent Application Publication No. WO 2015/120094A2; Kasaian et al., *BMC Cancer.,* 15:984, 2015; Vakil et al., *Neuro-Oncology,* 18:Supp. Supplement 3, pp. iii93. Abstract Number: LG-64, 17$^{th}$ International Symposium on Pediatric Neuro-Oncology, Liverpool, United Kingdom, 2016; Astsaturov et al., *Journal of Clinical Oncology,* 34:Supp. Supplement 15, Abstract Number: 11504, 2016 Annual Meeting of the American Society of Clinical Oncology, Chicago, IL; Heinrich et al., *Journal of Clinical Oncology,* 34:Supp. Supplement 15, Abstract Number: 11012, 2016 Annual Meeting of the American Society of Clinical Oncology, Chicago, IL; Hall et al., *Molecular Cancer Therapeutics*, Vol. 14, No. 12, Supp. 2, Abstract Number: B151, AACR-NCI-EORTC International Conference: Molecular Targets and Cancer Therapeutics, 2015; Reuther et al., *Journal of Molecular Diagnostics*, Vol. 17, No. 6, pp. 813, Abstract Number: ST02, 2015 Annual Meeting of the Association for Molecular Pathology, Austin, TX; Moeini et al., *Clin. Cancer. Res.,* 22(2):291-300, 2016; Schrock et al, *J Thorac. Oneal.* pii S1556-0864(18)30674-9, 2018. doi: 10.1016/j.jtho.2018.05.027; Pekmezci et al, *Acta Nurotaphol. Commun.* 6(1):47. doi: 10.1186/s40478-018-0551-z; Lowery et al. *Clin Cancer Res.* pii: clincanres.0078.2018. doi: 10.1158/1078-0432.CCR-18-0078; Ryland et al. *J Clin Pathol* pii: jclinpath-2018-205195, 2018. doi: 10.1136/jclinpath-2018-205195; Ferguson et al. *J Neuropathol Exp Neural* 77(6):437-442, 2018. doi: 10.1093/jnen/nly022; Wu et al, *BMC Cancer* 18(1):343, 2018. doi: 10.1186/s12885-018-4236-6; Shibata et al, *Cancer Sci* 109(5):1282-1291, 2018. doi: 10.1111/cas.13582; Papdopoulos et al, *Br J Cancer,* 1117(11):1592-1599, 2017. doi: 10.1038/bjc.2017.330; Hall et al, *PLoS One,* 11(9):e1062594, 2016. doi: 10.1371/journal.pone.0162594; Johnson et al, *Oncologist,* 22(12):1478-1490, 2017. doi: 10.1634/theoncologist.2017-0242; Yang et al, *Am J Hum Genet,* 98(5):843-856, 2016. doi: 10.1016/j.ajhg.2016.03.017; U.S. Patent Application Publication No. 2013/009621; Babina and Turner, *Nat Rev Cancer* 17(5): 318-332, 2017. doi: 10.1038/nrc.2017.8; Ryland et al, *J Clin Pathol.,* 2018 May 14. pii: jclinpath-2018-205195. doi: 10.1136/jclinpath-2018-205195; Kumar et al, *Am J Clin Pathol.* 143(5):738-748, 2015. doi: 10.1309/AJCPUD6W1JLQQMNA; Grand et al, *Genes Chromosomes* Cancer 40(1):78-83, 2004. doi: 10.1002/gcc.20023; Reeser, et al, *J Mol Diagn,* 19(5):682-696, 2017. doi: 10.1016/j.jmoldx.2017.05.006; Basturk, et al, *Mod Pathol,* 30(12):1760-1772, 2017. doi: 10.1038/modpathol.2017.60; Wang, et al, *Cancer* 123(20):3916-3924, 2017. doi: 10.1002/cncr.30837; Kim, et al, *Oncotarget,* 8(9):15014-15022, 2017. doi: 10.18632/oncotarget.14788; Busse, et al, *Genes Chromosomes Cancer,* 56(10):730-749, 2017. doi: 10.1002/gcc.22477; Shi, et al, *J Transl Med.,* 14(1):339, 2016. doi: 10.1186/s12967-016-1075-6, each of which is incorporated by reference herein.

FGFR point mutations are known in the art. See, e.g., UniParc entry UPI00000534B8; UniParc entry UPI0000001COF; UniParc entry UPI000002A99A; UniParc entry UPI000012A72A; UniParc entry UPI000059D1C2; UniParc entry UPI000002A9AC; Uniparc entry UPI000012A72C; Uniparc entry UPI000012A72D; Uniparc entry UPI000013EOB8; Uniparc entry UPI0001CE06A3; Gen bank entry BAD92868.1; Ang et al., *Diagn. Mol. Pathol*. Feb. 24, 2014; U.S. Patent Application Publication No. 2011/0008347; Gallo et al., *Cytokine Growth Factor Rev.* 26:425-449, 2015; Davies et al., *J. Cancer Res.* 65:7591, 2005; Kelleher et al., *Carcinogenesis* 34:2198, 2013; Cazier et al., *Nat. Commun.* 5:3756, 2014; Liu et al., *Genet. Mol. Res.* 13:1109, 2014; Trudel et al., *Blood* 107: 4039, 2006; Gallo et al., *Cytokine Growth Factor Rev.* 26:425, 2015; Liao et al., Cancer Res. 73:5195-5205, 2013; Martincorena et al., Science 348:880 (2015); U.S. Patent Application Publication No. US2016/0235744Al; U.S. Pat. No. 9,254,288B2; U.S. Pat. No. 9,267,176B2; U.S. Patent Application Publication No. 52016/0215350Al; European Patent Application Publication No. EP3023101Al; PCT Patent Application Publication No. WO2016105503Al; Rivera et al., *Acta. Neuropathol.,* 131(6):847-63, 2016; Lo Iacono et al., *Oncotarget,* 7(12):14394-404, 2016; Deeken et al., *Journal of Clinical Oncology,* 34:Supp. Supplement 15, pp. iii93. Abstract Number: el 7520, 2016 Annual Meeting of the American Society of Clinical Oncology, Chicago, IL; Sullivan et al., *Journal of Clinical Oncology,* 34:Supp. Supplement 15, pp. iii93. Abstract Number: 11596, 2016 Annual Meeting of the American Society of Clinical Oncology, Chicago, IL; Nguyen et al., *Molecular Cancer Therapeutics*, Vol. 14, No. 12, Supp.2, Abstract Number: C199, AACR-NCI-EORTC International Conference: Molecular Targets and Cancer Therapeutics, 2015; Li et al., *Hum. Pathol.,* 55:143-50, 2016; European Patent No. EP2203449B1; Yoza et al., *Genes Cells,* (10):1049-1058, 2016; U.S. Pat. No. 9,254,288B2; European Patent Application Publication No. 3023101Al; PCT Application Publication No. WO 2015/099127Al; European Patent No. EP2203449Bl; Yoza et al., *Genes Cells,* (10):1049-1058, 2016; Bunney et al., *EbioMedicine,* 2(3):194-204, 2015; Byron et al., *Neoplasia,* 15(8):975-88, 2013; European Patent Application Publication No. EP3023101Al; PCT Application Publication No. WO 2015/099127Al; Thussbas et al., *J. Clin. Oneal.,* 24(23):3747-55, 2006; Chell et al., *Oncogene,* 32(25):3059-70, 2013; Tanizaki et al, *Cancer Res.* 75(15):3149-3146 doi: 10.1158/0008-5472.CAN-14-3771; Yang et al, *EBioMedicine* pii S2352-3964(18)30218-4. doi: 10.1016/j.ebiom.2018.06.011; Jakobsen, et al *Oncotarget* 9(40):26195-26208, 2018. doi: 10.18632/oncotarget.25490; Stone, et al *Acta Neuropathol* 135(1):115-129, 2017. doi: 10.1007/s00401-017-1773-z; Pekmezci et al, Acta Nurotaphol. Commun. 6(1):47. doi: 10.1186/s40478-018-0551-z; De Mattos-Arruda et al, *Oncotarget* 9(29):20617-20630, 2018. doi:10.18632/oncotarget.25041; Oliveira et al, *J Exp Clin Cancer Res* 37(1):84, 2018. doi: 10.1186/s13046-018-0746-y; Cha et al, *Mol Oneal* 12(7):993-1003, 2018. doi: 10.1002/1878-0261.12194; Ikeda et al, *Oncologist,* 23(5): 586-593, 2018. doi: 10.1634/theoncologist.2017-0479; Pelaez-Garda et al, *PLoS One,* 8(5):e63695, 2013. doi: 10.1371/journal.pone.0063695; Shimada et al, *Oncotarget,* 8(55):93567-93579, 2017. doi: 10.18632/oncotarget.20510; Welander et al, *World J Surg,* 42(2):482-489, 2018. doi: 10.1007/s00268-01 7-4320-0; Chandrani et al, *Ann Oneal,* 28(3):597-603, 2017. doi: 10.1093/annonc/mdw636; Dalin et al, *Nat Commun,* 8(1):1197, 2017. doi: 10.1038/s41467-017-01178-z; Taurin et al, *Intl Gyneco/ Cancer,* 28(1):152-160, 2018. doi: 10.1097/IGC.0000000000001129; Haugh et al, *J Invest Dermatol* 138(2):384-393, 2018. doi: 10.1016/j.jid.2017.08.022; Babina and Turner, *Nat Rev Cancer* 17(5): 318-332, 2017. doi: 10.1038/nrc.2017.8; Greenman et al, *Nature* 446(7132):153-158, 2007. doi: 10.1038/nature05610; Helsten et al, *Clin Cancer Res,* 22(1):259-267, 2016. doi: 10.1158/1078-0432.CCR-14-3212; Kim et al, BMC Urol, 18:68, 2018. doi: 10.1186/s12894-018-0380-1; Goyal et al, *Cancer Discov,* 7(3):252-263, 2017. doi: 10.1158/2159-8290.CD-16-1000; Premov et al, *Oncogene,* 36(22):3168-3177, 2017. doi: 10.1038/onc.2016.464; Geelvink et al, *Int J Mol Sci.* 19(9): pii:E2548, 2018. doi: 10.3390/ijms19092548; Lee et al, *Exp Ther Med.* 16(2): 1343-1349, 2018. doi: 10.3892/etm.2018.6323; Kas et al, *Cancer Res,* 78(19):5668-5679, 2018. doi: 10.1158/0008-5472.CAN-18-0757; Chesi et al, *Blood,* 97(3):729-736, 2001. PMID: 11157491. Note that the deletion of FGFR3 isoform IIIe residues 795-808 also deletes the stop codon, elongating the protein by 99 amino acids (ATGPQQCEGSLAAHPAAGAQPLPGMRLSADGETATQSFGLCVCVCVCVCVCTSACACV RAHLASRCRGTLGVPAA VQRSPDWCCSTEGPLFWGDPVQNVSGPTRWDPVGQGAGPDMARPLPLHHGTSQGALG PSHTQS); Ge, et al, *Am J Cancer Res.* 7(7):1540-1553, 2017. PMID: 28744403; Jiao et al, *Nat Genet,* 45(12):1470-1473, 2013. doi: 10.1038/ng.2813; Jusakul et al, *Cancer Discov.* 7(10):1116-1135, 2017. doi: 10.1158/2159-8290.CD-17-0368; Guyard et al, *Respir Res.,* 18(1):120, 2018. doi: 10.1186/s12931-017-0605-y; Paik et al, *Clin Cancer Res.,* 23(18):5366-5373, 2017. doi: 10.1158/1078-

0432.CCR-17-0645; Roy et al, *Mod Patho/.,* 30(8):1133-1143, 2017. doi: 10.1038/modpathol.2017.33; Chakrabarty et al, *Br J Cancer,* 117(1):136-143, 2017. doi: 10.1038/bjc.2017.148; Hoang et al, *Sci Transl Med.,* 5(197): 197ra102. doi: 10.1126/scitranslmed.3006200; Kim et al, *Ann Oneal.,* 28(6):1250-1259. doi: 10.1093/annonc/mdx098, each of which is incorporated by reference herein.

Compounds of the disclosure have been found to inhibit FGFR1, FGFR2, FGFR3, and/or FGFR4 and are therefore believed to be useful for treating diseases and disorders which can be treated with an inhibitor of FGFR1, FGFR2, FGFR3 and/or FGFR4. For example, compounds of the disclosure can be useful in treating FGFR-associated diseases and disorders, e.g., proliferative disorders such as cancers, including hematological cancers and solid tumor, and angiogenesis-related disorders. Compounds of the disclosure may also be useful in treating disorders arising from autosomal dominant mutations in FGFR, e.g., FGFR3, including, for example, developmental disorders. Developmental disorders to be treated with compounds of the disclosure include Achondroplasia (Ach) and related chondrodysplasia syndromes, including Hypochondroplasia (Hch), Severe Achondroplasia with Developmental Delay and Acanthosis Nigricans (SADDAN), and Thanatophoric dysplasia (TD).

Non-limiting examples of FGFR-associated diseases and disorders include Acanthosis nigricans, Achondroplasia, Apert syndrome, Beare-Stevenson syndrome (BSS), Camptodactyly, tall stature, and hearing loss syndrome (CATSHL) syndrome, cleft lip and palate, congenital heart disease (e.g., associated with ambiguous genitalia), craniosynostosis, Crouzon syndrome, ectrodactyly, encephalocraniocutaneous lipomatosis, Hartsfield syndrome, hypochondroplasia, hypogonadoropic hypogonadism (e.g., hypogonadotropic hypogonadism 2 with or without anosmia, Kallman syndrome), ichthyosis vulgaris and/or atopic dermatitis, Jackson-Weiss syndrome, lethal pulmonary acinar dysplasia, microphthalmia, Muenke coronal craniosynostosis, osteoglophonic dysplasia, Pfeiffer syndrome, seborrheic keratosis, syndactyly, thanatophoric dysplasia (e.g., type I or type II), trigonocephaly 1 (also called metopic craniosynostosis), and tumor-induced osteomalacia. Non-limiting examples of FGFRl associated diseases and disorders include congenital heart disease (e.g., associated with ambiguous genitalia), craniosynostosis, encephalocraniocutaneous lipomatosis, Hartsfield syndrome, hypogonadotropic hypogonadism (e.g., hypogonadotropic hypogonadism 2 with or without anosmia, Kallman syndrome), ichthyosis vulgaris and/or atopic dermatitis, Jackson-Weiss syndrome, osteoglophonic dysplasia, Pfeiffer syndrome, trigonocephaly 1 (also called metopic craniosynostosis), and tumor-induced osteomalacia.

Non-limiting examples of FGFR2-associated diseases and disorders include Apert syndrome, Beare-Stevenson syndrome (BSS), Crouzon syndrome, ectrodactyly, Jackson-Weiss syndrome, lethal pulmonary acinar dysplasia, Pfeiffer syndrome, and syndactyly. Non-limiting examples of FGFR3-associated diseases and disorders include acanthosis nigricans, achondroplasia, Camptodactyly, tall stature, and hearing loss syndrome (CATSHL) syndrome, cleft lip and palate, craniosynostosis, hypochondroplasia, microphthalmia, Muenke coronal craniosynostosis, seborrheic keratosis, and thanatophoric dysplasia (e.g., type I or type II).

See also, See UniParc entry UPI00000534B8; UniParc entry UPI0000001COF; Uni Pare entry UPI000002A99A; UniParc entry UPI000012A72A; Yong-Xing et al., Hum. Mol. Genet. 9(13):2001-2008, 2000; Eeva-Maria Laitinen et al., PLoS One 7(6):e39450, 2012; Hart et al., Oncogene 19(29):3309-3320, 2000; Shiang et al., Cell 76:335-342, 1994; Rosseau et al., Nature 371:252-254, 1994; Tavormina et al., Nature Genet. 9:321-328, 1995; Bellus et al., Nature Genet. 10:357-359, 1995; Muenke et al., Nature Genet. 8:269-274, 1994; Rutland et al., Nature Genet. 9:173-176, 1995; Reardon et al., Nature Genet. 8:98-103, 1994; Wilkie et al., Nature Genet. 9:165-172, 1995; Jabs et al., Nature Genet. 8:275-279, 1994; Japanese Patent No. JP05868992B2; Ye et al., Plast. Reconstr. Surg., 137(3):952-61, 2016; U.S. Pat. No. 9,447,098B2; Bellus et al., Am. J. Med. Genet. 85(1):53-65, 1999; PCT Patent Application Publication No. WO2016139227Al; Australian Patent Application Publication No. AU2014362227Al; Chinese Patent No. CN102741256B; Ohishi et al., Am. J. Med. Genet. A., doi: 10.1002/ajmg.a.37992, 2016; Nagahara et al., Clin. Pediatr. Endocrinol., 25(3): 103-106, 2016; Hibberd et al., Am. J. Med. Genet. A., doi: 10.1002/ajmg.a.37862, 2016; Dias et al., Exp. Mol. Pathol., 101(1): 116-23, 2016; Lin et al., Mol. Med. Rep., 14(3):1941-6, 2016; Barnett et al., Hum. Mutat., 37(9):955-63, 2016; Krstevska-Konstantinova et al., Med. Arch., 70(2):148-50, 2016; Kuentz et al., Br. J. Dermatol., doi: 10.1111/bjd.14681, 2016; Ron et al., Am. J. Case Rep., 15; 17:254-8, 2016; Fernandes et al., Am. J. Med. Genet. A., 170(6):1532-7, 2016; Lindy et al., Am. J. Med. Genet. A., 170(6):1573-9, 2016; Bennett et al., Am. J. Hum. Genet., 98(3):579-87, 2016; lchiyama et al., J. Eur. Acad. Dermatol. Venereal., 30(3):442-5, 2016; Zhao et al., Int. J. Clin. Exp. Med., 8(10):19241-9, 2015; Hasegawa et al., Am. J. Med. Genet. A., 170A(5):1370-2, 2016; Legeai-Mallet, Endocr. Dev., 30:98-105, 2016; Takagi, Am. J. Med. Genet. A., 167A(ll): 2851-4, 2015; Goncalves, Fertil. Steril., 104(5):1261-7.el, 2015; Miller et al., Journal of Clinical Oncology, 34:Supp. Supplement 15, pp. iii93. Abstract Number: e22500, 2016 Annual Meeting of the American Society of Clinical Oncology, Chicago, IL; Sarabipour et al., J. Mol. Biol., 428(20): 3903-3910, 2016; Escobar et al., Am. J. Med. Genet. A., 170(7):1908-11, 2016; Mazen et al., Sex Dev., 10(1):16-22, 2016; Taylan et al., *J Allergy Clin lmmunol,* 136(2):507-9, 2015. doi: 10.1016/j.jaci.2015.02.010; Kant et al, *EuroJourn Endocrinol,* 172(6):763-770, 2015. doi: 10.1530/EJE-14-0945; Gonzalez-Del Angel et al, *Am J med Genet A,* 176 (1):161-166, 2018. doi: 10.1002/ajmg.a.38526; Lei and Deng, *Int J Biol Sci* 13(9):1163:1171, 2017. doi: 10.7150/ijbs.20792; Lajeunie et al, *Eur J Hum Genet,* 14(3):289-298, 2006. doi: 10.1038/sj.ejhg.5201558; Karadimas et al, *Prenat Diagn,* 26(3):258-261, 2006. doi: 10.1002/pd.1392; lbrahimi et al, *Hum Mo/ Genet* 13(19):2313-2324, 2004. doi: 10.1093/hmg/ddh235; Trarbach et al, *J Clin Endocrinol Metab.,* 91(10):4006-4012, 2006. doi: 10.1210/jc.2005-2793; Dode et al, *Nat Genet,* 33(4):463-465, 2003. doi: 10.1038/ng1122, each of which is incorporated by reference herein.

The term “angiogenesis-related disorder” means a disease characterized in part by an increased number or size of blood vessels in a tissue in a subject or patient, as compared to a similar tissue from a subject not having the disease. Non-limiting examples of angiogenesis-related disorders include: cancer (e.g., any of the exemplary cancers described herein, such as prostate cancer, lung cancer, breast cancer, bladder cancer, renal cancer, colon cancer, gastric cancer, pancreatic cancer, ovarian cancer, melanoma, hepatoma, sarcoma, and lymphoma), exudative macular degeneration, proliferative diabetic retinopathy, ischemic retinopathy, retinopathy of prematurity, neovascular glaucoma, iritis rubeosis, corneal neovascularization, cyclitis, sickle cell retinopathy, and pterygium.

Compounds of the disclosure inhibit wild-type FGFR1, FGFR2, FGFR3, and/or FGFR4. In other aspects, compounds of the disclosure inhibit a mutated FGFR1, FGFR2, FGFR3, and/or FGFR4. In other aspects, compounds of the disclosure inhibit FGFR1, FGFR2, FGFR3, and/or FGFR4 that includes an FGFR kinase inhibitor mutation.

In some embodiments of any of the methods or uses described herein, the cancer (e.g., FGFR-associated cancer) is a hematological cancer. In some embodiments of any of the methods or uses described herein, the cancer (e.g., FGFR-associated cancer) is a solid tumor. In some embodiments of any of the methods or uses described herein, the cancer (e.g., FGFR-associated cancer) is a lung cancer (e.g., small cell lung carcinoma, non-small cell lung carcinoma, squamous cell carcinoma, lung adenocarcinoma, large cell carcinoma, mesothelioma, lung neuroendocrine carcinoma, smoking-associated lung cancer), prostate cancer, colorectal cancer (e.g., rectal adenocarcinoma), endometrial cancer (e.g., endometrioid endometrial cancer, endometrial adenocarcinoma), breast cancer (e.g., hormone-receptor-positive breast cancer, triple-negative breast cancer, neuroendocrine carcinoma of the breast), skin cancer (e.g., melanoma, cutaneous squamous cell carcinoma, basal cell carcinoma, large squamous cell carcinoma), gallbladder cancer, liposarcoma (e.g., dedifferentiated liposarcoma, myxoid liposarcoma), pheochromocytoma, myoepithelial carcinoma, urothelial carcinoma, spermatocytic seminoma, stomach cancer, head and neck cancer (e.g., head and neck (squamous) carcinoma, head and neck adenoid cystic adenocarcinoma), brain cancer (e.g., glial neural tumors, glioma, neuroblastoma, glioblastoma, pilocytic astrocytoma, Rosette forming glioneural tumor, dysembryoplastic neuroepithelial tumor, anaplastic astrocytoma, medulloblastoma, ganglioglioma, oligodendroglioma), malignant peripheral nerve sheath tumor, sarcoma (e.g., soft tissue sarcoma (e.g., leiomyosarcoma), osteosarcoma), esophageal cancer (e.g., esophageal adenocarcinoma), lymphoma, bladder cancer (e.g., bladder urothelial (transition cell) carcinoma), cervical cancer (e.g., cervical squamous cell carcinoma, cervical adenocarcinoma), fallopian tube cancer (e.g., fallopian tube carcinoma), ovarian cancer (e.g., ovarian serous cancer, ovarian mucinous carcinoma), cholangiocarcinoma, adenoid cystic carcinoma, pancreatic cancer (e.g., pancreatic exocrine carcinoma, pancreatic ductal adenocarcinoma, pancreatic cancer intraepithelial neoplasia), salivary gland cancer (e.g., pleomorphic salivary gland adenocarcinoma, salivary adenoid cystic cancer), oral cancer (e.g., oral squamous cell carcinoma), uterine cancer, gastric or stomach cancer (e.g., gastric adenocarcinoma), gastrointestinal stromal tumors, myeloma (e.g., multiple myeloma), lymphoepithelioma, anal cancer (e.g., anal squamous cell carcinoma), prostate cancer (e.g., prostate adenocarcinoma), renal cell carcinoma, thymic cancer, gastroesophogeal junction adenocarcinoma, testicular cancer, rhabdomyosarcoma (e.g., alveolar rhabdomyosarcoma, embryonic rhabdomyosarcoma), renal papillary carcinoma, liver cancer (e.g., hepatocellular carcinoma, intrahepatic cholangiocarcinoma), carcinoid, myeloid proliferative disorders (also called myeloid proliferative neoplasms (MPN); e.g., 8pll myeloproliferative syndrome (EMS, also called stem cell leukemia/lymphoma), acute myeloid leukemia (AML), chronic myeloid leukemia (CML)), lymphoma (e.g., T-cell lymphoma, T-lymphoblastic lymphoma, acute lymphoblastic leukemia (ALL), B-cell lymphoma), myeloid and lymphoid neoplasms, chronic neutrophilic leukemia, phosphaturic mesenchymal tumor, thyroid cancer (e.g. anaplastic thyroid carcinoma), or biliary duct cancer.

In some embodiments of any of the methods or uses described herein, the cancer (e.g., FGFR-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and para nasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, para nasal sinus and nasal cavity cancer, parathyroid cancer, penile cancer, pharyngeal cancer, pheochromosytoma, pituitary cancer, plasma cell neoplasm, pleuropulmonary blastoma, pregnancy-associated breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, Spitz tumors, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are FGFR associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult Tcell ALL, AML with trilineage myelodysplasia (AML/TMDS), mixed lineage leukemia (MLL), myelodysplastic syndromes (MDSs), myeloproliferative disorders (MPD), and multiple myeloma (MM).

Additional examples of hematological cancers include myeloproliferative disorders (MPD) such as polycythemia vera (PV), essential thrombocytopenia (ET) and idiopathic primary myelofibrosis (IMF/IPF/PMF). In some embodiments, the hematological cancer (e.g., the hematological cancer that is a FGFR-associated cancer) is AML or CMML.

In some embodiments, the cancer (e.g., the FGFR-associated cancer) is a solid tumor. Examples of solid tumors (e.g., solid tumors that are FGFR-associated cancers) include, for example, lung cancer (e.g., lung adenocarcinoma, non-small-cell lung carcinoma, squamous cell lung cancer), bladder cancer, colorectal cancer, brain cancer, testicular cancer, bile duct cancer cervical cancer, prostate cancer, and sparmatocytic seminomas. See, for example, Turner and Grose, *Nat. Rev. Cancer,* 10(2):116-129, 2010.

In some embodiments, the cancer is selected from the group consisting of bladder cancer, brain cancer, breast cancer, cholangiocarcinoma, head and neck cancer, lung cancer, multiple myeloma, rhabdomyosarcoma, urethral cancer, and uterine cancer. In some embodiments, the cancer is selected from the group consisting of lung cancer, breast cancer, and brain cancer. In some embodiments, a FGFRl-associated cancer is selected from the group consisting of lung cancer, breast cancer, and brain cancer. In some embodiments, the cancer is selected from the group consisting of breast cancer, uterine cancer, cholangiocarcinoma, and lung cancer. In some embodiments, a FGFR2-associated cancer is selected from the group consisting of breast cancer, uterine cancer, cholangiocarcinoma, and lung cancer. In some embodiments, the cancer is selected from the group consisting of lung cancer, bladder cancer, urethral cancer, multiple myeloma, and head and neck cancer. In some embodiments, a FGFR3-associated cancer is selected from the group consisting of lung cancer, bladder cancer, urethral cancer, multiple myeloma, and head and neck cancer. In some embodiments, the cancer is selected from lung cancer, rhabdomyosarcoma, and breast cancer. In some embodiments, a FGFR4-associated cancer is selected from lung cancer, rhabdomyosarcoma, and breast cancer.

In some aspects, the compounds of the disclosure are useful in treating cancers associated with amplification or overexpression of FGFR1, for example, Breast cancer or carcinoma (e.g., hormone receptor-positive breast cancer, ductal carcinoma in situ (breast)), pancreatic ductal adenocarcinoma, pancreatic exocrine carcinoma, smoking-associated lung cancer, small cell lung cancer, lung adenocarcinoma, non-small cell lung cancer, squamous cell lung cancer or carcinoma, prostate cancer or carcinoma, ovarian cancer, fallopian tube carcinoma, bladder cancer, rhabdomyosarcoma, head and neck carcinoma (e.g., head and neck squamous cell carcinoma), esophageal cancer (e.g., esophageal squamous cell carcinoma), sarcoma (e.g., osteosarcoma), hepatocellular carcinoma, renal cell carcinoma, colorectal cancer (e.g., colorectal adenocarcinoma), prostate cancer, salivary gland tumors, glioblastoma multiforme, urinary bladder cancer, urothelial carcinoma, carcinoma of unknown primary, squamous non-lung tumors, gastric cancer, gastroesophageal junction carcinoma, adenoid cystic carcinoma, anal squamous cell carcinoma, oral squamous cell carcinoma, cholangiocarcinoma, hemangioendothelioma, leiomyosarcoma, melanoma, neuroendocrine carcinoma, squamous cell carcinoma, uterine carcinosarcoma.

In some aspects, the compounds of the disclosure are useful in treating cancers associated with amplification of FGFR2, for example, Gastric cancer, gastroesophageal junction adenocarcinoma, breast cancer (e.g., triple negative breast cancer), colon cancer, colorectal cancer (e.g., colorectal adenocarcinoma), urothelial cancer, bladder adenocarcinoma, carcinoma of unknown primary, cholangiocarcinoma, endometrial adenocarcinoma, esophageal adenocarcinoma, gallbladder carcinoma, ovarian cancer, fallopian tube carcinoma, pancreatic exocrine carcinoma, sarcoma, squamous cell carcinoma. In some aspects, the compounds of the disclosure are useful in treating cancers associated with overexpression of FGFR2, for example, Myxoid lipocarcinoma, rectal cancer, renal cell carcinoma, breast cancer.

In some aspects, the compounds of the disclosure are useful in treating cancers associated with upregulation of activity of FGFR3, for example, Colorectal cancer, hepatocellular carcinoma, pancreatic exocrine carcinoma. In some aspects, the compounds of the disclosure are useful in treating cancers associated with overexpression of activity of FGFR3, for example, Multiple myeloma, thyroid carcinoma. In some aspects, the compounds of the disclosure are useful in treating cancers associated with amplification of activity of FGFR3, for example, Bladder cancer and salivary adenoid cystic cancer, urothelial cancer, breast cancer, carcinoid, carcinoma of unknown primary, colorectal cancer (e.g., colorectal adenocarcinoma), gallbladder carcinoma, gastric cancer, gastroesophageal junction adenocarcinoma, glioma, mesothelioma, non-small cell lung carcinoma, small cell lung cancer, ovarian cancer, fallopian tube carcinoma, pancreatic exocrine carcinoma.

In some aspects, the compounds of the disclosure are useful in treating cancers associated with amplification of FGFR4, for example, Rhabdomyosarcoma, prostate cancer or carcinoma, breast cancer, urothelial cancer, carcinoid, carcinoma of unknown primary, esophageal adenocarcinoma, head and neck carcinoma, hepatocellular carcinoma, non-small cell lung carcinoma, ovarian cancer, fallopian tube carcinoma, peritoneal carcinoma, renal cell carcinoma.

In some aspects, the compounds of the disclosure are useful in treating cancers associated with upregulation of activity of FGFR4, for example, Colorectal cancer, hepatocellular carcinoma, adrenal carcinoma, breast cancer.

In some aspects, the compounds of the disclosure are useful in treating cancers associated with overexpression of activity of FGFR4, for example, Pancreatic intraepithelial neoplasia, and pancreatic ductal adenocarcinoma.

In some aspects, the compounds of the disclosure are more selective for one FGFR than for another. As used herein, the "selectivity" of a compound for a first target over a second target means that the compound has more potent activity at the first target than the second target. A fold selectivity can be calculated by any method known in the art. For example, a fold selectivity can be calculated by dividing the IC50 value (or Kd value) of a compound for the second target (e.g., FGFRl) by the IC50 value of the same compound for the first target (e.g., FGFR2 or FGFR3). An IC50 value can be determined by any method known in the art. In some embodiments, a compound is first determined to have an activity of less than 500 nM for the first target. In some embodiments, a compound is first determined to have an activity of less than 500 nM for the second target.

For example, in some aspects, the compounds of the disclosure are more selective for FGFR3 than for FGFR1. In some aspects, the compounds are at least 3-fold more selective for FGFR3 than for FGFR1. In some aspects, the compounds are 4, 5, 6, 7, 8, 9, 10, 15, 20, 30, 40, 50, 75, 100, 200, 500, or 1000 fold more selective for FGFR3 than for FGFR1.

In some aspects, the compounds of the disclosure are more selective for FGFR2 than for FGFR1. In some aspects, the compounds are at least 3-fold more selective for FGFR2 than for FGFR1. In some aspects, the compounds are 4, 5, 6, 7, 8, 9, 10, 15, 20, 30, 40, 50, 75, 100, 200, 500, or 1000 fold more selective for FGFR2 than for FGFR1.

In some aspects, the compounds of the disclosure are more selective for a first FGFR family member (e.g., FGFR2 or FGFR3) over a second FGFR family member (e.g., FGFR1 or FGFR4). In some aspects, the compounds of the disclosure are at least 3-fold more selective for a first FGFR family member over a second FGFR family member. In some aspects, the compounds are at least 10, 20, 30, 40, 50, 60, 70, 80, 90, 200, 300, 400, 500, 600, 700, 800, 900, or at least 1000 fold more selective for a first FGFR family member over a second FGFR family member.

In some aspects, the compounds of the disclosure are more selective for an FGFR kinase over another kinase that is not an FGFR kinase. For example, the compounds of the disclosure are at least 3-fold more selective for an FGFR kinase over another kinase that is not an FGFR kinase. In some aspects, the compounds of the disclosure are at least 10, 20, 30, 40, 50, 60, 70, 80, 90, 200, 300, 400, 500, 600, 700, 800, 900, or at least 1000 fold more selective for an FGFR kinase over another kinase that is not an FGFR kinase. Kinases that are not FGFR kinases include, for example, KDR kinase and Aurora B kinase.

In some embodiments, the compounds of the disclosure exhibit brain and/or central nervous system (CNS) penetrance. Such compounds are capable of crossing the blood brain barrier and inhibiting a FGFR kinase in the brain and/or other CNS structures. In some embodiments, the compounds provided herein are capable of crossing the blood brain barrier in a therapeutically effective amount. For example, treatment of a subject with cancer (e.g., a FGFR-associated cancer such as a FGFR-associated brain or CNS cancer) can include administration (e.g., oral administration) of the compound to the subject. In some such embodiments, the compounds provided herein are useful for treating a primary brain tumor or metastatic brain tumor. For example, a FGFR-associated primary brain tumor or metastatic brain tumor.

In some embodiments, the compounds of the disclosure, exhibit one or more of high GI absorption, low clearance, and low potential for drug-drug interactions.

In some aspects, compounds of the disclosure can be used for treating a subject diagnosed with (or identified as having) a FGFR-associated disease or disorder (e.g., a FGFR-associated cancer) that include administering to the subject a therapeutically effective amount of a compound of the disclosure. Also provided herein are methods for treating a subject identified or diagnosed as having a FGFR-associated disease or disorder (e.g., a FGFR-associated cancer) that include administering to the subject a therapeutically effective amount of a compound of the disclosure. In some embodiments, the subject that has been identified or diagnosed as having a FGFR-associated disease or disorder (e.g., a FGFR-associated cancer) through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit. In some embodiments, the FGFR-associated disease or disorder is a FGFR-associated cancer. For example, the FGFR-associated cancer can be a cancer that includes one or more FGFR inhibitor resistance mutations.

Also provided are methods for treating a disease or disorder in a subject in need thereof, the method comprising: (a) detecting a FGFR-associated disease or disorder in the subject; and (b) administering to the subject a therapeutically effective amount of a compound of the disclosure. Some embodiments of these methods further include administering to the subject an additional therapy or therapeutic agent (e.g., a second FGFR inhibitor, a second compound of the disclosure, or an immunotherapy. In some embodiments, the subject was previously treated with a first FGFR inhibitor or previously treated with another treatment. In some embodiments, the subject is determined to have a FGFR-associated disease or disorder through the use of a regulatory agency-approved, e.g., FDA approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit.

Also provided are methods for treating cancer in a subject in need thereof, the method comprising: (a) detecting a FGFR-associated cancer in the subject; and (b) administering to the subject a therapeutically effective amount of a compound of the disclosure. Some embodiments of these methods further include administering to the subject an additional therapy or therapeutic agent (e.g., a second FGFR inhibitor, a second compound of the disclosure, or an immunotherapy). In some embodiments, the subject was previously treated with a first FGFR inhibitor or previously treated with another anticancer treatment, e.g., at least partial resection of the tumor or radiation therapy. In some embodiments, the subject is determined to have a FGFR-associated cancer through the use of a regulatory agency-approved, e.g., FDA-approved test or assay for identifying dysregulation of a FGFR gene, a FGFR kinase, or expression or activity or level of any of the same, in a subject or a biopsy sample from the subject or by performing any of the non-limiting examples of assays described herein. In some embodiments, the test or assay is provided as a kit. In some embodiments, the cancer is a FGFR associated cancer. For example, the FGFR-associated cancer can be a cancer that includes one or more FGFR inhibitor resistance mutations. In some embodiments, the cancer is a FGFR associated cancer. For example, the FGFR-associated cancer can be a cancer that includes one or more FGFR activating mutations.

Also provided are methods of treating a subject that include performing an assay on a sample obtained from the subject to determine whether the subject has a dysregulation of a FGFR gene, a FGFR kinase, or expression or activity or level of any of the same, and administering (e.g., specifically or selectively administering) a therapeutically effective amount of a compound of the disclosure or pharmaceutically acceptable salt or solvate thereof to the subject determined to have a dysregulation of a FGFR gene, a FGFR kinase, or expression or activity or level of any of the same. Some embodiments of these methods further include administering to the subject an additional therapy or therapeutic agent (e.g., a second FGFR inhibitor, a second compound of the disclosure, or immunotherapy). In some embodiments of these methods, the subject was previously treated with a first FGFR inhibitor or previously treated with another anticancer treatment, e.g., at least partial resection of a tumor or radiation therapy. In some embodiments, the subject is a subject suspected of having a FGFR-associated disease or disorder (e.g., a FGFR-associated cancer), a subject presenting with one or more symptoms of a FGFR-associated disease or disorder (e.g., a FGFR-associated cancer), or a subject having an elevated risk of developing a FGFR-associated disease or disorder (e.g., a FGFR-associated cancer). In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a FGFR gene, a FGFR kinase, or expression or activity or level of any of the same includes one or more FGFR inhibitor resistance mutations or activating mutations.

Also provided herein are methods of selecting a treatment for a subject, wherein the methods include a step of performing an assay on a sample obtained from the subject to determine whether the subject has a dysregulation of a FGFR gene, a FGFR kinase, or expression or activity or level of any of the same (e.g., one or more FGFR inhibitor resistance mutations), and identifying or diagnosing a subject determined to have a dysregulation of a FGFR gene, a FGFR kinase, or expression or activity or level of any of the same, as having a FGFR-associated cancer. Some embodiments further include administering the selected treatment to the subject identified or diagnosed as having a FGFR-associated cancer. For example, in some embodiments, the selected treatment can include administration of a therapeutically effective amount of a compound of the disclosure to the subject identified or diagnosed as having a FGFR-associated cancer. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided herein are methods of treating a FGFR-associated cancer in a subject that include (a) administering one or more (e.g., two or more, three or more, four or more, five or more, or ten or more) doses of a first FGFR kinase inhibitor to a subject identified or diagnosed as having a FGFR associated cancer (e.g., any of the types of FGFR-associated cancers described herein) (e.g., identified or diagnosed as having a FGFR-associated cancer using any of the exemplary methods described herein or known in the art); (b) after step (a), determining a level of circulating tumor DNA in a biological sample (e.g., a biological sample comprising blood, serum, or plasma) obtained from the subject; (c) administering a therapeutically effective amount of a second FGFR inhibitor or a compound of the disclosure as a monotherapy or in conjunction with an additional therapy or therapeutic agent to a subject identified as having about the same or an elevated level of circulating tumor DNA as compared to a reference level of circulating tumor DNA (e.g., any of the reference levels of circulating tumor DNA described herein). In some examples of these methods, the reference level of circulating tumor DNA is a level of circulating tumor DNA in a biological sample obtained from the subject prior to step (a). Some embodiments of these methods further include determining the level of circulating tumor DNA in the biological sample obtained from the subject prior to step (a). In some examples of these methods, the reference level of circulating tumor DNA is a threshold level of circulating tumor DNA (e.g., an average level of circulating tumor DNA in a population of subjects having a similar FGFR-associated cancer and having a similar stage of the FGFR-associated cancer, but receiving a non-effective treatment or a placebo, or not yet receiving therapeutic treatment, or a level of circulating tumor DNA in a subject having a similar FGFR-associated cancer and having a similar stage of the FGFR-associated cancer, but receiving a non-effective treatment or a placebo, or not yet receiving therapeutic treatment). In some examples of these methods, the first FGFR inhibitor is: ARQ-087, ASP5878, AZD4547, B-701, BAY1179470, BAY1187982, BGJ398, brivanib, Debio-1347, dovitinib, E7090, erdafitinib, FPA144, HMPL-453, INCB054828, lenvatinib, lucitanib, LY3076226, MAX-40279, nintedanib, orantinib, pemigatinib, ponatinib, PRN1371, rogaratinib, sulfatinib, TAS-120 or RLY-4008.

Compounds of the disclosure can also be administered with additional therapy or therapeutic agents. In some aspects, the additional therapy or therapeutic agent includes one or more of radiation therapy, a chemotherapeutic agent (e.g., any of the exemplary chemotherapeutic agents described herein or known in the art), a checkpoint inhibitor (e.g., any of the exemplary checkpoint inhibitors described herein or known in the art), surgery (e.g., at least partial resection of the tumor), and one or more other kinase inhibitors (e.g., any of the kinase inhibitors described herein or known in the art).

Compounds of the disclosure may also be useful as adjuvants to cancer treatment, that is, they can be used in combination with one or more additional therapies or therapeutic agents, for example a chemotherapeutic agent that works by the same or by a different mechanism of action. In some embodiments, a compound of the disclosure can be used prior to administration of an additional therapeutic agent or additional therapy. For example, a subject in need thereof can be administered one or more doses of a compound of the disclosure for a period of time and then under go at least partial resection of the tumor. In some embodiments, the treatment with one or more doses of a compound of the disclosure reduces the size of the tumor (e.g., the tumor burden) prior to the at least partial resection of the tumor. In some embodiments, a subject has a cancer (e.g., a locally advanced or metastatic tumor) that is refractory or intolerant to standard therapy (e.g., administration of a chemotherapeutic agent, such as a first FGFR inhibitor or a multikinase inhibitor, immunotherapy, radiation, or a platinum-based agent (e.g., cisplatin)). In some embodiments, a subject has a cancer (e.g., a locally advanced or metastatic tumor) that is refractory or intolerant to prior therapy (e.g., administration of a chemotherapeutic agent, such as a first FGFR inhibitor or a multikinase inhibitor, immunotherapy, radiation, or a platinum-based agent (e.g., cisplatin)).

In some embodiments of any the methods described herein, the compound of the disclosure is administered in combination with a therapeutically effective amount of at least one additional therapeutic agent selected from one or more additional therapies or therapeutic (e.g., chemotherapeutic) agents.

Non-limiting examples of additional therapeutic agents include: other FGFR-targeted therapeutic agents (i.e. a first or second FGFR kinase inhibitor), other kinase inhibitors (e.g., receptor tyrosine kinase targeted therapeutic agents (e.g., Trk inhibitors or EGFR inhibitors)), signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy.

Also provided herein are methods of treating a disease or disorder, comprising administering to a subject in need thereof a pharmaceutical combination for treating the disease or disorder which comprises (a) a compound of the disclosure, (b) an additional therapeutic agent, and (c) optionally at least one pharmaceutically acceptable carrier for simultaneous, separate or sequential use for the treatment of the disease or disorder, wherein the amounts of the compound of the disclosure and the additional therapeutic agent are together effective in treating the disease or disorder. In some embodiments, the compound of the disclosure, and the additional therapeutic agent are administered simultaneously as separate dosages. In some embodiments, the compound of the disclosure, and the additional therapeutic agent are administered as separate dosages sequentially in any order, in jointly therapeutically effective amounts, e.g. in daily or intermittently dosages. In some embodiments, the compound of the disclosure, and the additional therapeutic agent are administered simultaneously as a combined dosage. In some embodiments, the disease or disorder is a FGFR-associated disease or disorder. In some embodiments, the subject has been administered one or more doses of a compound of of the disclosure, prior to administration of the pharmaceutical composition.

In some embodiments, the treatment period is at least 7 days (e.g., at least or about 8 days, at least or about 9 days, at least or about 10 days, at least or about 11 days, at least or about 12 days, at least or about 13 days, at least or about 14 days, at least or about 15 days, at least or about 16 days, at least or about 17 days, at least or about 18 days, at least or about 19 days, at least or about 20 days, at least or about 21 days, at least or about 22 days, at least or about 23 days, at least or about 24 days, at least or about 25 days, at least or about 26 days, at least or about 27 days, at least or about 28 days, at least or about 29 days, or at least or about 30 days).

In some embodiments, the treatment period is at least 21 days (e.g., at least or about 22 days, at least or about 23 days, at least or about 24 days, at least or about 25 days, at least or about 26 days, at least or about 27 days, at least or about 28 days, at least or about 29 days, at least or about 30 days, at least or about 31 days, at least or about 32 days, at least or about 33 days, at least or about 34 days, at least or about 35 days, at least or about 36 days, at least or about 37 days, at least or about 38 days, at least or about 39 days, or at least or about 40 days).

Also provided herein are pharmaceutical compositions that contain, as the active ingredient, a compound of the disclosure, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In some embodiments, the composition is formulated for oral administration. In some embodiments, the composition is formulated as a tablet or capsule.

The compositions comprising a compound of the disclosure can be formulated in a unit dosage form, each dosage containing from about 5 to about 1,000 mg (1 g), more usually about 100 mg to about 500 mg, of the active ingredient. The term "unit dosage form" refers to physically discrete units for human subjects and other subjects, each unit containing a predetermined quantity of active material (i.e., a compound of the disclosure) to produce the desired therapeutic effect, with a suitable pharmaceutical excipient.

In some embodiments, the compositions provided herein contain from about 5 mg to about 50 mg of the active ingredient, i.e., the compound of the disclosure. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient. In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient. In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

In some embodiments, the compounds of the disclosure can be especially advantageous in the context of the treatment of FGFR related cancers. In several embodiments, the compounds as disclosed herein are characterized by their ability to bind one or more of FGFR1, FGFR2, FGFR3, or FGFR4. In several embodiments, the compounds of the disclosure are characterized by a dissociation constant (Kd) for FGFR1 of equal to or less than about: 1200 nM, 1000 nM, 780 nM, 500 nM, 250 nM, 150 nM, 100 nM, 50 nM, 25 nM, 10 nM, 5 nM, 1 nM, 0.1 nM, 0.01 nM, or ranges including and/or spanning the aforementioned values. In several embodiments, the compounds of the disclosure are characterized by a Kd for FGFR2 of equal to or less than about: 250 nM, 150 nM, 100 nM, 50 nM, 25 nM, 10 nM, 5 nM, 1 nM, 0.1 nM, 0.01 nM, or ranges including and/or spanning the aforementioned values. In several embodiments, the compounds of the disclosure are characterized by a Kd for FGFR3 of equal to or less than about: 550 nM, 250 nM, 150 nM, 100 nM, 50 nM, 25 nM, 10 nM, 5 nM, 1 nM, 0.1 nM, 0.01 nM, or ranges including and/or spanning the aforementioned values. In several embodiments, the compounds of the disclosure are characterized by a dissociation constant (Kd) for FGFR4 of equal to or less than about: 1200 nM, 1000 nM, 780 nM, 500 nM, 250 nM, 150 nM, 100 nM, 50 nM, 25 nM, 10 nM, 5 nM, 1 nM, 0.1 nM, 0.01 nM, or ranges including and/or spanning the aforementioned values. In several embodiments, Kd values may be measured in aqueous 0.9% DMSO solution. In several embodiments, Kd is measured using liganded affinity beads as disclosed elsewhere herein. In several embodiments, Kd is measured by incubating kinases, liganded affinity beads, and compounds in 1× binding buffer (e.g., 20% SeaBlock, 0.17×PBS, 0.05% Tween 20, 6 mM DTT).

In several embodiments, not only can the compounds of the disclosure be used for therapy in patients with FGFR mutations (either point mutations or various fusions) to provide superior benefits, but in situations in which these mutations are likely to arise (such as in erdafitinib and/or infigratinib (BGJ398) pemigatinib, or TAS-120 therapy), where numerous activating and resistance mutations recur in patients, it may be especially advantageous. In several embodiments, the compounds of the disclosure can be used as a therapeutic intervention in patients bearing these mutations, either in combination with a pan-FGFR inhibitor or as a monotherapy where genomic testing supports mutations for which the compounds of the disclosure are active.

In several embodiments, a method of treating a cancer is provided. In several embodiments, the method of treating cancer includes administering one or more compounds of the disclosure. In several embodiments, the method comprises, in response to a determination of the presence of a FGFR mutant polypeptide or a FGFR mutant polynucleotide in a sample from the subject, administering to the subject an effective amount of compounds of the disclosure. This can thereby treat the cancer in the subject. In several embodiments, the FGFR mutant is one of the ones disclosed herein and/or an activating mutant (including a point mutation or FGFR fusion).

In several embodiments, the method of treating cancer includes administering one or more compounds of the disclosure to a patient who is suspected of having a cancer or being at risk of having a cancer. In several embodiments, the method comprises administering to the subject an effective amount of compound of the disclosure, this can be done with or without a diagnosis or analysis of the subject's kinases (including whether or not the kinases are wild-type or mutant).

In several embodiments, the FGFR mutants are fusions that can be caused by chromosomal translocations in cancers. These translocations can lead to fusion proteins that exert their oncogenic effects through overexpression of an otherwise normal gene or creation of a chimeric gene in which parts of two genes are fused together. Fusions of FGFR genes with other genes or parts of genes have been found most commonly in FGFR2 and FGFR3. The most common fusion partner reported for FGFR3 is TACC3 (Transforming Acidic Coiled-Coil Containing Protein). Table 0.1 Summarizes the Frequency of FGFR Specific Fusions:

TABLE 0.1

| Specific Fusion (N) | Tumor types (N) |
|---|---|
| FGFR3-TACC3 (11) | CUP (1), cervical carcinoma (1), Endometrial adeno-carcinoma (1), gallbladder carcinoma (1), glioma (1), NSCLC (1), renal cell carcinoma (1), urothelial carcinoma (4). |
| FGFR2-TACC3 (1) | Cholangiocarcinoma (1) |
| FGFR2-NPM1 (3) | Colorectal carcinoma (2), large cell lung carcinoma (1) |
| FGFR2-TACC2 (2) | CUP (1), Gastric/GE Junction adeno-carcinoma (1) |
| FGFR2-BICC1 (2) | CUP (1), Cholangiocarcinoma (1) |
| FGFR2-C10orf68 (1) | Gastric/GE Junction adeno-carcinoma (1) |
| FGFR3-JAKMIP1 (1) | Bladder urothelial (transition cell) carcinoma (1) |
| FGFR2-KIAA1598 (1) | Cholangiocarcinoma (1) |
| FGFR2-NCALD (1) | Breast carcinoma (1) |
| FGFR2-NOL4 (1) | Cholangiocarcinoma (1) |
| FGFR1-NTM (1) | Bladder urothelial (transition cell) carcinoma (1) |
| FGFR2-PPAPDC1A (1) | Prostate carcinoma (1) |
| FGFR3-TNIP2 (1) | Bladder urothelial (transition cell) carcinoma (1) |
| FGFR3-WHSC1 (1) | Breast carcinoma (1) |

An analysis of FGFR fusions identified in The Cancer Genome Atlas (TCGA) found a number of translocations which illustrate both the recurrence and lack of (absolute) tumor type specificity for FGFR1, 2, and 3 fusions (unpublished, Table 0.2).

TABLE 0.2

| Cancer | Fusion | Samples in Cancer Type |
|---|---|---|
| Acute Myeloid Leukemia | FGFR3--TACC3 | 1 |
| Bladder Urothelial Carcinoma | FGFR3--TACC3 | 7 |
| Brain Lower Grade Glioma | FGFR3--ELAVL3 | 1 |
| Brain Lower Grade Glioma | FGFR3--TACC3 | 2 |
| Brain Lower Grade Glioma | FGFR3--FBXO28 | 1 |
| Breast invasive carcinoma | ERLIN2--FGFR1 | 1 |
| Breast invasive carcinoma | FGFR2--CASP7 | 1 |
| Breast invasive carcinoma | FGFR2--CCDC6 | 1 |
| Cervical squamous cell carcinoma and endocervical adenocarcinoma | FGFR3--TACC3 | 5 |
| Cholangiocarcinoma | FGFR2--BICC1 | 2 |
| Cholangiocarcinoma | FGFR2--CCDC186 | 1 |
| Cholangiocarcinoma | FGFR2--FRK | 1 |
| Cholangiocarcinoma | FGFR2--SHTN1 | 1 |
| Esophageal carcinoma | FGFR3--TACC3 | 2 |
| Glioblastoma multiforme | FGFR3--AMBRA1 | 1 |
| Glioblastoma multiforme | FGFR3--TACC3 | 1 |
| Head and Neck squamous cell carcinoma | FGFR3--TACC3 | 2 |

TABLE 0.2-continued

| Cancer | Fusion | Samples in Cancer Type |
|---|---|---|
| Kidney renal papillary cell carcinoma | FGFR3--TACC3 | 2 |
| Liver hepatocellular carcinoma | FGFR2--BICC1 | 1 |
| Liver hepatocellular carcinoma | FGFR2--SMN1 | 1 |
| Lung squamous cell carcinoma | BAG4--FGFR1 | 1 |
| Lung squamous cell carcinoma | FGFR3--TACC3 | 6 |
| Lung squamous cell carcinoma | FGFR2--CCAR2 | 1 |
| Lung squamous cell carcinoma | FGFR2--EIF4A2 | 1 |
| Ovarian serous cystadenocarcinoma | FGFR3--MLLT10 | 1 |
| Prostate adenocarcinoma | FGFR3--AES | 1 |
| Stomach adenocarcinoma | FGFR3--TACC3 | 1 |
| Stomach adenocarcinoma | FGFR2--TACC2 | 1 |
| Thyroid carcinoma | FGFR2--OFD1 | 1 |
| Uterine Corpus Endometrial Carcinoma | FGFR2--SHTN1 | 1 |

In several embodiments, mutations in FGFR are polyclonal. Thus, when the FGFR or FGFR-fusion driven cancer metastasizes, the individual metastases can have distinct mutational patterns in the FGFR kinase domain. For example, a patient with distinct liver metastases can have a gatekeeper mutation in a subset of the metastases but not necessarily in all of them at the time of treatment or biopsy. The presence of the founding mutation from the primary tumor i.e. a FGFR fusion would likely remain in all patients. In several embodiments, it is that founding mutation that is targeted by any one or more of the methods provided herein. In several embodiments, both the founding mutation and other mutations are targeted by any one or more of the methods provided herein. In several embodiments, only the later mutations are targeted by one or more of the methods provided herein. In several embodiments, the method of any of the methods provided herein can be one where a compound of the disclosure is administered in an amount adequate to treat a tumor in a subject who has metastasized, and wherein the tumor that is being treated is the primary tumor. In several embodiments, any of the methods provided herein can use an adequate amount of a compound of the disclosure to treat a subset of the tumors in a subject. For example, the subset can include or focus on the tumors with a founding mutation (the primary tumor(s)). Thus, in several embodiments, the therapy need not be directed to, or include an amount of the disclosure to treat every tumor, but just a subset of the tumors (for example the primary tumors with the founding mutation). In several embodiments, the treated tumor is not the primary tumor, but may be a metastases with a detectable resistance or activating mutation not found in the primary tumor. In several embodiments, the method comprises administering a compound of the disclosure in an amount adequate to treat a tumor in a subject who has metastasized, and wherein the treated tumor is not the primary tumor, and wherein the treated tumor is a metastases with a detectable resistance or activating mutation not found in the primary tumor.

In several embodiments, a subject with any of the fusion arrangements in Tables 0.1 or 0.2 can obtain an enhanced benefit from a compound of a compound of the disclosure therapy. In several embodiments, any of the methods provided herein with respect to various point mutations can be applied to tumors or subjects that have any one or more of the above noted fusions. For example, a method of treating a subject having a cancer can comprise acquiring knowledge of a presence of an FGFR mutation (e.g., fusion) in a FGFR polynucleotide or FGFR polypeptide in said subject. The method can further comprise administering to the subject an effective amount of a compound of the disclosure. The FGFR mutation is at least one of the following fusions: BAG4-FGFR1, BCR-FGFR1, CEP110-FGFR1, CUX1-FGFR1, CNTRL-FGFR1, CFS1-FGFR1, ERLIN2-FGFR1, ETV6-FGFR1, FGFR1-NTM, FGFR1OP-FGFR1, FGFR1OP2-FGFR1, HERVK-FGFR1, LRRFIP-FGFR1, TRIM24-FGFR1, MYO18A-FGFR1, LRRFIP1-FGFR1, ZNF198-FGFR1, ZMYM2-FGFR1, MYO18A-FGFR1, RANBP2-FGFR1, TPR-FGFR1, FGFR2-BICC1, FGFR2-CIT, FGFR2-CASP7, FGFR2-CCAR2, FGFR2-CCDC186, FGFR2-CCDC6, FGFR2-EIF4A2, FGFR2-KIAA1967, SLC45A3-FGFR2, FGFR2-FRK, FGFR2-AFF3, FGFR2-OFD1, FGFR2-ZMYM4, FGFR2-OPTN, FGFR2-SHTN1, FGFR2-LZTFL1, FGFR2-SMN1, FGFR2-TACC1, FGFR2-C10orf68, FGFR2-KIAA1598, FGFR2-NCALD, FGFR2-NOL4, FGFR2-NPM1, FGFR2-PPAPDC1A, FGFR2-TACC2, FGFR2-TACC3, FGFR3-AES, FGFR3-AMBRA1, FGFR3-ELAVL3, FGFR3-FBXO28, FGFR3-MLLT10, FGFR3-TACC3, FGFR3-JAKMIP1, FGFR3-BAIAP2L1, FGFR3-TNIP2, FGFR3-WHSC1, FGFR3-PPHLN1.

In several embodiments, the compound can be used to treat subjects with other types of mutations in FGFR, including allosteric mutations, such as S249C.

In several embodiments, the tumor type to be treated is that designated as corresponding to the denoted particular fusion in one of Tables 0.1 or 0.2.

In several embodiments, a method of treating a subject having a cancer is provided. The method comprises acquiring knowledge of a presence of an FGFR mutation in a FGFR polynucleotide or FGFR polypeptide in said subject. The method can further comprise administering to the subject an effective amount of a compound of the disclosure. The FGFR mutant polypeptide or nucleic acid includes one or more of the following fusions: BAG4-FGFR1, BCR-FGFR1, CEP110-FGFR1, CUX1-FGFR1, CNTRL-FGFR1, CFS1-FGFR1, ERLIN2-FGFR1, ETV6-FGFR1, FGFR1-NTM, FGFR1OP-FGFR1, FGFR1OP2-FGFR1, HERVK-FGFR1, LRRFIP-FGFR1, TRIM24-FGFR1, MYO18A-FGFR1, LRRFIP1-FGFR1, ZNF198-FGFR1, ZMYM2-FGFR1, MYO18A-FGFR1, RANBP2-FGFR1, TPR-FGFR1, FGFR2-BICC1, FGFR2-CIT, FGFR2-CASP7, FGFR2-CCAR2, FGFR2-CCDC186, FGFR2-CCDC6, FGFR2-EIF4A2, FGFR2-KIAA1967, SLC45A3-FGFR2, FGFR2-FRK, FGFR2-AFF3, FGFR2-OFD1, FGFR2-ZMYM4, FGFR2-OPTN, FGFR2-SHTN1, FGFR2-LZTFL1, FGFR2-SMN1, FGFR2-TACC1, FGFR2-C10orf68, FGFR2-KIAA1598, FGFR2-NCALD, FGFR2-NOL4, FGFR2-NPM1, FGFR2-PPAPDC1A, FGFR2-TACC2, FGFR2-TACC3, FGFR3-AES, FGFR3-AMBRA1, FGFR3-ELAVL3, FGFR3-FBXO28, FGFR3-MLLT10, FGFR3-TACC3, FGFR3-JAKMIP1, FGFR3-BAIAP2L1, FGFR3-TNIP2, FGFR3-WHSC1, FGFR3-PPHLN1.

In several embodiments, a method of treating a cancer is provided. The method comprises, in response to a determination of the presence of a FGFR2 fusion polypeptide or a FGFR2 fusion polynucleotide in a sample from the subject, administering to the subject an effective amount of a compound of the disclosure. This treats the cancer in the subject. The administration of a compound of the disclosure is at least as effective on the fusion polypeptide as it is on the respective wild-type kinase of FGFR2. In several embodiments, a compound of the disclosure is at least 5, 10, 20, 30, 40, 50, 60, 70, 80, 90, 100, 110, 120, 130, 140, 150, 200, 300, 400, 500, 1000% more potent on the mutant FGFR as on the wild-type FGFR on inhibiting FGFR kinase activity. In several embodiments, the method and/or percent is determined by the method as provided in the present examples.

In several embodiments, a method of treating a subject having a cancer is provided. The method comprises acquiring knowledge of a presence of an FGFR mutation in a FGFR polynucleotide or FGFR polypeptide in said subject. The method can further comprise administering to the subject an effective amount of a compound of the disclosure. The FGFR mutant polypeptide includes at least one of: A) for FGFR1: V561M of FGFR1, B) for FGFR2: E565G, K526E, K641R, K659N, N549H, R612T, and V564F, C) for FGFR 3: G697C, K650E, K650M, K650Q, and/or V555M of FGFR3, or D) For FGFR4: N535K, V550E, V550L, and/or V550M of FGFR4.

In several embodiments, a method of treating a subject having a cancer is provided. The method comprises administering a compound of the disclosure to a subject. The subject has at least two FGFR point mutations. The at least two point mutations occur at two positions selected from at least two within any one of the following groupings: a) for FGFR2: 565, 526, 641, 659, 549, 612, and 564, b) for FGFR1: 561 of FGFR1, c) for FGFR 3: 697, 650, and/or 555 of FGFR3, or d) for FGFR4: 535 or 550 of FGFR4.

In several embodiments, one, two, three, four, or five or more mutations at these positions are present. In several embodiments at least two point mutations are selected from: a) for FGFR2: E565G, K526E, K641R, K659N, N549H, R612T, and V564F, b) for FGFR1: V561M of FGFR1, c) for FGFR 3: G697C, K650E, K650M, K650Q, and/or V555M of FGFR3, or d) For FGFR4: N535K, V550E, V550L, and/or V550M for FGFR4. In several embodiments, one, two, three, four, or five or more of these particular mutations are present.

In several embodiments, a method of treating a cancer is provided, the method comprises, in response to a determination of the presence of a FGFR activating mutation in a subject, administering to the subject an effective amount of a compound of the disclosure thereby treating the cancer in the subject, wherein the FGFR activating mutation is a driver in a non-fused cancer. In several embodiments, an effective amount of a compound of the disclosure is an amount that reduces the activity of the FGFR mutant to a level that is adequate to provide some treatment to the subject, for example, by reducing one or more symptoms. In several embodiments, the activity of the mutant FGFR is reduced by a compound of the disclosure to near, or lower than, wild-type activity. In several embodiments, the activity for the FGFR mutant, when a compound of the disclosure is administered, is reduced to 500, 400, 300, 200, 190, 180, 170, 160, 150, 140, 130, 120, 110, 105, 104, 103, 102, 101, 100, 95, 90, or lower percent of the activity of wild-type FGFR.

In several embodiments, a method of treating cancer in a subject in need thereof is provided. The method comprises administering an inhibitor of FGFR kinase activity to a subject determined to have a genetic fusion of FGFR and a second gene, wherein the inhibitor of FGFR is at least as effective against the genetic fusion of FGFR, as it is against a wild-type FGFR kinase. In several embodiments, the inhibitor can be a compound of the disclosure. In several embodiments, the inhibitor of FGFR kinase activity is at least 5, 10, 20, 30, 40, 50, 60, 70, 80, 90, 100, 110, 120, 130, 140, 150, 200, 300, 400, 500, 1000, 5000, or 10,000% more potent on the fused FGFR as on the wild-type FGFR. In several embodiments, a compound of the disclosure is at least 1.1, 2, 5, 10, 20, 30, 40, 50, 60, 70, 80, 90, or 100 fold as potent for the mutant as it is for wild-type. In several embodiments, the IC50 and/or Kd for a compound of the disclosure is 0.5, 0.1, 0.05, or 0.01% as large for the mutant FGFR as it is for wild type (that is, the numerical value for the IC50 is lower for the mutant).

In several embodiments, the $IC_{50}$ of a compound of the disclosure to the FGFR mutant or mutation is no higher than about 100 nM (e.g., it is at least as good in potency as 100 nM). In several embodiments, the $IC_{50}$ of a compound of the disclosure to the FGFR mutant or mutation is no higher than about 10 nM (e.g., it is at least as good in potency as 10 nM). In several embodiments, the $IC_{50}$ of a compound of the disclosure to the FGFR mutant or mutation is no higher than single digit nM (e.g., it is at least as good in potency as single digit nM). In several embodiments, the $IC_{50}$ of a compound of the disclosure to the FGFR mutant or mutation is at least as effective for the FGFR mutant or mutation as it is for a wild type FGFR.

In several embodiments of the method, the subject has been (or is still) on a multi-targeted kinase inhibitor ("MKI") or a targeted FGFR inhibitor. While on the MKI or the targeted FGFR inhibitor, the subject develops a tumor that has become resistant to the prior MKI or the targeted FGFR inhibitor. At this point, one can either simply administer a compound of the disclosure. In the alternative, one can determine if the subject now has a tumor that has a FGFR mutation in it (such as amino acid changes that result in resistance to the prior therapy). If the subject does have a tumor with the noted mutation, one can then dose the subject with a compound of the disclosure.

In several embodiments, the FGFR is a FGFR2 mutant. In several embodiments, the FGFR2 mutant includes at least one mutation as follows: E565G, K526E, K641R, K659N, N549H, R612T, and/or V564F of FGFR2.

In several embodiments, the FGFR is a FGFR1 mutant. In several embodiments, the FGFR1 mutant includes a mutation as follows: V561M and/or FGFR1OP-FGFR1 of FGFR1.

In several embodiments, the FGFR mutant is a FGFR3 mutant. In several embodiments, the FGFR3 includes a mutation as follows: G697C, K650E, K650M, K650Q, and/or V555M of FGFR3.

In several embodiments, the FGFR is an FGFR4. In several embodiments, the FGFR4 includes a mutation as follows: N535K, V550E, V550L, and/or V550M of FGFR4.

In several embodiments, the method of using a compound of the disclosure can be directed to treating a variety of cancers or cancer generically. In several embodiments, the cancer is one or more of: urothelial carcinoma, breast carcinoma, endometrial adenocarcinoma, ovarian carcinoma, primary glioma, cholangiocarcinoma, gastric adenocarcinoma, non-small cell lung carcinoma, pancreatic exocrine carcinoma, oral, prostate, bladder, colorectal carcinoma, renal cell carcinoma, neuroendocrine carcinoma, myeloproliferative neoplasms, head and neck (squamous), melanoma, leiomyosarcoma, and/or sarcomas. In several embodiments, the subject has an intrahepatic cholangiocarcinoma. This list denotes some, but not all of the FGFR mutant related cancers. In several embodiments, the cancer can include any of the previous options and/or any of the following: urothelial carcinoma, breast carcinoma, endometrial adenocarcinoma, ovarian carcinoma, primary glioma, cholangiocarcinoma, gastric adenocarcinoma, non-small cell lung carcinoma, pancreatic exocrine carcinoma, oral, prostate, bladder, colorectal carcinoma, renal cell carcinoma, neuroendocrine carcinoma, myeloproliferative neoplasms, head and neck (squamous), melanoma, leiomyosarcoma, and/or sarcomas. In several embodiments, the subject has an intrahepatic cholangiocarcinoma.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. Changes therein and other uses which are encompassed within the spirit of the disclosure as defined by the scope of the claims will occur to those skilled in the art.

EXAMPLES

Example Compounds 1-14 (shown in Table 1) were synthesized using the synthetic routes from Schemes 1-5. The routes of Scheme 1 were used to prepare Example Compounds 3, 4, 9, and 10. The routes of Scheme 2 were used to prepare Example Compounds 5 and 7. The routes of Scheme 3 were used to prepare Example Compounds 6 and 8. The routes of Scheme 4 were used to prepare Example Compounds 1 and 2. The routes of Scheme 5 were used to prepare Example Compounds 11, 12, 13, and 14. Kinase binding testing was then performed on Example Compounds 1-14. The results of the kinase binding assays can be found in Table 1.

Example 1. [3-[5-[1-(3,5-dichloro-4-pyridyl)ethoxy]-1H-indazol-3-yl]phenyl]imino-dimethyl-oxo-λ$^6$-sulfane

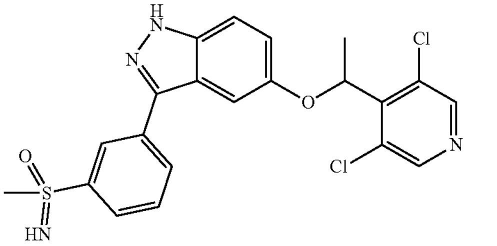 [SMILES: CC(Oc1ccc2[nH]nc(-c3cccc(S(C)(=N)=O)c3)c2c1)c1c(Cl)cncc1Cl]

[3-[5-[1-(3,5-dichloro-4-pyridyl)ethoxy]-1H-indazol-3-yl]phenyl]imino-dimethyl-oxo-λ$^6$-sulfane was synthesized according to the scheme shown below:

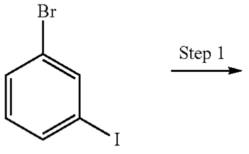

1-bromo-3-iodo-benzene

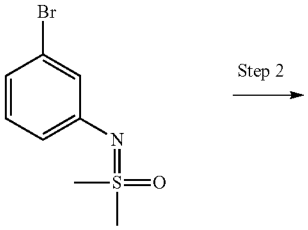

-continued

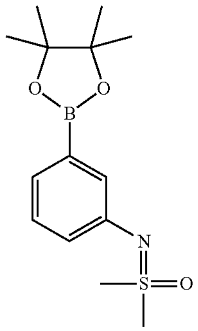

dimethyl-oxo-[3-(4,4,5,5-tetramethyl-1,3,2-dioxaborolan-2-yl)phenyl]imino-λ$^6$-sulfane

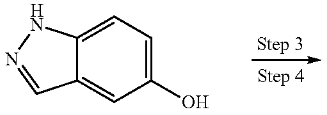

1H-indazol-5-ol

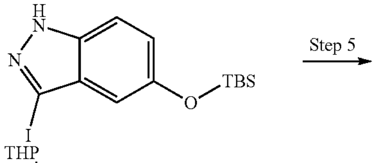

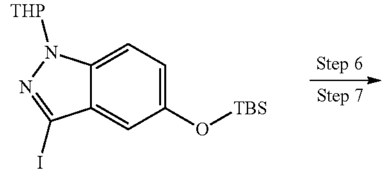

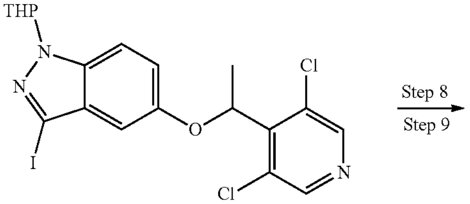

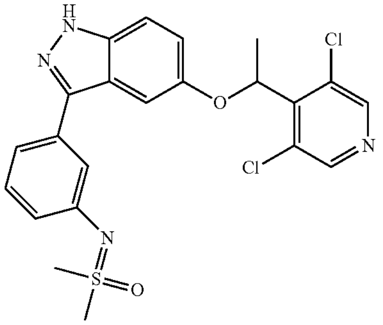

Example 1

Step 1. ((3-Bromophenyl)imino)dimethyl-λ$^6$-sulfanone. A solution of 1-bromo-3-iodo-benzene (500 mg, 1.76 mmol, 1.0 equiv), S,S-dimethylsulfoximine (190 mg, 2.12 mmol, 1.2 equiv), Xantphos (100 mg, 0.18 mmol, 0.1 equiv), tris(dibenzylideneacetone) dipalladium(0) (80 mg, 0.09 mmol, 0.05 equiv) and cesium carbonate (550 mg, 2.46 mmol, 1.4 equiv) in 1,4-dioxane (10 mL) was sparged with nitrogen for 15 min and then heated at 100° C. for 3 hours. After cooling to room temperature, the reaction mixture was filtered through Celite and the filtrate was concentrated under reduced pressure. The crude product was purified on a Büchi automated chromatography system (RediSep Rf Gold HP RP C18, 50 g column), eluting with a gradient of 0 to 70% acetonitrile in water to give (3-bromophenyl) imino-dimethyl-oxo-$\lambda^6$-sulfane (190 mg, 44% yield) as a pale yellow oil. Analysis: LCMS: m/z=247.2 (M+H).

Step 2. Dimethyl((3-(4,4,5,5-tetramethyl-1,3,2-dioxaborolan-2-yl)phenyl)imino)-$\lambda^6$-sulfanone. A solution of ((3-bromophenyl)imino)dimethyl-$\lambda^6$-sulfanone (190 mg, 0.77 mmol, 1.0 equiv), bis(pinacolato)diboron (230 mg, 0.93 mmol, 1.2 equiv), [1,1' bis(diphenylphosphino) ferrocene] dichloropalladium(II) (56 mg, 0.08 mmol, 0.1 equiv) and potassium acetate (113 mg, 1.20 mmol, 1.5 equiv) in 1,4-dioxane (10 mL) was sparged with nitrogen for 15 min and then heated at 100° C. for 16 h. After cooling to room temperature, the reaction mixture was filtered through Celite and the filtrate was concentrated under reduced pressure. The residue was suspended in saturated sodium bicarbonate solution (20 mL) and extracted with ethyl acetate (3×30 mL). The combined organic layers were dried over sodium sulfate, filtered and concentrated under reduced pressure. The residue was purified on a Büchi automated chromatography system (Sorbtech 25 g silica gel column), eluting with a gradient of 0 to 10% methanol in DCM to give a pale yellow oil (220 mg, 85% yield). Analysis: LCMS: m/z=296.1 (M+H)

Step 3. 5-((tert-Butyldimethylsilyl)oxy)-1H-indazole. A solution of 1H-indazol-5-ol (1.0 g, 7.50 mmol, 1.0 equiv), tert-butyldimethylsilyl chloride (1.35 g, 9.0 mmol, 1.2 equiv) and imidazole (760 mg, 11.2 mmol, 1.5 equiv) in anhydrous acetonitrile (10 mL) was stirred at room temperature for 16 h. The reaction mixture was concentrated under reduced pressure. The residue was diluted with saturated ammonium chloride (20 mL) and extracted with ethyl acetate (3×20 mL). The combined organic layers were dried over sodium sulfate, filtered and concentrated under reduced pressure. The residue was purified on a Büchi automated chromatography system (Sorbtech 25 g silica gel column), eluting with a gradient of 0 to 70% ethyl acetate in heptanes to give a light yellow solid (1.85 g, 99%). Analysis: LCMS: m/z=249.2 (M+H).

Step 4. 5-((tert-Butyldimethylsilyl)oxy)-3-iodo-1H-indazole: N-Iodosuccinimide (1.85 g, 8.2 mmol, 1.1 equiv) was added to a solution of 5-((tert-butyldimethylsilyl)oxy)-1H-indazole (1.85 g, 7.5 mmol, 1.0 equiv) in dichloromethane at 0° C. After stirring the reaction at room temperature for 4 h, water (20 mL) was added. The layers were separated and the aqueous layer was extracted with dichloromethane (2×15 mL). The combined organic layers were dried over sodium sulfate, filtered and concentrated under reduced pressure. The residue was purified on a Büchi automated chromatography system (Sorbtech 25 g silica gel column), eluting with a gradient of 0 to 20% ethyl acetate in heptanes to give a pale yellow solid (2.28 g, 99%). Analysis: LCMS: m/z=375.2 (M+H).

Step 5. 5-((tert-Butyldimethylsilyl)oxy)-3-iodo-1-(tetrahydro-2H-pyran-2-yl)-1H-indazole. Dihydropyran (1.5 g, 18.30 mmol, 3.0 equiv) and p-toluenesulfonic acid monohydrate (115 mg, 0.60 mmol, 0.1 equiv) were sequentially added to a solution of 5-((tert-butyldimethylsilyl)oxy)-3-iodo-1H-indazole (2.28 g, 6.09 mmol, 1.0 equiv) in tetrahydrofuran (25 mL). After stirring at room temperature for 16 hours the volatiles were removed under reduced pressure. The residue was suspended in saturated ammonium chloride (30 mL) and extracted with ethyl acetate (2×30 mL). The combined organic layers were dried over sodium sulfate, filtered and concentrated under reduced pressure. The residue was purified on a Büchi automated chromatography system (Sorbtech 40 g silica gel column), eluting with a gradient of 0 to 20% ethyl acetate in heptanes to give a light brown oil (1.6 g, 57% yield). Analysis: LCMS: m/z=458.1 (M+H).

Step 6. 3-Iodo-1-(tetrahydro-2H-pyran-2-yl)-1H-indazol-5-ol. 1M Tetrabutylammonium fluoride solution in THF (2.6 mL, 2.6 mmol, 1.1 equiv) was added to a solution of product step 5 (1.08 g, 2.40 mmol, 1.0 equiv) in THF (10 mL). After stirring at room temperature for 2 h, the reaction mixture was cooled to 10° C. followed by the addition of water (10 mL). The volatiles were removed under reduced pressure. The residue was diluted with saturated ammonium chloride (20 mL) and extracted with ethyl acetate (2×20 mL). The combined organic layers were dried over sodium sulfate, filtered and concentrated under reduced pressure to give a light brown oil (760 mg, 99% yield). Analysis: LCMS: m/z=345.2 (M+H).

Step 7. 5-(1-(3,5-Dichloropyridin-4-yl)ethoxy)-3-iodo-1-(tetrahydro-2H-pyran-2-yl)-1H-indazole. A mixture of 3-Iodo-1-(tetrahydro-2H-pyran-2-yl)-1H-indazol-5-ol (430 mg, 1.25 mmol, 1.0 equiv), 1-(3,5-dichloro-4-pyridyl)ethyl methanesulfonate (380 mg, 1.38 mmol, 1.1 equiv) and cesium carbonate (370 mg, 1.62 mmol, 1.30 equiv) in N,N-dimethylformamide (20 mL) was heated at 80° C. for 16 h. The reaction mixture was cooled to room temperature and diluted with water (20 mL). The solution was extracted with ethyl acetate (3×60 mL). The combined organic layers were dried over sodium sulfate, filtered and concentrated under reduced pressure. The crude product was purified on a Büchi automated chromatography system (Sorbtech 40 g silica gel column), eluting with a gradient of 0 to 20% ethyl acetate in heptanes to give a colorless oil (640 mg, 99% yield). Analysis: LCMS: m/z=519.2 (M+H).

Step 8. ((3-(5-(1-(3,5-Dichloropyridin-4-yl)ethoxy)-1-(tetrahydro-2H-pyran-2-yl)-1H-indazol-3-yl)phenyl)imino) dimethyl-$\lambda^6$-sulfanone. A solution of 5-(1-(3,5-dichloropyridin-4-yl)ethoxy)-3-iodo-1-(tetrahydro-2H-pyran-2-yl)-1H-indazole (340 mg, 0.67 mmol, 1.0 equiv), product step 2 (220 mg, 0.74 mmol, 1.1 equiv), [1,1' bis(diphenyl-phosphino)ferrocene]dichloropalladium(II) (49 mg, 0.07 mmol, 0.1 equiv) and potassium carbonate (184 mg, 1.34 mmol, 2.0 equiv) in 1,4-dioxane (10 mL) and water (1 mL) was sparged with nitrogen for 15 minutes and then heated at 80° C. for 16 hours. After cooling to room temperature, the reaction mixture was filtered through Celite and the filtrate was concentrated under reduced pressure. The residue was suspended in saturated sodium bicarbonate (20 mL) and extracted with ethyl acetate (3×30 mL). The combined organic layers were dried over sodium sulfate, filtered and concentrated under reduced pressure. The residue was purified on a Büchi automated chromatography system (Sorbtech 25 g silica gel column), eluting with a gradient of 0 to 10% methanol in dichloromethane to give a pale-yellow oil (190 mg, 44% yield). Analysis: LCMS: m/z=560.3 (M+H).

Step 9. ((3-(5-(1-(3,5-Dichloropyridin-4-yl)ethoxy)-1H-indazol-3-yl)phenyl)imino) dimethyl-$\lambda^6$-6-sulfanone. 4M HCl in 1,4-dioxane (0.5 mL, 1.92 mmol, 8.0 equiv) was added dropwise to a solution of ((3-(5-(1-(3,5-dichloropyridin-4-yl)ethoxy)-1-(tetrahydro-2H-pyran-2-yl)-1H-indazol-3-yl)phenyl)imino)dimethyl-$\lambda^6$-sulfanone (135 mg, 0.24 mmol, 1 equiv) in 1,4-dioxane (1.0 mL). The clear yellow solution was stirred at room temperature overnight, at which time LCMS analysis indicated reaction was complete. Solvent was evaporated under reduced pressure. The residue was purified on an Interchim automated chromatography system (Sorbtech 40 g silica gel column), eluting with a gradient of 0 to 6% methanol in dichloromethane to give an off-white solid (81 mg, 95% yield). Analysis: LCMS: m/z=475.1 (M); 1H NMR (400 MHz, DMSO-d6) δ 13.06 (br s, 1H), 8.60 (br s, 2H), 7.48 (br d, J=8.7 Hz, 1H), 7.38 (br s, 1H), 7.31 (br t, J=7.2 Hz, 1H), 7.27-7.20 (m, 1H), 7.14 (br s, 1H), 7.10 (br d, J=8.7 Hz, 1H), 6.97 (br d, J=6.7 Hz, 1H), 6.07 (br d, J=5.9 Hz, 1H), 3.30-3.21 (m, 6H), 1.76 (br d, J=5.6 Hz, 3H).

Example 2. (3-(5-(1-(3,5-Dichloropyridin-4-yl) ethoxy)-1H-indazol-3-yl)phenyl)(imino) (methyl)-$\lambda^6$-6-sulfanone

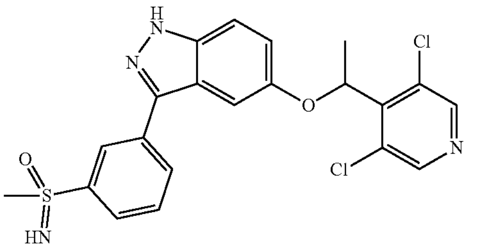 [SMILES: CC(Oc1ccc2[nH]nc(-c3cccc(S(C)(=N)=O)c3)c2c1)c1c(Cl)cncc1Cl]

Step 1. 5-(1-(3,5-Dichloropyridin-4-yl)ethoxy)-3-(3-(methylthio)phenyl)-1-(tetrahydro-2H-pyran-2-yl)-1H-indazole. A solution of 5-(1-(3,5-dichloropyridin-4-yl) ethoxy)-3-iodo-1-(tetrahydro-2H-pyran-2-yl)-1H-indazole (230 mg, 0.44 mmol, 1.0 equiv), (3-methylsulfanylphenyl) boronic acid (89 mg, 0.53 mmol, 1.2 equiv), [1,1' bis (diphenylphosphino)ferrocene]dichloropalladium(II) (32 mg, 0.04 mmol, 0.1 equiv) and potassium carbonate (120 mg, 0.88 mmol, 2.0 equiv) in 1,4-dioxane (10 mL) and water (1 mL) was sparged with nitrogen for 15 min and then heated at 80° C. for 16 h. After cooling to room temperature, the reaction mixture was filtered through Celite and the filtrate was concentrated under reduced pressure. The residue was suspended in saturated ammonium chloride (20 mL) and extracted with ethyl acetate (3×30 mL). The combined organic layers were dried over sodium sulfate, filtered and concentrated under reduced pressure. The residue was purified on a Büchi automated chromatography system (Sorbtech 25 g silica gel column), eluting with a gradient of 0 to 40% ethyl acetate in heptanes to give a pale-yellow oil (203 mg, 92% yield). Analysis: LCMS: m/z=513.2 (M+H).

Step 2. (3-(5-(1-(3,5-Dichloropyridin-4-yl)ethoxy)-1-(tetrahydro-2H-pyran-2-yl)-1H-indazol-3-yl)phenyl)(imino) (methyl)-$\lambda^6$-6-sulfanone. Ammonium acetate (47 mg, 0.62 mmol, 1.5 equiv) and (diacetoxyiodo)benzene (280 mg, 0.87 mmol, 2.1 equiv) were sequentially added to a solution of 5-(1-(3,5-dichloropyridin-4-yl)ethoxy)-3-(3-(methylthio) phenyl)-1-(tetrahydro-2H-pyran-2-yl)-1H-indazole (203 mg, 0.41 mmol, 1.0 equiv) in methanol (5 mL). After stirring at room temperature for 1 h, the reaction mixture was concentrated under reduced pressure. The residue was purified on a Büchi automated chromatography system (RediSep Rf Gold HP C18, 50 g column), eluting with a gradient of 0 to 80% acetonitrile in water to give a pale-yellow oil (155 mg, 72% yield). Analysis: LCMS: m/z=545.2 (M+H).

Step 3. (3-(5-(1-(3,5-Dichloropyridin-4-yl)ethoxy)-1H-indazol-3-yl)phenyl)(imino) (methyl)-$\lambda^6$-sulfanone. A solution of example 1 step 2 (155 mg, 0.28 mmol, 1.0 equiv) in 1,4-dioxane (1.0 mL) was treated with 4M HCl in 1,4-dioxane (0.6 mL, 2.28 mmol, 8.0 equiv). After stirring at room temperature for 16 h the volatiles were removed under reduced pressure. The residue was purified on an Interchim automated chromatography system (Sorbtech 40 g silica gel column), eluting with a gradient of 0 to 6% methanol in dichloromethane to give a white solid (51 mg, 39% yield). Analysis: LCMS: m/z=461.1 (M)+; $^1$H NMR (400 MHz, DMSO-d6) δ 8.46 (d, J=4.6 Hz, 3H), 8.10-7.96 (m, 2H), 7.76 (t, J=7.8 Hz, 1H), 7.48 (d, J=8.9 Hz, 1H), 7.27-7.14 (m, 2H), 6.20-6.09 (m, 1H), 3.25-3.19 (m, 3H), 1.82 (d, J=6.7 Hz, 3H).

Example 3. ([5-[(E)-2-[5-[(1R)-1-(3,5-dichloro-4-pyridyl)ethoxy]-1H-indazol-3-yl]vinyl]-2-pyridyl] imino-dimethyl-oxo-$\lambda^6$-sulfane

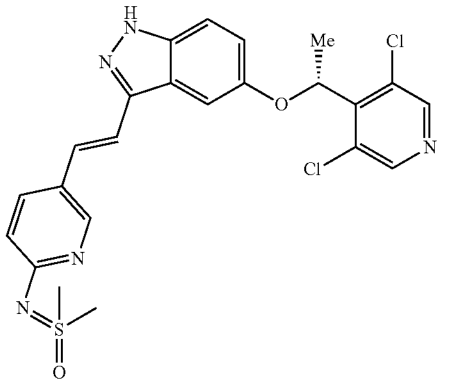 [SMILES: C[C@@H](Oc1ccc2[nH]nc(/C=C/c3ccc(N=S(C)(C)=O)nc3)c2c1)c1c(Cl)cncc1Cl]

([5-[(E)-2-[5-[(1R)-1-(3,5-dichloro-4-pyridyl)ethoxy]-1H-indazol-3-yl]vinyl]-2-pyridyl]imino-dimethyl-oxo-$\lambda^6$-sulfane was synthesized according to the scheme shown below:

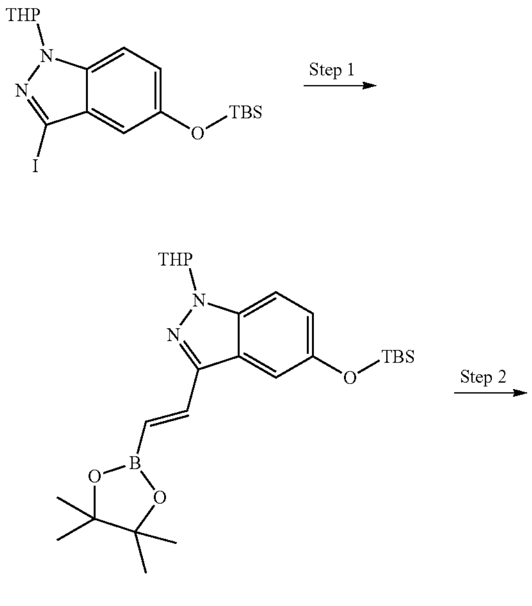

-continued

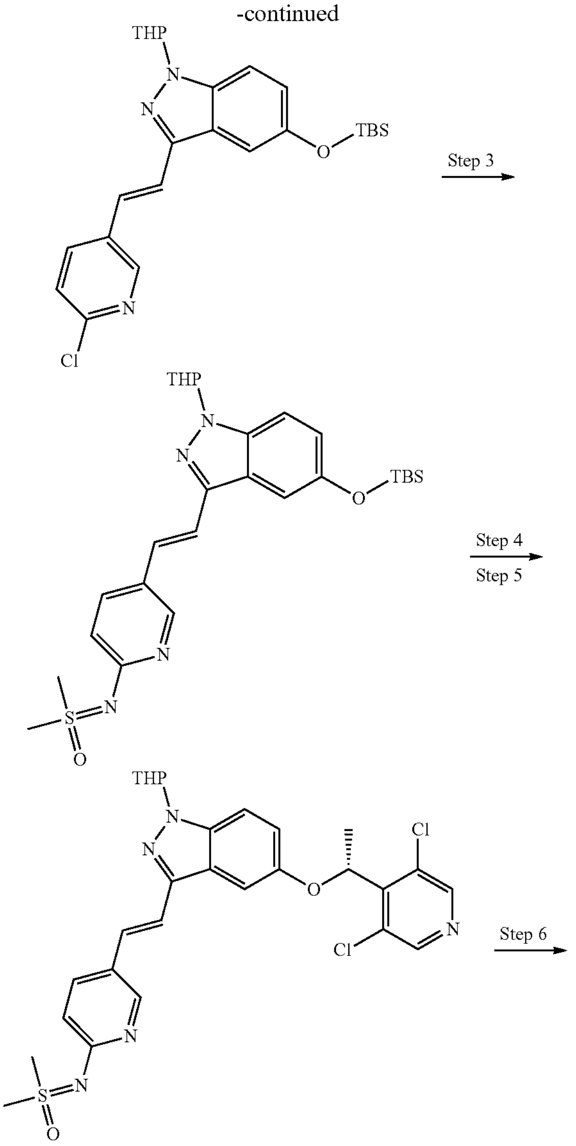

Example 3

Step 1. (E)-5-((tert-Butyldimethylsilyl)oxy)-1-(tetrahydro-2H-pyran-2-yl)-3-(2-(4,4,5,5-tetramethyl-1,3,2-dioxaborolan-2-yl)vinyl)-1H-indazole. A solution of 5-((tert-butyldimethylsilyl)oxy)-3-iodo-1-(tetrahydro-2H-pyran-2-yl)-1H-indazole (4.58 g, 10.0 mmol, 1 equiv), tri-tert-butylamine (2.9 mL, 12.0 mmol, 1.2 equiv) and vinylboronic acid pinacol ester (2.37 mL, 14.0 mmol, 1.4 equiv) in anhydrous N,N-dimethylformamide (50 mL) was sparged with nitrogen for 30 minutes. Bis(triphenylphosphine)palladium(II) dichloride (0.35 g, 0.5 mmol, 0.05 equiv) was added and reaction mixture was sparged with nitrogen for an additional 5 minutes. The reaction was heated at 90° C. for 16 h. After cooling to room temperature, the reaction was concentrated under reduced pressure. The residue was diluted with water (200 mL) and dichloromethane (200 mL). The layers were separated. The organic layer was dried over sodium sulfate, filtered and concentrated under reduced pressure. The crude product was pre-absorbed on silica gel (10 g) and purified on an Interchim automated chromatography system (Sorbtech 120 g silica gel cartridge), eluting with a gradient of 0 to 70% ethyl acetate in heptanes to give a tan solid (2.3 g, 47% yield). Analysis: LCMS: m/z=485 (M+H).

Step 2. (E)-5-((tert-Butyldimethylsilyl)oxy)-3-(2-(6-chloropyridin-3-yl)vinyl)-1-(tetrahydro-2H-pyran-2-yl)-1H-indazole. A solution of the product from step 1 (1.13 g, 2.33 mmol, 1 equiv) and 2-chloro-5-iodopyridine (0.73 g, 3.03 mmol, 1.3 equiv) in 6 to 1 mixture of 1,4-dioxane and water (58 mL) was sparged with nitrogen for 25 min. Potassium carbonate (0.96 g, 6.99 mmol, 3 equiv) and (1,1'-bis(diphenylphosphino)ferrocene) palladium(II) dichloride (0.128 g, 0.174 mmol, 0.075 equiv)) were added and the reaction mixture was sparged with nitrogen for an additional 5 minutes. The reaction was heated at 80-85° C. for 3 h. After cooling to room temperature, the reaction was concentrated under reduced pressure. The residue was diluted with water (50 mL) and dichloromethane (50 mL). The layers were separated. The organic layer was dried over sodium sulfate, filtered and concentrated under reduced pressure. The crude product was pre-absorbed on silica gel (5 g) and purified on an Interchim automated chromatography system (Sorbtech 80 g silica gel cartridge), eluting with a gradient of 0 to 30% ethyl acetate in heptanes to give a white solid (0.805 g, 74% yield). Analysis: LCMS: m/z=470 (M+H).

Step 3. (E)-((5-(2-(5-((tert-Butyldimethylsilyl)oxy)-1-(tetrahydro-2H-pyran-2-yl)-1H-indazol-3-yl)vinyl)pyridin-2-yl)imino)dimethyl-$\lambda^6$-sulfanone. A solution of product from step 2 (0.805 g, 1.72 mmol, 1 equiv), S,S-dimethylsulfoximine (0.32 g, 3.43 mmol, 2 equiv), and potassium acetate (0.336 g, 3.43 mmol, 2 equiv) in 6 to 1 mixture of 1,4-dioxane and water (35 mL) was sparged with nitrogen for 20 minutes. BINAP Pd(allyl)Cl (0.147 g, 0.172 mmol, 0.1 equiv) was added and reaction mixture was sparged with nitrogen for an additional 5 minutes. The reaction was heated at 85° C. for 3 h. After cooling to room temperature, the reaction was concentrated under reduced pressure. The residue was diluted with water (50 mL) and dichloromethane (50 mL). The layers were separated. The organic layer was dried over sodium sulfate, filtered and concentrated under reduced pressure. The crude product was pre-absorbed on silica gel (3 g) and purified on an Interchim automated chromatography system (Sorbtech 80 g silica gel cartridge), eluting with a gradient of 0 to 5% methanol in dichloromethane to give a white solid (769 mg, 85% yield). Analysis: LCMS: m/z=527 (M+H).

Step 4. (E)-((5-(2-(5-Hydroxy-1-(tetrahydro-2H-pyran-2-yl)-1H-indazol-3-yl)vinyl) pyridin-2-yl)imino)dimethyl-$\lambda^6$-sulfanone. 1M Tetrabutylammonium fluoride in THF (1.84 mL, 1.84 mmol, 1.0 equiv) was added dropwise at 0° C. to a solution of step 3 (0.86 g, 1.84 mmol, 1 equiv) in anhydrous THF (15 mL). The reaction was warmed to room temperature, stirred for 1 hour, quenched with water (1 mL) and concentrated under reduced pressure. The residue was diluted with water (50 mL) and extracted with dichloromethane (50 mL). The organic layer was dried over sodium sulfate, filtered and concentrated under reduced pressure. The crude product was pre-absorbed onto silica gel (2 g) and purified on an Interchim automated chromatography system (Sorbtech 80 g silica gel cartridge), eluting with a gradient of 0 to 8% methanol in dichloromethane to give a tan solid (0.69 g, 91% yield). Analysis: LCMS: m/z=413 (M+H).

Step 5. ((5-((E)-2-(5-((R)-1-(3,5-Dichloropyridin-4-yl) ethoxy)-1-(tetrahydro-2H-pyran-2-yl)-1H-indazol-3-yl)vinyl)pyridin-2-yl)imino)dimethyl-λ$^6$-sulfanone. A solution of step 4 (0.206 g, 0.5 mmol, 1 equiv) and cesium carbonate (0.171 g, 0.525 mmol, 1.05 equiv) in an anhydrous acetonitrile (5 mL) added [(1S)-1-(3,5-dichloro-4-pyridyl)ethyl] methanesulfonate (0.154 g, 0.57 mmol, 1.14 equiv) and the reaction was heated at 60° C. for 16 h. After cooling to room temperature, the reaction was diluted with saturated brine (30 mL) and extracted with dichloromethane (30 mL). The organic layer was dried over sodium sulfate, filtered and concentrated under reduced pressure. The crude product was pre-absorbed onto silica gel (1 g) and purified on an Interchim automated chromatography system (Sorbtech 40 g silica gel cartridge), eluting with a gradient of 0 to 5% methanol in dichloromethane to give a tan solid (0.265 g, 90% yield). Analysis: LCMS m/z=586 (M+H); $^1$H NMR (400 MHz, CDCl3) δ 8.51-8.39 (m, 2H), 8.34 (br d, J=2.2 Hz, 1H), 7.77 (br dd, J=2.5, 8.7 Hz, 1H), 7.46 (br dd, J=3.5, 9.1 Hz, 1H), 7.24-7.16 (m, 3H), 7.16-7.12 (m, 1H), 6.84-6.78 (m, 1H), 6.09 (q, J=6.8 Hz, 1H), 5.70-5.55 (m, 1H), 4.03 (br s, 1H), 3.72 (br s, 1H), 3.41 (s, 6H), 2.52 (br d, J=8.7 Hz, 1H), 2.14 (br s, 1H), 2.03 (br s, 1H), 1.83 (br d, J=6.6 Hz, 3H), 1.74 (br s, 2H), 1.63 (br s, 1H).

Step 6. ([5-[(E)-2-[5-[(1R)-1-(3,5-dichloro-4-pyridyl) ethoxy]-1H-indazol-3-yl]vinyl]-2-pyridyl]imino-dimethyl-oxo-λ$^6$-sulfane. Step 5 product (0.265 g, 0.452 mmol, 1 equiv) was treated with 4N HCl in 1-4 dioxane (4×0.45 mL, 4×1.8 mmol, 4×4 equiv), which was added in 3 h intervals at room temperature. The reaction mixture was stirred for 16 hours. The reaction mixture was adjusted to pH 8 with saturated sodium bicarbonate and extracted with dichloromethane (3×10 mL). The combined organic layers were dried over sodium sulfate, filtered and concentrated under reduced pressure. The crude product was pre-absorbed onto silica gel (1 g) and purified on an Interchim automated chromatography system (Sorbtech 40 g silica gel cartridge), eluting with a gradient of 0 to 6% methanol in dichloromethane to give a solid, which was triturated with hexanes (5 mL), filtered, washed with diethyl ether (10 mL), and dried under high vacuum for 16 h to give a beige foam (77 mg, 34% yield). Analysis: LCMS: m/z=502 (M+H); $^1$H NMR (400 MHz, CDCl3) δ 10.16 (br s, 1H), 8.45 (s, 2H), 8.35 (d, J=2.2 Hz, 1H), 7.78 (dd, J=2.4, 8.6 Hz, 1H), 7.35 (d, J=9.0 Hz, 1H), 7.25-7.08 (m, 4H), 6.82 (d, J=8.4 Hz, 1H), 6.09 (q, J=6.7 Hz, 1H), 3.41 (s, 6H), 1.83 (d, J=6.6 Hz, 3H).

Example 4. ([5-[(E)-2-[5-[(1S)-1-(3,5-dichloro-4-pyridyl)ethoxy]-1H-indazol-3-yl]vinyl]-2-pyridyl] imino-dimethyl-oxo-λ$^6$-sulfane

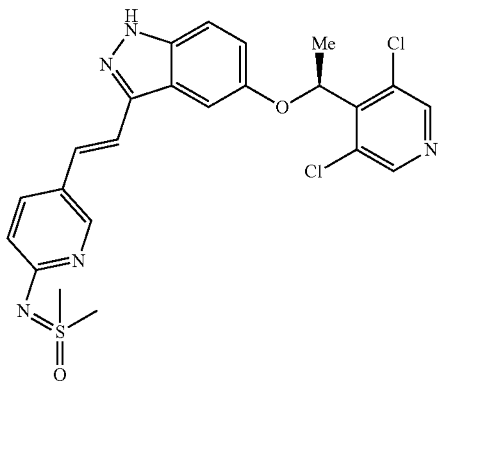 [SMILES: C[C@H](Oc1ccc2[nH]nc(/C=C/c3ccc(N=S(C)(C)=O)nc3)c2c1)c1c(Cl)cncc1Cl]

Step 1. ((5-((E)-2-(5-((S)-1-(3,5-Dichloropyridin-4-yl) ethoxy)-1-(tetrahydro-2H-pyran-2-yl)-1H-indazol-3-yl)vinyl)pyridin-2-yl)imino)dimethyl-λ$^6$-sulfanone. A solution of (E)-((5-(2-(5-hydroxy-1-(tetrahydro-2H-pyran-2-yl)-1H-indazol-3-yl)vinyl)pyridin-2-yl) imino)dimethyl-λ$^6$-sulfanone (0.208 g, 0.506 mmol, 1 equiv), and cesium carbonate (0.173 g, 0.532 mmol, 1.05 equiv) in an anhydrous acetonitrile (5 mL) was heated to 60° C. as [(1R)-1-(3,5-dichloro-4-pyridyl)ethyl] methanesulfonate (0.146 g, 0.54 mmol, 1.07 equiv) was added. The reaction was heated at 60° C. for 20 h. After cooling to room temperature, the reaction was diluted with saturated brine (30 mL) and extracted with dichloromethane (30 mL). The organic layer was dried over sodium sulfate, filtered and concentrated under reduced pressure. The crude product was pre-absorbed onto silica gel (1 g) and purified on an Interchim automated chromatography system (Sorbtech 40 g silica gel cartridge), eluting with a gradient of 0 to 5% methanol in dichloromethane to give a tan solid (0.250 g, 84% yield). Analysis: LCMS: m/z=413 (M+H); $^1$H NMR (400 MHz, CDCl3) δ 8.43 (s, 2H), 8.34 (d, J=2.4 Hz, 1H), 7.77 (dd, J=2.4, 8.6 Hz, 1H), 7.46 (dd, J=3.5, 9.0 Hz, 1H), 7.25-7.18 (m, 3H), 7.13 (dd, J=2.3, 9.0 Hz, 1H), 6.81 (d, J=8.6 Hz, 1H), 6.09 (q, J=6.6 Hz, 1H), 5.61 (ddd, J=2.6, 5.7, 9.4 Hz, 1H), 4.07-4.00 (m, 1H), 3.75-3.67 (m, 1H), 3.43-3.39 (m, 6H), 2.51 (br d, J=9.4 Hz, 1H), 2.13 (br s, 1H), 2.05-1.98 (m, 1H), 1.84-1.82 (m, 3H), 1.78-1.70 (m, 2H), 1.65-1.61 (m, 1H).

Step 2. ([5-[(E)-2-[5-[(1R)-1-(3,5-dichloro-4-pyridyl) ethoxy]-1H-indazol-3-yl] vinyl]-2-pyridyl]imino-dimethyl-oxo-λ$^6$-sulfane. The product from step 1 (0.250 g, 0.43 mmol, 1 equiv) in methanol (5 mL) was treated with 4N HCl in 1-4 dioxane (0.85 mL, 3.4 mmol, 8 equiv). The reaction mixture was stirred for 16 hours. Additional 4N HCl in 1-4 dioxane (0.43 mL, 1.7 mmol, 4 equiv) was added and the reaction mixture was stirred for 4 hours. The reaction mixture was adjusted to pH 8 with saturated sodium bicarbonate and extracted with dichloromethane (3×10 mL). The combined organic layers were dried over sodium sulfate, filtered and concentrated under reduced pressure. The crude product was pre-absorbed onto silica gel (1 g) and purified on an Interchim automated chromatography system (Sorbtech 40 g silica gel cartridge), eluting with a gradient of 0 to 6% methanol in dichloromethane to give a solid that was triturated with diethyl ether (10 mL), filtered, washed with diethyl ether (3×3 mL), and dried under high vacuum for 16 hours to give a beige foam (62 mg, 29% yield). Analysis: LCMS: m/z=502 (M+H); $^1$H NMR (400 MHz, CDCl3) δ 10.30 (br s, 1H), 8.44 (s, 2H), 8.35 (d, J=2.2 Hz, 1H), 7.78 (dd, J=2.4, 8.6 Hz, 1H), 7.35 (d, J=9.0 Hz, 1H), 7.25-7.08 (m, 4H), 6.82 (d, J=8.6 Hz, 1H), 6.09 (q, J=6.7 Hz, 1H), 3.41 (d, J=1.0 Hz, 6H), 1.83 (d, J=6.6 Hz, 3H).

Example 5. 5-[1-(3,5-dichloro-4-pyridyl)ethoxy]-N-[4-[[dimethyl(oxo)-λ$^6$-sulfanylidene] amino]phenyl]-1H-indazole-3-carboxamide

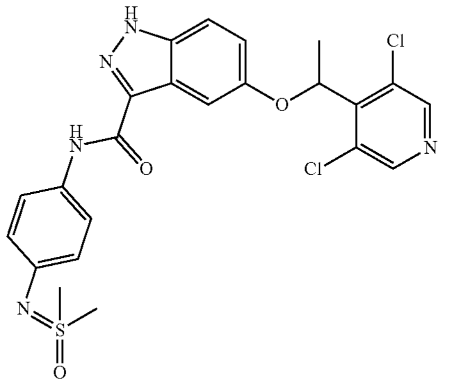 [SMILES: CC(Oc1ccc2[nH]nc(C(=O)Nc3ccc(N=S(C)(C)=O)cc3)c2c1)c1c(Cl)cncc1Cl]

Step 1. 5-(1-(3,5-Dichloropyridin-4-yl)ethoxy)-N-(4-((dimethyl(oxo)-λ$^6$-sulfaneylidene)amino)phenyl)-1-(tetrahydro-2H-pyran-2-yl)-1H-indazole-3-carboxamide. 1-Bis (dimethylamino)methylene]-1H-1,2,3-triazolo[4,5-b] pyridinium 3-oxid hexafluorophosphate (210 mg, 0.55 mmol, 1.2 equiv) and diisopropylethylamine (0.23 mL, 1.35 mmol, 3.0 equiv) were sequentially added at room temperature to a solution of 5-[1-(3,5-dichloro-4-pyridyl)ethoxy]-1-tetrahydropyran-2-yl-indazole-3-carboxylic acid (200 mg, 0.46 mmol, 1.0 equiv) in N,N-dimethylformamide (5 mL). After stirring for 30 minutes, 4-[[dimethyl(oxo)-λ$^6$-sulfanylidene]amino]aniline (130 mg, 0.55 mmol, 1.2 equiv) was added and the reaction was stirred for 16 hours. The reaction mixture was diluted with water (5 mL) and extracted with ethyl acetate (3×30 mL) The combined organic layer was dried over sodium sulfate, filtered and concentrated under reduced pressure. The crude product was purified on a Büchi automated chromatography system (Sorbtech 25 g silica gel column), eluting with a gradient of 0 to 5% methanol in dichloromethane to give a light brown oil (370 mg, >100% yield). Analysis: LCMS: m/z=618.2 (M+H).

Step 2. 5-[1-(3,5-dichloro-4-pyridyl)ethoxy]-N-[4-[[dimethyl(oxo)-λ$^6$-sulfanylidene] amino]phenyl]-1H-indazole-3-carboxamide. A solution of the product from step 1 (360 mg, 1.2 mmol, 1 equiv) in 1,4-dioxane (1.0 mL) was treated with 4M HCl in 1,4-dioxane (2.4 mL, 9.5 mmol, 8.0 equiv). After stirring at room temperature for 16 hours the volatiles were removed under reduced pressure. The residue was suspended in saturated sodium bicarbonate (30 mL) and extracted with ethyl acetate (3×30 mL). The combined organic layers were dried over sodium sulfate, filtered and concentrated under reduced pressure. The residue was purified on a Büchi automated chromatography system (Sorbtech 25 g silica gel column), eluting with a gradient of 0 to 5% methanol in dichloromethane to give a white solid (175 mg, 74% yield). Analysis: LCMS: m/z=518.1 (M+H); $^1$H NMR (400 MHz, DMSO-d6) δ 13.59 (s, 1H), 9.96 (s, 1H), 8.59 (s, 2H), 7.65-7.60 (m, 2H), 7.55 (d, J=9.0 Hz, 1H), 7.50 (d, J=2.3 Hz, 1H), 7.15 (dd, J=2.4, 9.0 Hz, 1H), 6.93-6.87 (m, 2H), 6.07 (q, J=6.6 Hz, 1H), 3.20 (s, 6H), 1.75 (d, J=6.6 Hz, 3H).

Example 6. 5-(1-(3,5-Dichloropyridin-4-yl)ethoxy)-N-(6-(S-methylsulfonimidoyl) pyridine-3-yl)-1H-indazole-3-carboxamide

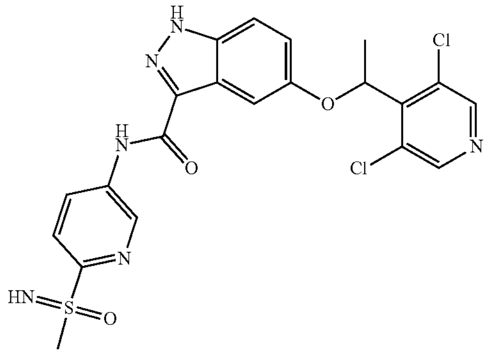 [SMILES: CC(Oc1ccc2[nH]nc(C(=O)Nc3ccc(S(C)(=N)=O)nc3)c2c1)c1c(Cl)cncc1Cl]

Step 1. 5-(1-(3,5-Dichloropyridin-4-yl)ethoxy)-N-(6-(methylthio)pyridin-3-yl)-1-(tetrahydro-2H-pyran-2-yl)-1H-indazole-3-carboxamide. A solution of 5-[1-(3,5-dichloro-4-pyridyl)ethoxy]-1-tetrahydropyran-2-yl-indazole-3-carboxylic acid (200 mg, 0.46 mmol, 1.0 equiv), 1-[bis (dimethylamino)methylene]-1H-1,2,3-triazolo[4,5-b] pyridinium 3-oxid hexafluorophosphate (210 mg, 0.55 mmol, 1.2 equiv) and diisopropylethylamine (0.23 mL, 1.35 mmol, 3.0 equiv) in N,N-dimethylformamide (5 mL) was stirred at room temperature for 30 minutes. 6-Methylsulfanylpyridin-3-amine (77 mg, 0.55 mmol, 1.2 equiv) was added to the solution and stirred for 16 hours. The reaction mixture was diluted with water (5 mL) and extracted with ethyl acetate (3×30 mL) The combined organic layers were dried over sodium sulfate, filtered and concentrated under reduced pressure. The crude product was purified on a Büchi automated chromatography system (Sorbtech 25 g silica gel column), eluting with a gradient of 0 to 5% methanol in dichloromethane to give a light brown oil (160 mg, 62% yield). Analysis: LCMS: m/z=559.4 (M+H).

Step 2. 5-(1-(3,5-Dichloropyridin-4-yl)ethoxy)-N-(6-(S-methylsulfonimidoyl) pyridin-3-yl)-1-(tetrahydro-2H-pyran-2-yl)-1H-indazole-3-carboxamide. Ammonium acetate (33 mg, 0.43 mmol, 1.5 equiv) and (diacetoxyiodo) benzene (190 mg, 0.60 mmol, 2.1 equiv) were sequentially added to a solution of the product from step 1 (160 mg, 0.29 mmol, 1.0 equiv) in methanol (5 mL) and 1,4-dioxane (5 mL. After stirring at room temperature for 16 hours, additional ammonium acetate (33 mg, 0.43 mmol, 1.5 equiv) and (diacetoxyiodo)benzene (190 mg, 0.60 mmol, 2.1 equiv) were added and the reaction was stirred for another 16 hours. The reaction mixture was concentrated under reduced pressure. The crude product was purified on a Büchi automated chromatography system (Sorbtech 25 g silica gel column), eluting with a gradient of 0 to 5% methanol in dichloromethane to give as a pale-yellow oil (150 mg, 89% yield). Analysis: LCMS: m/z=589.5 (M+H).

Step 3. 5-(1-(3,5-Dichloropyridin-4-yl)ethoxy)-N-(6-(S-methylsulfonimidoyl) pyridin-3-yl)-1H-indazole-3-carboxamide. 4M HCl in 1,4-dioxane (0.67 mL, 2.71 mmol, 8.0 equiv) was added to a solution of product from step 2 (200 mg, 0.34 mmol, 1.0 equiv) in 1,4-dioxane (1.0 mL). After stirring at room temperature for 16 hours the volatiles were removed under reduced pressure the residue was purified on an Büchi automated chromatography system (Sorbtech 25 g silica gel column), eluting with a gradient of 0 to 5% methanol in dichloromethane to give a white solid (60 mg, 50% yield). Analysis: LCMS: m/z=505.1 (M+H); $^{1}$H NMR (400 MHz, DMSO-d6) δ=13.84 (br s, 1H), 10.86 (s, 1H), 9.13 (d, J=2.0 Hz, 1H), 8.60 (s, 2H), 8.54 (dd, J=2.4, 8.6 Hz, 1H), 8.07 (d, J=8.7 Hz, 1H), 7.60 (d, J=9.2 Hz, 1H), 7.51 (d, J=2.3 Hz, 1H), 7.18 (dd, J=2.4, 9.1 Hz, 1H), 6.08 (q, J=6.7 Hz, 1H), 4.29 (s, 1H), 3.15 (s, 3H), 1.76 (d, J=6.6 Hz, 3H).

Example 7. 5-[1-(3,5-dichloro-4-pyridyl)ethoxy]-N-[3-[[dimethyl(oxo)-λ$^{6}$-sulfanylidene] amino]phenyl]-1H-indazole-3-carboxamide

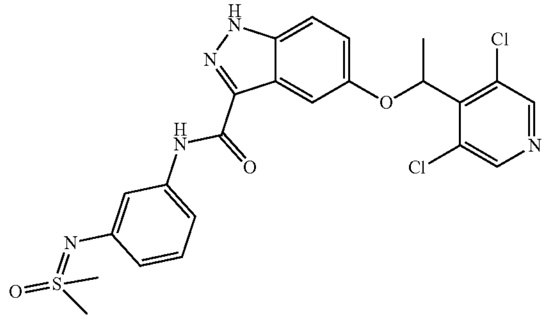 [SMILES: CC(Oc1ccc2[nH]nc(C(=O)Nc3cccc(N=S(C)(C)=O)c3)c2c1)c1c(Cl)cncc1Cl]

This example was synthesized using the procedure for Example 5 with 3-[[dimethyl(oxo)-λ$^{6}$-sulfanylidene]amino] aniline in step 1. Deprotection of the THP intermediate (240 mg, 0.4 mmol, 1 equiv) gave a white solid (142 mg, 69% yield). Analysis: LCMS: m/z=518.1 (M+H); $^{1}$H NMR (400 MHz, DMSO-d6) δ 13.62 (s, 1H), 10.00 (s, 1H), 8.59 (s, 2H), 7.56 (d, J=9.0 Hz, 1H), 7.50 (d, J=2.3 Hz, 1H), 7.46 (t, J=2.0 Hz, 1H), 7.35 (ddd, J=0.9, 1.8, 8.1 Hz, 1H), 7.18-7.09 (m, 2H), 6.65 (ddd, J=0.9, 2.1, 7.9 Hz, 1H), 6.07 (q, J=6.6 Hz, 1H), 3.26 (s, 6H), 1.76 (d, J=6.7 Hz, 3H).

Example 8. 5-[1-(3,5-dichloro-4-pyridyl)ethoxy]-N-[6-[[dimethyl(oxo)-λ$^{6}$-sulfanylidene] amino]-3-pyridyl]-1H-indazole-3-carboxamide

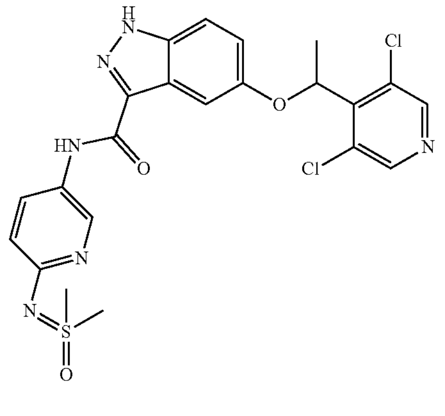 [SMILES: CC(Oc1ccc2[nH]nc(C(=O)Nc3ccc(N=S(C)(C)=O)nc3)c2c1)c1c(Cl)cncc1Cl]

Step 1. N-(6-Bromopyridin-3-yl)-5-(1-(3,5-dichloropyridin-4-yl)ethoxy)-1-(tetrahydro-2H-pyran-2-yl)-1H-indazole-3-carboxamide. 1-[Bis(dimethylamino)methylene]-1H-1,2,3-triazolo[4,5-b]pyridinium 3-oxid hexafluorophosphate (310 mg, 0.83 mmol, 1.2 equiv) and diisopropylethylamine (0.36 mL, 2.07 mmol, 3.0 equiv) were sequentially added at room temperature to a solution of 5-[1-(3,5-dichloro-4-pyridyl)ethoxy]-1-tetrahydropyran-2-yl-indazole-3-carboxylic acid (300 mg, 0.69 mmol, 1.0 equiv) in N,N-dimethylformamide (5 mL). After stirring for 30 minutes, 6-bromopyridin-3-amine (143 mg, 0.83 mmol, 1.2 equiv) was added and the reaction was stirred for 16 h. The reaction mixture was diluted with water (5 mL) and the resulting solids were filtered to give a white solid (350 mg, 88% yield). Analysis: LCMS: m/z=589.1 (M+H).

Step 2. 5-(1-(3,5-Dichloropyridin-4-yl)ethoxy)-N-(6-((dimethyl(oxo)-λ$^{6}$-sulfaneylidene)amino)pyridin-3-yl)-1-(tetrahydro-2H-pyran-2-yl)-1H-indazole-3-carboxamide. A solution of the product from step 1 (450 mg, 0.76 mmol, 1.0 equiv), S,S-dimethylsulfoximine (85 mg, 0.91 mmol, 1.2 equiv), Xantphos (44 mg, 0.08 mmol, 0.1 equiv), tris(dibenzylideneacetone)-dipalladium(0) (34 mg, 0.04 mmol, 0.05 equiv) and cesium carbonate (345 mg, 1.07 mmol, 1.4 equiv) in 1,4-dioxane (10 mL) was sparged with nitrogen for 15 minutes. After heating at 100° C. for 3 h, the reaction was cooled to room temperature and filtered through Celite. The filtrate was concentrated under reduced pressure. The residue was suspended in saturated sodium bicarbonate (30 mL) and extracted with ethyl acetate (3×30 mL). The combined organic layers were dried over sodium sulfate, filtered and concentrated under reduced pressure. The residue was purified on a Büchi automated chromatography system (Sorbtech 25 g silica gel column), eluting with a gradient of 0 to 5% methanol in dichloromethane to give a light brown oil (390 mg, 87% yield). Analysis: LCMS: m/z=602.1 (M+H).

Step 3. 5-[1-(3,5-dichloro-4-pyridyl)ethoxy]-N-[6-[[dimethyl(oxo)-λ$^{6}$-sulfanylidene]amino]-3-pyridyl]-1H-indazole-3-carboxamide. A solution of step 2 (390 mg, 0.4 mmol, 1 equiv) in 1,4-dioxane (1.0 mL) was treated with 4M HCl in 1,4-dioxane (0.8 mL, 3.2 mmol, 8.0 equiv). After stirring at room temperature for 16 h, the volatiles were removed under reduced pressure. The residue was suspended in saturated sodium bicarbonate solution (30 mL) and extracted with ethyl acetate (3×30 mL). The combined organic layers were dried over sodium sulfate, filtered and concentrated under reduced pressure. The residue was purified on a Büchi automated chromatography system (Sorbtech 25 g silica gel column), eluting with a gradient of 0 to 3% methanol in dichloromethane to give a pale yellow solid (96 mg, 21% yield). Analysis: LCMS: m/z=519.1 (M+H); $^{1}$H NMR (400 MHz, DMSO-d6) δ 13.65 (s, 1H), 10.16 (s, 1H), 8.59 (s, 2H), 8.52 (d, J=2.6 Hz, 1H), 7.95 (dd, J=2.8, 8.7 Hz, 1H), 7.56 (d, J=9.0 Hz, 1H), 7.49 (d, J=2.3 Hz, 1H), 7.15 (dd, J=2.4, 9.0 Hz, 1H), 6.65 (d, J=8.8 Hz, 1H), 6.06 (q, J=6.6 Hz, 1H), 3.38-3.35 (m, 6H), 1.75 (d, J=6.7 Hz, 3H).

Example 9. [5-[(E)-2-[5-[(1R)-1-(3,5-dichloro-4-pyridyl)ethoxy]-1H-indazol-3-yl]vinyl]-2-pyridyl]-imino-methyl-oxo-λ$^6$-sulfane

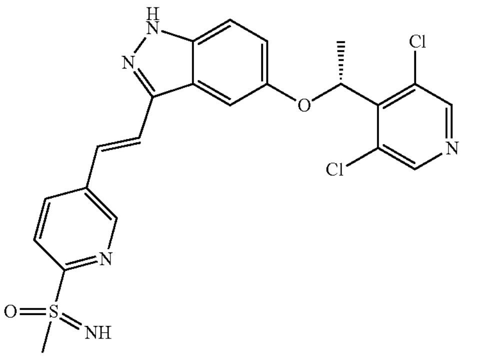 [SMILES: C[C@@H](Oc1ccc2[nH]nc(/C=C/c3ccc(S(C)(=N)=O)nc3)c2c1)c1c(Cl)cncc1Cl]

[5-[(E)-2-[5-[(1R)-1-(3,5-dichloro-4-pyridyl)ethoxy]-1H-indazol-3-yl]vinyl]-2-pyridyl]-imino-methyl-oxo-λ$^6$-sulfane was synthesized according to the scheme shown below:

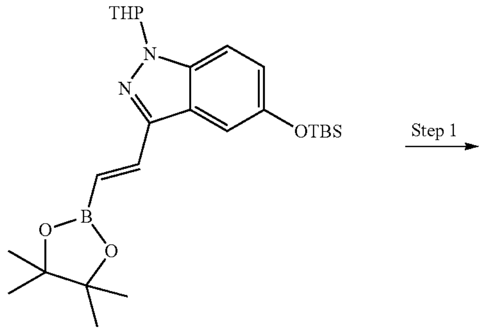

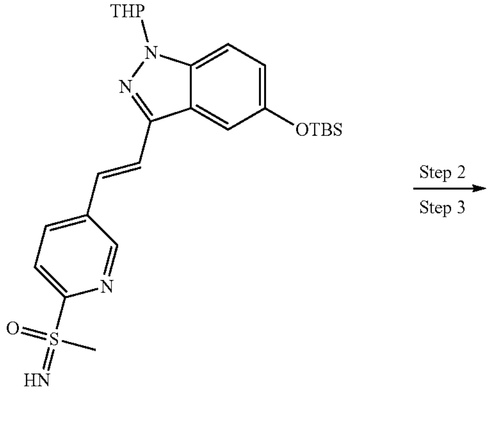

-continued

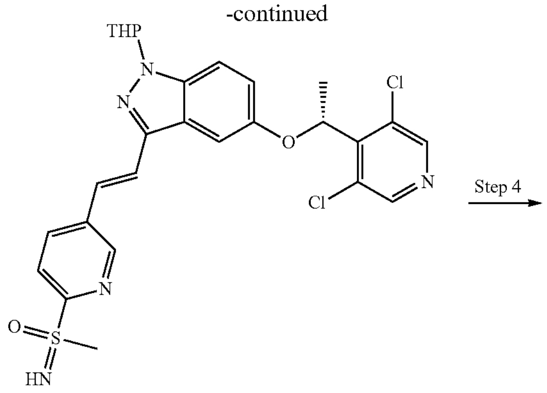

Example 9

Step 1. tert-butyl-dimethyl-[3-[(E)-2-[6-(methylsulfonimidoyl)-3-pyridyl]vinyl]-1-tetrahydropyran-2-yl-indazol-5-yl]oxy-silane. A solution of (E)-5-((tert-butyldimethylsilyl) oxy)-1-(tetrahydro-2H-pyran-2-yl)-3-(2-(4,4,5,5-tetramethyl-1,3,2-dioxaborolan-2-yl)vinyl)-1H-indazole (0.63 g, 1.3 mmol, 1 equiv) and (5-bromo-2-pyridyl)-imino-methyl-oxo-λ$^6$-sulfane (0.34 g, 1.44 mmol, 1.1 equiv) in 4 to 1 mixture of 1,4-dioxane and water (50 mL) was sparged with nitrogen for 20 minutes. Potassium carbonate (0.54 g, 3.93 mmol, 3 equiv) and (1,1'-bis(diphenylphosphino) ferrocene palladium(II) dichloride (0.096 g, 0.13 mmol, 0.1 equiv) were added and the reaction was sparged with nitrogen for another 5 minutes. The reaction was heated at 90° C. for 2 h. After cooling to room temperature, the reaction was concentrated under reduced pressure. The residue was diluted with water (30 mL) and dichloromethane (30 mL). The layers were separated and the organic layer was dried over sodium sulfate, filtered and concentrated under reduced pressure. The crude product was pre-absorbed onto silica gel (2 g) and purified on an Interchim automated chromatography system (Sorbtech 40 g silica gel cartridge), eluting with a gradient of 0 to 10% methanol in dichloromethane to give a mixture of THP protected (0.32 g, 29% yield; LCMS: m/z=513 (M+H)) and deprotected compound (150 mg, 18% yield; LCMS: m/z=399 (M+H) as yellow solid.

Step 2. (E)-(5-(2-(5-Hydroxy-1-(tetrahydro-2H-pyran-2-yl)-1H-indazol-3-yl)vinyl) pyridin-2-yl)(imino)(methyl)-λ$^6$-sulfanone. 1M Tetrabutylammonium fluoride in THF (0.68 mL, 0.68 mmol, 1.1 equiv) was added dropwise at 0° C. to a solution of step 1 product (0.32 g, 0.625 mmol, 1 equiv) in anhydrous THF (5 mL). The reaction was warmed to room temperature and stirred for 1 hour. The reaction was diluted with saturated brine (30 mL) and extracted with dichloromethane (30 mL). The organic layer was dried over sodium sulfate, filtered and concentrated under reduced pressure. The crude product was pre-absorbed onto silica gel (1 g) and purified on an Interchim automated chromatography system (Sorbtech 40 g silica gel cartridge), eluting with a gradient of 0 to 10% methanol in dichloromethane to give a tan solid (0.098 g, 39% yield). Analysis: LCMS: m/z=399 (M+H).

Step 3. (5-((E)-2-(5-((R)-1-(3,5-Dichloropyridin-4-yl) ethoxy)-1-(tetrahydro-2H-pyran-2-yl)-1H-indazol-3-yl)vinyl)pyridin-2-yl)(imino)(methyl)-λ$^6$-sulfanone. A solution of step 2 product (0.098 g, 0.236 mmol, 1 equiv) and cesium carbonate (0.084 g, 0.258 mmol, 1.05 equiv) in a mixture of acetonitrile (4 mL) and N,N-dimethylformamide (7 mL) was heated to 60° C. (S)-1-(3,5-Dichloropyridin-4-yl)ethyl methanesulfonate (0.007 g, 0.026 mmol, 0.11 equiv) and cesium carbonate (0.084 g, 0.258 mmol, 1.05 equiv) was added. The reaction was heated at 60° C. for 3 hours. After cooling to room temperature additional mesylate (0.07 g, 0.258 mmol, 1.05 equiv) and cesium carbonate (0.008 g, 0.026 mmol, 0.11 equiv) were added and the reaction was heated at 60° C. for another 3 hours. After cooling to room temperature, the reaction was diluted with saturated brine (30 mL) and extracted with dichloromethane (30 mL). The organic layer was dried over sodium sulfate, filtered and concentrated under reduced pressure. The crude product was pre-absorbed onto silica gel (1 g) and purified on an Interchim automated chromatography system (Sorbtech 40 g silica gel cartridge), eluting with a gradient of 0 to 10% methanol in dichloromethane to give a tan solid (0.12 g, 85% yield). Analysis: LCMS: m/z=572 (M+H).

Step 4. (5-((E)-2-(5-((R)-1-(3,5-Dichloropyridin-4-yl) ethoxy)-1H-indazol-3-yl) vinyl) pyridin-2-yl)(imino) (methyl)-λ$^6$-sulfanone. The product from step 3 (0.1 g, 0.18 mmol, 1 equiv) was dissolved in 1 to 1 mixture of methanol and THF (10 mL) and 4N HCl in 1,4-dioxane (0.36 mL, 1.43 mmol, 8 equiv) was added dropwise at room temperature. After stirring for 2 hours, additional 4N HCl in 1,4-dioxane (0.36 mL, 1.43 mmol, 8 equiv) was added. After stirring for another 2.5 hours, the reaction was quenched with saturated sodium bicarbonate (10 mL) and extracted with dichloromethane (3×10 mL). The combined organic layers were dried over sodium sulfate, filtered and concentrated under reduced pressure. The crude product was pre-absorbed onto silica gel (1 g) and purified on an Interchim automated chromatography system (Sorbtech 40 g silica gel cartridge), eluting with a gradient of 0 to 10% methanol in dichloromethane to give a yellow solid (40 mg, 49% yield). Analysis: LCMS: m/z=488 (M+H); $^1$H NMR (400 MHz, DMSO-d6) δ 13.28 (br s, 1H), 8.97 (d, J=2.0 Hz, 1H), 8.61 (s, 2H), 8.39 (dd, J=2.1, 8.3 Hz, 1H), 8.09 (d, J=8.2 Hz, 1H), 7.74 (d, J=16.9 Hz, 1H), 7.49 (d, J=8.9 Hz, 1H), 7.42 (d, J=1.8 Hz, 1H), 7.33 (d, J=16.8 Hz, 1H), 7.10 (dd, J=2.3, 9.0 Hz, 1H), 6.18 (q, J=6.7 Hz, 1H), 4.42 (s, 1H), 3.20 (d, J=1.0 Hz, 3H), 1.79 (d, J=6.7 Hz, 3H).

Example 10. [5-[(E)-2-[5-[(1S)-1-(3,5-dichloro-4-pyridyl)ethoxy]-1H-indazol-3-yl]vinyl]-2-pyridyl]-imino-methyl-oxo-λ$^6$-sulfane

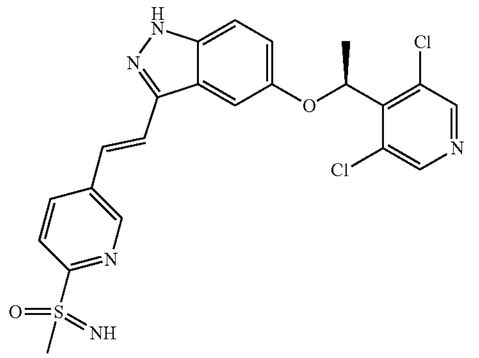 [SMILES: C[C@H](Oc1ccc2[nH]nc(/C=C/c3ccc(S(C)(=N)=O)nc3)c2c1)c1c(Cl)cncc1Cl]

This example was synthesized using the method for Example 9 with (R)-1-(3,5-dichloropyridin-4-yl)ethyl methanesulfonate. LCMS: m/z=488 (M+H).

Example 11. (S)-4-(5-(5-(1-(3,5-Dichloropyridin-4-yl)ethoxy)-1H-indazol-3-yl)pyridin-2-yl)-1-imino-1λ$^6$-thiomorpholine 1-oxide

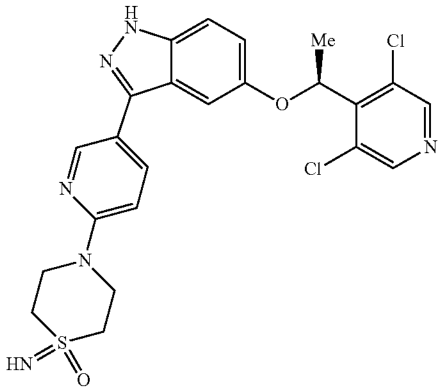 [SMILES: C[C@H](Oc1ccc2[nH]nc(-c3ccc(N4CCS(=N)(=O)CC4)nc3)c2c1)c1c(Cl)cncc1Cl]

(S)-4-(5-(5-(1-(3,5-Dichloropyridin-4-yl)ethoxy)-1H-indazol-3-yl)pyridin-2-yl)-1-imino-1λ$^6$-thiomorpholine 1-oxide was synthesized according to the scheme shown below:

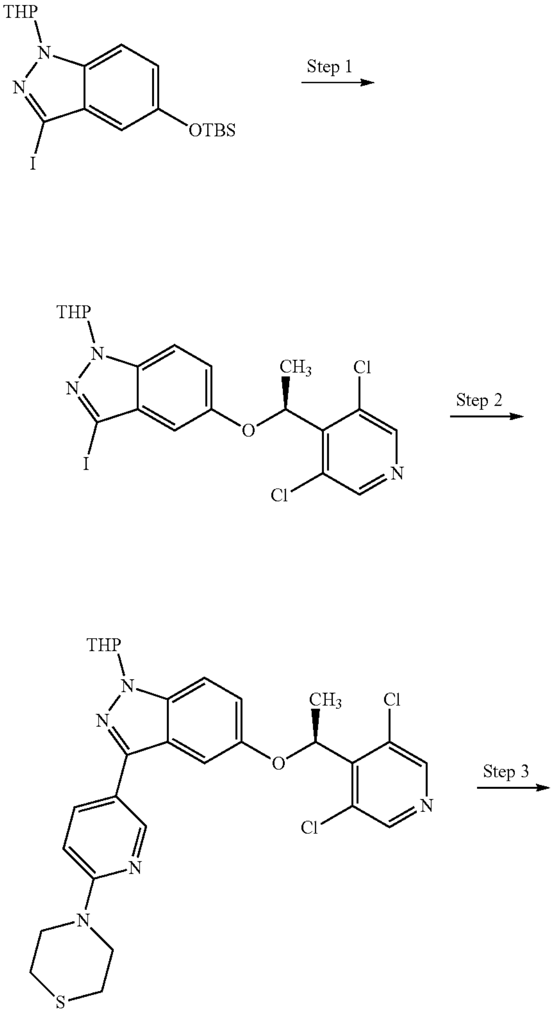

-continued

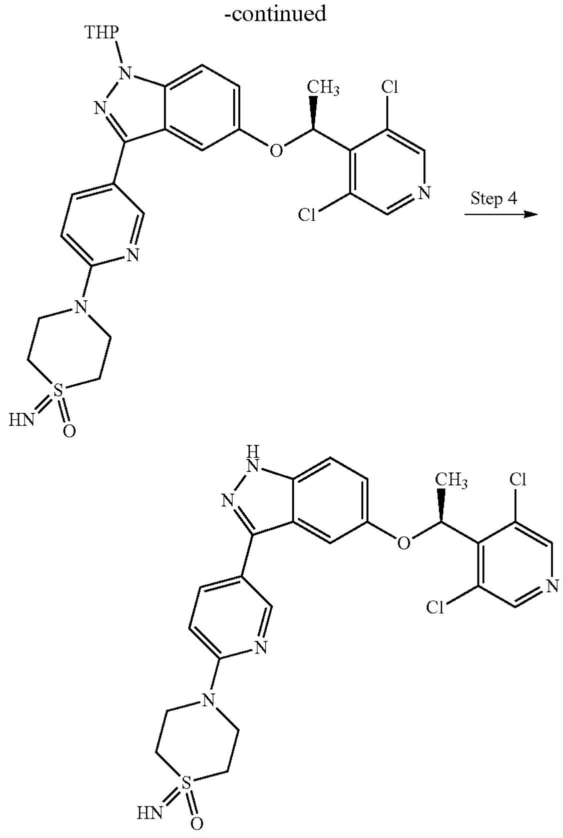

Example 11

Step 1. 5-((S)-1-(3,5-Dichloropyridin-4-yl)ethoxy)-3-iodo-1-(tetrahydro-2H-pyran-2-yl)-1H-indazole. A mixture of 3-iodo-1-tetrahydropyran-2-yl-indazol-5-ol (1.0 g, 2.90 mmol, 1.0 equiv), (R)-1-(3,5-dichloropyridin-4-yl)ethyl methanesulfonate (780 mg, 2.90 mmol, 1.0 equiv) and cesium carbonate (1.41 g, 14.45 mmol, 1.5 equiv) in N,N-dimethylformamide (20 mL) was heated at 130° C. for 16 h. After cooling to room temperature, the volatiles were removed under reduced pressure and the resulting crude was suspended in saturated ammonium chloride solution (50 mL). The solution was extracted with ethyl acetate (3×50 mL). The combined organic layers were dried over sodium sulfate, filtered and concentrated under reduced pressure. The crude product was purified on a Büchi automated chromatography system (Sorbtech 40 g silica gel column), eluting with a gradient of 0 to 30% ethyl acetate in heptanes to give a white solid (1.36 g, 91% yield). Analysis: LCMS: m/z=517.2 (M+H).

Step 2. 4-(5-(5-((S)-1-(3,5-Dichloropyridin-4-yl)ethoxy)-1-(tetrahydro-2H-pyran-2-yl)-1H-indazol-3-yl)pyridin-2-yl) thiomorpholine. A solution of product step 1 (250 mg, 0.49 mmol, 1.0 equiv), 4-[5-(4,4,5,5-tetramethyl-1,3,2-dioxaborolan-2-yl)-2-pyridyl] thiomorpholine (160 mg, 0.53 mmol, 1.1 equiv), [1,1' bis(diphenylphosphino) ferrocene] dichloropalladium(II) (36 mg, 0.048 mmol, 0.1 equiv) and potassium carbonate (133 mg, 0.96 mmol, 2.0 equiv) in 1,4-dioxane (10 mL) and water (1 mL) was sparged with nitrogen for 15 minutes. After heating at 80° C. for 16 hours, the reaction was cooled to room temperature and filtered through Celite and the filtrate was concentrated under reduced pressure. The residue was suspended in saturated ammonium chloride (20 mL) and extracted with ethyl acetate (2×30 mL). The combined organic layers were dried over sodium sulfate, filtered and concentrated under reduced pressure. The residue was purified on a Büchi automated chromatography system (Sorbtech 40 g silica gel column), eluting with a gradient of 0 to 30% ethyl acetate in heptanes to give a pale-yellow oil (270 mg, 99% yield). Analysis: LCMS: m/z=570.2 (M+H).

Step 3. 4-(5-(5-((S)-1-(3,5-Dichloropyridin-4-yl)ethoxy)-1-(tetrahydro-2H-pyran-2-yl)-1H-indazol-3-yl)pyridin-2-yl)-1-imino-1λ$^6$-thiomorpholine 1-oxide. Ammonium acetate (56 mg, 0.73 mmol, 1.5 equiv) and (diacetoxyiodo) benzene (324 mg, 1.05 mmol, 2.1 equiv) were sequentially added to a solution of product from step 2 (270 mg, 0.48 mmol, 1.0 equiv) in a mixture of methanol (10 mL) and dichloromethane (5 mL). After stirring at room temperature for 1 hour, the reaction mixture was concentrated under reduced pressure. The residue was purified on a Büchi automated chromatography system (Sorbtech 24 g silica gel column), eluting with a gradient of 0 to 10% methanol in dichloromethane to give an off white solid (52 mg, 19% yield). Analysis: LCMS: m/z=600.1 (M+H).

Step 4. (S)-4-(5-(5-(1-(3,5-Dichloropyridin-4-yl)ethoxy)-1H-indazol-3-yl)pyridin-2-yl)-1-imino-1λ$^6$-thiomorpholine 1-oxide. 4M HCl in 1,4-dioxane (0.2 mL, 0.69 mmol, 8.0 equiv) was added to a solution of product from step 3 (52 mg, 0.09 mmol, 1.0 equiv) in 1,4-dioxane (1.0 mL). After stirring at room temperature for 16 hours the volatiles were removed under reduced pressure. The crude was suspended in saturated sodium bicarbonate solution (30 mL) and extracted with ethyl acetate (3×30 mL). The combined organic layers were dried over sodium sulfate, filtered and concentrated under reduced pressure. The residue was purified on a Büchi automated chromatography system (Sorbtech 24 g silica gel column), eluting with a gradient of 0 to 5% methanol in dichloromethane to give an off white solid (8.2 mg, 18% yield). Analysis: LCMS: m/z=517.1 (M+H)$^1$H NMR (400 MHz, CD3OD) δ 8.54 (d, J=1.8 Hz, 1H), 8.47 (s, 2H), 7.94 (dd, J=2.4, 8.9 Hz, 1H), 7.44 (d, J=9.0 Hz, 1H), 7.16 (dd, J=2.2, 9.0 Hz, 1H), 7.12-7.06 (m, 2H), 6.10 (q, J=6.7 Hz, 1H), 4.37 (td, J=4.5, 15.0 Hz, 2H), 4.11-4.02 (m, 2H), 3.19 (t, J=5.1 Hz, 4H), 1.81 (d, J=6.6 Hz, 3H).

Example 12. (R)-4-(5-(5-(1-(3,5-Dichloropyridin-4-yl)ethoxy)-1H-indazol-3-yl)pyridin-2-yl)-1-imino-1λ$^6$-thiomorpholine 1-oxide

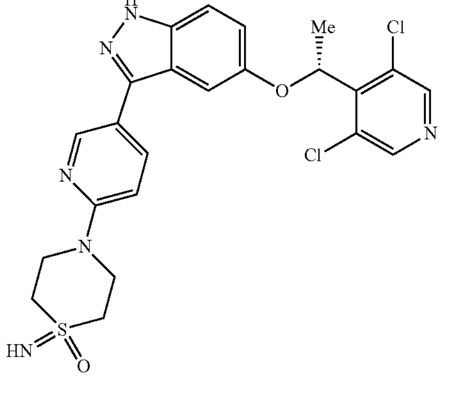

This example was synthesized using the procedure for Example 11 with (S)-1-(3,5-dichloropyridin-4-yl)ethyl methanesulfonate Analysis: LCMS: m/z=517.1 (M+H); $^1$H NMR (400 MHz, DMSO-d6) δ 13.04 (s, 1H), 8.60 (s, 2H), 8.58 (d, J=2.1 Hz, 1H), 7.91 (dd, J=2.4, 8.9 Hz, 1H), 7.47 (d, J=9.0 Hz, 1H), 7.18-7.13 (m, 2H), 7.10 (dd, J=2.3, 8.9 Hz, 1H), 6.10 (q, J=6.6 Hz, 1H), 4.33-4.22 (m, 2H), 3.96-3.87 (m, 2H), 3.82 (s, 1H), 3.10-2.98 (m, 4H), 1.76 (d, J=6.6 Hz, 3H).

Example 13. (R)-4-(4-(5-(1-(3,5-Dichloropyridin-4-yl)ethoxy)-1H-indazol-3-yl)phenyl)-1-imino-1λ$^6$-thiomorpholine 1-oxide

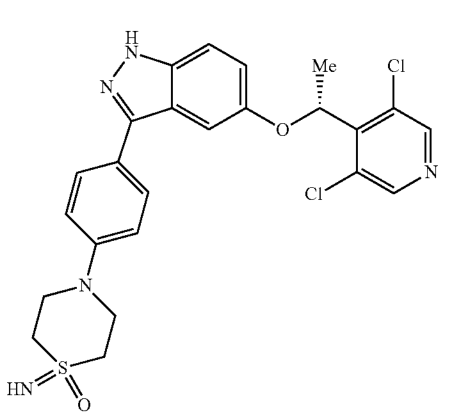 [SMILES: C[C@@H](Oc1ccc2[nH]nc(-c3ccc(N4CCS(=N)(=O)CC4)cc3)c2c1)c1c(Cl)cncc1Cl]

Step 1. 3-(4-Bromophenyl)-5-((R)-1-(3,5-dichloropyridin-4-yl)ethoxy)-1-(tetrahydro-2H-pyran-2-yl)-1H-indazole (55-2): A solution of 5-[(1R)-1-(3,5-dichloro-4-pyridyl) ethoxy]-3-iodo-1-tetrahydropyran-2-yl-indazole (300 mg, 0.58 mmol, 1 equiv) and 4-bromophenylboronic acid (116.3 mg, 0.58 mmol, 1 equiv) in 4 to 1 mixture of 1,4-dioxane and water (12.5 mL) was sparged with nitrogen for 20 minutes. Potassium carbonate (240 mg, 1.74 mmol, 3 equiv) and [1,1' bis(diphenylphosphino)ferrocene]palladium(II) dichloride (20 mg, 0.027 mmol, 0.047 equiv) were added and reaction mixture was sparged with nitrogen for an additional 5 minutes. The reaction was heated at 75° C. for 3 hours. After cooling to room temperature, the reaction was diluted with DI water (30 mL) and dichloromethane (30 mL). The layers were separated. The organic layer was dried over sodium sulfate, filtered and concentrated under reduced pressure. The crude product was pre-absorbed on silica gel (2 g) and purified on an Interchim automated chromatography system (Sorbtech 40 g silica gel cartridge), eluting with a gradient of 0 to 30% ethyl acetate in heptanes to give a yellowish solid (219 mg, 69% yield). Analysis: LCMS: m/z=548 (M+H).

Step 2. 4-(4-(5-((R)-1-(3,5-Dichloropyridin-4-yl)ethoxy)-1-(tetrahydro-2H-pyran-2-yl)-1H-indazol-3-yl)phenyl)-1-imino-1-λ$^6$-thiomorpholine 1-oxide. A solution of product from step 1 (219 mg, 0.4 mmol, 1 equiv) in anhydrous dimethylsulfoxide (4 mL) was sparged with nitrogen for 20 minutes. 1-Imino-1,4-thiazinane 1-oxide (166 mg, 0.8 mmol, 2 equiv), cesium carbonate (1.04 g, 3.2 mmol, 8 equiv) and BINAP Pd(allyl)Cl (34 mg, 0.04 mmol, 0.1 equiv) were added reaction mixture was sparged with nitrogen for an additional 5 minutes. The reaction was heated at 130° C. for 3 hours. After cooling to room temperature, the reaction was diluted with saturated brine (50 mL) and extracted with dichloromethane (30 mL). The aqueous layer was extracted with dichloromethane (2×10 mL). The organic combined layers were dried over sodium sulfate, filtered and concentrated under reduced pressure. The crude product was pre-absorbed on silica gel (2 g) and purified on an Interchim automated chromatography system twice (Sorbtech 40 g silica gel cartridge), eluting with a gradient of 0 to 10% methanol in dichloromethane to give a white solid (50 mg, 21% yield). Analysis: LCMS: m/z=600 (M+H); $^1$H NMR (300 MHz, CDCl3) δ 8.42 (d, J=1.2 Hz, 2H), 7.68-7.64 (dd, J=8.1, 1.8 Hz 2H), 7.49 (dd, J=8.9, 1.8 Hz, 1H), 7.26-7.20 (m, 3H), 7.13 (dd, J=9.0, 2.1 Hz, 1H), 6.05 (q, J=6.3 Hz, 1H), 5.70-5.60 (m, 1H), 4.05 (m, 1H), 3.75 (m, 1H), 3.5-3.3 (m, 6H), 3.2-3.1 (m, 2H), 2.6 (m, 1H), 2.1-2.2 (m, 2H), 1.81 (d, J=6.6 Hz, 3H), 1.7-1.6 (m, 3H).

Step 3. (R)-4-(4-(5-(1-(3,5-Dichloropyridin-4-yl)ethoxy)-1H-indazol-3-yl)phenyl)-1-imino-1λ$^6$-thiomorpholine 1-oxide. 4N HCl in 1,4-dioxane (0.25 mL, 0.83 mmol, 10 equiv) was added to a solution of product from step 2 (50 mg, 0.083 mmol, 1 equiv) in a 1 to 1 mixture of THF and methanol (5 mL). The reaction was stirred at room temperature for 3 h. Additional 4N HCl in 1,4-dioxane (0.25 mL, 0.83 mmol, 10 equiv) was added and the reaction was stirred for another 3 hours. The reaction was cooled to 0° C. and quenched with saturated sodium bicarbonate (50 mL) and extracted with dichloromethane (15 mL). The organic layer was dried over sodium sulfate, filtered and concentrated under reduced pressure. The crude product was pre-absorbed on silica gel (1 g) and purified on an Interchim automated chromatography system (Sorbtech 40 g silica gel cartridge), eluting with a gradient of 0 to 10% methanol in dichloromethane to give a white solid (33 mg, 77% yield). Analysis: LCMS: m/z=516 (M+H); $^1$H NMR (400 MHz, $CDCl_3$) δ 8.43 (s, 2H), 7.71-7.64 (m, 2H), 7.34 (d, J=8.9 Hz, 1H), 7.26-7.20 (m, 3H), 7.13 (dd, J=2.3, 9.0 Hz, 1H), 6.05 (q, J=6.6 Hz, 1H), 3.47-3.39 (m, 2H), 3.38-3.30 (m, 4H), 3.22-3.14 (m, 2H), 1.81 (d, J=6.7 Hz, 3H).

Example 14. (S)-4-(4-(5-(1-(3,5-Dichloropyridin-4-yl)ethoxy)-1H-indazol-3-yl)phenyl)-1-imino-1λ$^6$-thiomorpholine 1-oxide

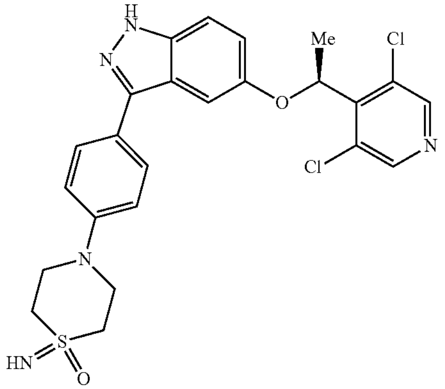 [SMILES: C[C@H](Oc1ccc2[nH]nc(-c3ccc(N4CCS(=N)(=O)CC4)cc3)c2c1)c1c(Cl)cncc1Cl]

This example was synthesize using the procedure for Example 13 with 5-[(1S)-1-(3,5-dichloro-4-pyridyl) ethoxy]-3-iodo-1-tetrahydropyran-2-yl-indazole to give a white solid (23 mg, 45% yield). Analysis: LCMS: m/z=516 (M+H); $^1$H NMR (400 MHz, CDCl3) δ 8.43 (s, 2H), 7.69 (s, 1H), 7.67 (s, 1H), 7.35 (dd, J=0.4, 9.0 Hz, 1H), 7.26-7.22 (m, 2H), 7.21 (d, J=2.2 Hz, 1H), 7.13 (dd, J=2.4, 9.0 Hz, 1H), 6.05 (q, J=6.7 Hz, 1H), 3.47-3.39 (m, 2H), 3.39-3.29 (m, 4H), 3.22-3.14 (m, 2H), 1.82 (d, J=6.6 Hz, 3H).

Example 15. 1-Imino-4-(5-(5-(pyrimidin-4-ylmethoxy)-1H-indazol-3-yl)pyridin-2-yl)-1λ$^6$-thiomorpholine 1-oxide

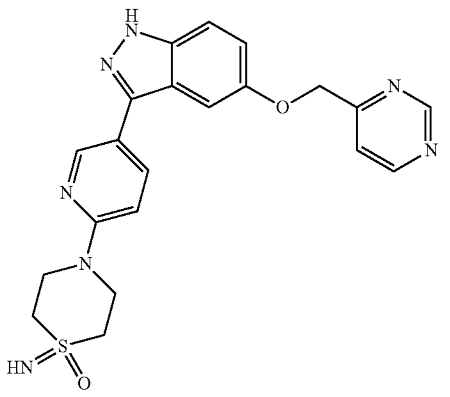 [SMILES: N=S1(=O)CCN(c2ccc(-c3n[nH]c4ccc(OCc5ccncn5)cc34)cn2)CC1]

Step 1. tert-Butyl (1-oxido-4-(5-(5-(pyrimidin-4-ylmethoxy)-1-(tetrahydro-2H-pyran-2-yl)-1H-indazol-3-yl)pyridin-2-yl)-1-λ$^6$-thiomorpholin-1-ylidene)carbamate. A mixture of tert-butyl N-[4-[5-(5-hydroxy-1-tetrahydropyran-2-yl-indazol-3-yl)-2-pyridyl]-1-oxo-1,4-thiazinan-1-ylidene]carbamate (70 mg, 0.13 mmol, 1.0 equiv), pyrimidin-4-ylmethyl methanesulfonate (28 mg, 0.15 mmol, 1.1 equiv) and cesium carbonate (64 mg, 0.2 mmol, 1.5 equiv) in acetonitrile (10 mL) was heated at 80° C. for 16 h. After cooling to room temperature, the volatiles were removed under reduced pressure and the resulting crude was suspended in saturated ammonium chloride (20 mL). The solution was extracted with ethyl acetate (2×25 mL). The combined organic layers were dried over sodium sulfate, filtered and concentrated under reduced pressure. The crude product was purified on a Büchi automated chromatography system (Sorbtech 25 g silica gel column), eluting with a gradient of 0 to 100% ethyl acetate in heptanes to give an off-white solid (64 mg, 78% yield). Analysis: LCMS: m/z=604.2 (M+H).

Step 2. 1-Imino-4-(5-(5-(pyrimidin-4-ylmethoxy)-1H-indazol-3-yl)pyridin-2-yl)-1λ$^6$-thiomorpholine 1-oxide. A solution of step 1 product (64 mg, 0.1 mmol, 1.0 equiv) in 1,4-dioxane (1 mL) was treated with 4M HCl in 1,4-dioxane (0.40 mL, 1.65 mmol, 16.0 equiv). After stirring at room temperature for 16 hours the volatiles were removed under reduced pressure. The residue was suspended in saturated sodium bicarbonate (20 mL) and extracted with ethyl acetate (3×20 mL). The combined organic layers were dried over sodium sulfate, filtered and concentrated under reduced pressure. The residue was purified on a Büchi automated chromatography system (RediSep Rf Gold HP C18, 50 g column), eluting with a gradient of 0 to 50% acetonitrile in water to give an off-white solid (15.6 mg, 35% yield). Analysis: LCMS: m/z=436.2 (M+H); $^1$H NMR (400 MHz, DMSO-d6) δ 13.12 (br s, 1H), 9.20 (d, J=1.0 Hz, 1H), 8.84 (d, J=5.1 Hz, 1H), 8.76 (d, J=2.1 Hz, 1H), 8.13 (dd, J=2.3, 8.9 Hz, 1H), 7.71 (d, J=5.0 Hz, 1H), 7.57-7.48 (m, 2H), 7.21 (dd, J=2.1, 9.0 Hz, 1H), 7.14 (d, J=8.8 Hz, 1H), 5.34 (s, 2H), 4.27 (br d, J=15.2 Hz, 2H), 3.95-3.86 (m, 2H), 3.82 (br s, 1H), 3.08-2.97 (m, 4H).

Example 16. 1-Imino-4-(5-(5-(1-(pyrimidin-4-ylethoxy)-1H-indazol-3-yl)pyridin-2-yl)-1λ$^6$-thiomorpholine 1-oxide

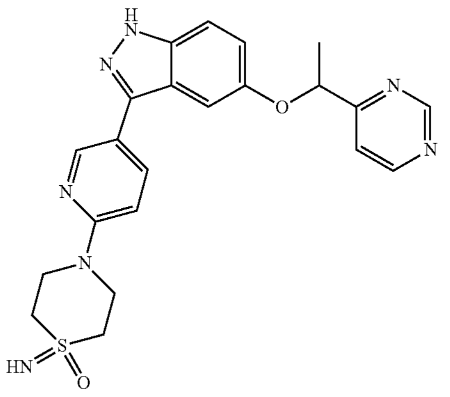 [SMILES: CC(Oc1ccc2[nH]nc(-c3ccc(N4CCS(=N)(=O)CC4)nc3)c2c1)c1ccncn1]

This example was synthesized using the procedure for Example 15 with 1-pyrimidin-4-ylethyl methanesulfonate to give a white solid (21.0 mg, 52% yield). Analysis: LCMS: m/z=450.2 (M+H); $^1$H NMR (400 MHz, DMSO-d6) δ 13.07 (br s, 1H), 9.19 (d, J=1.1 Hz, 1H), 8.77 (d, J=5.3 Hz, 1H), 8.65 (d, J=2.1 Hz, 1H), 8.02 (dd, J=2.3, 8.9 Hz, 1H), 7.63 (dd, J=1.1, 5.3 Hz, 1H), 7.49 (d, J=8.9 Hz, 1H), 7.37 (d, J=1.8 Hz, 1H), 7.20-7.09 (m, 2H), 5.63 (q, J=6.5 Hz, 1H), 4.33-4.20 (m, 2H), 3.95-3.85 (m, 2H), 3.82 (br s, 1H), 3.10-2.96 (m, 4H), 1.62 (d, J=6.5 Hz, 3H).

Example 17. 1-Imino-4-(5-(5-((2-methylpyrimidin-4-yl)methoxy)-1H-indazol-3-yl) pyridin-2-yl)-1λ$^6$-thiomorpholine 1-oxide

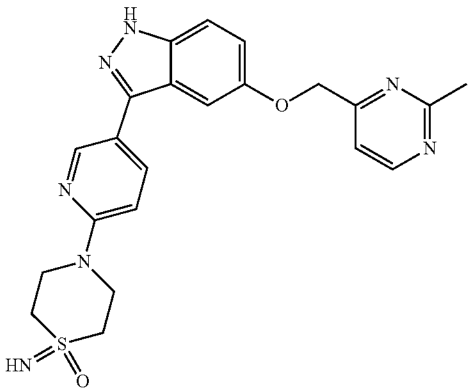 [SMILES: Cc1nccc(COc2ccc3[nH]nc(-c4ccc(N5CCS(=N)(=O)CC5)nc4)c3c2)n1]

This example was synthesized using the procedure for Example 15 with (2-methylpyrimidin-4-yl)methyl methanesulfonate to give a white solid (12.0 mg, 20% yield). Analysis: LCMS: m/z=450 (M+H); $^1$H NMR (400 MHz, DMSO-d6) δ 13.03 (br s, 1H), 8.75 (d, J=2.1 Hz, 1H), 8.72 (d, J=5.1 Hz, 1H), 8.14 (dd, J=2.4, 8.9 Hz, 1H), 7.53 (br d, J=8.9 Hz, 1H), 7.50 (d, J=2.1 Hz, 1H), 7.48 (d, J=5.1 Hz, 1H), 7.20 (dd, J=2.3, 9.0 Hz, 1H), 7.14 (d, J=8.9 Hz, 1H), 5.28 (s, 2H), 4.27 (br d, J=15.3 Hz, 2H), 3.90 (ddd, J=2.9, 7.9, 14.4 Hz, 2H), 3.81 (br s, 1H), 3.08-2.97 (m, 4H), 2.65 (s, 3H).

Example 18. 1-Imino-4-(5-(5-(1-(2-methylpyrimidin-4-yl)ethoxy)-1H-indazol-3-yl) pyridin-2-yl)-1λ$^6$-thiomorpholine 1-oxide

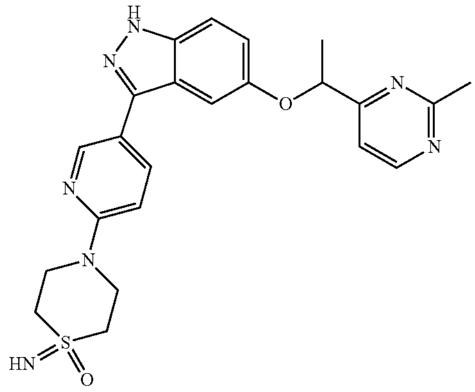

This example was synthesized using the procedure for Example 15 with 1-(2-methylpyrimidin-4-yl)ethyl methanesulfonate to give a white solid (12.5 mg, 22% yield). Analysis: LCMS: m/z=464 (M+H); $^1$H NMR (400 MHz, DMSO-d6) δ 13.02 (s, 1H), 8.65 (d, J=5.1 Hz, 1H), 8.60 (d, J=2.2 Hz, 1H), 8.04 (dd, J=2.3, 8.8 Hz, 1H), 7.47 (d, J=9.0 Hz, 1H), 7.41 (d, J=5.1 Hz, 1H), 7.34 (d, J=2.0 Hz, 1H), 7.16-7.10 (m, 2H), 5.52 (q, J=6.5 Hz, 1H), 4.30-4.23 (m, 2H), 3.90 (ddd, J=3.0, 8.0, 14.4 Hz, 2H), 3.81 (s, 1H), 3.08-2.98 (m, 4H), 2.66 (s, 3H), 1.61 (d, J=6.5 Hz, 3H).

Example 19. (R)—N-(5-(1-(3,5-Dichloropyridin-4-yl)ethoxy)-1H-indazol-3-yl)-6-((dimethyl(oxo)-λ$^6$-sulfaneylidene)amino)nicotinamide

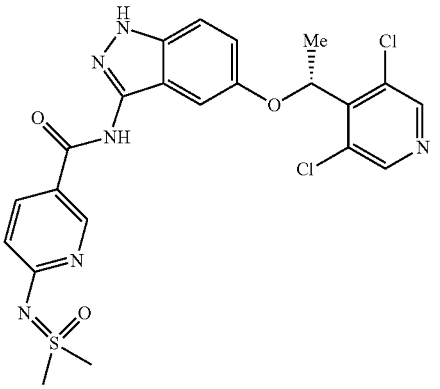 [SMILES: C[C@@H](Oc1ccc2[nH]nc(NC(=O)c3ccc(N=S(C)(C)=O)nc3)c2c1)c1c(Cl)cncc1Cl]

Step 1. tert-Butyl (5-((R)-1-(3,5-dichloropyridin-4-yl) ethoxy)-1-(tetrahydro-2H-pyran-2-yl)-1H-indazol-3-yl)carbamate. A mixture of tert-butyl N-(5-hydroxy-1-tetrahydropyran-2-yl-indazol-3-yl)carbamate (250 mg, 0.75 mmol, 1.0 equiv), (S)-1-(3,5-dichloropyridin-4-yl)ethyl methanesulfonate (230 mg, 0.83 mmol, 1.1 equiv) and cesium carbonate (370 mg, 1.13 mmol, 1.5 equiv) in acetonitrile (15 mL) was heated at 80° C. for 16 h. After cooling to room temperature, the volatiles were removed under reduced pressure and the resulting residue was suspended in saturated ammonium chloride solution (10 mL). The solution was extracted with ethyl acetate (3×20 mL). The combined organic layers were dried over sodium sulfate, filtered and concentrated under reduced pressure. The crude product was purified on a Büchi automated chromatography system (Sorbtech 25 g silica gel column), eluting with a gradient of 0 to 50% ethyl acetate in heptanes to give a white solid (250 mg, 65% yield). Analysis: LCMS: m/z=506.1 (M+H).

Step 2. (R)-5-(1-(3,5-Dichloropyridin-4-yl)ethoxy)-1H-indazol-3-amine. A solution of step 1 product (250 mg, 0.49 mmol, 1.0 equiv) in 1,4-dioxane (5.0 mL) was treated with 4M HCl in 1,4-dioxane (2.0 mL, 8.55 mmol, 16.0 equiv). After stirring at room temperature for 16 hours, the volatiles were removed under reduced pressure. The crude was dissolved in 20% methanol in dichloromethane (10 mL) followed by the addition of MP-carbonate (3.15 g, 9.8 mmol, 20.0 equiv). After stirring at room temperature for 1 hour, the suspension was filtered and the filtrate was concentrated under reduced pressure. The residue was purified on a Büchi automated chromatography system (RediSep Rf Gold HP C18, 50 g column), eluting with a gradient of 0 to 70% acetonitrile in water to give a white solid (130 mg, 82% yield). Analysis: LCMS: m/z=322.1 (M+H).

Step 3. (R)—N-(5-(1-(3,5-Dichloropyridin-4-yl)ethoxy)-1H-indazol-3-yl)-6-((dimethyl (oxo)-λ$^6$-sulfaneylidene) amino)nicotinamide. 6-[[Dimethyl(oxo)-λ$^6$-sulfanylidene] amino] pyridine-3-carbonyl chloride (100 mg, 0.43 mmol, 1.1 equiv) was added to a solution of product from step 2 (126 mg, 0.39 mmol, 1.0 equiv) in pyridine (10 mL) at 0° C. The reaction mixture was warmed to room temperature over 30 minutes and stirred for 16 h. The volatiles were removed under reduced pressure and the crude residue was absorbed onto Celite (10.0 g) and purified first on a Büchi automated chromatography system (RediSep Rf Gold HP C18, 50 g column), eluting with a gradient of 0 to 70% acetonitrile in water to give a light grey solid (17 mg, 8% yield). Analysis: LCMS: m/z=519.1 (M+H); $^1$H NMR (400 MHz, DMSO-d6) δ 12.70 (br s, 1H), 10.52 (br s, 1H), 8.80 (d, J=2.0 Hz, 1H), 8.54 (s, 2H), 8.16 (dd, J=2.5, 8.6 Hz, 1H), 7.38 (d, J=9.0 Hz, 1H), 7.05 (dd, J=2.4, 8.9 Hz, 1H), 6.84 (d, J=2.4 Hz, 1H), 6.75 (dd, J=0.6, 8.6 Hz, 1H), 5.91 (q, J=6.7 Hz, 1H), 3.45 (s, 6H), 1.71 (d, J=6.7 Hz, 3H).

Example 20. 4-[5-[5-[1-(3,5-difluoro-4-pyridyl) ethoxy]-1H-indazol-3-yl]-2-pyridyl]-1-imino-1,4-thiazinane 1-oxide

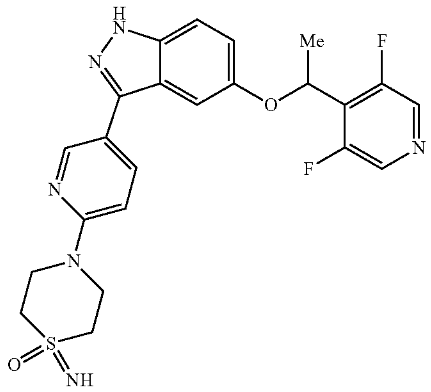 [SMILES: CC(Oc1ccc2[nH]nc(-c3ccc(N4CCS(=N)(=O)CC4)nc3)c2c1)c1c(F)cncc1F]

Step 1. 5-(1-(3,5-Difluoropyridin-4-yl)ethoxy)-3-iodo-1-(tetrahydro-2H-pyran-2-yl)-1H-indazole. A solution of 3-iodo-1-tetrahydropyran-2-yl-indazol-5-ol (0.6 g, 1.74 mmol, 1 equiv), cesium carbonate (0.681 g, 2.09 mmol, 1.2 equiv) and 1-(3,5-difluoro-4-pyridyl)ethanol (0.496 g, 2.09 mmol, 1.2 equiv) in a 1 to 1 mixture of acetonitrile and N,N-dimethylformamide (10 mL) was heated at 70° C. for 2 h. After cooling to room temperature, the reaction was diluted with water (50 mL) and extracted with ethyl acetate (3×25 mL). The combined organic layers were dried over sodium sulfate, filtered and concentrated under reduced pressure. The crude product was pre-absorbed on Celite (2 g) and purified on an Interchim automated chromatography system (Sorbtech 40 g silica gel cartridge), eluting with a gradient of 10 to 40% ethyl acetate in heptanes to give a white solid (0.69 g, 82% yield). Analysis: LCMS: m/z=486 (M+H).

Step 2. 3-(6-Chloropyridin-3-yl)-5-(1-(3,5-difluoropyridin-4-yl)ethoxy)-1-(tetrahydro-2H-pyran-2-yl)-1H-indazole. A solution of step 1 product (0.69 g, 1.4 mmol, 1 equiv) and 2-chloro-5-(4,4,5,5-tetramethyl-1,3,2-dioxaborolan-2-yl)pyridine (0.412 g, 1.72 mmol, 1.2 equiv) in a 20 to 1 mixture of 1,4-dioxane and water (15 mL) was sparged with nitrogen for 10 minutes. Potassium carbonate (0.395 g mg, 2.86 mmol, 2 equiv) and [1,1' bis(diphenylphosphino)-ferrocene]palladium(II) dichloride (104 mg, 0.143 mmol, 0.1 equiv) were added and reaction mixture was sparged with nitrogen for an additional 5 minutes. The reaction was heated at 90° C. for 16 h. After cooling to room temperature, the reaction was concentrated under reduced pressure. The residue was diluted with water (40 mL) and dichloromethane (40 mL). The layers were separated. The organic layer was dried over sodium sulfate, filtered and concentrated under reduced pressure. The crude product was pre-absorbed on silica gel (2 g) and purified on an Interchim automated chromatography system (Sorbtech 40 g silica gel cartridge), eluting with a gradient of 5 to 20% ethyl acetate in heptanes to give a yellow solid (0.45 g, 67% yield). Analysis: LCMS: m/z=471 (M+H).

Step 3. 4-(5-(5-(1-(3,5-Difluoropyridin-4-yl)ethoxy)-1-(tetrahydro-2H-pyran-2-yl)-1H-indazol-3-yl)pyridin-2-yl)-1-imino-1λ$^6$-thiomorpholine 1-oxide. A solution of step 2 product (0.2 g, 0.425 mmol, 1 equiv) in DMSO (4 mL) was sparged with nitrogen for 15 minutes. 1-Imino-1,4-thiazinane 1-oxide (0.18 g, 0.85 mmol, 2 equiv), cesium carbonate (0.83 g, 2.55 mmol, 6 equiv) and BinapPd(allyl)Cl (36 mg, 0.042 mmol, 0.1 equiv) were added and the reaction mixture was sparged with nitrogen for an additional 5 minutes. The reaction was heated at 110° C. for 16 h. After cooling to room temperature, the reaction was diluted with saturated brine (30 mL) and extracted with ethyl acetate (30 mL). The organic layer was dried over sodium sulfate, filtered and concentrated under reduced pressure. The crude product was combined with a 50 mg impure fraction, pre-absorbed on Celite (2 g) and purified on an Interchim automated chromatography system (Sorbtech 40 g silica gel cartridge), eluting with a gradient of 0 to 10% methanol in dichloromethane to give a white solid (0.211 g, 70% yield). Analysis: LCMS: m/z=569 (M+H).

Step 4. 4-[5-[5-[1-(3,5-difluoro-4-pyridyl)ethoxy]-1H-indazol-3-yl]-2-pyridyl]-1-imino-1,4-thiazinane 1-oxide. A solution of step 3 product (0.211 g, 0.37 mmol, 1 equiv) in 2 to 1 mixture of acetonitrile and water (15 mL) was treated with 4N HCl in 1,4-dioxane (9.3 mL, 37.2 mmol, 100 equiv) in microwave reactor at 110° C. for 1 hour. After cooling to room temperature, the reaction mixture was concentrated under reduced pressure to dryness. The residue was dissolved in methanol (20 mL), treated with MP-carbonate (3.2 mmol/g, 2 g), stirred for 30 minutes, filtered and concentrated under reduced pressure. The residue was pre-absorbed on Celite (1 g) and purified on an Interchim automated chromatography system (RediSep Rf Gold HP C18, 15.5 g column), eluting with a gradient of 0 to 100% acetonitrile in water. The pure fractions were collected and lyophilized to give a white solid (100 mg, 56% yield). Analysis: LCMS: m/z=485 (M+H); $^1$H NMR (400 MHz, DMSO-d6) δ 13.07 (br s, 1H), 8.57 (dd, J=0.6, 2.4 Hz, 1H), 8.50 (s, 2H), 7.98 (dd, J=2.5, 8.5 Hz, 1H), 7.45 (d, J=9.0 Hz, 1H), 7.43 (d, J=1.8 Hz, 1H), 7.06 (dd, J=2.3, 9.0 Hz, 1H), 6.86 (dd, J=0.6, 8.4 Hz, 1H), 5.98 (q, J=6.6 Hz, 1H), 3.73-3.63 (m, 2H), 3.37-3.33 (m, 2H), 3.25-3.17 (m, 2H), 3.13-2.98 (m, 2H), 1.76 (d, J=6.5 Hz, 3H).

Example 21. (R)-((5-(5-(1-(3,5-Dichloropyridin-4-yl)ethoxy)-1H-indazol-3-yl)pyridin-2-yl)imino)dimethyl-λ$^6$-sulfanone

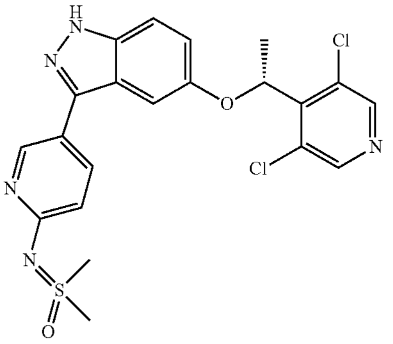 [SMILES: C[C@@H](Oc1ccc2[nH]nc(-c3ccc(N=S(C)(C)=O)nc3)c2c1)c1c(Cl)cncc1Cl]

(R)-((5-(5-(1-(3,5-Dichloropyridin-4-yl)ethoxy)-1H-indazol-3-yl)pyridin-2-yl)imino)dimethyl-λ$^6$-sulfanone was synthesized according to the scheme shown below:

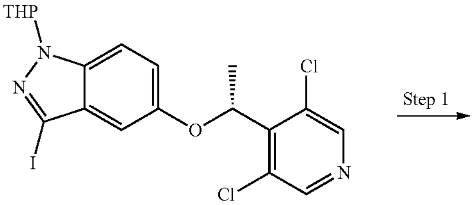

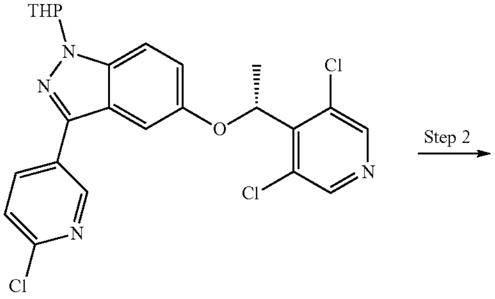

-continued

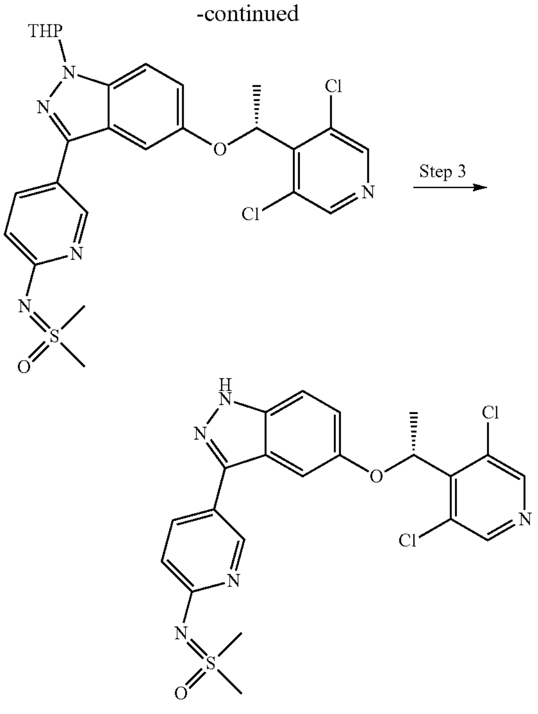

Example 21

Step 1. 5-((R)-1-(3,5-Dichloropyridin-4-yl)ethoxy)-3-iodo-1-(tetrahydro-2H-pyran-2-yl)-1H-indazole. A mixture of 3-iodo-1-tetrahydropyran-2-yl-indazol-5-ol (1.0 g, 2.90 mmol, 1.0 equiv), [(1S)-1-(3,5-dichloro-4-pyridyl)ethyl] methanesulfonate (780 mg, 2.90 mmol, 1.0 equiv) and cesium carbonate (1.41 g, 14.45 mmol, 1.5 equiv) in N,N-dimethylformamide (20 mL) was heated at 130° C. for 16 h. The volatiles were removed under reduced pressure and the residue was suspended in saturated ammonium chloride (50 mL). The solution was extracted with ethyl acetate (3×50 mL). The combined organic layers were dried over sodium sulfate, filtered and concentrated under reduced pressure. The crude product was purified on a Büchi automated chromatography system (Sorbtech 40 g silica gel column), eluting with a gradient of 0 to 30% ethyl acetate in heptanes to give a white solid (1.01 g, 88% yield). Analysis: LCMS: m/z=517.2 (M+H).

Step 2. ((5-(5-((R)-1-(3,5-Dichloropyridin-4-yl)ethoxy)-1-(tetrahydro-2H-pyran-2-yl)-1H-indazol-3-yl)pyridin-2-yl) imino)dimethyl-$\lambda^6$-sulfanone. A solution of 3-(6-chloro-3-pyridyl)-5-[(1R)-1-(3,5-dichloro-4-pyridyl)ethoxy]-1-tetrahydropyran-2-yl-indazole (200 mg, 0.4 mmol, 1.0 equiv), S,S-dimethylsulfoximine (45 mg, 0.48 mmol, 1.2 equiv), Xantphos (23 mg, 0.04 mmol, 0.1 equiv), tris(dibenzylideneacetone)dipalladium(0) (18 mg, 0.02 mmol, 0.05 equiv) and cesium carbonate (200 mg, 0.6 mmol, 1.5 equiv) in 1,4-dioxane (10 mL) was sparged with nitrogen for 15 minutes. After heating at 100° C. for 3 h, the reaction was cooled to room temperature and filtered through a bed of Celite. The filtrate was concentrated under reduced pressure. The residue was purified on a Büchi automated chromatography system (RediSep Rf Gold HP C18, 50 g column), eluting with a gradient of 0 to 80% acetonitrile in water to give a white solid (150.0 mg, 68% yield). Analysis: LCMS: m/z=560.1 (M+H).

Step 3. (R)-((5-(5-(1-(3,5-Dichloropyridin-4-yl)ethoxy)-1H-indazol-3-yl)pyridin-2-yl)imino)dimethyl-$\lambda^6$-sulfanone. A solution of step 1 product (150 mg, 0.27 mmol, 1.0 equiv) in 1,4-dioxane (2.0 mL) was treated with 4M HCl in 1,4-dioxane (0.53 mL, 2.14 mmol, 8.0 equiv). After stirring at room temperature for 16 h the volatiles were removed under reduced pressure. The residue was suspended in 10% methanol in dichloromethane (10 mL) and treated with MP-carbonate resin (860 mg, 2.7 mmol, 10.0 equiv) at room temperature for 1 h. The solids were filtered and washed with 10% methanol in dichloromethane (10 mL). The filtrated was concentrated under reduced pressure. The residue was purified on a Büchi automated chromatography system (RediSep Rf Gold HP C18, 50 g column), eluting with a gradient of 0 to 70% acetonitrile in water to give an off-white solid (40 mg, 31% yield). Analysis: LCMS: m/z=476.1 (M+H); $^1$H NMR (400 MHz, DMSO-d6) δ 13.08 (br s, 1H), 8.59 (s, 2H), 8.50 (dd, J=0.7, 2.4 Hz, 1H), 7.86 (dd, J=2.4, 8.4 Hz, 1H), 7.47 (d, J=9.2 Hz, 1H), 7.13 (d, J=2.1 Hz, 1H), 7.09 (dd, J=2.3, 8.9 Hz, 1H), 6.79 (dd, J=0.7, 8.6 Hz, 1H), 6.10 (q, J=6.6 Hz, 1H), 3.45 (s, 3H), 3.44 (s, 3H), 1.76 (d, J=6.6 Hz, 3H).

Example 22. (S)-((5-(5-(1-(3,5-Dichloropyridin-4-yl)ethoxy)-1H-indazol-3-yl)pyridin-2-yl)imino)dimethyl-$\lambda^6$-sulfanone

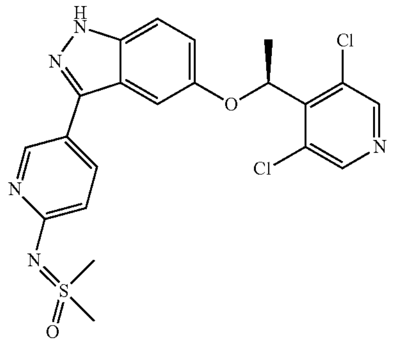 [SMILES: C[C@H](Oc1ccc2[nH]nc(-c3ccc(N=S(C)(C)=O)nc3)c2c1)c1c(Cl)cncc1Cl]

This example was synthesized with 3-(6-chloro-3-pyridyl)-5-[(1S)-1-(3,5-dichloro-4-pyridyl)ethoxy]-1-tetrahydropyran-2-yl-indazole using the procedure for Example 21 to give an off-white solid (36.0 mg, 33% yield). Analysis: LCMS: m/z=476.1 (M+H); $^1$H NMR (400 MHz, DMSO-d6) δ 13.06 (s, 1H), 8.59 (s, 2H), 8.50 (dd, J=0.5, 2.5 Hz, 1H), 7.88 (dd, J=2.3, 8.6 Hz, 1H), 7.47 (d, J=8.9 Hz, 1H), 7.14 (d, J=1.6 Hz, 1H), 7.09 (dd, J=2.3, 9.0 Hz, 1H), 6.80 (d, J=8.4 Hz, 1H), 6.10 (q, J=6.7 Hz, 1H), 3.45 (s, 3H), 3.45 (s, 3H), 1.76 (d, J=6.6 Hz, 3H).

Example 23. 4-[5-[5-[1-(3-chloro-5-fluoro-4-pyridyl)ethoxy]-1H-indazol-3-yl]-2-pyridyl]-1-imino-1,4-thiazinane 1-oxide

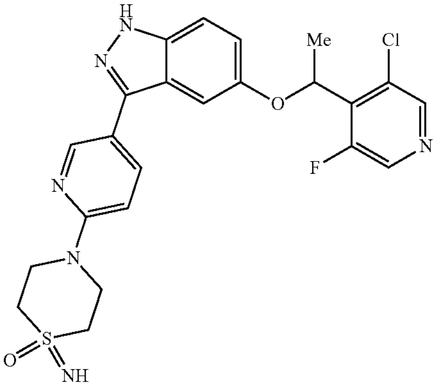 [SMILES: CC(Oc1ccc2[nH]nc(-c3ccc(N4CCS(=N)(=O)CC4)nc3)c2c1)c1c(F)cncc1Cl]

This example was synthesized using 1-(3-chloro-5-fluoro-4-pyridyl)ethyl methanesulfonate and the procedure for Example 20 to give a white solid (14 mg, 4% yield). Analysis: LCMS: m/z=501 (M+H); $^1$H NMR (400 MHz, CD3OD) δ=8.51 (dd, J=0.6, 2.4 Hz, 1H), 8.43 (s, 1H), 8.36 (d, J=1.8 Hz, 1H), 7.95 (dd, J=2.4, 8.4 Hz, 1H), 7.44 (dd, J=0.5, 9.0 Hz, 1H), 7.20 (d, J=2.1 Hz, 1H), 7.14 (dd, J=2.3, 9.0 Hz, 1H), 6.96 (dd, J=0.7, 8.5 Hz, 1H), 5.97 (q, J=6.7 Hz, 1H), 3.82-3.75 (m, 2H), 3.45-3.35 (m, 4H), 3.29-3.23 (m, 2H), 1.80 (d, J=6.6 Hz, 3H).

Example 24. 4-[5-[5-[(1R)-1-(3,5-dichloro-4-pyridyl)ethoxy]-1H-indazol-3-yl]-2-pyridyl]-1-methylimino-1,4-thiazinane 1-oxide

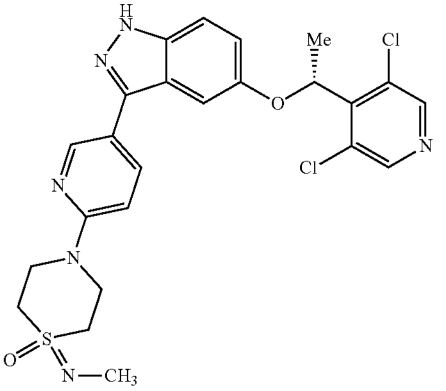 [SMILES: CN=S1(=O)CCN(c2ccc(-c3n[nH]c4ccc(O[C@H](C)c5c(Cl)cncc5Cl)cc34)cn2)CC1]

This example was synthesized using 1-methylimino-1,4-thiazinane 1-oxide and 5-[(1R)-1-(3,5-dichloro-4-pyridyl)ethoxy]-3-iodo-1-tetrahydropyran-2-yl-indazole with the procedure for Example 11 to give a white solid (40 mg, 47% yield). Analysis: LCMS: m/z=531.1 (M+H); $^1$H NMR (400 MHz, DMSO-d6) δ 13.05 (br s, 1H), 8.60 (s, 2H), 8.58 (d, J=2.0 Hz, 1H), 7.92 (dd, J=2.4, 8.8 Hz, 1H), 7.47 (d, J=8.9 Hz, 1H), 7.16 (s, 1H), 7.15 (d, J=7.2 Hz, 1H), 7.09 (dd, J=2.3, 9.0 Hz, 1H), 6.10 (q, J=6.7 Hz, 1H), 4.30 (td, J=2.6, 14.2 Hz, 2H), 3.89-3.80 (m, 2H), 3.25-3.19 (m, 2H), 3.10-3.01 (m, 2H), 2.69 (s, 3H), 1.76 (d, J=6.6 Hz, 3H).

Example 25. [5-[5-[(1R)-1-(3,5-dichloro-4-pyridyl)ethoxy]-1H-indazol-3-yl]-3-fluoro-2-pyridyl]imino-dimethyl-oxo-λ$^6$-sulfane

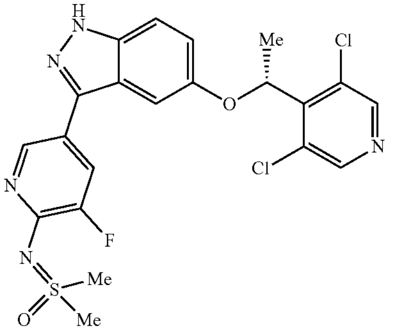 [SMILES: C[C@@H](Oc1ccc2[nH]nc(-c3cnc(N=S(C)(C)=O)c(F)c3)c2c1)c1c(Cl)cncc1Cl]

This example was synthesized using the procedure for Example 21. Analysis: LCMS: m/z=494.1 (M+H); $^1$H NMR (400 MHz, $CDCl_3$) δ 9.99 (br s, 1H), 8.48 (d, J=1.3 Hz, 1H), 8.44 (s, 2H), 7.70 (dd, J=2.0, 11.1 Hz, 1H), 7.41-7.36 (m, 1H), 7.18-7.13 (m, 2H), 6.05 (q, J=6.8 Hz, 1H), 3.51-3.47 (m, 6H), 1.83 (d, J=6.6 Hz, 3H).

Example 26. [5-[5-[(1R)-1-(3,5-dichloro-4-pyridyl)ethoxy]-1H-indazol-3-yl]pyrimidin-2-yl]imino-dimethyl-oxo-λ$^6$-sulfane

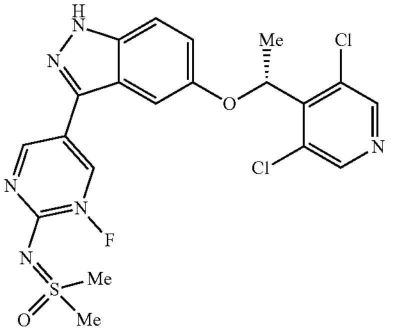

This example was synthesized using the procedure for Example 21. Analysis: LCMS: m/z=477.1 (M+H); $^1$H NMR (400 MHz, $CDCl_3$) δ 10.62 (br s, 1H), 8.95 (s, 2H), 8.42 (s, 2H), 7.41 (d, J=9.0 Hz, 1H), 7.22-7.10 (m, 2H), 6.06 (q, J=6.6 Hz, 1H), 3.47 (s, 6H), 1.81 (d, J=6.6 Hz, 3H).

Example 27. 4-[5-[5-[(1R)-1-(3,5-dichloro-4-pyridyl)ethoxy]-1H-indazol-3-yl]pyrimidin-2-yl]imino-1,4-oxathiane 4-oxide

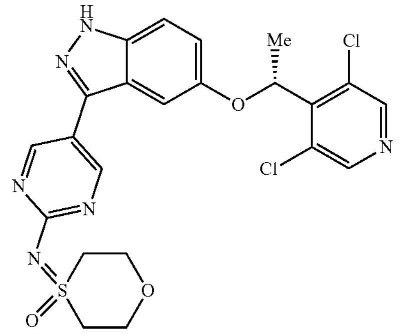 [SMILES: C[C@@H](Oc1ccc2[nH]nc(-c3cnc(N=S4(=O)CCOCC4)nc3)c2c1)c1c(Cl)cncc1Cl]

This example was synthesized using the procedure for Example 21. Analysis: LCMS: m/z=519.1 (M+H); $^1$H NMR (400 MHz, $CDCl_3$) δ 10.21 (br s, 1H), 8.94 (s, 2H), 8.43 (s, 2H), 7.44-7.37 (m, 1H), 7.20-7.13 (m, 2H), 6.07 (q, J=6.6 Hz, 1H), 4.31-4.15 (m, 4H), 3.91 (br dd, J=2.7, 14.1 Hz, 2H), 3.61-3.51 (m, 2H), 1.82 (d, J=6.6 Hz, 3H).

Example 28. [5-[5-[(1R)-1-(3,5-dichloro-4-pyridyl)ethoxy]-1H-indazol-3-yl]-2-pyridyl]-imino-methyl-oxo-λ$^6$-sulfane

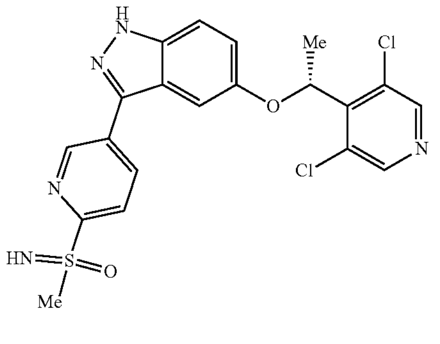 [SMILES: C[C@@H](Oc1ccc2[nH]nc(-c3ccc(S(C)(=N)=O)nc3)c2c1)c1c(Cl)cncc1Cl]

This example was synthesized using the procedure for Example 2. Analysis: LCMS: m/z=462.1 (M+H); $^1$H NMR (400 MHz, $CDCl_3$) δ 10.57 (br s, 1H), 9.25 (br s, 1H), 8.44 (d, J=2.6 Hz, 2H), 8.34 (ddd, J=2.1, 5.6, 8.0 Hz, 1H), 8.23 (br d, J=7.9 Hz, 1H), 7.48-7.44 (m, 1H), 7.23-7.18 (m, 2H), 6.08 (q, J=6.6 Hz, 1H), 3.34 (s, 3H), 1.84 (d, J=6.7 Hz, 3H).

Example 29. 4-[5-[5-[(1R)-1-(3,5-dichloro-4-pyridyl)ethoxy]-1H-indazol-3-yl]-3-fluoro-2-pyridyl]-1-methylimino-1,4-thiazinane 1-oxide

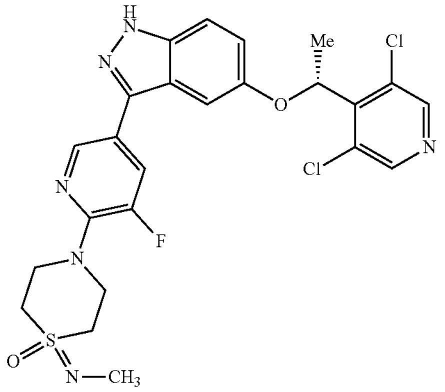 [SMILES: CN=S1(=O)CCN(c2ncc(-c3n[nH]c4ccc(O[C@H](C)c5c(Cl)cncc5Cl)cc34)cc2F)CC1]

This example was synthesized using the procedure for Example 24. Analysis: LCMS: m/z=549.1 (M+H); $^1$H NMR (400 MHz, $CDCl_3$) δ 13.22 (br s, 1H), 8.57 (s, 2H), 8.48 (t, J=1.7 Hz, 1H), 7.84 (dd, J=1.9, 14.4 Hz, 1H), 7.50 (d, J=9.0 Hz, 1H), 7.21 (d, J=2.2 Hz, 1H), 7.11 (dd, J=2.3, 9.0 Hz, 1H), 6.14 (q, J=6.6 Hz, 1H), 4.11 (br d, J=16.3 Hz, 2H), 3.77 (ddd, J=2.0, 8.9, 14.0 Hz, 2H), 3.36-3.33 (m, 2H), 3.27-3.10 (m, 3H), 2.69 (s, 3H), 1.78-1.76 (m, 3H).

Example 30. [5-[5-[(1R)-1-(3,5-dichloro-2-methyl-4-pyridyl)ethoxy]-1H-indazol-3-yl]-2-pyridyl]imino-dimethyl-oxo-λ$^6$-sulfane

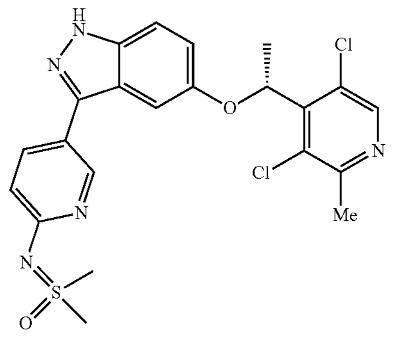 [SMILES: Cc1ncc(Cl)c([C@@H](C)Oc2ccc3[nH]nc(-c4ccc(N=S(C)(C)=O)nc4)c3c2)c1Cl]

[5-[5-[(1R)-1-(3,5-dichloro-2-methyl-4-pyridyl)ethoxy]-1H-indazol-3-yl]-2-pyridyl]imino-dimethyl-oxo-λ$^6$-sulfane was synthesized according to the scheme shown below:

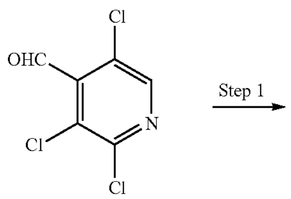

-continued

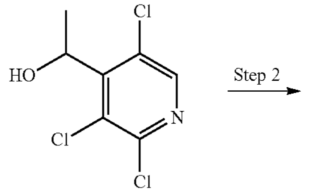

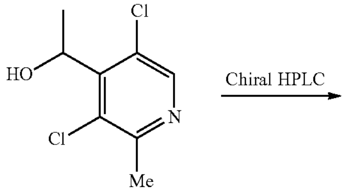

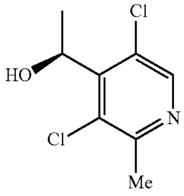

(1S)-1-(3,5-dichloro-2-methyl-4-pyridyl) ethanol

+

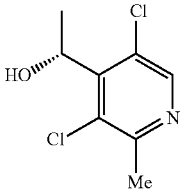

(1R)-1-(3,5-dichloro-2-methyl-4-pyridyl) ethanol

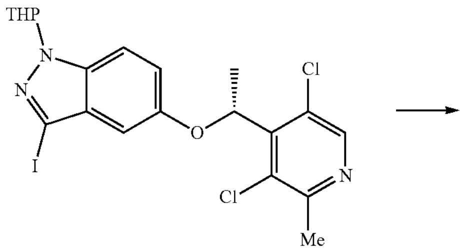

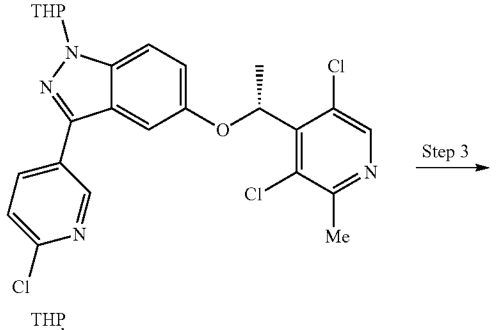

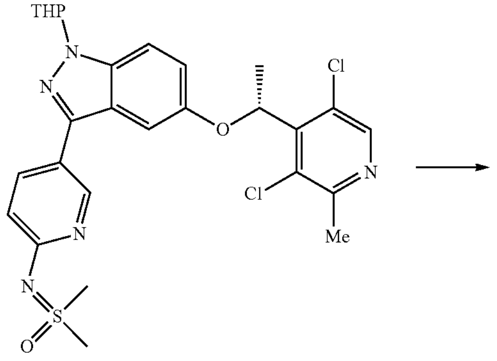

-continued

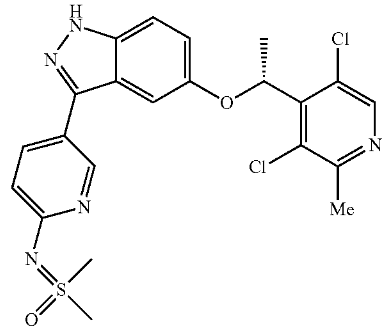

Example 30

Step 1. Trichloro-4-pyridyl)ethanol. A 500 mL three-neck round bottom flask was charged with 2,3,5-trichloropyridine-4-carbaldehyde (40 g, 0.19 mol) and THF (200 mL). MeMgBr (70 mL, 0.21 mol) was added in portions and the mixture was stirred at −70° C. for 1 h. The reaction was quenched with aqueous ammonium chloride solution, extracted with ethyl acetate (200 mL×3), dried over $Na_2SO_4$ and concentrated. The residue was purified by silica gel column (PE/EA=30/1) to give (33 g) a yellow liquid (33 g, 77%). Analysis: LCMS: m/z=227 (M+H).

Step 2. 1-(3,5-Dichloro-2-methyl-4-pyridyl)ethanol. A mixture of product step 1 (33 g, 0.147 mmol), methylboronic acid (26.3 g, 0.429 mmol) $K_2CO_3$ (40 g, 0.290 mmol) and $Pd(PPh_3)_2Cl_2$ (3 g) in dioxane (300 mL) was stirred at 110° C. overnight. The resulting mixture was filtered and the filtrate was concentrated in vacuo to give the crude product, which was further purified by silica gel column chromatography to give a yellow liquid (15 g, 50%). LCMS: m/z=206.1 (M+H). The product was separated by Prep-HPLC (Chiralpak ID 5×25 cm, hexanes/ethanol (80/20), 60 mL/min. 38 C.°) to give (S)-1-(3,5-dichloro-2-methyl-4-pyridyl)ethanol (5 g) and (R)-1-(3,5-dichloro-2-methyl-4-pyridyl)ethanol R (5 g) as yellow liquid. Peak 1 5.5 min; (S)-1-(3,5-dichloro-2-methyl-4-pyridyl)ethanol. Analysis: LCMS: m/z=206.1 (M+H). $^1H$ NMR (400 MHz, $CDCl_3$) δ 8.36 (s, 1H), 5.57 (m, 1H), 2.93 (b, 1H), 2.64 (s, 3H), 1.65 (d, 3H). Peak 2 6.9 min; (R)-1-(3,5-dichloro-2-methyl-4-pyridyl)ethanol. Analysis: LCMS: m/z=206.1 (M+H). $^1H$ NMR (400 MHz, $CDCl_3$) δ 8.36 (s, 1H), 5.57 (m, 1H), 2.93 (b, 1H), 2.64 (s, 3H), 1.65 (d, 3H).

[5-[5-[(1R)-1-(3,5-dichloro-2-methyl-4-pyridyl)ethoxy]-1H-indazol-3-yl]-2-pyridyl] imino-dimethyl-oxo-$\lambda^6$-sulfane. This example was synthesized using 3-iodo-1-tetrahydropyran-2-yl-indazol-5-ol and S)-1-(3,5-dichloro-2-methyl-4-pyridyl)ethanol by the method for Example 21 and Example 11. LCMS: m/z=490.1 (M+H); δ $^1H$ NMR (400 MHz, DMSO-d6) δ=13.05 (s, 1H), 8.44 (s, 1H), 8.42 (d, J=2.1 Hz, 1H), 7.88 (dd, J=2.5, 8.5 Hz, 1H), 7.47 (d, J=9.0 Hz, 1H), 7.09 (dd, J=2.3, 9.0 Hz, 1H), 7.06 (d, J=1.8 Hz, 1H), 6.77 (dd, J=0.6, 8.4 Hz, 1H), 6.09 (q, J=6.7 Hz, 1H), 3.45 (s, 3H), 3.44 (s, 3H), 2.57 (s, 3H), 1.76 (d, J=6.7 Hz, 3H).

Example 31. [5-[5-[(1S)-1-(3,5-dichloro-2-methyl-4-pyridyl)ethoxy]-1H-indazol-3-yl]-2-pyridyl]imino-dimethyl-oxo-$\lambda^6$-sulfane

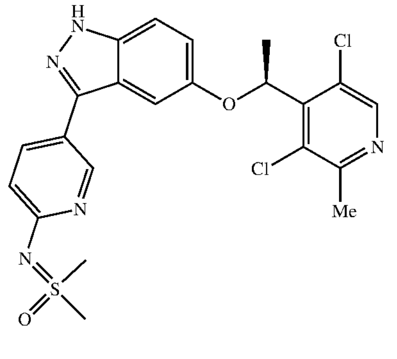 [SMILES: Cc1ncc(Cl)c([C@H](C)Oc2ccc3[nH]nc(-c4ccc(N=S(C)(C)=O)nc4)c3c2)c1Cl]

This example was synthesized using (R)-1-(3,5-dichloro-2-methyl-4-pyridyl)ethanol by the method for Example 21. LCMS: m/z=490.1 (M+H); $^1$H NMR (400 MHz, DMSO-d6) δ=13.05 (s, 1H), 8.43 (s, 1H), 8.42 (d, J=2.1 Hz, 1H), 7.88 (dd, J=2.4, 8.6 Hz, 1H), 7.47 (d, J=9.0 Hz, 1H), 7.09 (dd, J=2.3, 8.9 Hz, 1H), 7.06 (d, J=1.7 Hz, 1H), 6.77 (dd, J=0.7, 8.5 Hz, 1H), 6.09 (q, J=6.7 Hz, 1H), 3.45 (s, 3H), 3.44 (s, 3H), 2.57 (s, 3H), 1.75 (d, J=6.6 Hz, 3H).

Example 32. 1-[[5-[5-[(1R)-1-(3,5-Dichloro-4-pyridyl)ethoxy]-1H-indazol-3-yl]-2-pyridyl]imino] thiolane 1-oxide

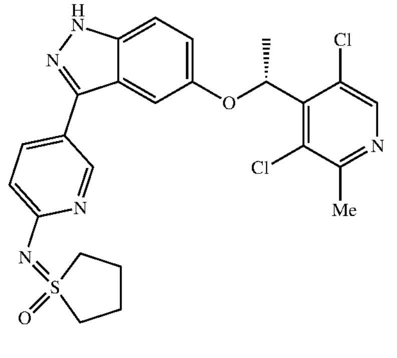 [SMILES: Cc1ncc(Cl)c([C@@H](C)Oc2ccc3[nH]nc(-c4ccc(N=S5(=O)CCCC5)nc4)c3c2)c1Cl]

This example was synthesized using the procedure for example 21 with (S)-1-(3,5-dichloro-4-pyridyl)ethanol and 1-iminothiolane 1-oxide. LCMS: m/z=502.1 (M+H). 1H NMR (400 MHz, DMSO-d6) δ=13.04 (br s, 1H), 8.60 (s, 2H), 8.51 (dd, J=0.7, 2.4 Hz, 1H), 7.89 (dd, J=2.5, 8.5 Hz, 1H), 7.49 (d, J=9.0 Hz, 1H), 7.13 (d, J=2.1 Hz, 1H), 7.09 (dd, J=2.3, 9.0 Hz, 1H), 6.85 (dd, J=0.7, 8.4 Hz, 1H), 6.09 (q, J=6.6 Hz, 1H), 3.66-3.58 (m, 2H), 3.38 (td, J=6.5, 13.2 Hz, 2H), 2.30-2.21 (m, 2H), 2.19-2.10 (m, 2H), 1.76 (d, J=6.6 Hz, 3H).

Example A Kinase Assays

Kinase-tagged T7 phage strains were prepared in an *E. coli* host derived from the BL21 strain. *E. coli* were grown to log-phase and infected with T7 phage and incubated with shaking at 32° C. until lysis. The lysates were centrifuged and filtered to remove cell debris. Streptavidin-coated magnetic beads were treated with biotinylated small molecule ligands for 30 minutes at room temperature to generate affinity resins for kinase assays. The liganded beads were blocked with excess biotin and washed with blocking buffer SeaBlock (Pierce), 1% BSA, 0.05% Tween 20, 1 mM DTT to remove unbound ligand and to reduce non-specific binding. Binding reactions were assembled by combining kinases, liganded affinity beads, and test compounds in 1× binding buffer (20% SeaBlock, 0.17×PBS, 0.05% Tween 20, 6 mM DTT).

Test compounds were prepared as 111× stocks in 100% DMSO. Kds were determined using an 11-point 3-fold compound dilution series with three DMSO control points. All compounds for Kd measurements are distributed by acoustic transfer (non-contact dispensing) in 100% DMSO. The compounds were then diluted directly into the assays such that the final concentration of DMSO was 0.9%. All reactions performed in polypropylene 384-well plate. Each was a final volume of 0.02 ml. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Binding Constants (Kds)

Binding constants were calculated with a standard dose-response curve using the Hill equation:

$$\text{Response} = \text{Background} + \frac{\text{Signal} - \text{Background}}{1 + \left(\frac{Kd^{Hill\ Slope}}{\text{Dose}^{Hill\ Slope}}\right)}$$

The Hill Slope was set to −1. Curves were fitted using a non-linear least square fit with the Levenberg-Marquardt algorithm.

Results are shown below in Table 2.

TABLE 2

| FGFR Family Binding Constants (nM) | | | | |
|---|---|---|---|---|
| Example | FGFR1 (Kd nM) | FGFR2 (Kd nM) | FGFR3 (Kd nM) | FGFR3(V555M) (Kd nM) |
| 1 | 770 | 550 | 76 | 30 |
| 2 | 1200 | 400 | 120 | 43 |
| (R)-3 | 0.9 | 2.6 | 1.5 | 0.5 |
| (S)-4 | 21 | 17 | 12 | 2.8 |
| 5 | 71 | 51 | 19 | 3.5 |
| 6 | 260 | 120 | 47 | 10 |
| 7 | 240 | 110 | 68 | 9.6 |
| 8 | 13 | 100 | 38 | 4.5 |
| (R)-9 | 0.6 | 1.2 | 0.5 | 0.24 |
| (S)-10 | 30 | 17 | 16 | 4.1 |
| (S)-11 | 110 | 92 | 10 | 4.2 |
| (R)-12 | 8.0 | 3.3 | 0.8 | 0.34 |
| 13 | 6.7 | 4.2 | 0.62 | 0.32 |
| 14 | 24 | 65 | 5.3 | 2.0 |
| 15 | 3100 | 1700 | 250 | 97 |
| 16 | 1200 | 450 | 77 | 39 |
| 17 | 3500 | 1200 | 180 | 56 |
| 18 | 2100 | 540 | 87 | 31 |
| 19 | 5.1 | 16 | 3.4 | 0.9 |
| 20 | 590 | 320 | 67 | 18 |
| 21 | 9.9 | 5 | 1.1 | 1.1 |
| 22 | 350 | 190 | 66 | 26 |
| 23 | 580 | 67 | 32 | 11 |
| 24 | 3.9 | 2.2 | 0.5 | 0.3 |

TABLE 2-continued

| FGFR Family Binding Constants (nM) | | | | |
|---|---|---|---|---|
| Example | FGFR1 (Kd nM) | FGFR2 (Kd nM) | FGFR3 (Kd nM) | FGFR3(V555M) (Kd nM) |
| 25 | 12 | 6.3 | 0.8 | 0.7 |
| 26 | 17 | 14 | 3.6 | 1.8 |
| 27 | 13 | 10 | 2.7 | 1.1 |
| 28 | 22 | 15 | 1.9 | 1.1 |
| 29 | 3.4 | 4.4 | 0.6 | 0.6 |
| 30 | 23.0 | 16.0 | 2.0 | 0.6 |
| 31 | 390.0 | 290.0 | 66.0 | 24 |
| 32 | 14.0 | 15.0 | 1.9 | 1.2 |

Example B. RT112/84 Cell Viability Assay

Cell Titer-Glo® 2.0 Luminescent cell viability assay reagent was purchased from Promega (Madison, WI). RT112/84 cell line was purchased from American Type Culture Collection (Manassas, VA). RT112/84 cells were cultured in RPMI1640 media supplemented with 10% fetal bovine serum. Cultures were maintained at 37° C. in a humidified atmosphere of 5% CO2 and 95% air.

Procedure: Cells were plated in 96-well clear bottom/white plates (Corning #3903) at 10,000 cells/well in 100 µl of media, incubated overnight. The next day, test compound DMSO stock solutions were made at 10 mM and 2 µM final concentration. Compounds were then added to cells in a 9-dose, 10-fold dilution series starting at 30 µM with an HP 300e Digital Dispenser (each dose was applied in triplicate). DMSO was backfilled to each well up to 301 nL total volume of test compound+DMSO, and a total of 301 nL DMSO was added to a control/no test compound well in triplicate. The cells in cell culture plates were incubated with the compounds at 37° C. and 5% $CO_2$ for 72 hours. Then 50 µl of Cell Titer Glo 2.0 reagent was added to each well of the cell culture plates. The contents were covered from light and mixed on an orbital shaker at room temperature for 10 min. Luminescence was recorded by a Synergy H1 Microplate Reader (Biotek, Winooski, VT). Cells were assessed as a percentage of DMSO only treated control cells. Curves were plotted and IC50 values were calculated using the GraphPad Prism 8 program based on a sigmoidal dose-response equation (4 parameter).

TABLE 4

| Cell Lines Used for Cell Viability Assays | | |
|---|---|---|
| Cell line | Mutation or Fusion | Source |
| Ba/F3 FGFR1 | FGFR1-BCR | Advanced Cellular Dynamics, (Seattle, WA) |
| Ba/F3 FGFR3 | FGFR3--BAIAP2L1 fusion | Advanced Cellular Dynamics, (Seattle, WA) |
| RT112/84 (Bladder Cancer) | FGFR3-TACC3 fusion | American Type Culture Collection (Manassas, VA) |
| UM-UC-14 (Bladder Cancer) | FGFR3(S249C) | Sigma, (St. Louis, MO) |
| KG-1 (Acute Myeloid Leukemia) | FGFR1OP2-FGFR1 fusion | American Type Culture Collection (Manassas, VA) |

Ba/F3 Cell Viability Assays

Experimental Purpose: Recombinant kinase fusions are transduced into parental Ba/F3, which becomes dependent upon this constitutive kinase activity for IL3-independent survival. Inhibition of kinase activity leads to cell death, which is monitored using CellTiter-Glo® 2.0 (Promega) which measures intracellular ATP concentration that in turn serves as a marker for viability. FGFR1-BCR Ba/F3 and FGFR3-BAIAP2L1 Ba/F3 were obtained from Advanced Cellular Dynamics (Seattle, WA)

Cell Viability Assay Procedure: Cell Titer-Glo® 2.0 Luminescent cell viability assay reagent was purchased from Promega (Madison, WI). FGFR1-BCR Ba/F3 and FGFR3-BAIAP2L1 Ba/F3 cells were cultured in RPMI1640 media supplemented with 10% fetal bovine serum. Cultures were maintained at 37° C. in a humidified atmosphere of 5% CO2 and 95% air. Cells were plated in 96-well clear bottom/white plates (Corning #3903) at 10,000 cells/well in 100 µl of media, incubated overnight. The next day, test compound DMSO stock solutions were made at 10 mM and 2 µM final concentration. Compounds were then added to cells in a 9-dose, 10-fold dilution series starting at 30 µM with an HP 300e Digital Dispenser (each dose was applied in triplicate). DMSO was backfilled to each well up to 301 nL total volume of test compound+DMSO, and a total of 301 nL DMSO was added to a control/no test compound well in triplicate. The cells in cell culture plates were incubated with the compounds at 37° C. and 5% $CO_2$ for 48 hours. Then 50 µl of Cell Titer Glo 2.0 reagent was added to each well of the cell culture plates. The contents were covered from light and mixed on an orbital shaker at room temperature for 10 min. Luminescence was recorded by a Synergy H1 Microplate Reader (Biotek, Winooski, VT). Cells were assessed as a percentage of DMSO only treated control cells. Curves were plotted and $IC_{50}$ values were calculated using the GraphPad Prism 8 program based on a sigmoidal dose-response equation (4 parameter).

RT112/84, UM-UC-14 and KG-1 Cancer Cell Line Cell Viability Assays

Experimental Purpose: To detect the change of intracellular ATP by Cell Titer-Glo® and to evaluate the inhibitory effect of the compounds on cancer cell lines by determining the in vitro $IC_{50}$ value of the compounds.

Cell Titer-Glo® 2.0 Luminescent cell viability assay reagent was purchased from Promega (Madison, WI). RT112/84 and KG-1 cell lines were purchased from American Type Culture Collection (Manassas, VA). UM-UC-14 cell line was purchased from Sigma (St. Louis, MO). RT112/84, UM-UC-14, and KG-1 cells were cultured in RPMI1640 media supplemented with 10% fetal bovine serum. Cultures were maintained at 37° C. in a humidified atmosphere of 5% CO2 and 95% air.

Cell Viability Assay Procedure: Cells were plated in 96-well clear bottom/white plates (Corning #3903) at 10,000 cells/well in 100 µl of media, incubated overnight. The next day, test compound DMSO stock solutions were made at 10 mM and 2 µM final concentration. Compounds were then added to cells in a 9-dose, 10-fold dilution series starting at 30 µM with an HP 300e Digital Dispenser (each dose was applied in triplicate). DMSO was backfilled to each well up to 301 nL total volume of test compound+DMSO, and a total of 301 nL DMSO was added to a control/no test compound well in triplicate. The cells in cell culture plates were incubated with the compounds at 37° C. and 5% $CO_2$ for 72 hours. Then 50 µl of Cell Titer Glo 2.0 reagent was added to each well of the cell culture plates. The contents were covered from light and mixed on an orbital shaker at room temperature for 10 min. Luminescence was recorded by a Synergy H1 Microplate Reader (Biotek, Winooski, VT). Cells were assessed as a percentage of DMSO only treated control cells. Curves were plotted and $IC_{50}$ values were calculated using the GraphPad Prism 8 program based on a sigmoidal dose-response equation (4 parameter).

Results are shown in Table 5.

TABLE 5

| IC50 Values (nM) | | | | | |
|---|---|---|---|---|---|
| | | | Cancer Cell Viability Assays | | |
| | Ba/F3 Cells | | RT112/84 | UM-UC-14 | KG-1 |
| Example | FGFR3 (IC50 nM) | FGFR1 (IC50 nM) | FGFR3 (IC50 nM) | FGFR3 (IC50 nM) | FGFR1 (IC50 nM) |
| 3 | 0.9 | 10 | 20 | | 0.4 |
| 9 | 0.2 | 1 | | | |
| 11 | 29 | 179 | | | |
| 12 | 5.9 | 140 | 4.3 | 5.9 | 45 |
| 13 | 26 | 294 | 16 | | |
| 14 | 100 | 1275 | 75 | | |
| 19 | 29 | | 39 | | |
| 20 | 572 | 4968 | | | |
| 21 | 13 | 189 | 11 | 19 | 103 |
| 22 | 222 | 3167 | | | |
| 23 | 160 | 3134 | | | |
| 24 | 5.5 | 123 | 8.4 | 12 | 169 |
| 25 | 9.1 | 143 | 14 | 19 | 81 |
| 26 | 18 | 221 | 22 | 29 | 123 |
| 27 | 36 | 254 | | | |
| 28 | 7.2 | 219 | 28 | 44 | |
| 29 | 4 | 73 | | | |
| 30 | 14 | 230 | 38 | 47 | |
| 31 | 250 | 483 | | | |

TABLE 6

| Ba/F3 FGFR1/FGFR3 Selectivity | |
|---|---|
| Example | Ba/F3 FGFR1/FGFR3 Selectivity |
| 3 | 11 |
| 9 | 5 |
| 11 | 6 |
| 12 | 24 |
| 13 | 11 |
| 14 | 13 |
| 20 | 8 |
| 21 | 15 |
| 22 | 14 |
| 23 | 7 |
| 24 | 22 |
| 25 | 16 |
| 26 | 12 |
| 27 | 7 |
| 28 | 31 |
| 29 | 18 |
| 30 | 16 |
| 31 | 2 |

Aspects

Aspect 1. A compound of Formula (I) or a pharmaceutically acceptable salt thereof:

(I)

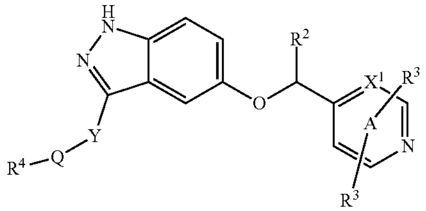

where

Y is —C(O)—$NR^8$—, —$NR^8$C(O)—, —$CR^1$═$CR^1$—, or Y is absent;

each instance of $R^1$, where present, is independently selected from the group consisting —H, —F, —Cl, and -Me;

$R^8$, where present, is selected from —H and -Me;

$R^2$ is selected from the group consisting of —H and optionally substituted $C_1$-$C_3$ alkyl and $R^2$ may be in the (R) or (S) configuration;

$X^1$ is selected from the group consisting of $CR^3$ and N;

each instance of $R^3$ can replace any —H of a CH within Ring A and each instance of $R^3$ is independently selected from the group consisting of —H, —F, —Cl, optionally substituted $C_1$-$C_3$-alkyl, $C_3$-$C_6$-cycloalkyl, and —$OR^9$;

each instance of $R^9$, where present, is independently selected from the group consisting of —H and optionally substituted $C_1$-$C_3$-alkyl;

Q is selected from the group consisting of optionally substituted phenyl, optionally substituted pyridine, optionally substituted pyrimidine, optionally substituted pyridazine, optionally substituted pyrazole, and optionally substituted imidazole;

$R^4$ is selected from the group consisting of:

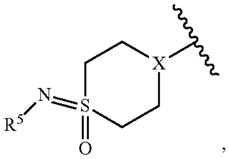

,

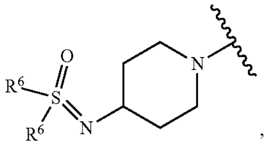

,

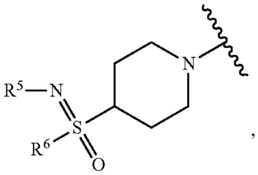

,

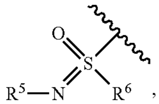

,

-continued

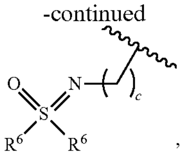

,

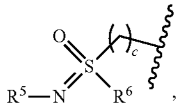

,

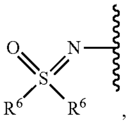

and

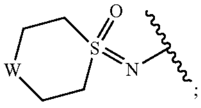

;

X is C—H or N;

$R^5$ is selected from the group consisting of —H, optionally substituted $C_1$-$C_6$-alkyl, and optionally substituted $C_3$-$C_6$-cycloalkyl;

each instance of $R^6$ is independently selected from optionally substituted $C_1$-$C_6$-alkyl, and optionally substituted $C_3$-$C_6$-cycloalkyl;

W is selected from the group consisting of —$CH_2$—, —C(O)—, CH(OH), and —$N(R^7)$—;

$R^7$ is selected from the group consisting of —H, optionally substituted —$C_1$-$C_6$-alkyl, —$C_1$-$C_6$-alkenyl, and optionally substituted —$C_3$-$C_6$-cycloalkyl;

c is an integer equal to 1 or 2;

wherein each instance of Q, phenyl, pyridine, pyrimidine, pyridazine, pyrazole, imidazole, $C_1$-$C_6$-alkyl, and $C_3$-$C_6$-cycloalkyl, when substituted, is independently substituted with one or more of —F, —Cl, —OH, $C_1$-$C_6$-alkyl, —$OR^9$, and —$N(R^9)_2$; and each instance of $R^9$, where present, is independently selected from the group consisting of —H and optionally substituted $C_1$-$C_3$-alkyl.

Aspect 2. The compound of Aspect 1, or a pharmaceutically acceptable salt thereof, further represented by Formula (IA):

(IA)

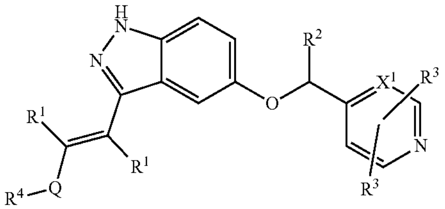

where each instance of $R^1$ is independently selected from the group consisting —H, —F, —Cl, and -Me;

$R^2$ is selected from the group consisting of —H and optionally substituted $C_1$-$C_3$ alkyl;

$X^1$ is selected from the group consisting of $CR^3$ and N;

each instance of $R^3$ is independently selected from the group consisting of —H, —F, —Cl, optionally substituted $C_1$-$C_3$-alkyl, $C_3$-$C_6$-cycloalkyl, and —$OR^9$;

each instance of $R^9$, where present, is independently selected from the group consisting of —H and optionally substituted $C_1$-$C_3$-alkyl;

Q is selected from the group consisting of optionally substituted phenyl, optionally substituted pyridine, optionally substituted pyrimidine, optionally substituted pyridazine, optionally substituted pyrazole, and optionally substituted imidazole;

$R^4$ is selected from the group consisting of:

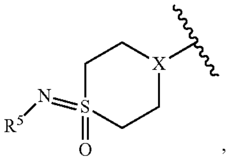

,

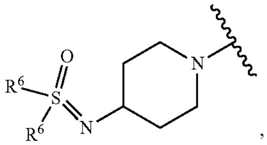

,

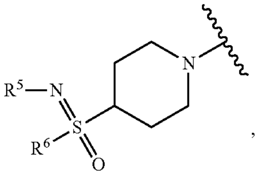

,

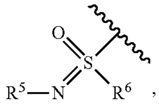

,

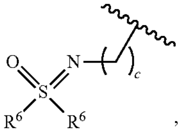

,

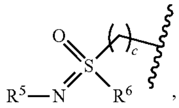

,

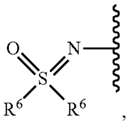

and

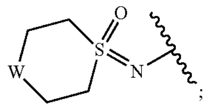

;

X is C—H or N;

$R^5$, where present, is selected from the group consisting of —H, optionally substituted $C_1$-$C_6$-alkyl, and optionally substituted $C_3$-$C_6$-cycloalkyl;

each instance of $R^6$, where present, is independently selected from optionally substituted $C_1$-$C_6$-alkyl, and optionally substituted $C_3$-$C_6$-cycloalkyl;

W, where present, is selected from the group consisting of —$CH_2$—, —C(O)—, and —$N(R^7)$—;

$R^7$, where present, is selected from the group consisting of —H, optionally substituted —$C_1$-$C_6$-alkyl, —$C_1$-$C_6$-alkenyl, and optionally substituted —$C_3$-$C_6$-cycloalkyl; and c is an integer equal to 1 or 2;

wherein each instance of Q, phenyl, pyridine, pyrimidine, pyridazine, pyrazole, imidazole, $C_1$-$C_6$-alkyl, and $C_3$-$C_6$-cycloalkyl, when substituted, is independently substituted with one or more of —F, —Cl, —OH, $C_1$-$C_6$-alkyl, —$OR^9$, and —$N(R^9)_2$; and each instance of $R^9$, where present, is independently selected from the group consisting of —H and optionally substituted $C_1$-$C_3$-alkyl.

Aspect 3. The compound of Aspect 2 or a pharmaceutically acceptable salt thereof, further represented by Formula (IAi):

(IAi)

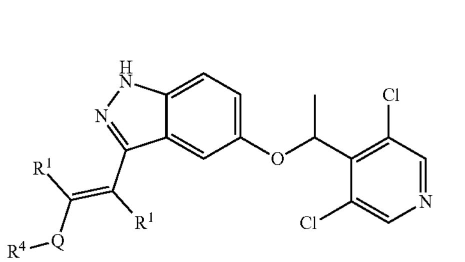

where each instance of $R^1$ is independently selected from the group consisting —H, —F, —Cl, and -Me;

Q is selected from the group consisting of optionally substituted phenyl, pyridine, pyrimidine, pyridazine, pyrazole, and imidazole;

$R^4$ is selected from the group consisting of:

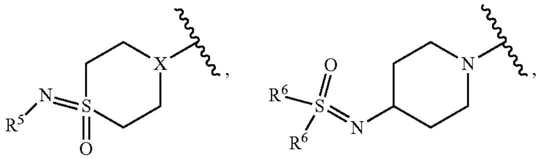

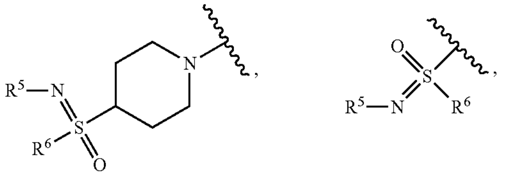

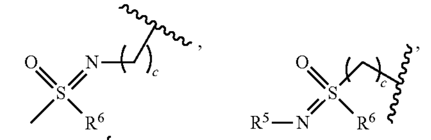

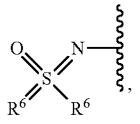

and

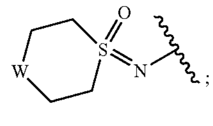

X is C—H or N;

$R^5$ is selected from the group consisting of —H or -Me;

each instance of $R^6$ is -Me;

W is selected from the group consisting of —$CH_2$— and —$N(R^7)$—;

$R^7$, where present, is selected from the group consisting of —H and —$C_1$-$C_6$-alkyl;

c, where present, is an integer equal to 1 or 2;

each instance of phenyl may independently be substituted with one or more of —F, —Cl, —OH, —$OR^9$, and —$N(R^9)_2$, and $R^9$, where present, is independently selected from the group consisting of —H and optionally substituted $C_1$-$C_3$-alkyl; and each instance of $R^9$, where present, is independently selected from the group consisting of —H and optionally substituted $C_1$-$C_3$-alkyl.

Aspect 4. The compound of Aspect 3, where:

each instance of $R^1$ is —H;

Q is selected from the group consisting of pyridine and pyridazine;

$R^4$ is selected from the group consisting of:

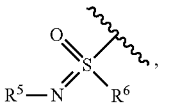

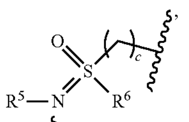

and

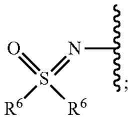

$R^5$ is selected from the group consisting of —H or -Me;

each instance of $R^6$ is -Me; and c is 1.

Aspect 5. The compound of Aspect 2 or a pharmaceutically acceptable salt thereof, further represented by Formula (IAii):

(IAii)

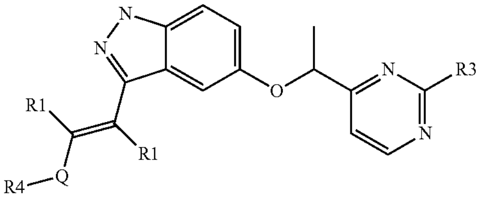

where each instance of $R^1$ is independently selected from the group consisting —H, —F, —Cl, and -Me;

Q is selected from the group consisting of optionally substituted phenyl, pyridine, pyrimidine, pyridazine, pyrazole, and imidazole;

$R^3$ is selected from $C_1$-$C_3$-alkyl, $C_3$-$C_6$-cycloalkyl $R^4$ is selected from the group consisting of:

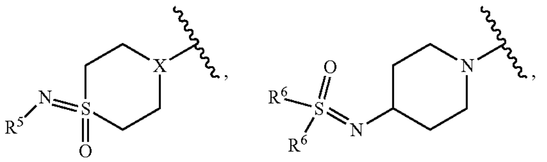

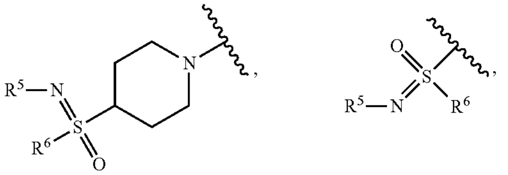

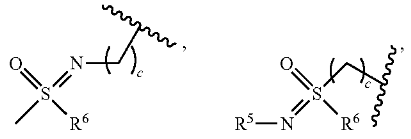

-continued

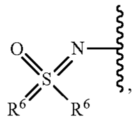

and

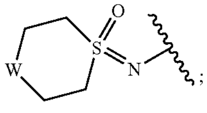

;

X is C—H or N;

$R^5$ is selected from the group consisting of —H or -Me;

each instance of $R^6$ is -Me;

W is selected from the group consisting of —$CH_2$— and —$N(R^7)$—;

$R^7$, where present, is selected from the group consisting of —H and —$C_1$-$C_6$-alkyl;

c, where present, is an integer equal to 1 or 2;

each instance of phenyl may independently be substituted with one or more of —F, —Cl, —OH, —$OR^9$, and —$N(R^9)_2$, and $R^9$, where present, is independently selected from the group consisting of —H and optionally substituted $C_1$-$C_3$-alkyl; and each instance of $R^9$, where present, is independently selected from the group consisting of —H and optionally substituted $C_1$-$C_3$-alkyl.

Aspect 6. The compound of Aspect 1, or a pharmaceutically acceptable salt thereof, further represented by Formula (IB):

(IB)

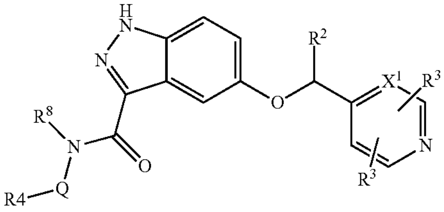

where $R^8$ is selected from —H and -Me;

$R^2$ is selected from the group consisting of —H and optionally substituted $C_1$-$C_3$ alkyl;

$X^1$ is selected from the group consisting of $CR^3$ and N;

each instance of $R^3$ is independently selected from the group consisting of —H, —F, —Cl, optionally substituted $C_1$-$C_3$-alkyl, $C_3$-$C_6$-cycloalkyl, and —$OR^9$;

Q is selected from the group consisting of optionally substituted phenyl, optionally substituted pyridine, optionally substituted pyrimidine, optionally substituted pyridazine, optionally substituted pyrazole, and optionally substituted imidazole;

$R^4$ is selected from the group consisting of:

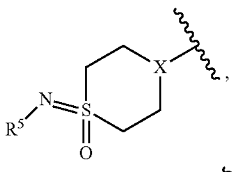

,

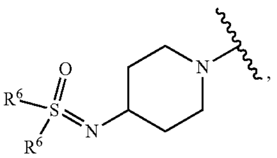

,

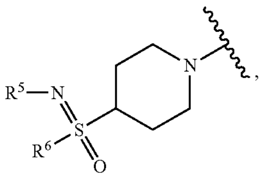

,

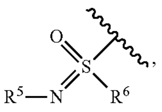

,

-continued

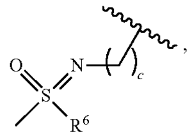

,

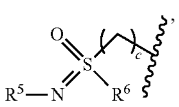

,

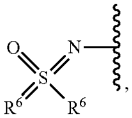

, and

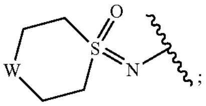

;

X is C—H or N;

$R^5$ is selected from the group consisting of —H, optionally substituted $C_1$-$C_6$-alkyl, and optionally substituted $C_3$-$C_6$-cycloalkyl;

each instance of $R^6$ is independently selected from optionally substituted $C_1$-$C_6$-alkyl, and optionally substituted $C_3$-$C_6$-cycloalkyl;

W is selected from the group consisting of —$CH_2$—, —C(O)—, CH(OH), and —$N(R^7)$—;

$R^7$ is selected from the group consisting of —H, optionally substituted —$C_1$-$C_6$-alkyl, —$C_1$-$C_6$-alkenyl, and optionally substituted —$C_3$-$C_6$-cycloalkyl;

c is an integer equal to 1 or 2; and wherein each instance of Q, phenyl, pyridine, pyrimidine, pyridazine, pyrazole, imidazole, $C_1$-$C_6$-alkyl, and $C_3$-$C_6$-cycloalkyl, when substituted, is independently substituted with one or more of —F, —Cl, —OH, $C_1$-$C_6$-alkyl, —$OR^9$, and —$N(R^9)_2$; and each instance of $R^9$, where present, is independently selected from the group consisting of —H and optionally substituted $C_1$-$C_3$-alkyl.

Aspect 7. The compound of Aspect 6 or a pharmaceutically acceptable salt thereof, further represented by Formula (IBi):

(IBi)

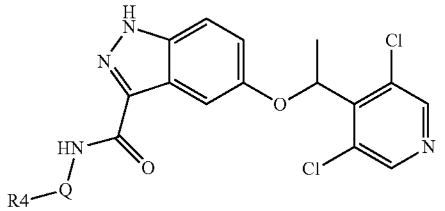

where

Q is selected from the group consisting of optionally substituted phenyl, pyridine, pyrimidine, pyridazine, pyrazole, and imidazole;

$R^4$ is selected from the group consisting of:

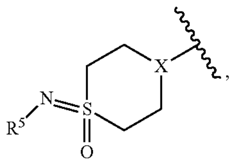

,

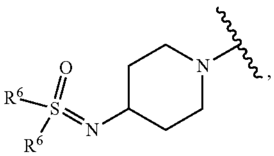

,

-continued

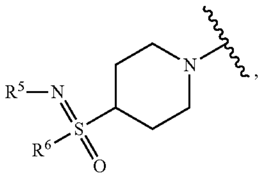

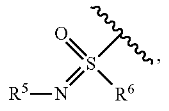

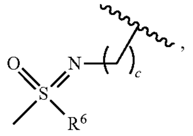

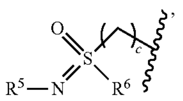

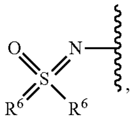

and

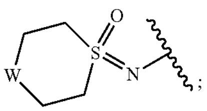

X is C—H or N;

$R^5$ is selected from the group consisting of —H or -Me;

each instance of $R^6$ is -Me;

W is selected from the group consisting of —$CH_2$— and —$N(R^7)$—;

$R^7$, where present, is selected from the group consisting of —H and —$C_1$-$C_6$-alkyl;

c, where present, is an integer equal to 1 or 2;

each instance of phenyl may independently be substituted with one or more of —F, —Cl, —OH, —$OR^9$, and —$N(R^9)_2$, and $R^9$, where present, is independently selected from the group consisting of —H and optionally substituted $C_1$-$C_3$-alkyl; and each instance of $R^9$, where present, is independently selected from the group consisting of —H and optionally substituted $C_1$-$C_3$-alkyl.

Aspect 8. The compound of Aspect 7, where:

each instance of $R^1$ is —H;

Q is selected from the group consisting of pyridine and pyridazine;

$R^4$ is selected from the group consisting of:

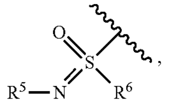

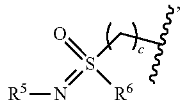

and

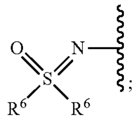

$R^5$ is selected from the group consisting of —H or -Me;

each instance of $R^6$ is -Me; and c is 1.

Aspect 9. The compound of Aspect 6, further represented by Formula (IBii) or a pharmaceutically acceptable salt thereof:

(IBii)

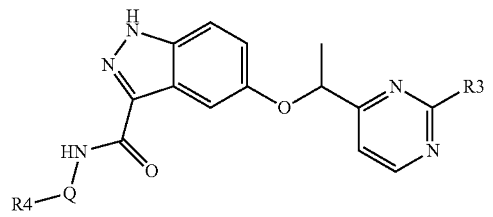

where

Q is selected from the group consisting of optionally substituted phenyl, pyridine, pyrimidine, pyridazine, pyrazole, and imidazole;

$R^3$ is selected from $C_1$-$C_3$-alkyl, $C_3$-$C_6$-cycloalkyl $R^4$ is selected from the group consisting of:

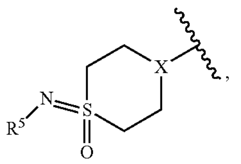

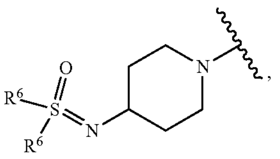

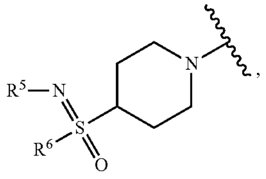

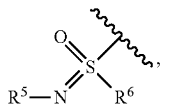

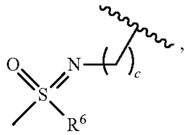

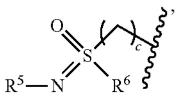

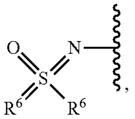

and

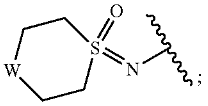

X is C—H or N;

$R^5$ is selected from the group consisting of —H or -Me;

each instance of $R^6$ is -Me;

W is selected from the group consisting of —$CH_2$— and —$N(R^7)$—;

$R^7$, where present, is selected from the group consisting of —H and —$C_1$-$C_6$-alkyl;

c, where present, is an integer equal to 1 or 2;

each instance of phenyl may independently be substituted with one or more of —F, —Cl, —OH, —$OR^9$, and —$N(R^9)_2$, and $R^9$, where present, is independently selected from the group consisting of —H and optionally substituted $C_1$-$C_3$-alkyl; and each instance of $R^9$, where present, is independently selected from the group consisting of —H and optionally substituted $C_1$-$C_3$-alkyl.

Aspect 10. The compound of Aspect 1, or a pharmaceutically acceptable salt thereof, further represented by Formula (IC):

(IC)

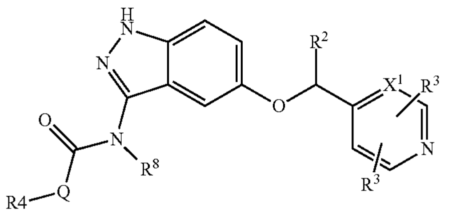

where $R^8$ is selected from —H and -Me;

$R^2$ is selected from the group consisting of —H and optionally substituted $C_1$-$C_3$ alkyl;

$X^1$ is selected from the group consisting of $CR^3$ and N;

each instance of $R^3$ is independently selected from the group consisting of —H, —F, —Cl, optionally substituted $C_1$-$C_3$-alkyl, $C_3$-$C_6$-cycloalkyl, and —$OR^9$;

Q is selected from the group consisting of optionally substituted phenyl, optionally substituted pyridine, optionally substituted pyrimidine, optionally substituted pyridazine, optionally substituted pyrazole, and optionally substituted imidazole;

$R^4$ is selected from the group consisting of:

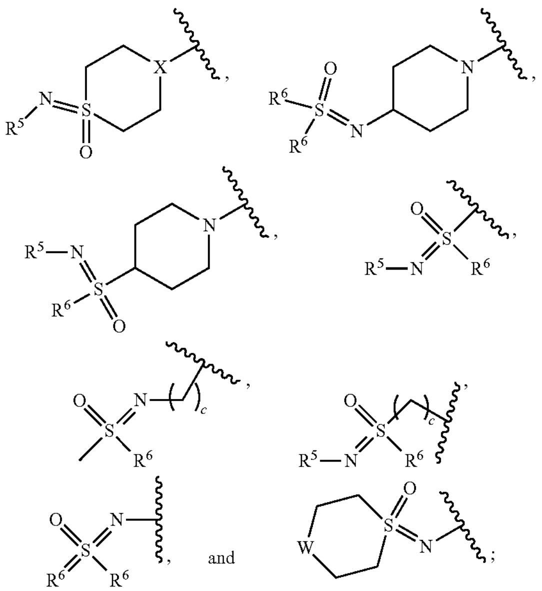

and

X is C—H or N;

$R^5$ is selected from the group consisting of —H, optionally substituted $C_1$-$C_6$-alkyl, and optionally substituted $C_3$-$C_6$-cycloalkyl;

each instance of $R^6$ is independently selected from optionally substituted $C_1$-$C_6$-alkyl, and optionally substituted $C_3$-$C_6$-cycloalkyl;

W is selected from the group consisting of —$CH_2$—, —C(O)—, CH(OH), and —$N(R^7)$—;

$R^7$ is selected from the group consisting of —H, optionally substituted —$C_1$-$C_6$-alkyl, —$C_1$-$C_6$-alkenyl, and optionally substituted —$C_3$-$C_6$-cycloalkyl;

c is an integer equal to 1 or 2; and wherein each instance of Q, phenyl, pyridine, pyrimidine, pyridazine, pyrazole, imidazole, $C_1$-$C_6$-alkyl, and $C_3$-$C_6$-cycloalkyl, when substituted, is independently substituted with one or more of —F, —Cl, —OH, $C_1$-$C_6$-alkyl, —$OR^9$, and —$N(R^9)_2$; and each instance of $R^9$, where present, is independently selected from the group consisting of —H and optionally substituted $C_1$-$C_3$-alkyl.

Aspect 11. The compound of Aspect 1, or a pharmaceutically acceptable salt thereof, further represented by Formula (ID):

(ID)

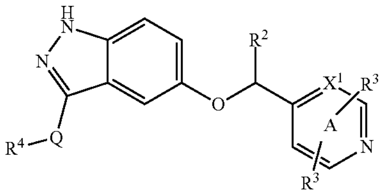

where

Q is selected from the group consisting of optionally substituted phenyl, pyridine, pyrimidine, pyridazine, pyrazole, and imidazole;

$R^4$ is selected from the group consisting of:

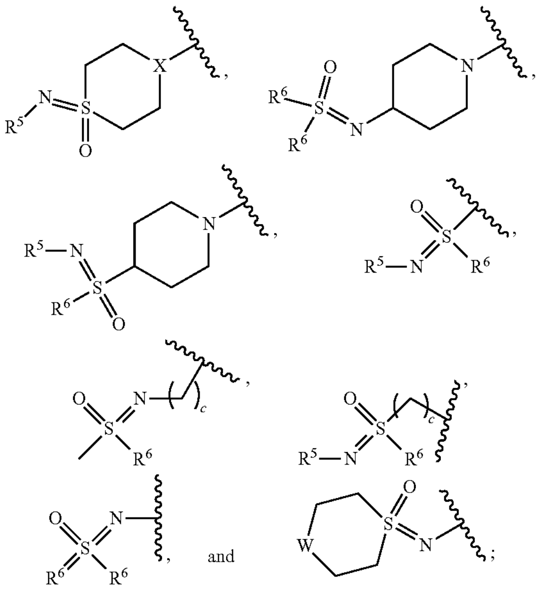

and

X is C—H or N;

$R^5$ is selected from the group consisting of —H or -Me;

each instance of $R^6$ is -Me;

W is selected from the group consisting of —$CH_2$— and —$N(R^7)$—;

$R^7$, where present, is selected from the group consisting of —H and —$C_1$-$C_6$-alkyl;

c, where present, is an integer equal to 1 or 2;

wherein each instance of Q, phenyl, pyridine, pyrimidine, pyridazine, pyrazole, imidazole, when substituted, is independently substituted with one or more of —F, —Cl, —OH, $C_1$-$C_6$-alkyl, —$OR^9$, and —$N(R^9)_2$; and each instance of $R^9$, where present, is independently selected from the group consisting of —H and $C_1$-$C_3$-alkyl.

Aspect 12. The compound of Aspect 11, further represented by Formula (IDi) or a pharmaceutically acceptable salt thereof:

(IDi)

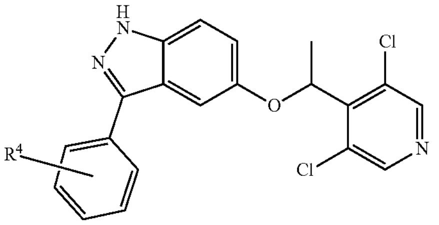

$R^4$ is selected from the group consisting of:

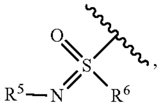

,

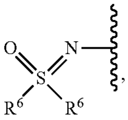

, and

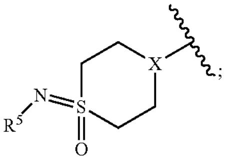

;

X is C—H or N;

$R^5$ is selected from the group consisting of —H or -Me; and each instance of $R^6$ is -Me.

Aspect 13. The compound of Aspect 11, further represented by Formula (IDi) or a pharmaceutically acceptable salt thereof:

(IDii)

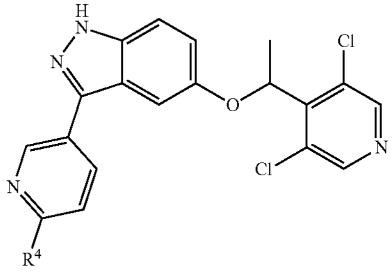

where $R^4$ is selected from the group consisting of:

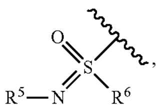

,

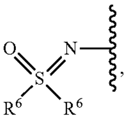

, and

-continued

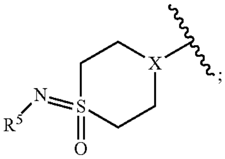

;

X is C—H or N;

$R^5$ is selected from the group consisting of —H or -Me; and each instance of $R^6$ is -Me.

Aspect 14. The compound of Aspect 1 or a pharmaceutically acceptable salt thereof further represented by one of the following structures:

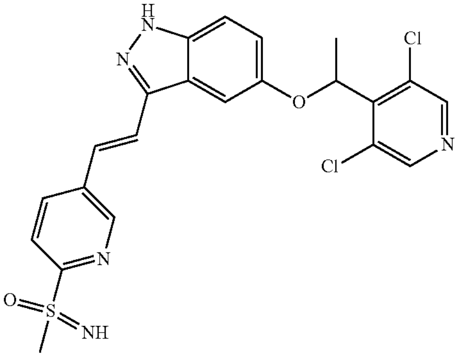

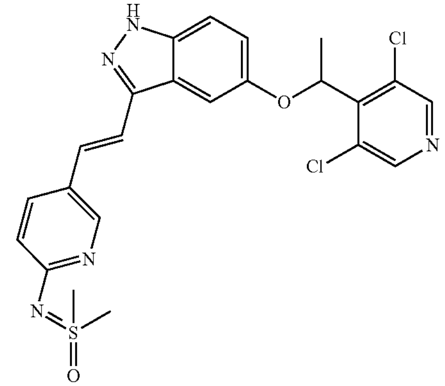

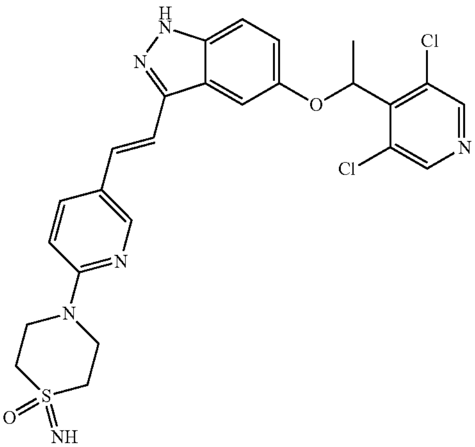

-continued
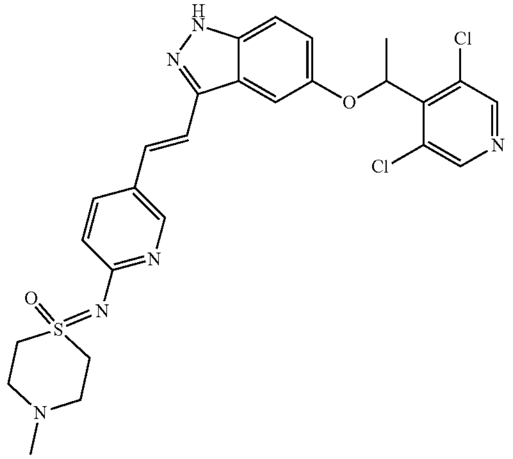
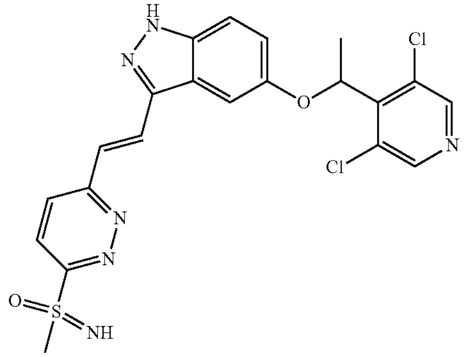
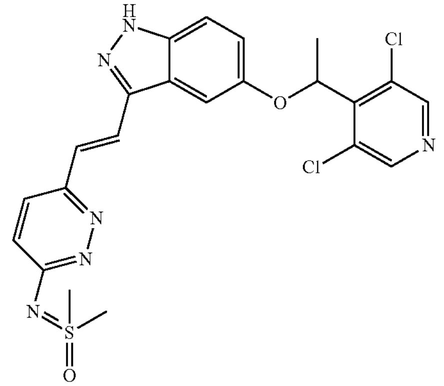
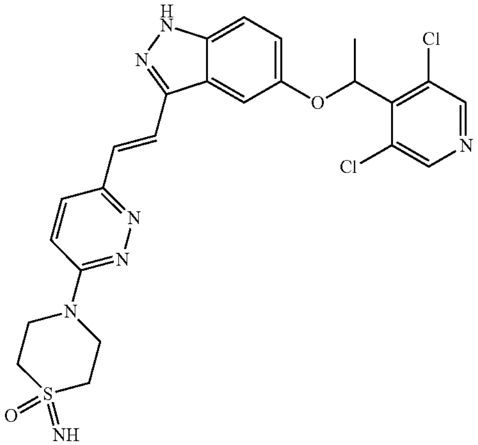
-continued
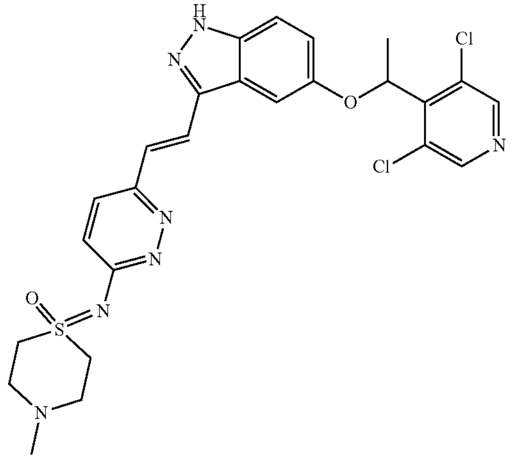
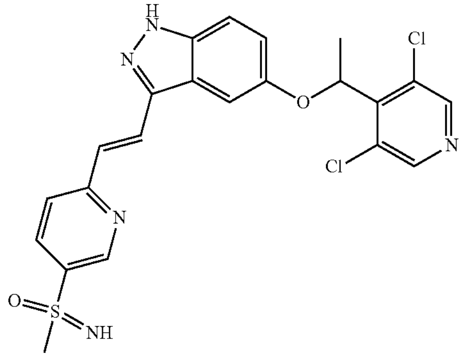
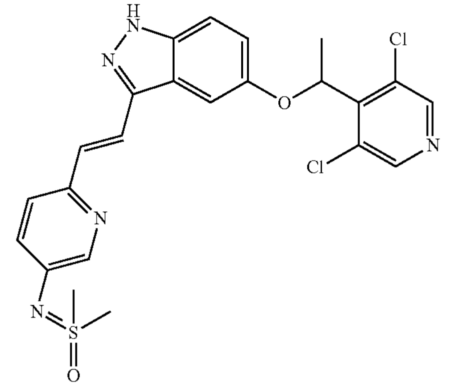
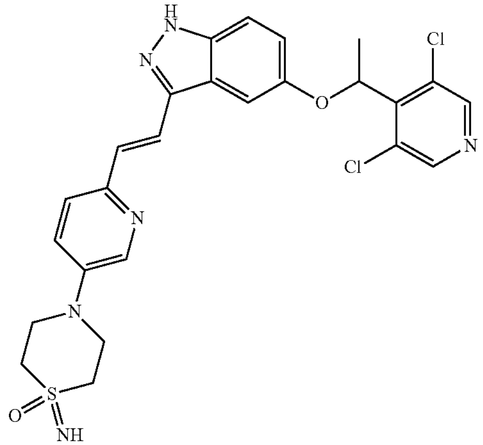

-continued
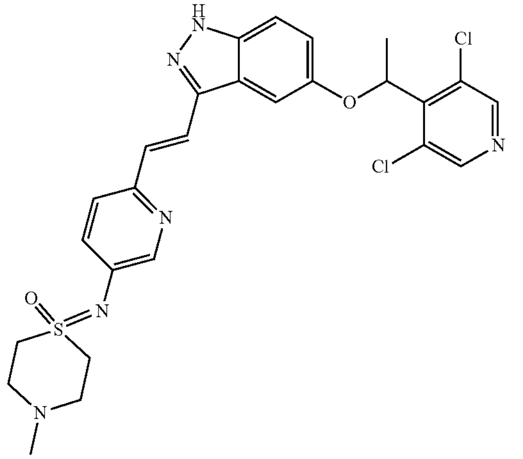
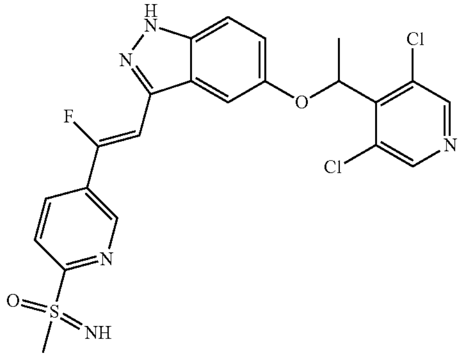
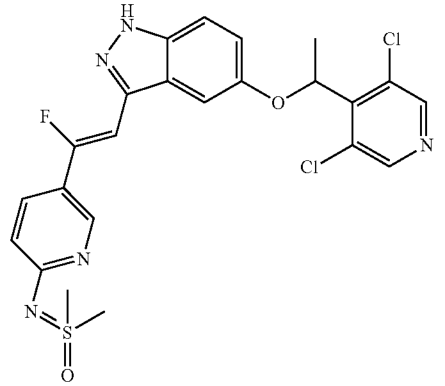
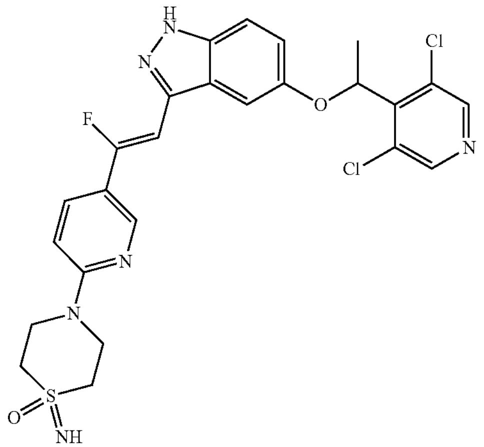
-continued
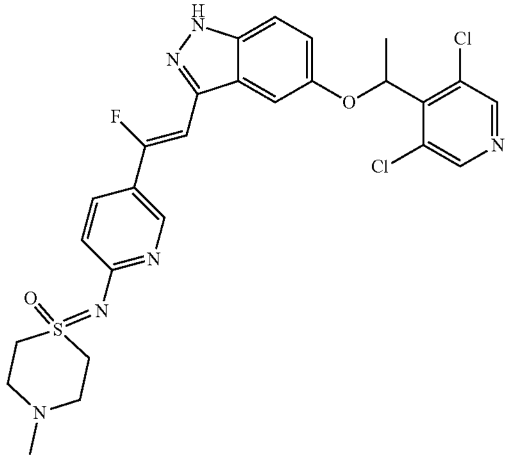
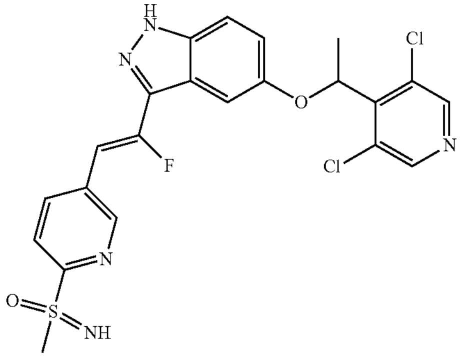
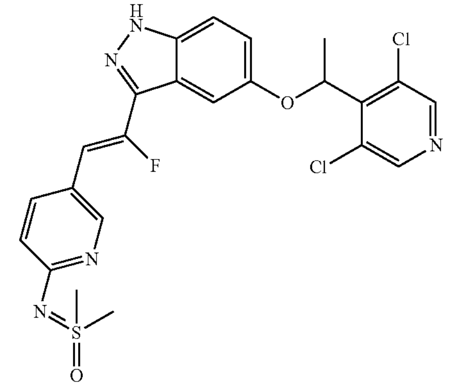
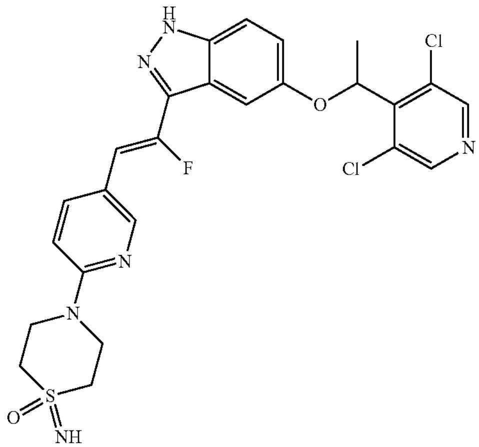

-continued
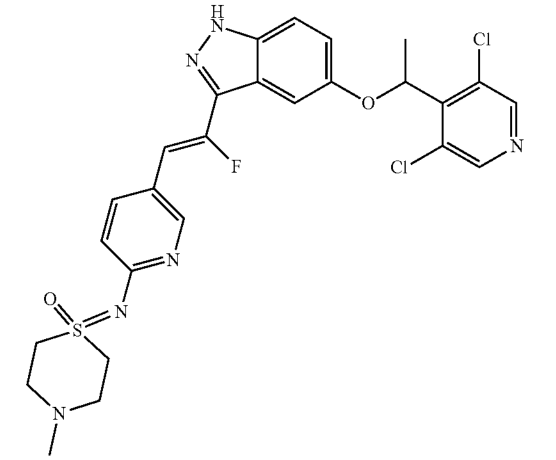
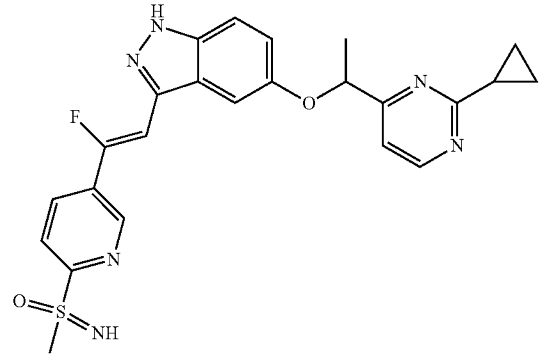
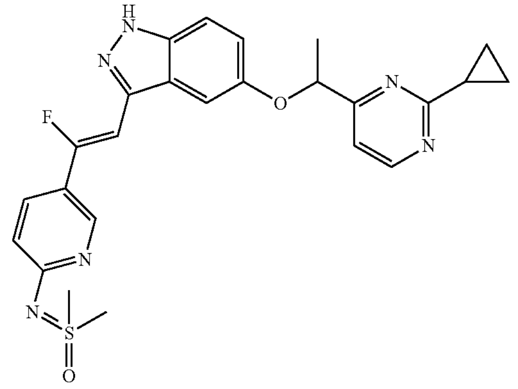
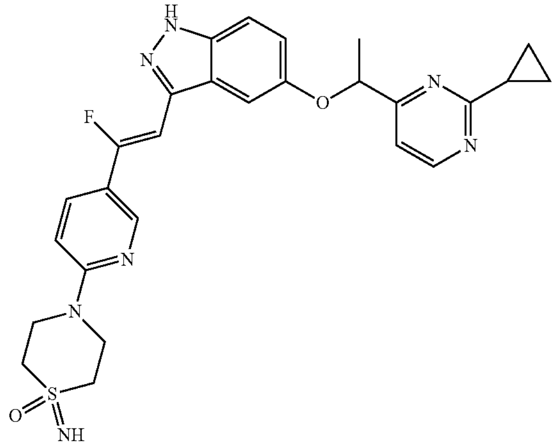
-continued
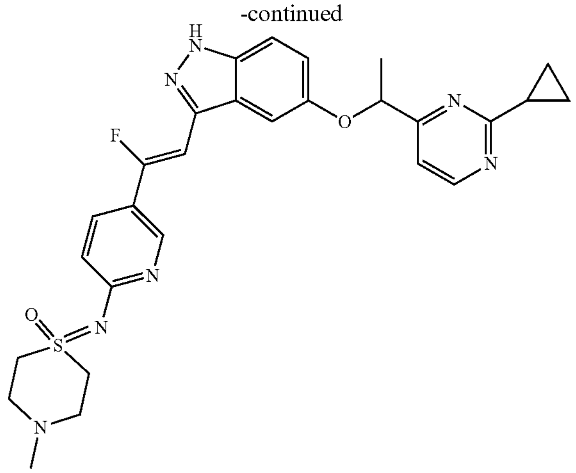
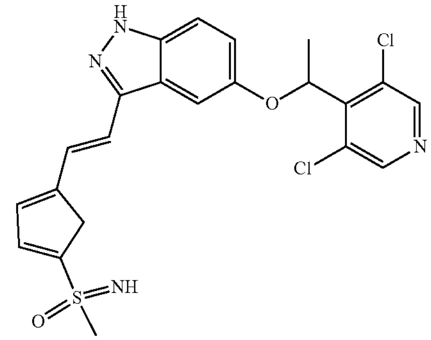
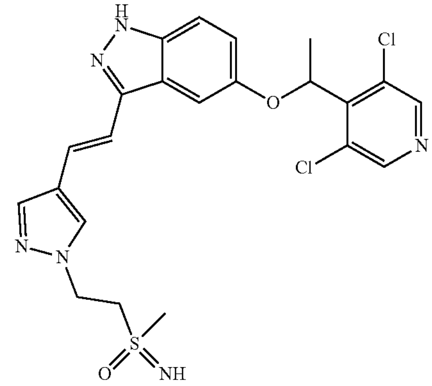
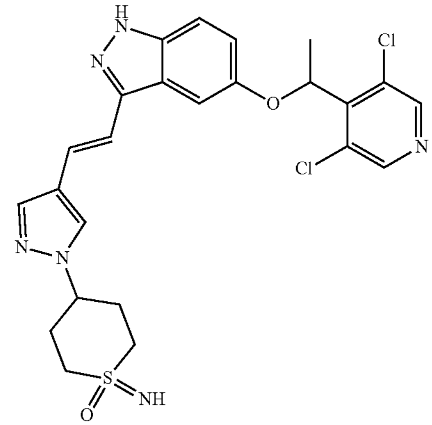

-continued
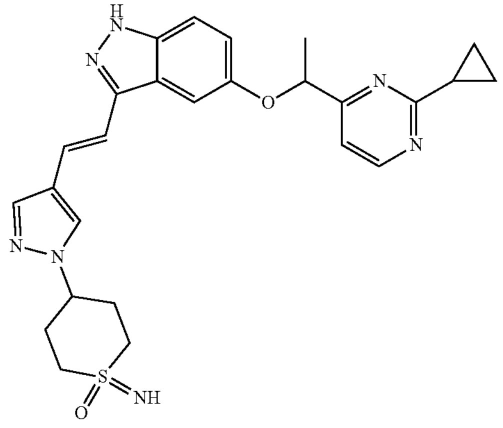
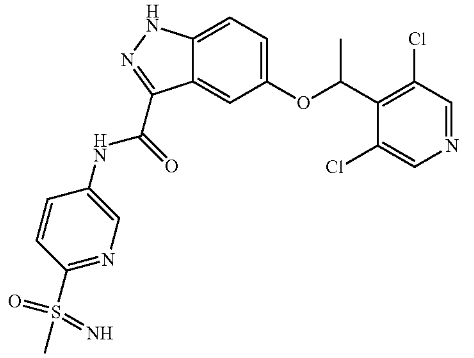
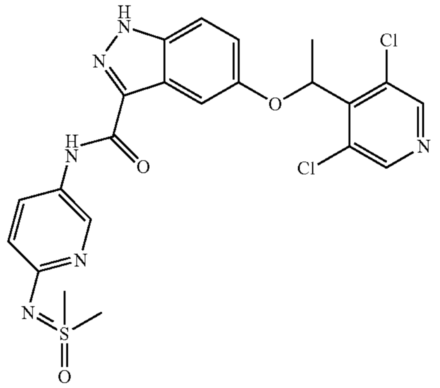
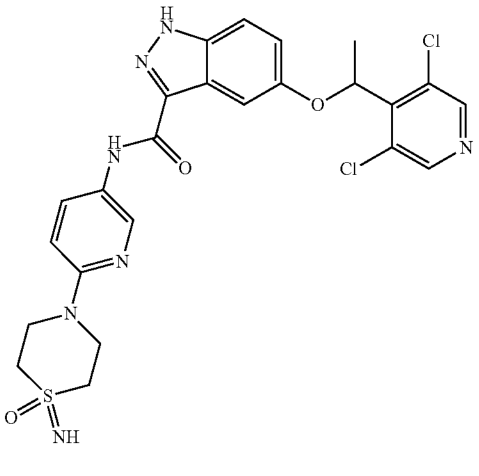
-continued
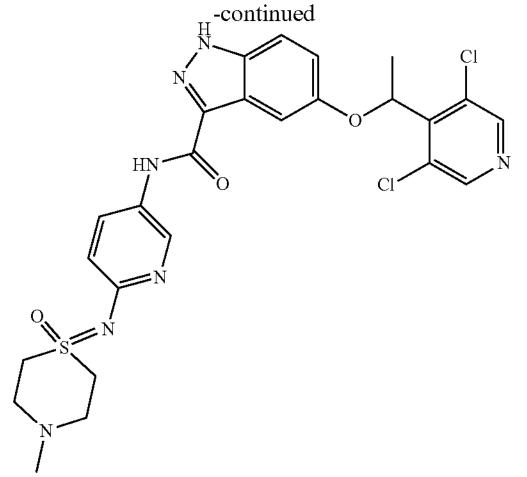
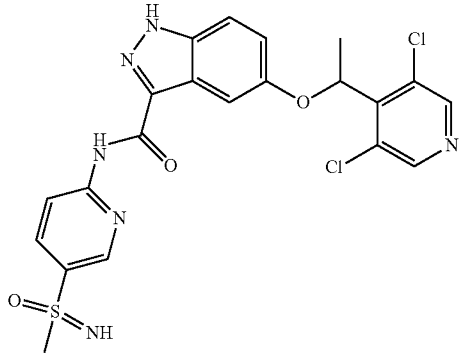
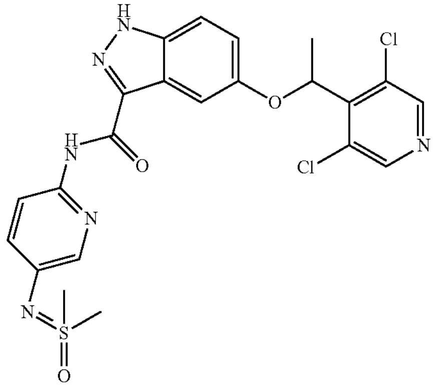
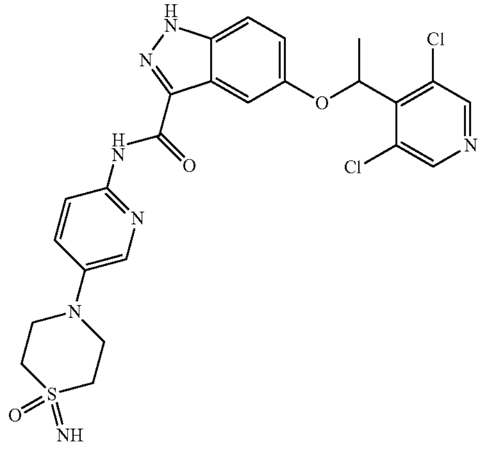

-continued
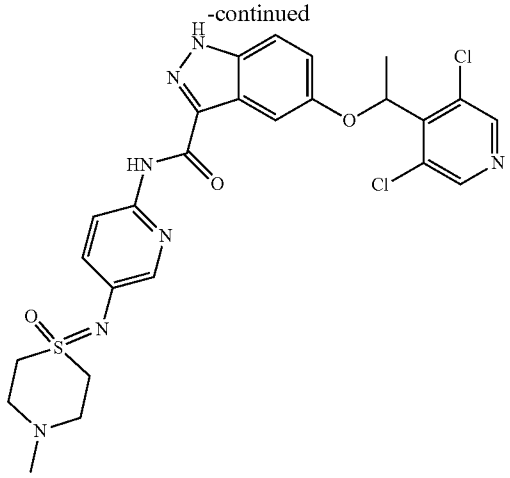
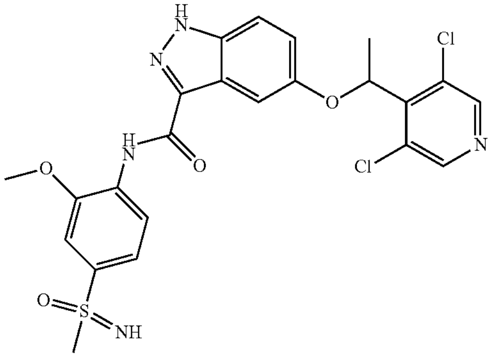
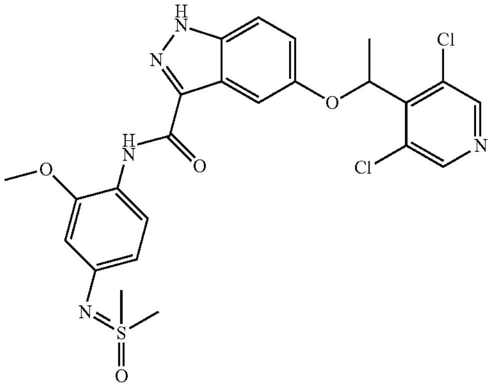
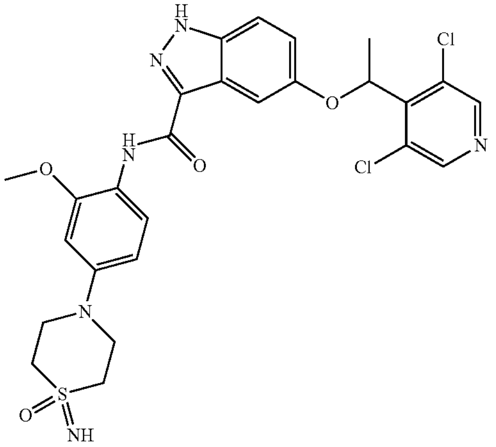
-continued
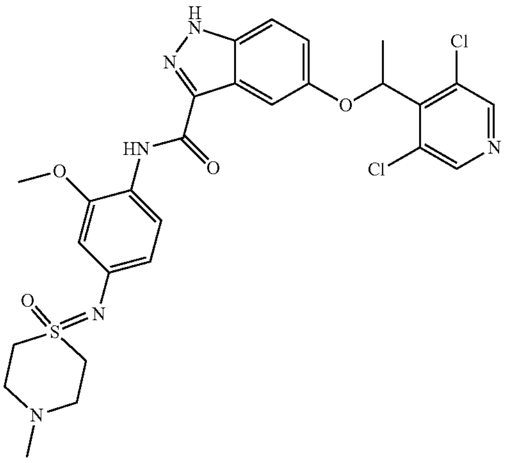
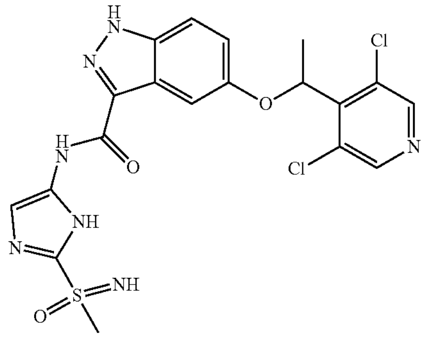
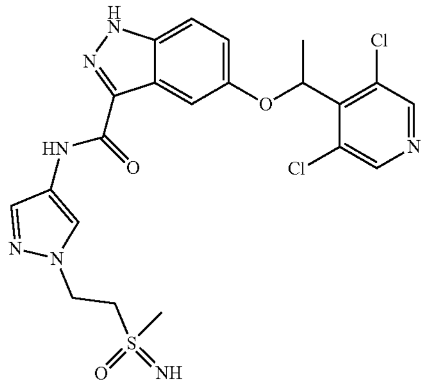
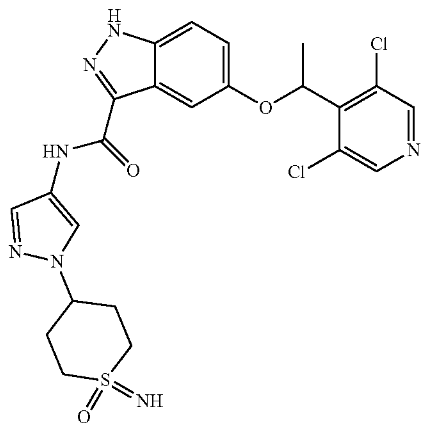

-continued
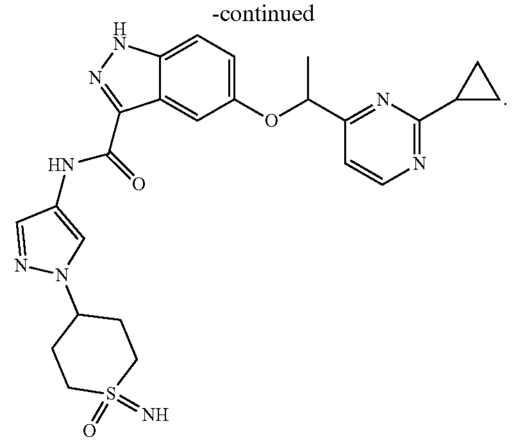
Aspect 15. The compound of Aspect 1 or a pharmaceutically acceptable salt thereof further represented by one of the following structures:
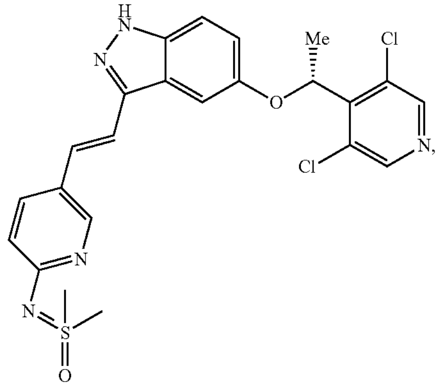
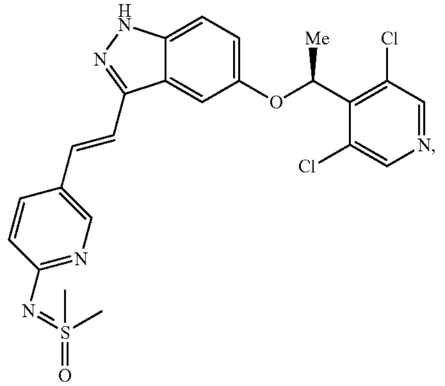
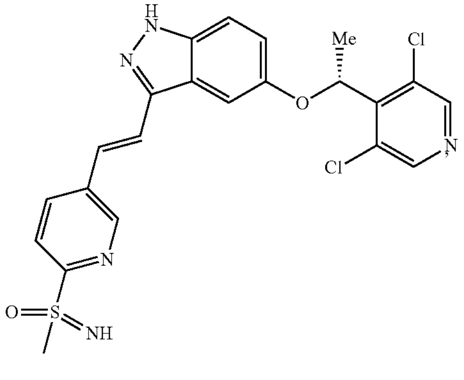
-continued
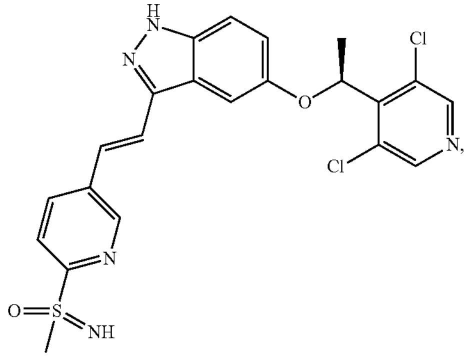
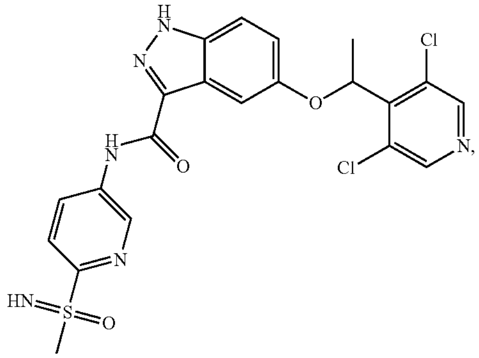
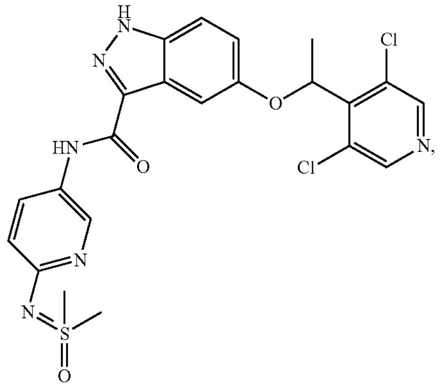
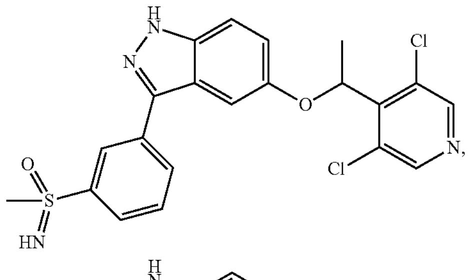
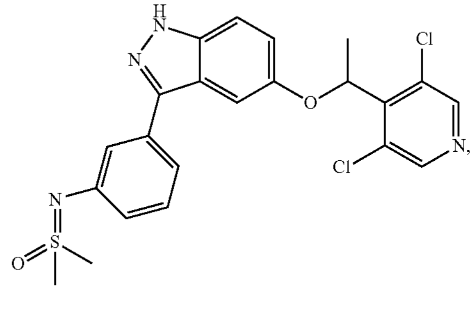

-continued
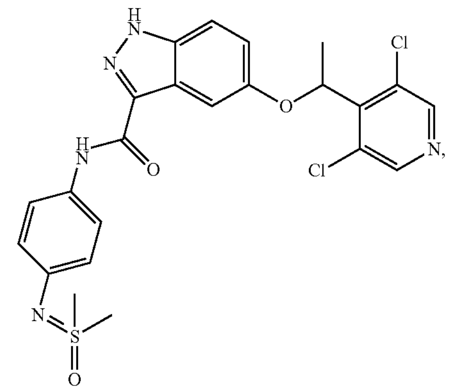
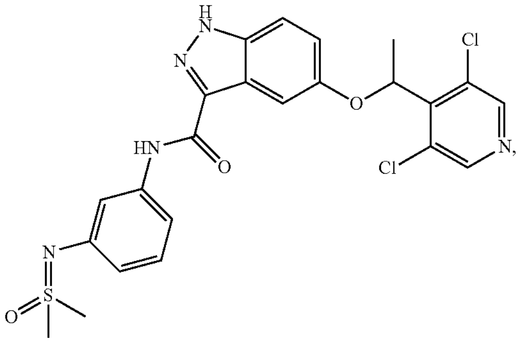
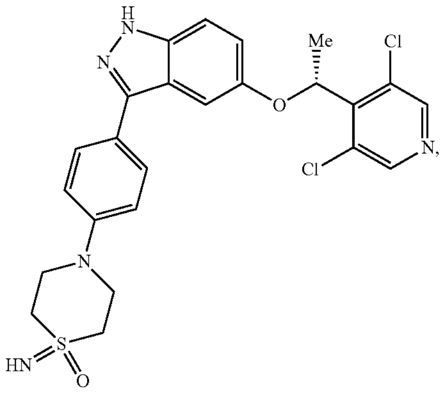
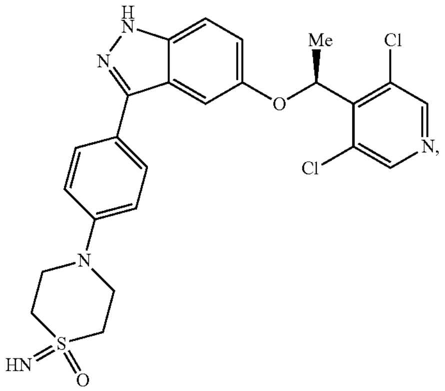
-continued
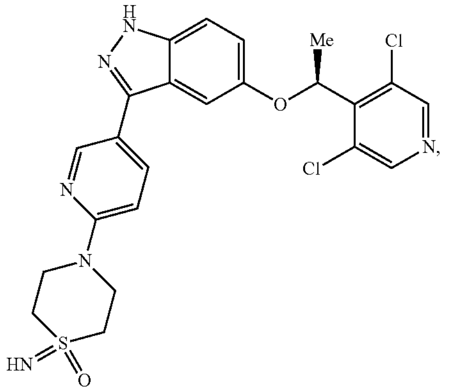
and
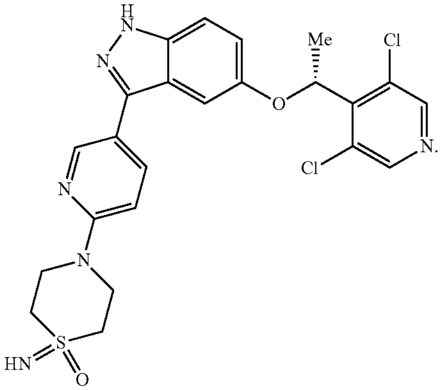
Aspect 16. The compound of Aspect 1 or a pharmaceutically acceptable salt thereof further represented by one of the following structures:
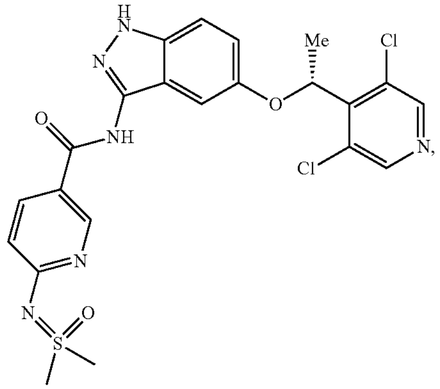
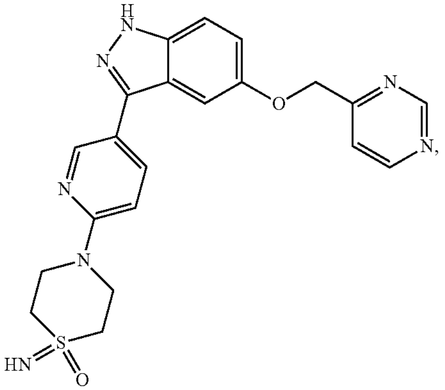

-continued
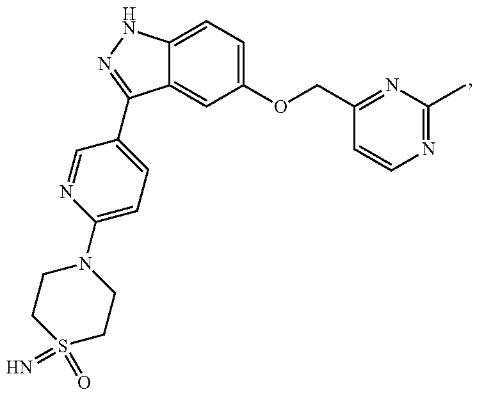
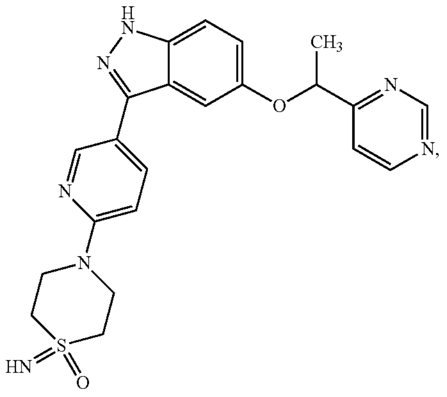
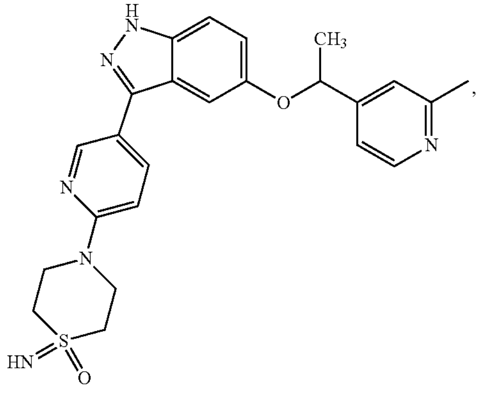
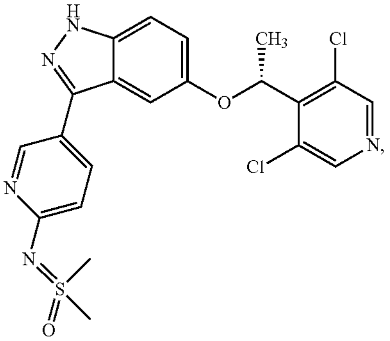
-continued
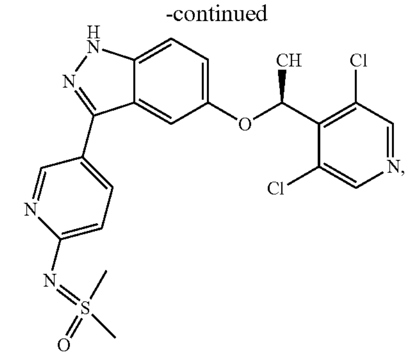
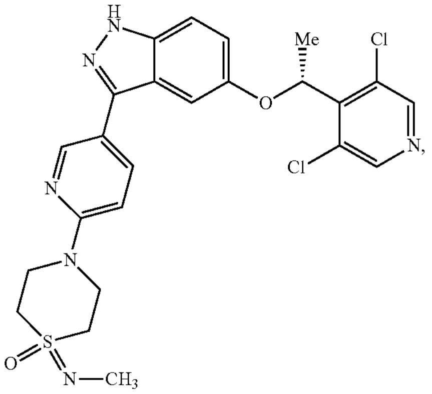
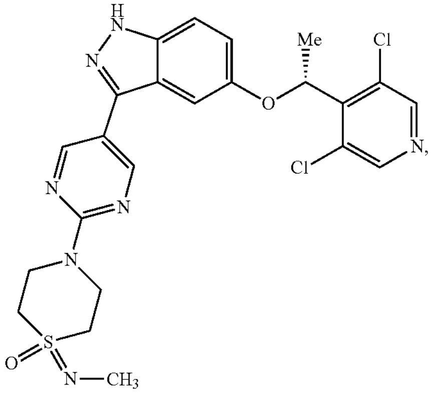
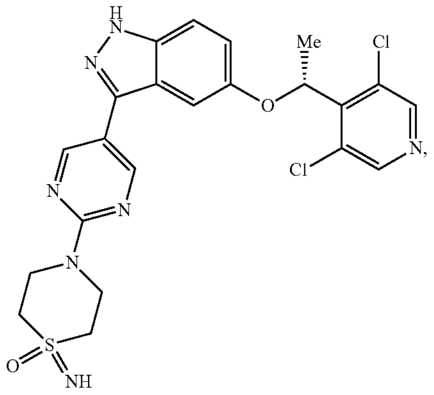

-continued
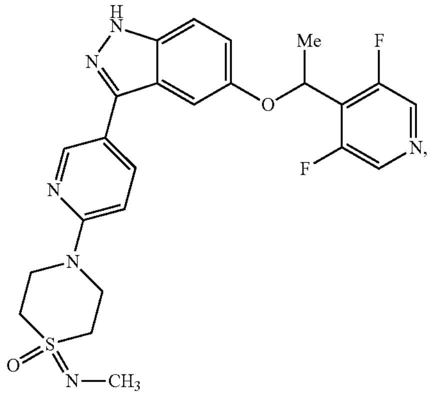
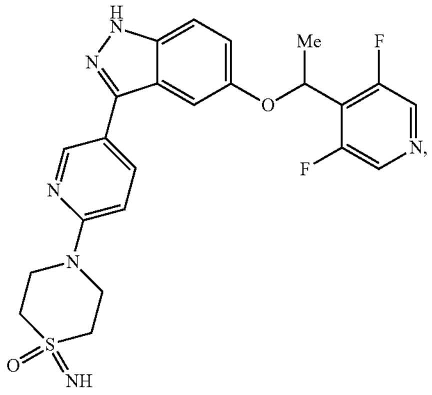
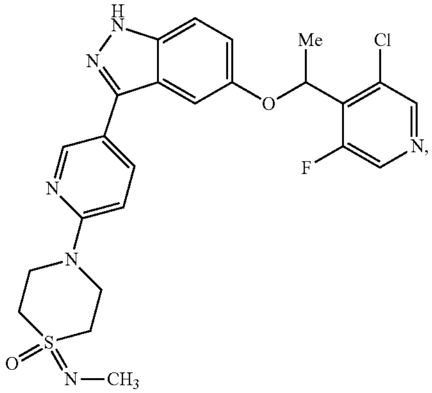
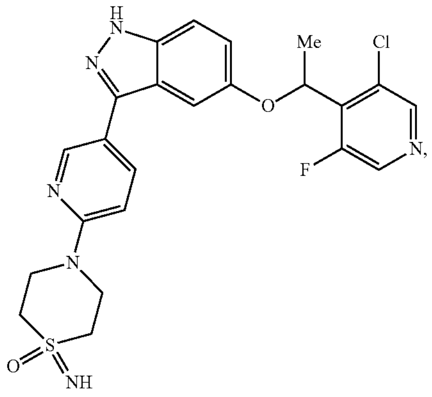
-continued
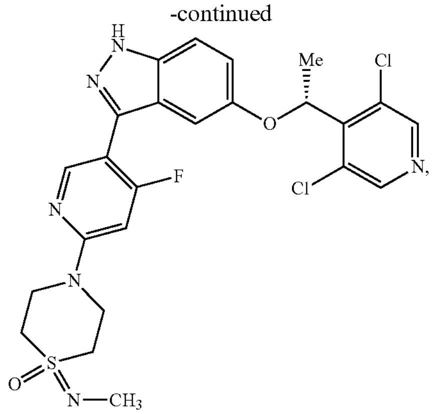
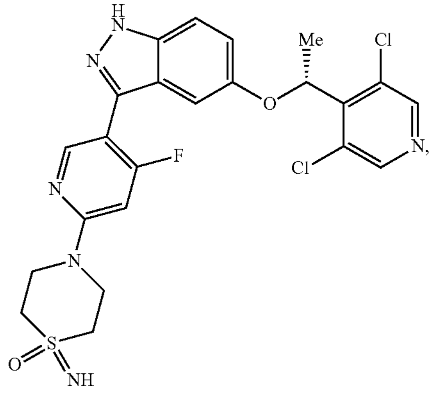
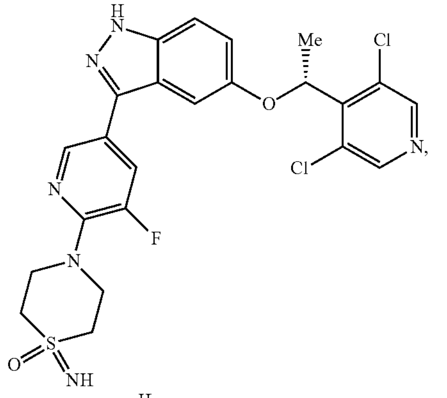
and
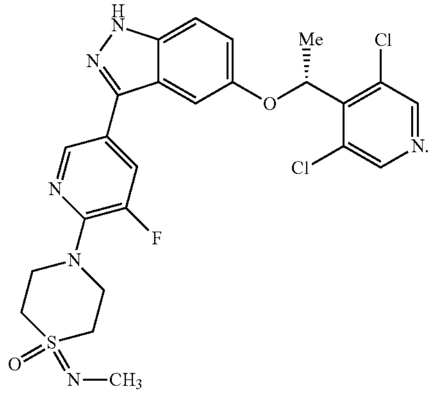
Aspect 17. A method of treating a cancer, the method comprising:
in response to a determination of the presence of a FGFR mutant polypeptide or a FGFR mutant polynucleotide in a sample from a subject, administering to the subject an effective amount the compound of any one of Aspects 1 to 16 thereby treating the cancer in the subject.

Aspect 18. A formulation comprising or consisting essentially of the compounds of any one of Aspects 1 to 16.

What is claimed is:

1. A compound of Formula (I) or a pharmaceutically acceptable salt thereof:

(I)

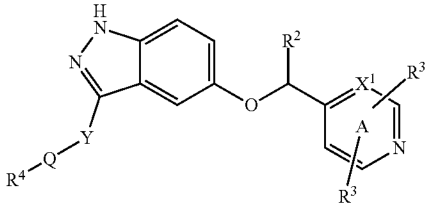

wherein

Y is —C(O)—$NR^8$—, —$NR^8$C(O)—, —$CR^1$═$CR^1$—, or Y is absent;

each $R^1$, where present, is independently —H, —F, —Cl, —$C_{1-6}$alkyl, $C_{1-6}$haloalkyl, $C_{1-6}$alkoxy, or $C_{1-6}$hydroxyalkyl;

$R^8$, where present, is —H or —$C_{1-6}$alkyl;

$R^2$ is —H or optionally substituted $C_1$-$C_3$ alkyl;

$X^1$ is CH, $CR^3$, or N;

each instance of $R^3$ can replace any —H of a CH within Ring A and each instance of $R^3$ is independently —F, —Cl, —Br, optionally substituted $C_1$-$C_6$-alkyl, $C_{1-6}$haloalkyl, $C_3$-$C_6$-cycloalkyl, or —$OR^9$;

each instance of $R^9$, where present, is independently —H, optionally substituted $C_1$-$C_6$-alkyl, or $C_{1-6}$haloalkyl;

Q is optionally substituted phenyl, optionally substituted pyridinyl, optionally substituted pyrimidinyl, optionally substituted pyridazinyl, optionally substituted pyrazolyl, optionally substituted imidazolyl, optionally substituted thiazolyl, or optionally substituted pyrrolopyridinyl;

$R^4$ is:

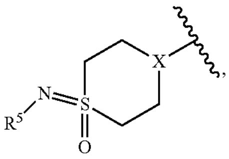

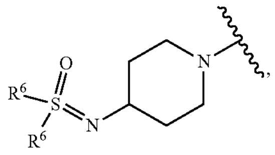

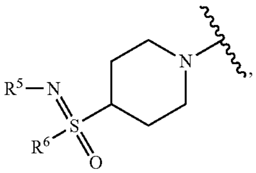

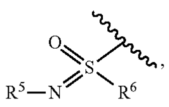

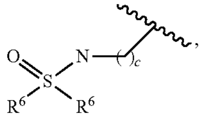

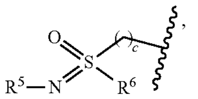

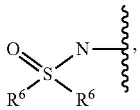

or

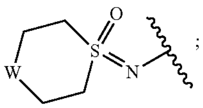

;

X is C—H or N;

$R^5$ is —H, optionally substituted $C_1$-$C_6$-alkyl, or optionally substituted $C_3$-$C_6$-cycloalkyl;

each instance of $R^6$ is independently optionally substituted $C_1$-$C_6$-alkyl, or optionally substituted $C_3$-$C_6$-cycloalkyl; or two $R^6$ groups, together with the atoms to which they are attached, form a 4- to 7-membered ring;

W is —$CH_2$—, —C(O)—, CH(OH), or —N($R^7$)—;

$R^7$ is —H, optionally substituted —$C_1$-$C_6$-alkyl, —$C_1$-$C_6$-alkenyl, or optionally substituted —$C_3$-$C_6$-cycloalkyl;

c is 1 or 2;

wherein when Q, $C_1$-$C_6$-alkyl, or $C_3$-$C_6$-cycloalkyl is substituted, the substituent is one or more of —F, —Cl, Br, —OH, $C_1$-$C_6$-alkyl, —$OR^9$, or —N($R^9$)$_2$.

2. The compound of claim 1, wherein Y is —C(O)—$NR^8$—.

3. The compound of claim 1, wherein Y is —$NR^8$C(O)—.

4. The compound of claim 1, wherein Y is —$CR^1$═$CR^1$—.

5. The compound of claim 1, wherein Y is absent.

6. The compound of claim 1, wherein $R^4$ is

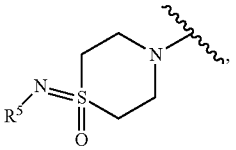

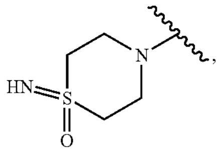

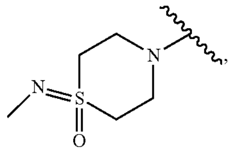

or

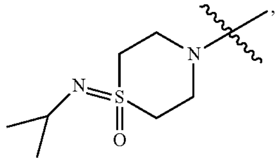

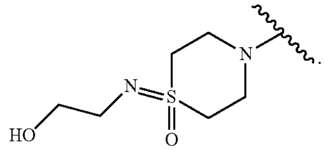

7. The compound of claim 1, wherein $R^4$ is

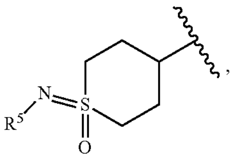

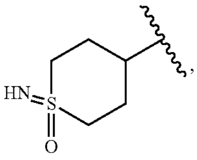
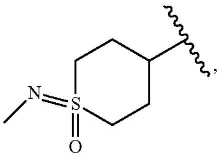
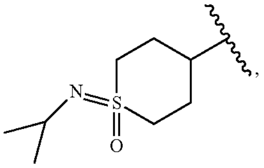
or
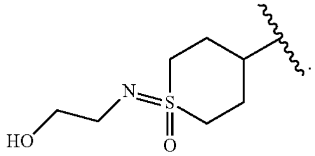
8. The compound of claim 1, wherein $R^4$ is
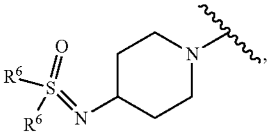
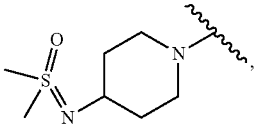
or
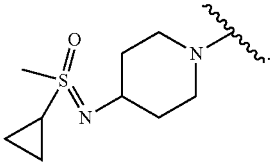
9. The compound of claim 1, wherein $R^4$ is
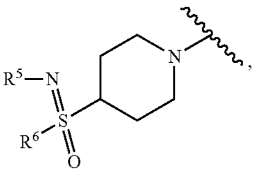
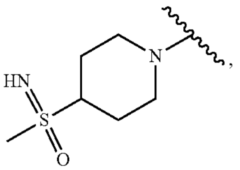
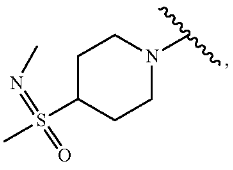
-continued
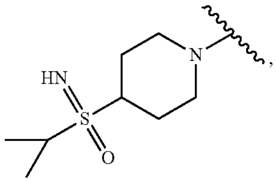
or
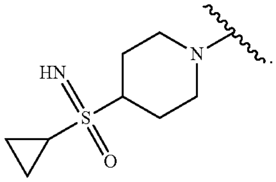
10. The compound of claim 1, wherein $R^4$ is
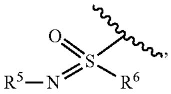
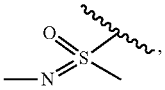
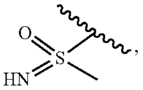
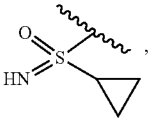
or
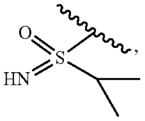
11. The compound of claim 1, wherein $R^4$ is
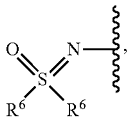
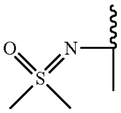
or
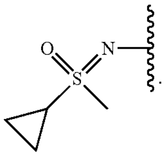
12. The compound of claim 1, wherein $R^4$ is
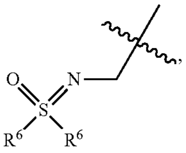

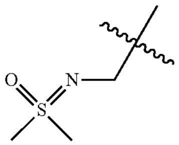
or
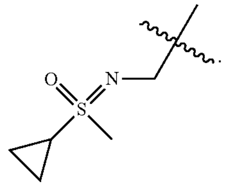
13. The compound of claim 1, wherein $R^4$ is
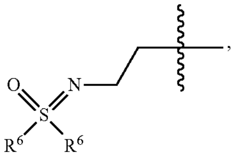
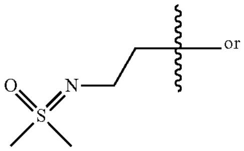
or
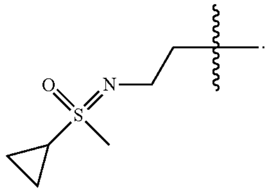
14. The compound of claim 1, wherein $R^4$ is
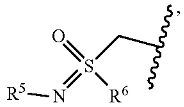
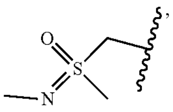
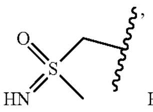
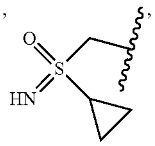
or
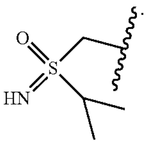
15. The compound of claim 1, wherein $R^4$ is
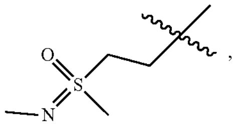
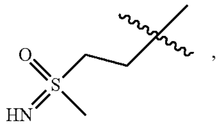
-continued
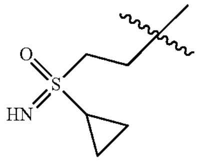
or
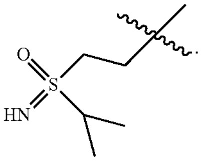
16. The compound of claim 1, wherein $R^4$ is
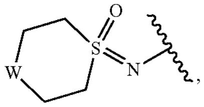
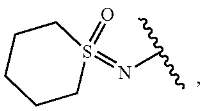
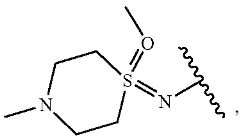
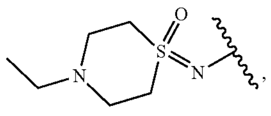
or
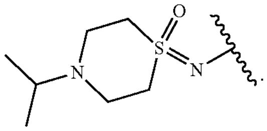
17. The compound of claim 1, wherein $R^4$ is
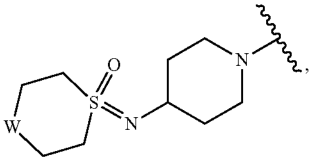
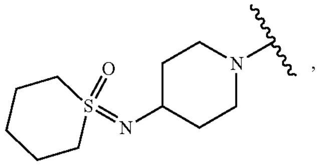
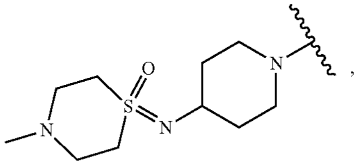
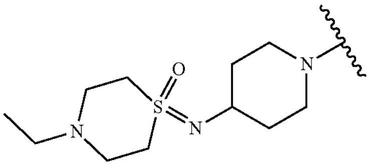
or -continued

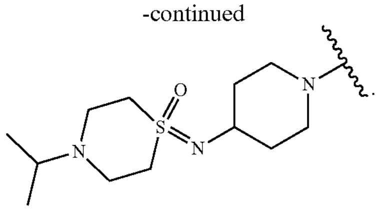

18. A pharmaceutically acceptable salt of a compound of claim 1.

19. A pharmaceutical composition comprising a compound of claim 1 and a pharmaceutically acceptable excipient.

20. A method of treating cancer in a subject comprising administering to the subject a therapeutically effective amount of a compound of claim 1, or a pharmaceutically acceptable salt thereof.

21. The method of claim 20, wherein the cancer is urothelial carcinoma, breast carcinoma, endometrial adenocarcinoma, ovarian carcinoma, primary glioma, cholangiocarcinoma, gastric adenocarcinoma, non-small cell lung carcinoma, pancreatic exocrine carcinoma, oral, prostate, bladder, colorectal carcinoma, renal cell carcinoma, neuroendocrine carcinoma, myeloproliferative neoplasms, head and neck (squamous), melanoma, leiomyosarcoma, or a sarcoma.

22. The method of claim 20, wherein the subject has an intrahepatic cholangiocarcinoma.

23. The method of claim 20, wherein the cancer is an FGFR-mutant cancer.

* * * * *